US011806335B2

(12) United States Patent
Guo et al.

(10) Patent No.: US 11,806,335 B2
(45) Date of Patent: Nov. 7, 2023

(54) HETEROCYCLIC CARBOXYLATE COMPOUNDS AS GLYCOLATE OXIDASE INHIBITORS

(71) Applicant: Lilac Therapeutics, Inc., Walnut Creek, CA (US)

(72) Inventors: Hongyan Guo, San Mateo, CA (US); Amy S. Lee, Palo Alto, CA (US); Hyung-Jung Pyun, Fremont, CA (US); Devleena M. Shivakumar, Menlo Park, CA (US); Manoj C. Desai, Martinez, CA (US); Lianhong Xu, Palo Alto, CA (US); John E. Knox, Alameda, CA (US); Zachary E R Newby, San Francisco, CA (US)

(73) Assignee: Lilac Therapeutics, Inc., Walnut Creek, CA (US)

( * ) Notice: Subject to any disclaimer, the term of this patent is extended or adjusted under 35 U.S.C. 154(b) by 45 days.

(21) Appl. No.: 17/081,940

(22) Filed: Oct. 27, 2020

(65) Prior Publication Data

US 2021/0128532 A1 May 6, 2021

Related U.S. Application Data

(60) Provisional application No. 63/093,094, filed on Oct. 16, 2020, provisional application No. 62/929,476, filed on Nov. 1, 2019.

(51) Int. Cl.

| | | |
|---|---|---|
| *A61K 31/4192* | (2006.01) | |
| *A61K 31/19* | (2006.01) | |
| *A61K 31/194* | (2006.01) | |
| *A61K 31/351* | (2006.01) | |
| *A61K 31/381* | (2006.01) | |
| *A61K 31/382* | (2006.01) | |
| *A61K 31/415* | (2006.01) | |
| *A61K 31/4164* | (2006.01) | |
| *A61K 31/422* | (2006.01) | |
| *A61K 31/427* | (2006.01) | |
| *A61K 31/428* | (2006.01) | |
| *A61K 31/433* | (2006.01) | |
| *A61K 31/4439* | (2006.01) | |
| *A61K 31/454* | (2006.01) | |
| *A61K 31/4709* | (2006.01) | |
| *A61K 31/4725* | (2006.01) | |
| *A61K 31/497* | (2006.01) | |
| *A61K 31/501* | (2006.01) | |
| *A61K 31/506* | (2006.01) | |
| *A61K 31/5377* | (2006.01) | |
| *A61K 31/675* | (2006.01) | |
| *A61K 31/7048* | (2006.01) | |
| *A61K 38/51* | (2006.01) | |
| *A61K 45/06* | (2006.01) | |
| *C07D 231/14* | (2006.01) | |

(Continued)

(52) U.S. Cl.
CPC .......... *A61K 31/4192* (2013.01); *A61K 31/19* (2013.01); *A61K 31/194* (2013.01); *A61K 31/351* (2013.01); *A61K 31/381* (2013.01); *A61K 31/382* (2013.01); *A61K 31/415* (2013.01); *A61K 31/4164* (2013.01); *A61K 31/422* (2013.01); *A61K 31/427* (2013.01); *A61K 31/428* (2013.01); *A61K 31/433* (2013.01); *A61K 31/4439* (2013.01); *A61K 31/454* (2013.01); *A61K 31/4709* (2013.01); *A61K 31/4725* (2013.01); *A61K 31/497* (2013.01); *A61K 31/501* (2013.01); *A61K 31/506* (2013.01); *A61K 31/5377* (2013.01); *A61K 31/675* (2013.01); *A61K 31/7048* (2013.01); *A61K 38/51* (2013.01); *A61K 45/06* (2013.01); *C07D 231/14* (2013.01); *C07D 233/90* (2013.01); *C07D 249/06* (2013.01); *C07D 401/04* (2013.01); *C07D 401/10* (2013.01); *C07D 401/12* (2013.01); *C07D 401/14* (2013.01); *C07D 403/04* (2013.01); *C07D 403/10* (2013.01); *C07D 403/14* (2013.01); *C07D 405/04* (2013.01); *C07D 405/10* (2013.01); *C07D 405/14* (2013.01); *C07D 413/10* (2013.01); *C07D 417/04* (2013.01); *C07D 417/10* (2013.01); *C07F 9/65583* (2013.01); *C12N 15/113* (2013.01); *C12N 2310/14* (2013.01)

(58) Field of Classification Search
CPC ............................ A61K 31/4192; A61K 31/19
See application file for complete search history.

(56) References Cited

U.S. PATENT DOCUMENTS

| 5,439,813 A | 8/1995 | Anton et al. |
| 9,221,805 B2 | 12/2015 | Flynn |

(Continued)

FOREIGN PATENT DOCUMENTS

| CN | 109988784 A | 7/2019 |
| WO | 199406925 A1 | 3/1994 |

(Continued)

OTHER PUBLICATIONS

Reimlinger et. al. (Chemische Berichte (1964) 97:3493-3502). (Year: 1964).*

(Continued)

*Primary Examiner* — Marcos L Sznaidman
(74) *Attorney, Agent, or Firm* — Young Basile Hanlon & MacFarlane, P.C.

(57) ABSTRACT

The present disclosure relates generally to modulators of human glycolate oxidase enzyme and methods of use and manufacture thereof.

12 Claims, 4 Drawing Sheets

(51) Int. Cl.
| | |
|---|---|
| C07D 233/90 | (2006.01) |
| C07D 249/06 | (2006.01) |
| C07D 401/04 | (2006.01) |
| C07D 401/10 | (2006.01) |
| C07D 401/12 | (2006.01) |
| C07D 401/14 | (2006.01) |
| C07D 403/04 | (2006.01) |
| C07D 403/10 | (2006.01) |
| C07D 403/14 | (2006.01) |
| C07D 405/04 | (2006.01) |
| C07D 405/10 | (2006.01) |
| C07D 405/14 | (2006.01) |
| C07D 413/10 | (2006.01) |
| C07D 417/04 | (2006.01) |
| C07D 417/10 | (2006.01) |
| C07F 9/6558 | (2006.01) |
| C12N 15/113 | (2010.01) |

(56) References Cited

U.S. PATENT DOCUMENTS

| | | |
|---|---|---|
| 9,833,455 B2 | 12/2017 | Flynn |
| 2015/0202186 A1 | 7/2015 | Duron et al. |
| 2018/0125848 A1 | 5/2018 | Flynn |

FOREIGN PATENT DOCUMENTS

| | | |
|---|---|---|
| WO | 94/20631 A2 | 9/1994 |
| WO | 95/01443 A1 | 1/1995 |
| WO | 95/01444 A1 | 1/1995 |
| WO | 2015100436 A1 | 7/2015 |
| WO | 2016057893 A1 | 4/2016 |
| WO | 2016205323 A1 | 12/2016 |
| WO | 2017100266 A1 | 6/2017 |
| WO | 2017100268 A1 | 6/2017 |
| WO | 2019014491 A1 | 1/2019 |
| WO | 2019133770 A2 | 7/2019 |
| WO | 2019133813 A1 | 7/2019 |
| WO | 20200010309 A1 | 1/2020 |
| WO | 2020257487 A1 | 12/2020 |

OTHER PUBLICATIONS

Barawkar et al., Discovery of pyrazole carboxylic acids as potent inhibitors of rat long chain I-2-hydroxy acid oxidase, Bioorganic & Medicinal Chemistry Letters, vol. 22, Issue 13, 2012, pp. 4341-4347.

* cited by examiner

US 11,806,335 B2

HETEROCYCLIC CARBOXYLATE COMPOUNDS AS GLYCOLATE OXIDASE INHIBITORS

CROSS-REFERENCE TO RELATED APPLICATIONS

This application claims the benefit under 35 U.S.C. § 119(e) of United States Provisional Application Nos. 62/929,476, filed Nov. 1, 2019, and 63/093,094, filed Oct. 16, 2020, each of which are hereby incorporated by reference in their entirety.

FIELD

The present disclosure relates to compounds, compositions, and methods for the treatment of primary hyperoxaluria type 1 and recurrent kidney stone formers. The present disclosure is directed to novel substituted heterocyclic carboxylate compounds and methods for their preparation and use as therapeutic or prophylactic agents. In particular, the present disclosure provides novel inhibitors of human glycolate oxidase enzyme, pharmaceutical compositions containing such compounds, and methods for using these compounds to treat primary hyperoxaluria type 1 and recurrent kidney stone formers.

BACKGROUND

Kidney stones affect a large human population. In the United States, the prevalence of kidney stones was 8.8% with 10.6% among men and 7.1% among women. The diseases also occur in primary hyperoxaluria type 1 (PHI), which can be caused by genetically defective enzyme activity. Due to the high activity of glycolate oxidase, those patients can show a significant increase in glyoxylate and oxalate production and deposition of calcium oxalate stones. The medical procedures to remove kidney stones exist and are effective. However, the recurrence of kidney stones following those procedures can be high (e.g., over 50%). Accordingly, there is a need for agents that inhibit glycolate oxidase enzyme activity to treat PHI patients and reduce the rate of kidney stone recurrence in kidney stone formers.

SUMMARY

The present disclosure is directed to novel substituted heterocyclic carboxylate compounds, inhibiting human glycolate oxidase activity, including stereoisomers, pharmaceutically acceptable salts and prodrugs thereof, and the use of such compounds in the treatment of primary hyperoxaluria type 1. The compounds of the disclosure may be used to treat recurrent kidney stone formers.

In one aspect, provided is a compound having the structure of Formula I:

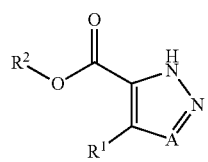

I or a pharmaceutically acceptable salt, tautomer, stereoisomer, mixture of stereoisomers, or deuterated analog thereof, wherein A, $R^1$ and $R^2$ are as described herein.

In certain embodiments, the disclosure provides pharmaceutical compositions comprising a therapeutically effective amount of a compound of the disclosure (e.g. a compound of Formula I or additional Formulas described throughout), and at least one pharmaceutically acceptable excipient. In certain embodiments, provided herein is a pharmaceutical composition comprising a compound, or a pharmaceutically acceptable salt, tautomer, stereoisomer, mixture of stereoisomers, or deuterated analog thereof.

Some embodiments provide a method of using (or administering) the compounds of Formula I, or additional Formula(s) described throughout, in the treatment of a disease or condition in a mammal, particularly a human, that is amenable to treatment by an inhibitor of human glycolate oxidase enzyme.

Some embodiments provide a method of using (or administering) a compound as described herein in the treatment of a disease or condition in a mammal, particularly a human, that is amenable to treatment by an inhibitor of human glycolate oxidase enzyme.

DETAILED DESCRIPTION

Definitions and General Parameters

Figure 1:
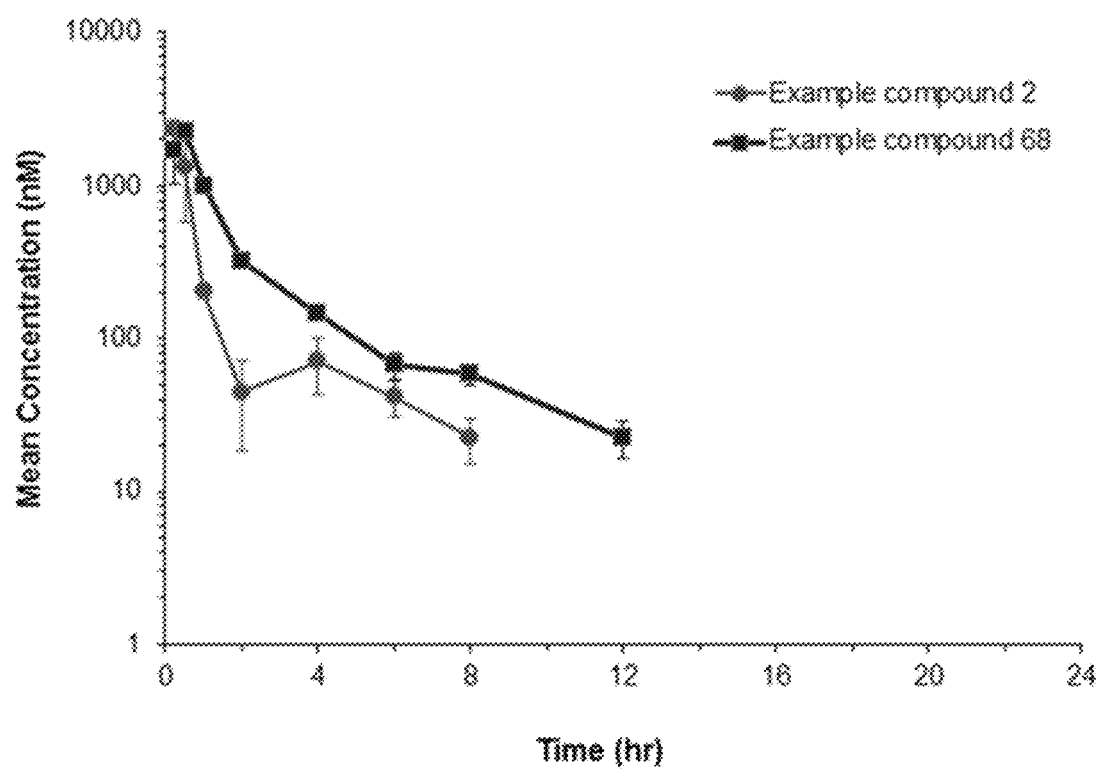
FIG. 1 shows the plasma concentration-time profiles of Example 2 and Example 68 following an oral dose of Example 2 at 5.0 mg/kg in SD rats (mean±SD, n=3).

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

The modifier "about" used in connection with a quantity is inclusive of the stated value and has the meaning dictated by the context (e.g., includes the degree of error associated with measurement of the particular quantity). Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Acyl" refers to a group —C(O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Imino" refers to a group —C(NR)R, wherein each R is alkyl, cycloalkyl, heterocyclyl, aryl, heteroalkyl, or heteroaryl; each of which may be optionally substituted, as defined herein.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —$OCH_3$, —$CH_2OCH_3$, —$SCH_3$, —$CH_2SCH_3$, —$NRCH_3$, and —$CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Non-limiting examples of heteroaryl groups include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl. The fused-heteroaryl rings can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen, and optionally one or more oxo groups. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g. 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro [3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno [2,3-c]pyridinyl, indolinyl, and isoindolinyl (e.g., 2-methylisoquinolin-1(2H)-one), where the heterocyclyl can be bound via either ring of the fused system.

"Oxo" refers to the group (=O) or (O).

"Sulfonyl" refers to the group —S(O)$_2$R, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

"Alkylsulfonyl" refers to the group —S(O)$_2$R, where R is alkyl.

"Alkylsulftnyl" refers to the group —S(O)R, where R is alkyl.

"Thiol" refers to the group —SR, where R is alkyl, haloalkyl, heterocyclyl, cycloalkyl, heteroaryl, or aryl.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., $HN(alkyl)_2$), trialkyl amines (i.e., $N(alkyl)_3$), substituted alkyl amines (i.e., $NH_2$(substituted alkyl)), di(substituted alkyl) amines (i.e., $HN$(substituted alkyl)$_2$), tri (substituted alkyl) amines (i.e., $N$(substituted alkyl)$_3$), alkenyl amines (i.e., $NH_2$(alkenyl)), dialkenyl amines (i.e., $HN(alkenyl)_2$), trialkenyl amines (i.e., $N(alkenyl)_3$), substituted alkenyl amines (i.e., $NH_2$(substituted alkenyl)), di(substituted alkenyl) amines (i.e., $HN$(substituted alkenyl)$_2$), tri(substituted alkenyl) amines (i.e., $N$(substituted alkenyl)$_3$, mono-, di- or tri-cycloalkyl amines (i.e., $NH_2$(cycloalkyl), $HN(cycloalkyl)_2$, $N(cycloalkyl)_3$), mono-, di- or tri-arylamines (i.e., $NH_2$(aryl), $HN(aryl)_2$, $N(aryl)_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

In certain embodiments, as used herein, the phrase "one or more" refers to one to five. In certain embodiments, as used herein, the phrase "one or more" refers to one to three.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Compounds

Provided herein are compounds that function as inhibitors of glycolate oxidase. In certain embodiments, provided herein is a compound of Formula I:

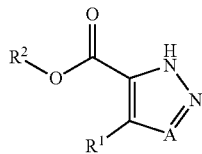

I or a pharmaceutically acceptable salt, tautomer, stereoisomer, mixture of stereoisomers, or deuterated analog thereof, wherein A is N or CH;

$R^1$ is alkynyl, cycloalkyl, aryl, heteroaryl or heterocyclyl, wherein each is optionally substituted with one to three $R^3$;

$R^2$ is hydrogen, —$(CH_2CH_2O)_{1-9}CH_2CH_2OCH_3$, $C_{1-6}$ alkyl optionally substituted with one to three $R^4$, cycloalkyl, or heteroaryl optionally substituted with one to three $R^5$;

each $R^3$ is independently cyano, halo, -L-$C_{1-9}$ alkyl, -L-$C_{1-4}$ haloalkyl, -L-$OC_{1-4}$ haloalkyl, —$NR^7R^8$, —$C(O)NR^7R^8$, —$S(O)_2NR^7R^8$, —$NR^7C(O)R^8$, —$OR^7$, -L-aryl, -L-heteroaryl or -L-heterocyclyl, wherein each is optionally substituted with one to three $R^6$, and each L is independently —C≡C— or absent;

each $R^4$ is independently halo, hydroxy, —$OC_{1-6}$alkyl, —$NH_2$, —$NHC_{1-6}$ alkyl, —$N(C_{1-6}alkyl)_2$, —$OC(O)R^a$, —$OC(O)OR^a$, —$OP(O)(OR^b)_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —$OC_{1-4}$alkyl, $C_{1-4}$ haloalkyl, or —$OC_{1-4}$ haloalkyl;

each $R^6$ is independently cyano, halo, —$C(O)R^7$, —$C(O)OR^7$, —$C(O)NR^7R^8$, —$S(O)_2NR^7R^8$, —$NR^7C(O)R^8$, —$OR^7$, $C_{1-4}$ alkyl, —$OC_{1-4}$alkyl, $C_{1-4}$ haloalkyl, —$OC_{1-4}$ haloalkyl, phenyl, heterocyclyl, or heteroaryl; wherein each is optionally substituted with one to three $C_{1-4}$ alkyl, —$C(O)OH$ or $C_{1-4}$ haloalkyl;

$R^7$ and $R^8$ are each independently hydrogen, $C_{1-4}$ alkyl or phenyl, pyridyl, or $R^7$ and $R^8$ together with the nitrogen atom to which they are attached form a heterocyclyl;

each $R^a$ is independently $C_{1-6}$ alkyl optionally substituted with —$NH_2$, —$NHC_{1-6}$ alkyl, —$N(C_{1-6}alkyl)_2$, or —$OP(O)(OR^b)_2$;

each $R^b$ is independently hydrogen or $C_{1-4}$ alkyl.

In some embodiments, when A is N, at least one of the following is true:

1) $R^1$ is a fused tricyclic ring optionally substituted with one to three $R^3$;

2) $R^1$ is an optionally substituted fused bicyclic ring substituted with at least one $R^3$ selected from cyano, —C≡C—$C_{1-9}$ alkyl, —$C_{1-9}$ alkyl substituted with one to three $R^6$, —C≡C—$C_{1-4}$ haloalkyl, —C≡C—$OC_{1-4}$ haloalkyl, —$NR^7R^8$, —$C(O)NR^7R^8$, —$S(O)_2NR^7R^8$, —$NR^7C(O)R^8$, —O—$C_{1-4}$ alkyl, —O-phenyl, -L-aryl, -L-heteroaryl or -L-heterocyclyl, wherein each is further optionally substituted with one to three $R^6$, and each L is independently —C≡C— or absent;

3) $R^1$ is a substituted monocyclic ring, substituted with at least one $R^3$ selected from:

i) cyano, —C≡C—$C_{1-9}$ alkyl, —C≡C—$C_{1-4}$ haloalkyl, —C≡C—$OC_{1-4}$ haloalkyl, —$NR^7R^8$, —$C(O)NR^7R^8$, —$S(O)_2NR^7R^8$, —$NR^7C(O)R^8$, —C≡C-aryl, —C≡C-heteroaryl, or —C≡C— heterocyclyl, wherein each is further optionally substituted with one to three $R^6$;

ii) monocyclic aryl, monocyclic heteroaryl, or monocyclic heterocyclyl, wherein each is further substituted with one to three cyano, —$C(O)R^7$, —$C(O)OR^7$, —$C(O)NR^7R^8$, —$S(O)_2NR^7R^8$, —$NR^7C(O)R^8$, $C_{1-4}$ alkyl, —$OC_{1-4}$alkyl, $C_{1-4}$ haloalkyl, phenyl, heterocyclyl, or heteroaryl; wherein each is optionally substituted with one to three $C_{1-4}$ alkyl, —$C(O)OH$ or $C_{1-4}$ haloalkyl;

iii) optionally substituted fused aryl, optionally substituted fused heteroaryl or optionally substituted fused heterocyclyl, wherein each is further optionally substituted with one to three $R^6$; or iv) a substituent of formula -$L^3$-$L^2$, wherein $L^1$ is aryl, heteroaryl or heterocyclyl, wherein each is optionally substituted with one to three $R^6$; and $L^2$ is phenyl, heterocyclyl, or heteroaryl, wherein each is optionally substituted with one to three $C_{1-4}$ alkyl, —$C(O)OH$ or $C_{1-4}$ haloalkyl; or 4) $R^2$ is —$(CH_2CH_2O)_{1-9}CH_2CH_2OCH_3$, $C_{1-6}$ alkyl substituted with one to three $R^4$, cycloalkyl, or heteroaryl optionally substituted with one to three $R^5$; and In some embodiments, when A is CH, $R^1$ is not 10-membered heteroaryl substituted with methoxy and methyl; or $R^1$ is not $C_6$ aryl optionally substituted 1-3 substituents independently selected from cyano, halo, $C_{1-4}$ alkyl, —$OR^7$, $C_{1-4}$ haloalkyl, and $NR^7R^8$, wherein $R^7$ and $R^8$ are each independently hydrogen or $C_{1-4}$ alkyl; or $R^1$ is not unsubstituted $C_{10}$ aryl; or $R^1$ is not unsubstituted heterocyclyl.

In one aspect, provided is a compound having structure of Formula I:

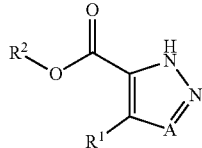

or a pharmaceutically acceptable salt, tautomer, stereoisomer, mixture of stereoisomers, or deuterated analog thereof, wherein A is N or CH;

$R^1$ is alkynyl, cycloalkyl, aryl, heteroaryl or heterocyclyl, wherein each is optionally substituted with one to three $R^3$;

$R^2$ is hydrogen, —$(CH_2CH_2O)_{1-9}CH_2CH_2OCH_3$, $C_{1-6}$ alkyl optionally substituted with one to three $R^4$, or heteroaryl optionally substituted with one to three $R^5$;

each $R^3$ is independently cyano, halo, -L-$C_{1-9}$ alkyl, -L-$C_{1-4}$ haloalkyl, -L-$OC_{1-4}$ haloalkyl, —$NR^7R^8$, —$C(O)NR^7R^8$, —$S(O)_2NR^7R^8$, —$NR^7C(O)R^8$, —$OR^7$, -L-aryl, -L-heteroaryl or -L-heterocyclyl, wherein each is optionally substituted with one to three $R^6$, and each L is independently a bond or —C≡C—;

each $R^4$ is independently halo, hydroxy, —$OC_{1-6}$alkyl, —$NH_2$, —$NHC_{1-6}$ alkyl, —$N(C_{1-6}alkyl)_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —$OC_{1-4}$alkyl, $C_{1-4}$ haloalkyl, or —$OC_{1-4}$ haloalkyl;

each $R^6$ is independently cyano, halo, —$C(O)R^7$, —$C(O)OR^7$, —$C(O)NR^7R^8$, —$S(O)_2NR^7R^8$, —$NR^7C(O)R^8$, —$OR^7$, $C_{1-4}$ alkyl, —$OC_{1-4}$alkyl, $C_{1-4}$ haloalkyl, —$OC_{1-4}$ haloalkyl, phenyl, heterocyclyl, or heteroaryl; wherein each is optionally substituted with one to three $C_{1-4}$ alkyl, —C(O)OH or $C_{1-4}$ haloalkyl;

$R^7$ and $R^8$ are each independently hydrogen, $C_{1-4}$ alkyl or phenyl, pyridyl, or $R^7$ and $R^8$ together with the nitrogen atom to which they are attached form a heterocyclyl.

In certain embodiments, when $R^1$ is phenyl, then $R^3$ is aryl or heteroaryl, each of which is optionally substituted with one to three $R^6$.

In certain embodiments, when $R^1$ is heteroaryl, then $R^2$ is not unsubstituted $C_{1-6}$ alkyl.

In certain embodiments,

A is N or CH;

$R^1$ is alkynyl, cycloalkyl, aryl, heteroaryl or heterocyclyl, wherein each is optionally substituted with one to three $R^3$;

$R^2$ is hydrogen, —$(CH_2CH_2O)_{1-9}CH_2CH_2OCH_3$, $C_{1-6}$ alkyl optionally substituted with one to three $R^4$, or heteroaryl optionally substituted with one to three $R^5$;

each $R^3$ is independently halo, -L-$C_{1-9}$ alkyl, —$C(O)NR^7R^8$, —$S(O)_2NR^7R^8$, —$NR^7C(O)R^8$, —$OR^7$, -L-5-6 membered heteroaryl or -L-5-6 membered heterocyclyl, wherein each is optionally substituted with one to three $R^6$, and each L is independently a bond or —C≡C—;

each $R^4$ is independently halo, hydroxy, —$OC_{1-6}$alkyl, —$NH_2$, —$NHC_{1-6}$ alkyl, —$N(C_{1-6}alkyl)_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —$OC_{1-4}$alkyl, $C_{1-4}$ haloalkyl, or —$OC_{1-4}$ haloalkyl;

each $R^6$ is independently cyano, halo, $C_{1-4}$ alkyl, hydroxy, —$OC_{1-4}$alkyl, $C_{1-4}$ haloalkyl, or —$OC_{1-4}$ haloalkyl; and $R^7$ and $R^8$ are each independently hydrogen or $C_{1-4}$ alkyl, or $R^7$ and $R^8$ together with the nitrogen atom to which they are attached form a —$(CH_2)_2$—O—$(CH_2)_2$—.

Also provided is a compound of Formula IIa:

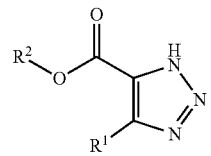

or a pharmaceutically acceptable salt, tautomer, stereoisomer, mixture of stereoisomers, or deuterated analog thereof, wherein $R^1$ is alkynyl, cycloalkyl, aryl, heteroaryl or heterocyclyl, wherein each is optionally substituted with one to three $R^3$;

$R^2$ is hydrogen, —$(CH_2CH_2O)_{1-9}CH_2CH_2OCH_3$, $C_{1-6}$ alkyl optionally substituted with one to three $R^4$, or heteroaryl optionally substituted with one to three $R^5$;

each $R^3$ is independently cyano, halo, $C_{1-9}$ alkyl, $C_{1-4}$ haloalkyl, —$OC_{1-4}$ haloalkyl, —$NR^7R^8$, —$C(O)NR^7R^8$, —$S(O)_2NR^7R^8$, —$NR^7C(O)R^8$, —$OR^7$, aryl, heteroaryl or heterocyclyl, wherein each is optionally substituted with one to three $R^6$, and each L is independently a bond or —C≡C—;

each $R^4$ is independently halo, hydroxy, —$OC_{1-6}$alkyl, —$NH_2$, —$NHC_{1-6}$ alkyl, —$N(C_{1-6}alkyl)_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —$OC_{1-4}$alkyl, $C_{1-4}$ haloalkyl, or —$OC_{1-4}$ haloalkyl;

each $R^6$ is independently cyano, halo, —$C(O)R^7$, —$C(O)OR^7$, —$C(O)NR^7R^8$, —$S(O)_2NR^7R^8$, —$NR^7C(O)R^8$, —$OR^7$, $C_{1-4}$ alkyl, —$OC_{1-4}$alkyl, $C_{1-4}$ haloalkyl, —$OC_{1-4}$ haloalkyl, phenyl, heterocyclyl, or heteroaryl; wherein each is optionally substituted with one to three $C_{1-4}$ alkyl, —C(O)OH or $C_{1-4}$ haloalkyl;

$R^7$ and $R^8$ are each independently hydrogen, $C_{1-4}$ alkyl or phenyl, pyridyl, or $R^7$ and $R^8$ together with the nitrogen atom to which they are attached form a heterocyclyl.

In certain embodiments, provided is a compound of Formula IIa:

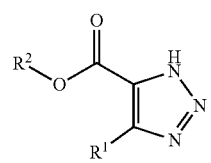

or a pharmaceutically acceptable salt, tautomer, stereoisomer, mixture of stereoisomers, or deuterated analog thereof, wherein $R^1$ is alkynyl, cycloalkyl, aryl, heteroaryl or heterocyclyl, wherein each is optionally substituted with one to three $R^3$;

$R^2$ is hydrogen, —$(CH_2CH_2O)_{1-9}CH_2CH_2OCH_3$, $C_{1-6}$ alkyl optionally substituted with one to three $R^4$, cycloalkyl, or heteroaryl optionally substituted with one to three $R^5$;

each $R^3$ is independently cyano, halo, -L-$C_{1-9}$ alkyl, -L-$C_{1-4}$ haloalkyl, -L-$OC_{1-4}$ haloalkyl, —$NR^7R^8$, —$C(O)NR^7R^8$, —$S(O)_2NR^7R^8$, —$NR^7C(O)R^8$, —$OR^7$, -L-aryl, -L-heteroaryl or -L-heterocyclyl, wherein each is optionally substituted with one to three $R^6$, and each L is independently —C≡C— or absent;

each $R^4$ is independently halo, hydroxy, —$OC_{1-6}$alkyl, —$NH_2$, —$NHC_{1-6}$ alkyl, —$N(C_{1-6}alkyl)_2$, —$OC(O)R^a$, —$OC(O)OR^a$, —$OP(O)(OR^b)_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —$OC_{1-4}$alkyl, $C_{1-4}$ haloalkyl, or —$OC_{1-4}$ haloalkyl;

each $R^6$ is independently cyano, halo, —$C(O)R^7$, —$C(O)OR^7$, —$C(O)NR^7R^8$, —$S(O)_2NR^7R^8$, —$NR^7C(O)R^8$, —$OR^7$, $C_{1-4}$ alkyl, —$OC_{1-4}$alkyl, $C_{1-4}$ haloalkyl, —$OC_{1-4}$ haloalkyl, phenyl, heterocyclyl, or heteroaryl; wherein each is optionally substituted with one to three $C_{1-4}$ alkyl, —C(O)OH or $C_{1-4}$ haloalkyl;

$R^7$ and $R^8$ are each independently hydrogen, $C_{1-4}$ alkyl or phenyl, pyridyl, or $R^7$ and $R^8$ together with the nitrogen atom to which they are attached form a heterocyclyl; each $R^a$ is independently $C_{1-6}$ alkyl optionally substituted with —$NH_2$, —$NHC_{1-6}$ alkyl, —$N(C_{1-6}alkyl)_2$, or —$OP(O)(OR^b)_2$;

each $R^b$ is independently hydrogen or $C_{1-4}$ alkyl.

In some embodiments, for compounds of formula IIa, at least one of the following is true:

1) $R^1$ is a fused tricyclic ring optionally substituted with one to three $R^3$;
2) $R^1$ is an optionally substituted fused bicyclic ring substituted with at least one $R^3$ selected from cyano, —C≡C—$C_{1-9}$ alkyl, —$C_{1-9}$ alkyl substituted with one to three $R^6$, —C≡C—$C_{1-4}$ haloalkyl, —C≡C—$OC_{1-4}$ haloalkyl, —$NR^7R^8$, —$C(O)NR^7R^8$, —$S(O)_2NR^7R^8$, —$NR^7C(O)R^8$, —O—$C_{1-4}$ alkyl, —O-phenyl, -L-aryl, -L-heteroaryl or -L-heterocyclyl, wherein each is further optionally substituted with one to three $R^6$, and each L is independently —C≡C— or absent;
3) $R^1$ is a substituted monocyclic ring, substituted with at least one $R^3$ selected from:
   i) cyano, —C≡C—$C_{1-9}$ alkyl, —C≡C—$C_{1-4}$ haloalkyl, —C≡C—$OC_{1-4}$ haloalkyl, —$NR^7R^8$, —$C(O)NR^7R^8$, —$S(O)_2NR^7R^8$, —$NR^7C(O)R^8$, —C≡C-aryl, —C≡C-heteroaryl, or —C≡C— heterocyclyl, wherein each is further optionally substituted with one to three $R^6$;
   ii) monocyclic aryl, monocyclic heteroaryl, or monocyclic heterocyclyl, wherein each is further substituted with one to three cyano, —$C(O)R^7$, —$C(O)OR^7$, —$C(O)NR^7R^8$, —$S(O)_2NR^7R^8$, —$NR^7C(O)R^8$, $C_{1-4}$ alkyl, —$OC_{1-4}$alkyl, $C_{1-4}$ haloalkyl, phenyl, heterocyclyl, or heteroaryl; wherein each is optionally substituted with one to three $C_{1-4}$ alkyl, —C(O)OH or $C_{1-4}$ haloalkyl;
   iii) optionally substituted fused aryl, optionally substituted fused heteroaryl or optionally substituted fused heterocyclyl, wherein each is further optionally substituted with one to three $R^6$; or
   iv) a substituent of formula -$L^1$-$L^2$, wherein $L^1$ is aryl, heteroaryl or heterocyclyl, wherein each is optionally substituted with one to three $R^6$; and $L^2$ is phenyl, heterocyclyl, or heteroaryl, wherein each is optionally substituted with one to three $C_{1-4}$ alkyl, —C(O)OH or $C_{1-4}$ haloalkyl; or
4) $R^2$ is —$(CH_2CH_2O)_{1-9}CH_2CH_2OCH_3$, $C_{1-6}$ alkyl substituted with one to three $R^4$, cycloalkyl, or heteroaryl optionally substituted with one to three $R^5$.

Also provided is a compound of Formula IIb:

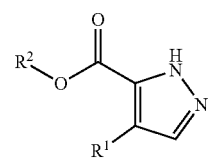

or a pharmaceutically acceptable salt, tautomer, stereoisomer, mixture of stereoisomers, or deuterated analog thereof, wherein $R^1$ is alkynyl, cycloalkyl, aryl, heteroaryl or heterocyclyl, wherein each is optionally substituted with one to three $R^3$;

$R^2$ is hydrogen, —$(CH_2CH_2O)_{1-9}CH_2CH_2OCH_3$, $C_{1-6}$ alkyl optionally substituted with one to three $R^4$, cycloalkyl, or heteroaryl optionally substituted with one to three $R^5$;

each $R^3$ is independently cyano, halo, -L-$C_{1-4}$ alkyl, -L-$C_{1-4}$ haloalkyl, -L-$OC_{1-4}$ haloalkyl, —$NR^7R^8$, —$C(O)NR^7R^8$, —$S(O)_2NR^7R^8$, —$NR^7C(O)R^8$, —$OR^7$, -L-aryl, -L-heteroaryl or -L-heterocyclyl, wherein each is optionally substituted with one to three $R^6$, and each L is independently —C≡C— or absent;

each $R^4$ is independently halo, hydroxy, —$OC_{1-6}$alkyl, —$NH_2$, —$NHC_{1-6}$ alkyl, —$N(C_{1-6}alkyl)_2$, —$OC(O)R^a$, —$OC(O)OR^a$, —$OP(O)(OR^b)_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —$OC_{1-4}$alkyl, $C_{1-4}$ haloalkyl, or —$OC_{1-4}$ haloalkyl;

each $R^6$ is independently cyano, halo, —$C(O)R^7$, —$C(O)OR^7$, —$C(O)NR^7R^8$, —$S(O)_2NR^7R^8$, —$NR^7C(O)R^8$, —$OR^7$, $C_{1-4}$ alkyl, —$OC_{1-4}$alkyl, $C_{1-4}$ haloalkyl, —$OC_{1-4}$ haloalkyl, phenyl, heterocyclyl, or heteroaryl; wherein each is optionally substituted with one to three $C_{1-4}$ alkyl, —C(O)OH or $C_{1-4}$ haloalkyl;

$R^7$ and $R^8$ are each independently hydrogen, $C_{1-4}$ alkyl or phenyl, pyridyl, or $R^7$ and $R^8$ together with the nitrogen atom to which they are attached form a heterocyclyl;

each $R^a$ is independently $C_{1-6}$ alkyl optionally substituted with —$NH_2$, —$NHC_{1-6}$ alkyl, —$N(C_{1-6}alkyl)_2$, or —$OP(O)(OR^b)_2$;

each $R^b$ is independently hydrogen or $C_{1-4}$ alkyl.

In some embodiments, for compounds of formula IIb, $R^1$ is not 10-membered heteroaryl substituted with methoxy and methyl; or $R^1$ is not $C_6$ aryl optionally substituted 1-3 substituents independently selected from cyano, halo, $C_{1-4}$ alkyl, —$OR^7$, $C_{1-4}$ haloalkyl, and $NR^7R^8$, wherein $R^7$ and $R^8$ are each independently hydrogen or $C_{1-4}$ alkyl; or $R^1$ is not unsubstituted $C_{10}$ aryl; or $R^1$ is not unsubstituted heterocyclyl.

In certain embodiments, A is N. In certain embodiments, A is CH.

In certain embodiments, $R^1$ is aryl optionally substituted with one to three $R^3$.

In certain embodiments, $R^1$ is heteroaryl optionally substituted with one to three $R^3$.

In certain embodiments, $R^1$ is heterocyclyl optionally substituted with one to three $R^3$.

In certain embodiments, $R^1$ is cycloalkyl optionally substituted with one to three $R^3$.

In certain embodiments, $R^1$ is

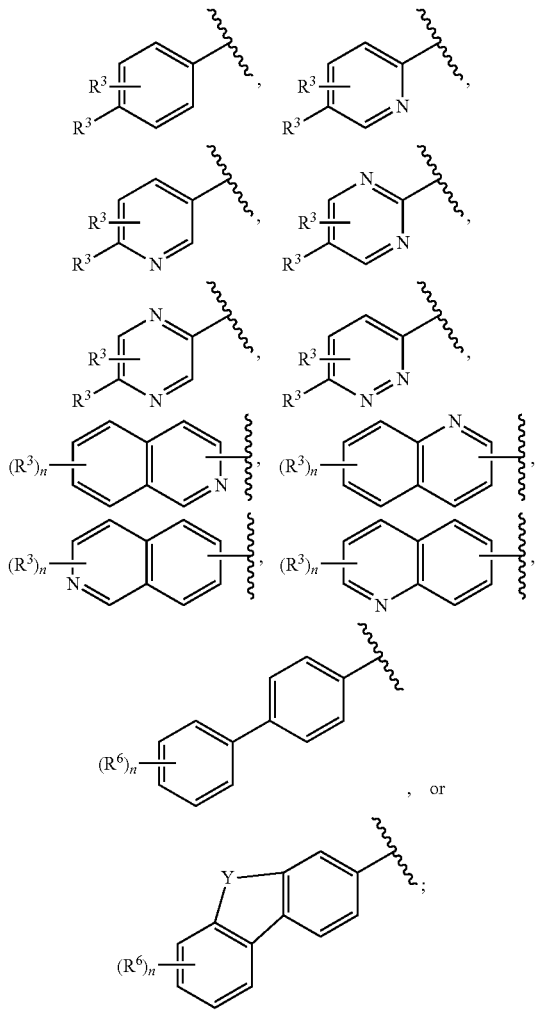

each n is independently one, two or three, and Y is $CR^8R^9$, C(O), O, or $NR^{10}$; each of $R^8$ and $R^9$ are independently hydrogen, halo or $C_{1-4}$ alkyl; and $R^{10}$ is hydrogen or $C_{1-4}$ alkyl.

In certain embodiments, L is a bond (i.e. absent). In certain embodiments, L is —C≡C—.

In certain embodiments, each of $R^8$ and $R^9$ are halo. In certain embodiments, each of $R^8$ and $R^9$ are fluoro.

In certain embodiments, each of $R^8$ and $R^9$ are hydrogen.

In certain embodiments, $R^2$ is hydrogen.

In certain embodiments, $R^3$ is halo, $C_{1-9}$ alkyl, $C_{1-4}$ haloalkyl or —$OR^7$.

In certain embodiments, at least one $R^3$ is halo, $C_{1-9}$ alkyl or —$OR^7$. In certain embodiments, $R^3$ is halo, $C_{1-9}$ alkyl or —$OR^7$.

In certain embodiments, at least one $R^3$ is fluoro, chloro, bromo, methyl, tert-butyl, methoxy or phenoxy. In certain embodiments, $R^3$ is fluoro, chloro, bromo, methyl, tert-butyl, methoxy or phenoxy.

In certain embodiments, $R^3$ is aryl optionally substituted with one to three $R^6$.

In certain embodiments, $R^3$ is

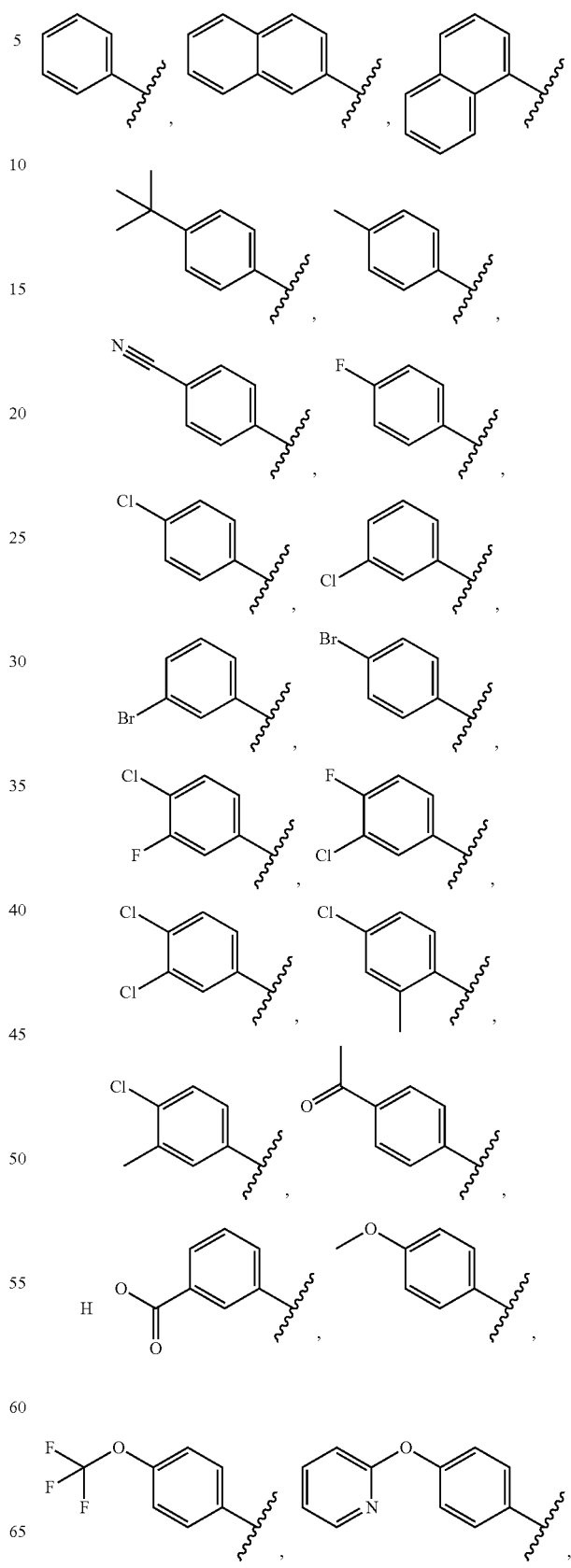

In certain embodiments, at least one R³ is aryl substituted with phenyl, heterocyclyl or heteroaryl. In certain embodiments, R³ is aryl substituted with phenyl, heterocyclyl or heteroaryl.

In certain embodiments, at least one R³ is

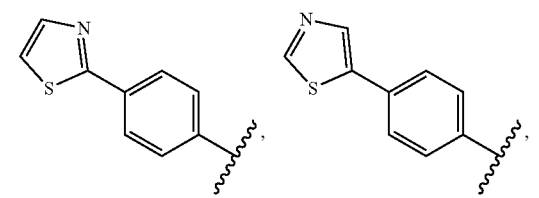
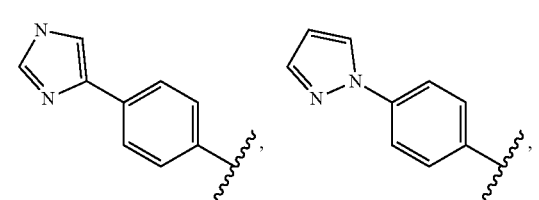
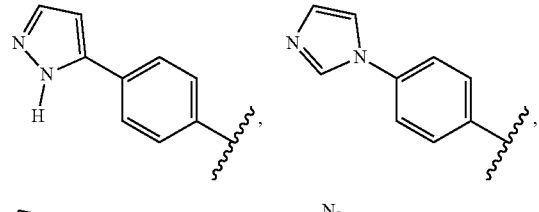
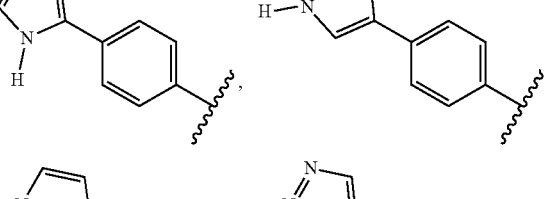
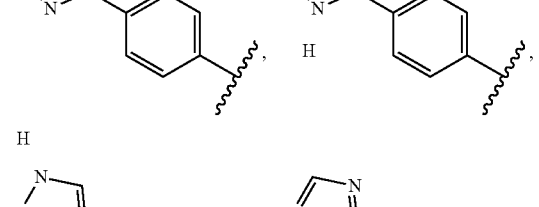
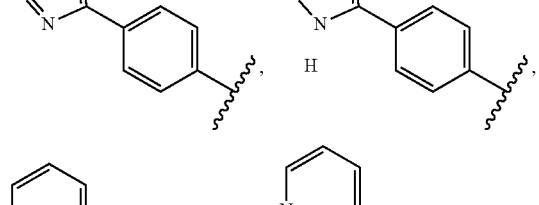
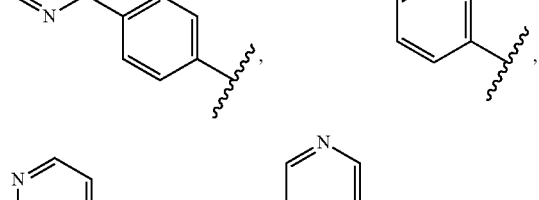
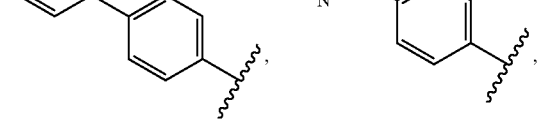
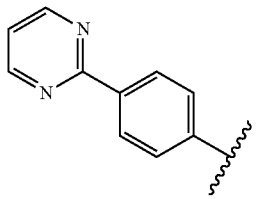
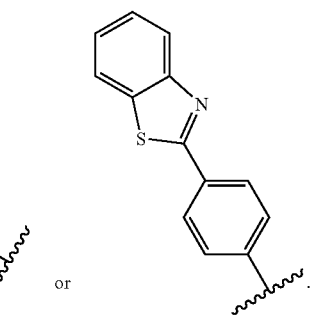
or
In certain embodiments, R³ is
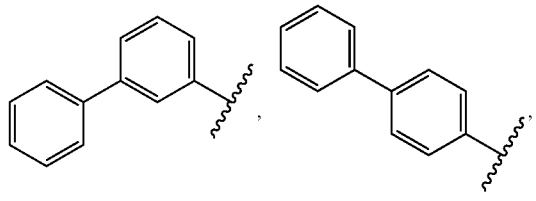
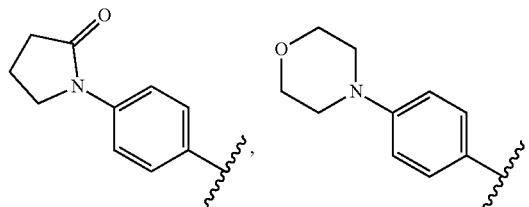
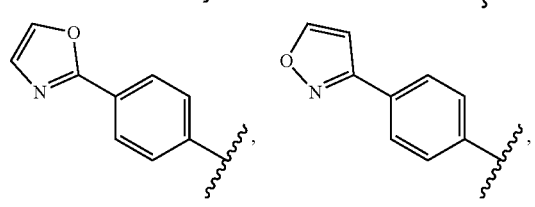
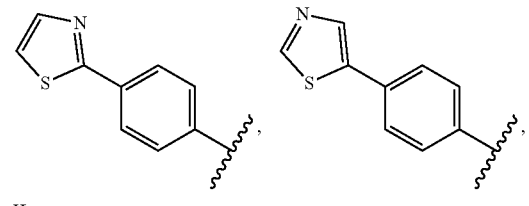
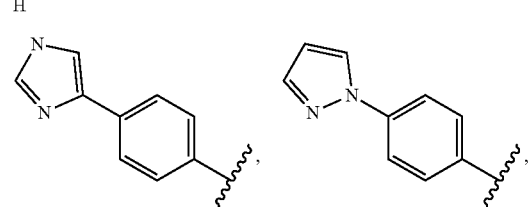
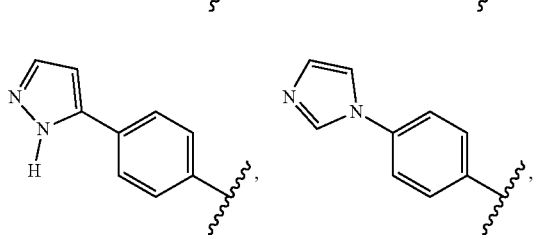

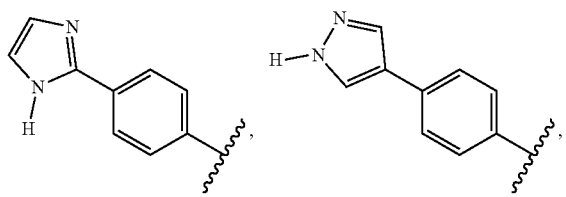
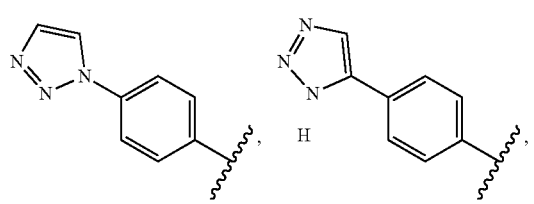
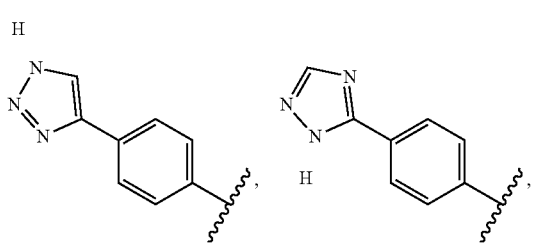
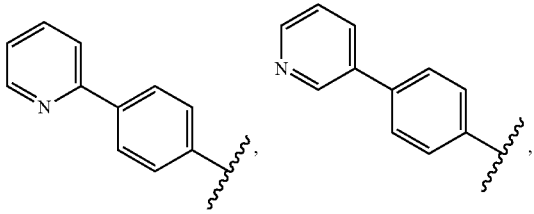
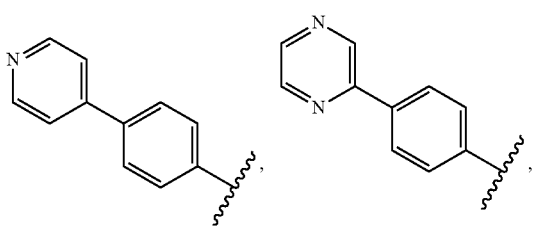
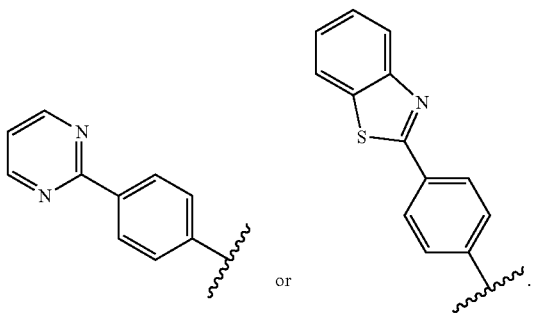
or
In certain embodiments, at least one $R^3$ is aryl substituted with heteroaryl, which heteroaryl is substituted with $C_{1-4}$ alkyl, —C(O)OH or $C_{1-4}$ haloalkyl. In certain embodiments, $R^3$ is aryl substituted with heteroaryl, which heteroaryl is substituted with $C_{1-4}$ alkyl, —C(O)OH or $C_{1-4}$ haloalkyl.
In certain embodiments, at least one $R^3$ is
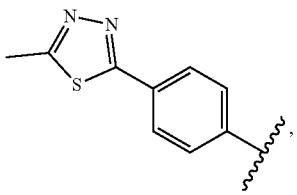
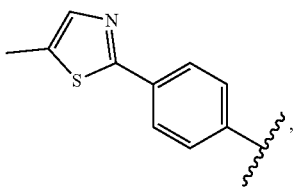
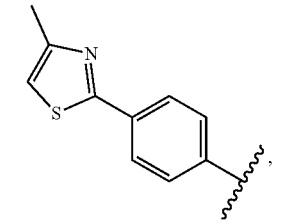
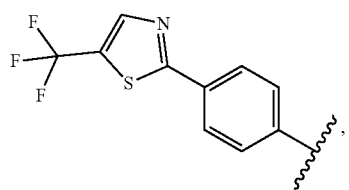
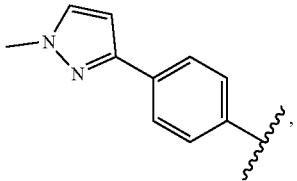
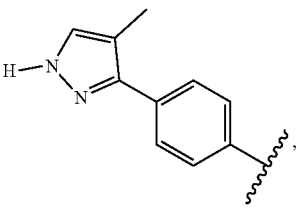
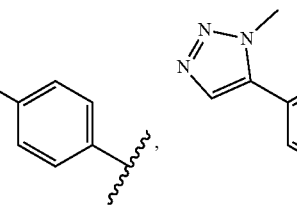
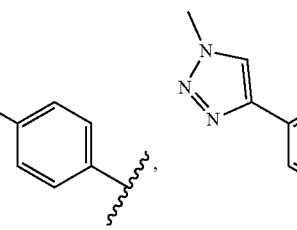

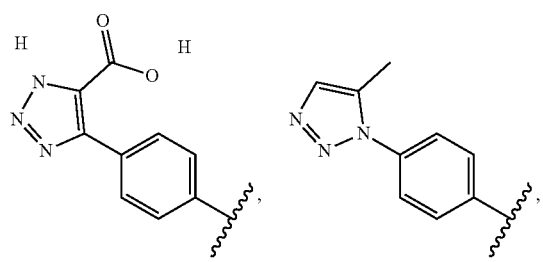
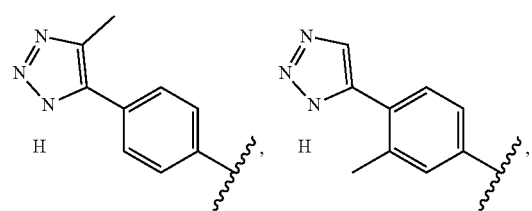
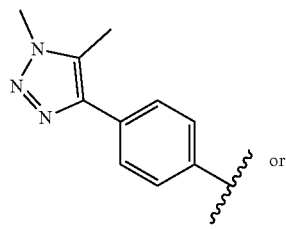
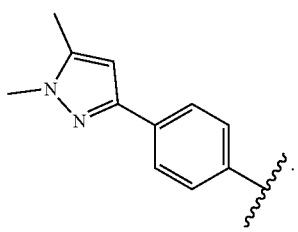
In certain embodiments, R³ is
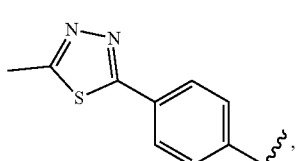
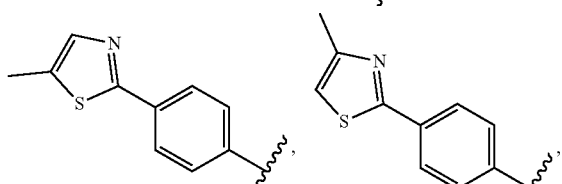
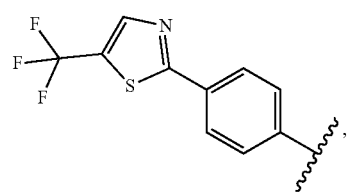
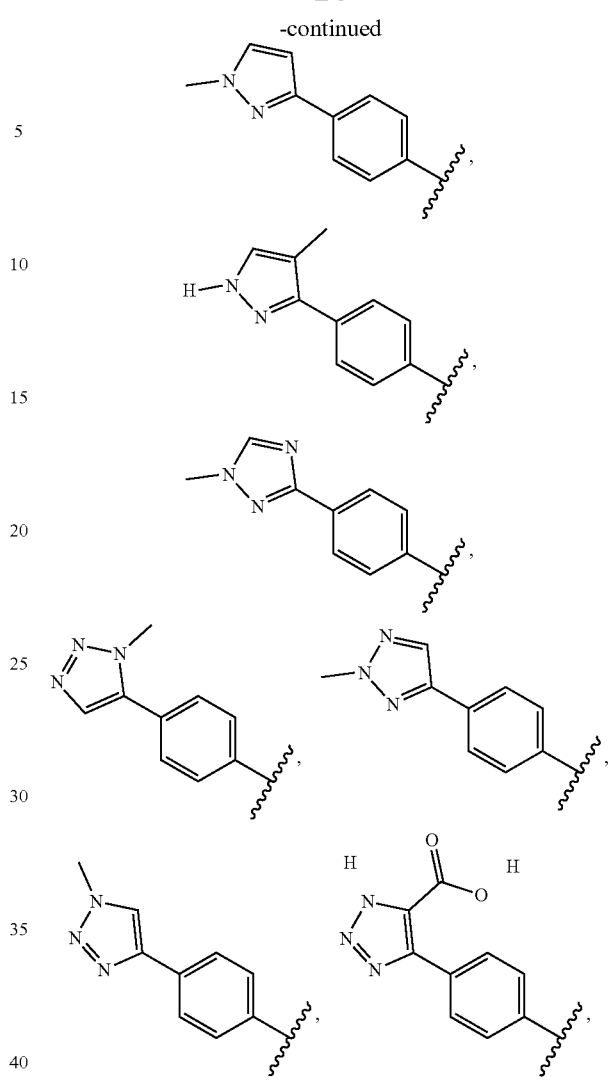
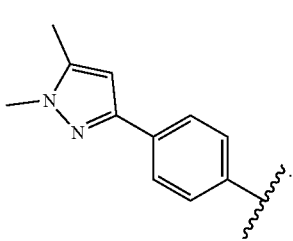

In certain embodiments, at least one $R^3$ is heterocyclyl optionally substituted with one to three $R^6$. In certain embodiments, $R^3$ is heterocyclyl optionally substituted with one to three $R^6$.

In certain embodiments, at least one $R^3$ is

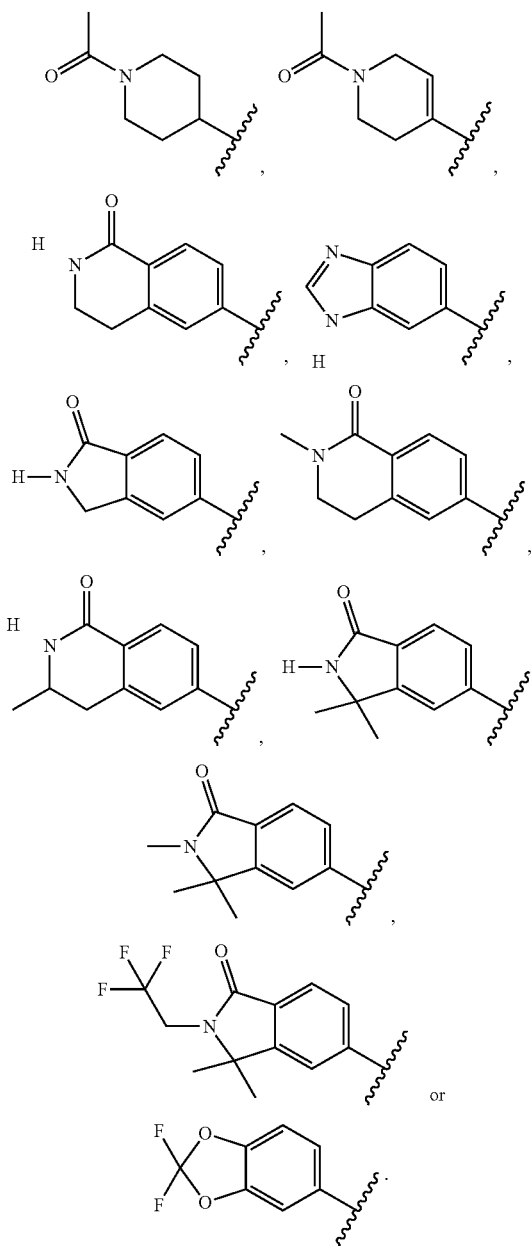

In certain embodiments, $R^3$ is

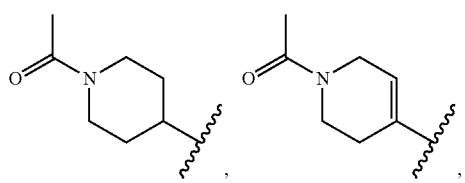

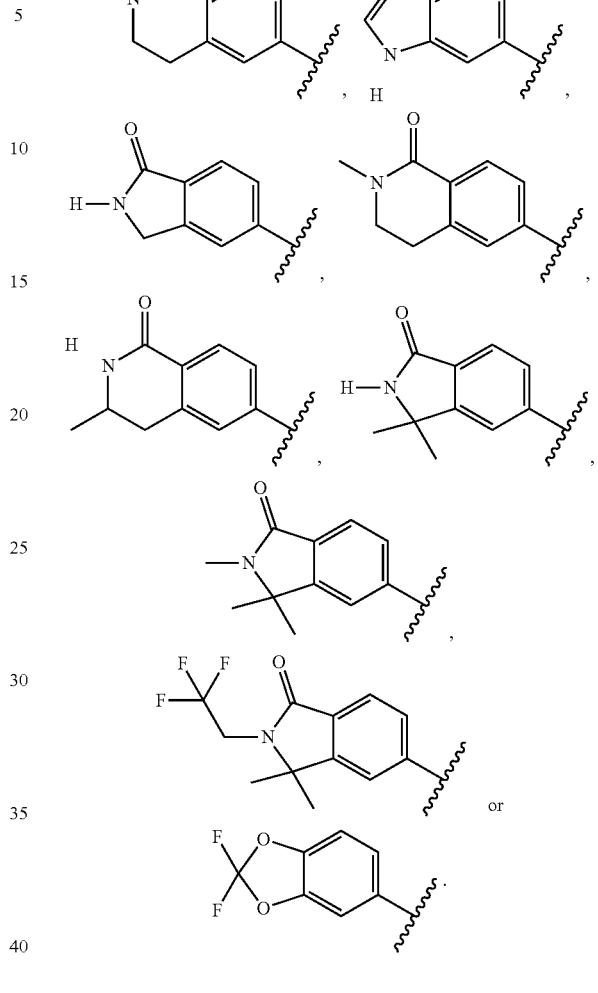

In certain embodiments, at least one $R^3$ is heteroaryl optionally substituted with one to three $R^6$. In certain embodiments, $R^3$ is heteroaryl optionally substituted with one to three $R^6$.

In certain embodiments, at least one $R^3$ is

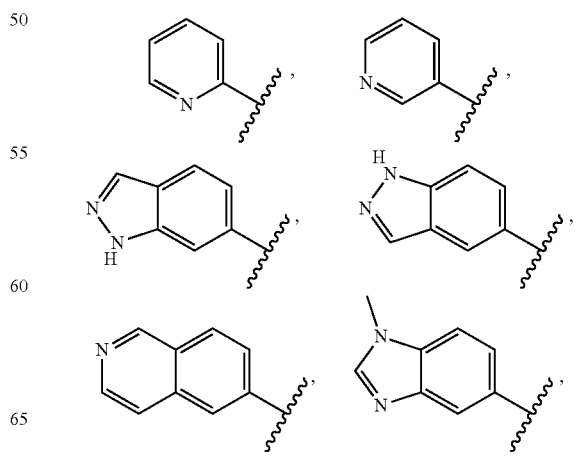

-continued

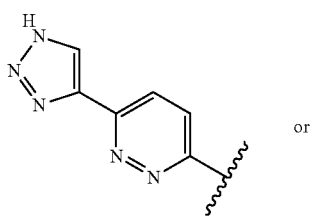

or

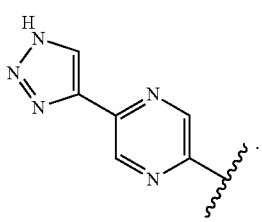

In certain embodiments, R³ is

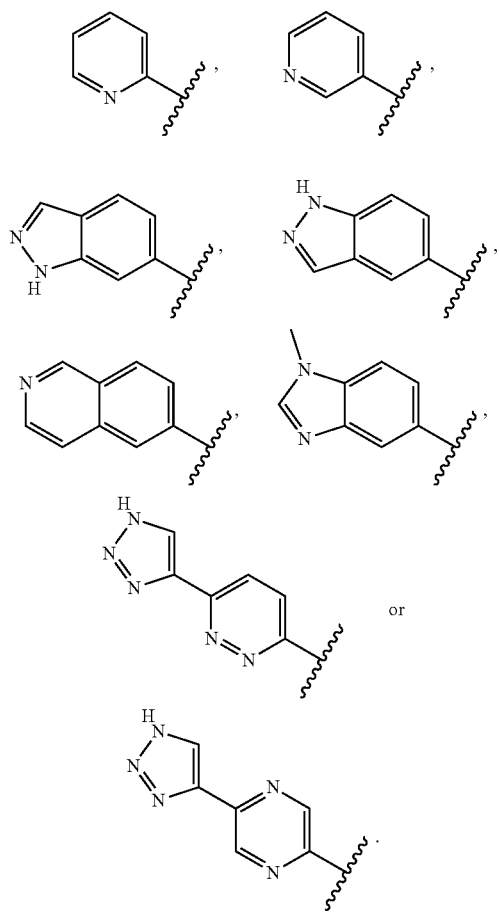

In certain embodiments, R² is hydrogen, $C_{1-6}$ alkyl optionally substituted with one to three $R^4$, or cycloalkyl; each $R^4$ is independently —OC(O)$R^a$, —OC(O)O$R^a$, —OP(O)(O$R^b$)$_2$, or monocyclic heterocyclyl; provided only one $R^4$ is heterocyclyl; each $R^a$ is independently $C_{1-6}$ alkyl optionally substituted with —NH$_2$ or —OP(O)(O$R^b$)$_2$; and $R^b$ is hydrogen.

In certain embodiments, provided herein is a compound of formula III:

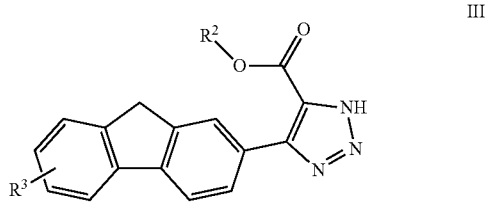

III or a pharmaceutically acceptable salt, tautomer, stereoisomer, mixture of stereoisomers, or deuterated analog thereof, wherein:

$R^2$ is hydrogen, —(CH$_2$CH$_2$O)$_{1-9}$CH$_2$CH$_2$OCH$_2$, $C_{1-6}$ alkyl optionally substituted with one to three $R^4$, cycloalkyl, or heteroaryl optionally substituted with one to three $R^5$;

each $R^3$ is independently aryl, heteroaryl, or heterocyclyl, wherein each is optionally substituted with one to three $R^6$;

each $R^4$ is independently halo, hydroxy, —OC$_{1-6}$alkyl, —NH$_2$, —NHC$_{1-6}$ alkyl, —N(C$_{1-6}$alkyl)$_2$, —OC(O)$R^a$, —OC(O)O$R^a$, —OP(O)(O$R^b$)$_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —OC$_{1-4}$alkyl, $C_{1-4}$ haloalkyl, or —OC$_{1-4}$ haloalkyl;

each $R^6$ is independently cyano, halo, —C(O)$R^7$, —C(O)O$R^7$, —C(O)N$R^7R^8$, —S(O)$_2$N$R^7R^8$, —N$R^7$C(O)$R^8$, —O$R^7$, $C_{1-4}$ alkyl, —OC$_{1-4}$alkyl, $C_{1-4}$ haloalkyl, —OC$_{1-4}$ haloalkyl, phenyl, heterocyclyl, or heteroaryl; wherein each is optionally substituted with one to three $C_{1-4}$ alkyl, —C(O)OH or $C_{1-4}$ haloalkyl;

$R^7$ and $R^8$ are each independently hydrogen, $C_{1-4}$ alkyl, phenyl, or pyridyl, or $R^7$ and $R^8$ together with the nitrogen atom to which they are attached form a heterocyclyl;

each $R^a$ is independently $C_{1-6}$ alkyl optionally substituted with —NH$_2$, —NHC$_{1-6}$ alkyl, —N(C$_{1-6}$alkyl)$_2$, or —OP(O)(O$R^b$)$_2$; and each $R^b$ is independently hydrogen or $C_{1-4}$ alkyl.

In certain embodiments, provided herein is a compound of formula IV:

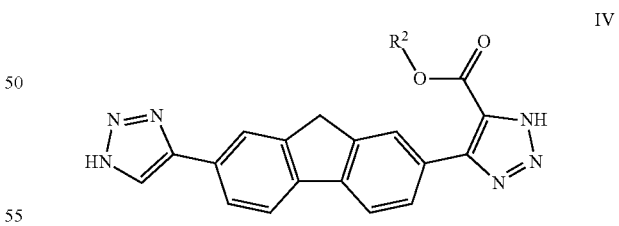

IV or a pharmaceutically acceptable salt, tautomer, stereoisomer, mixture of stereoisomers, or deuterated analog thereof, wherein:

$R^2$ is hydrogen, —(CH$_2$CH$_2$O)$_{1-9}$CH$_2$CH$_2$OCH$_3$, $C_{1-6}$ alkyl optionally substituted with one to three $R^4$, cycloalkyl, or heteroaryl optionally substituted with one to three $R^5$;

each $R^4$ is independently halo, hydroxy, —OC$_{1-6}$alkyl, —NH$_2$, —NHC$_{1-6}$ alkyl, —N(C$_{1-6}$alkyl), —OC(O)$R^a$, —OC(O)O$R^a$, —OP(O)(O$R^b$)$_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —$OC_{1-4}$alkyl, $C_{1-4}$ haloalkyl, or —$OC_{1-4}$ haloalkyl;

each $R^a$ is independently $C_{1-6}$ alkyl optionally substituted with —$NH_2$, —$NHC_{1-6}$ alkyl, —$N(C_{1-6}alkyl)_2$, or —$OP(O)(OR^b)_2$; and each $R^b$ is independently hydrogen or $C_{1-4}$ alkyl.

In certain embodiments, $R^2$ is hydrogen, $C_{1-6}$ alkyl optionally substituted with one to three $R^4$, or cycloalkyl. In certain embodiments, $R^2$ is hydrogen or $C_{1-6}$ alkyl optionally substituted with one to three $R^4$. In certain embodiments, $R^2$ is hydrogen or $C_{1-6}$ alkyl optionally substituted with one $R^4$. In certain embodiments, $R^2$ is hydrogen. In certain embodiments, $R^2$ is $C_{1-6}$ alkyl optionally substituted with one to three $R^4$. In certain embodiments, $R^2$ is $C_{1-6}$ alkyl. In certain embodiments, $R^2$ is $C_{1-4}$ alkyl.

In certain embodiments, $R^2$ is hydrogen, $C_{1-6}$ alkyl optionally substituted with one to three $R^4$, or cycloalkyl; each $R^4$ is independently —$OC_{1-6}$alkyl, —$OC(O)R^a$, —$OC(O)OR^a$, —$OP(O)(OR^b)_2$, or monocyclic heterocyclyl; each $R^a$ is independently $C_{1-6}$ alkyl optionally substituted with —$NH_2$ or —$OP(O)(OR^b)_2$; and $R^b$ is hydrogen.

In certain embodiments, each $R^4$ is independently —$OC_{1-6}$alkyl, —$OC(O)R^a$, —$OC(O)OR^a$, —$OP(O)(OR^b)_2$, or monocyclic heterocyclyl; wherein each $R^a$ is independently $C_{1-6}$ alkyl optionally substituted with —$NH_2$ or —$OP(O)(OR^b)_2$, and $R^b$ is hydrogen.

In certain embodiments, each $R^4$ is independently —$OC(O)R^a$, —$OC(O)OR^a$, —$OP(O)(OR^b)_2$, or monocyclic heterocyclyl; wherein each $R^a$ is independently $C_{1-6}$ alkyl optionally substituted with —$NH_2$ or —$OP(O)(OR^b)_2$, and $R^b$ is hydrogen.

In certain embodiments, provided is a compound selected from Table 1 or a pharmaceutically acceptable salt, tautomer, stereoisomer, mixture of stereoisomers, or deuterated analog thereof. In certain embodiments, the compound is selected from a compound of Table 1:

TABLE 1

| No. | Structure |
|---|---|
| 1 | [structure] |
| 2 | [structure] |
| 3 | [structure] |
| 4 | [structure] |
| 5 | [structure] |
| 6 | [structure] |
| 7 | [structure] |
| 8 | [structure] |
| 9 | [structure] |
| 10 | [structure] |
| 11 | [structure] |

TABLE 1-continued
| No. | Structure |
|---|---|
| 12-19 | 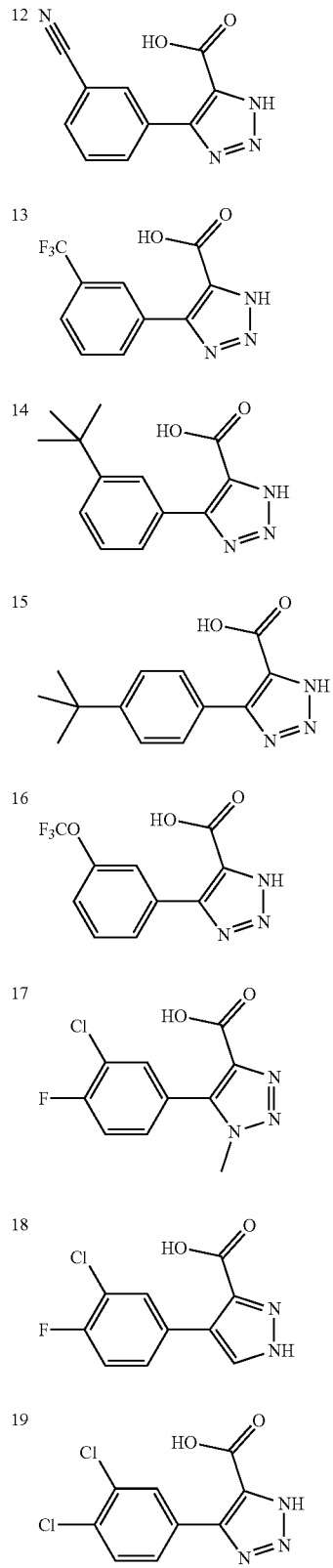 |
| 20-26 | 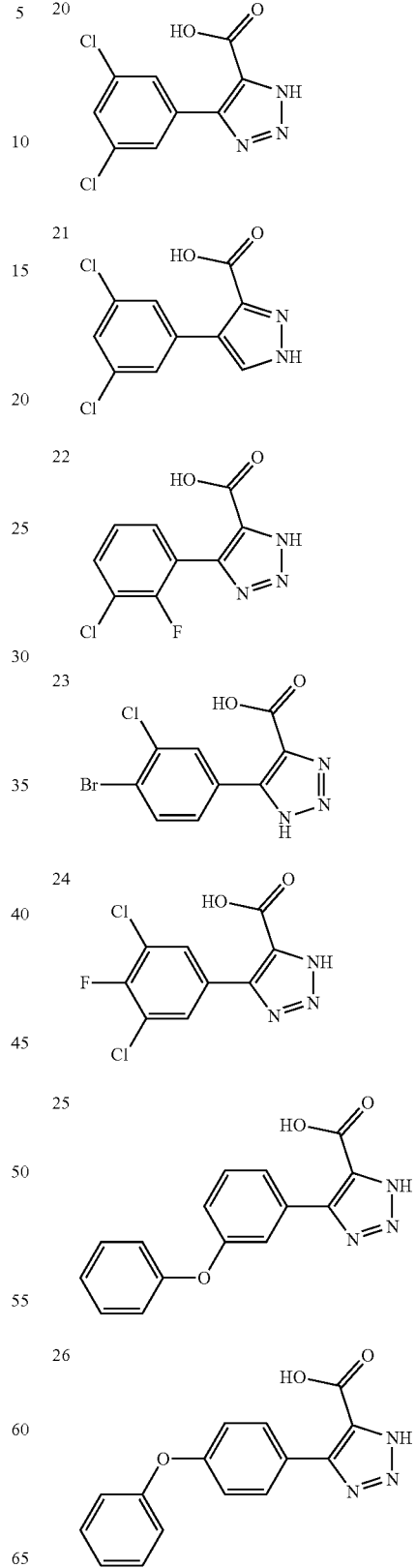 |

TABLE 1-continued
No. Structure
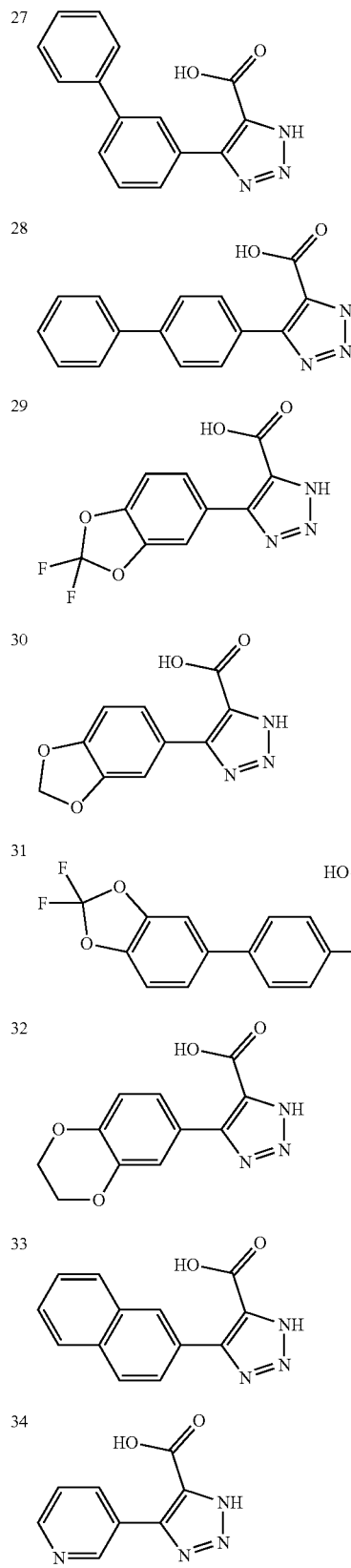
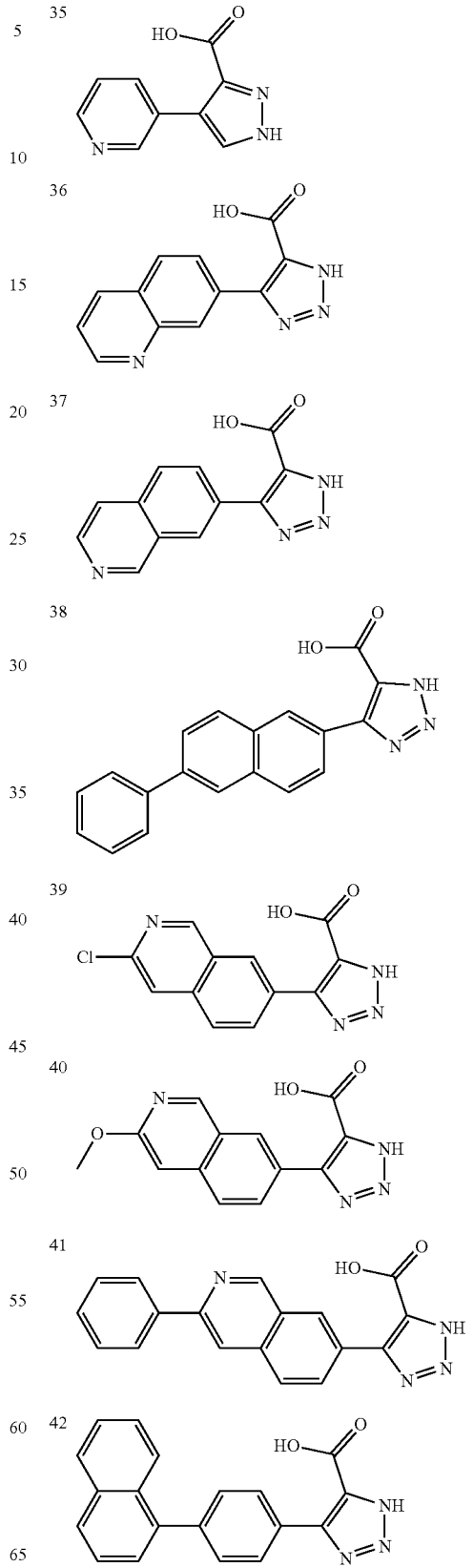

TABLE 1-continued
| No. | Structure |
|---|---|
| 43 | 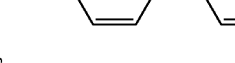 |
| 44 | 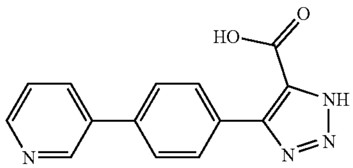 [SMILES: O=C(O)c1[nH]nnc1-c1ccc(-c2cccnc2)cc1] |
| 45 | 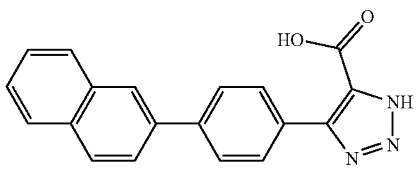 [SMILES: O=C(O)c1[nH]nnc1-c1ccc(-c2ccc3ccccc3c2)cc1] |
| 46 | 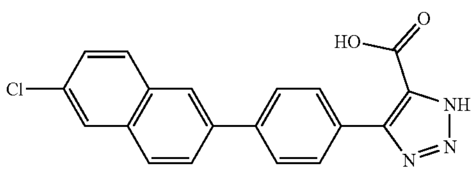 [SMILES: O=C(O)c1[nH]nnc1-c1ccc(-c2ccc3cc(Cl)ccc3c2)cc1] |
| 47 | 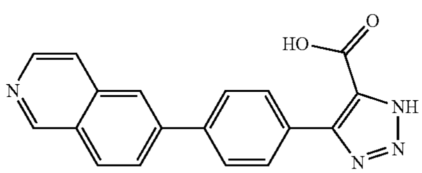 [SMILES: O=C(O)c1[nH]nnc1-c1ccc(-c2ccc3cnccc3c2)cc1] |
| 48 | 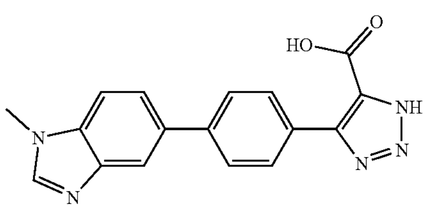 [SMILES: Cn1cnc2cc(-c3ccc(-c4nn[nH]c4C(=O)O)cc3)ccc21] |
| 49 | 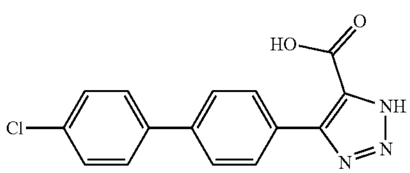 [SMILES: O=C(O)c1[nH]nnc1-c1ccc(-c2ccc(Cl)cc2)cc1] |
| 50 | 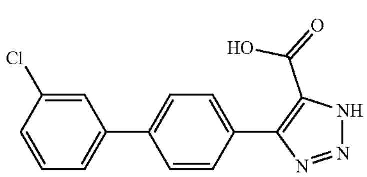 [SMILES: O=C(O)c1[nH]nnc1-c1ccc(-c2cccc(Cl)c2)cc1] |
| 51 | 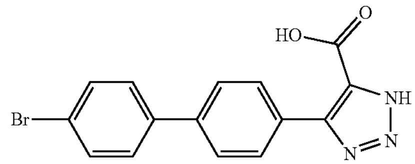 |
| 52 | 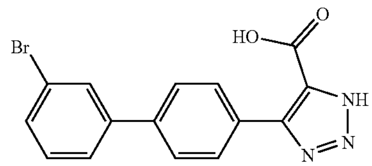 [SMILES: O=C(O)c1[nH]nnc1-c1ccc(-c2cccc(Br)c2)cc1] |
| 53 | 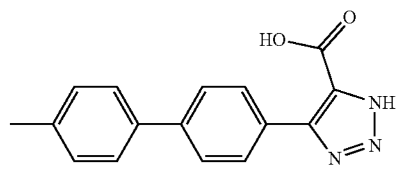 [SMILES: Cc1ccc(-c2ccc(-c3nn[nH]c3C(=O)O)cc2)cc1] |
| 54 | 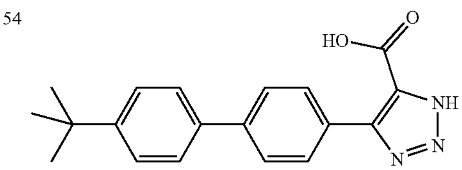 |
| 55 | 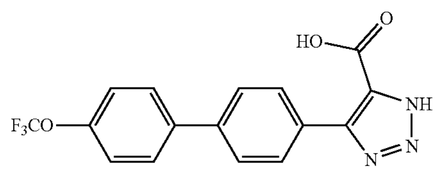 [SMILES: O=C(O)c1[nH]nnc1-c1ccc(-c2ccc(OC(F)(F)F)cc2)cc1] |
| 56 | 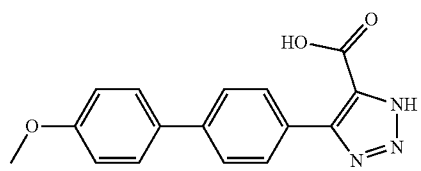 [SMILES: COc1ccc(-c2ccc(-c3nn[nH]c3C(=O)O)cc2)cc1] |
| 57 | 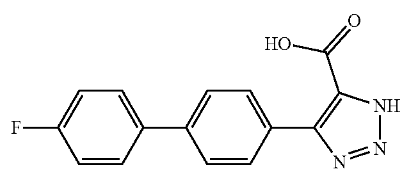 [SMILES: O=C(O)c1[nH]nnc1-c1ccc(-c2ccc(F)cc2)cc1] |
| 58 | 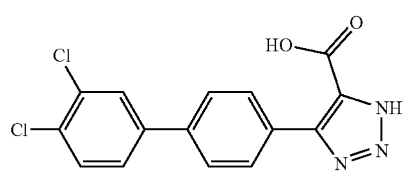 [SMILES: O=C(O)c1[nH]nnc1-c1ccc(-c2ccc(Cl)c(Cl)c2)cc1] |
| 59 | 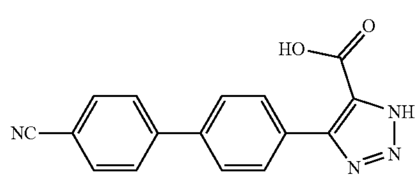 |

TABLE 1-continued

| No. | Structure |
|---|---|
| 60 | 3'-fluoro-4'-chloro-biphenyl-triazole-carboxylic acid |
| 61 | 3'-chloro-4'-fluoro-biphenyl-triazole-carboxylic acid |
| 62 | 3'-phenoxy-biphenyl-triazole-carboxylic acid |
| 63 | 4'-phenoxy-biphenyl-triazole-carboxylic acid |
| 64 | 4'-(pyridin-2-yloxy)-biphenyl-triazole-carboxylic acid |
| 65 | 4'-acetyl-biphenyl-triazole-carboxylic acid |
| 66 | 3'-carbamoyl-biphenyl-triazole-carboxylic acid |
| 67 | 3'-(N-methylcarbamoyl)-biphenyl-triazole-carboxylic acid |
| 68 | 4'-carbamoyl-biphenyl-triazole-carboxylic acid |
| 69 | 4'-(N-methylcarbamoyl)-biphenyl-triazole-carboxylic acid |
| 70 | 4'-(N,N-dimethylcarbamoyl)-biphenyl-triazole-carboxylic acid |
| 71 | 4'-carbamoyl-3'-chloro-biphenyl-triazole-carboxylic acid |
| 72 | 3'-sulfamoyl-biphenyl-triazole-carboxylic acid |
| 73 | 3'-(N,N-dimethylsulfamoyl)-biphenyl-triazole-carboxylic acid |

TABLE 1-continued

| No. | Structure |
|---|---|
| 74 | 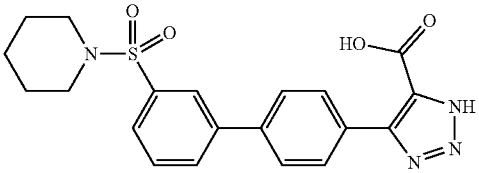 [SMILES: O=C(O)c1[nH]nnc1-c1ccc(-c2cccc(S(=O)(=O)N3CCCCC3)c2)cc1] |
| 75 | 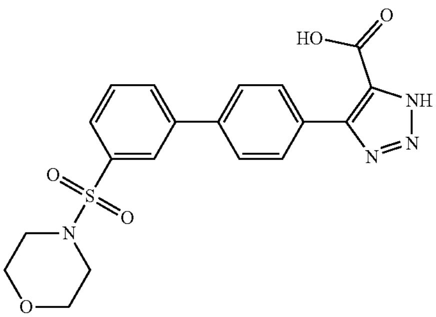 [SMILES: O=C(O)c1[nH]nnc1-c1ccc(-c2cccc(S(=O)(=O)N3CCOCC3)c2)cc1] |
| 76 | 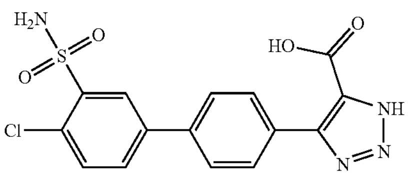 [SMILES: NS(=O)(=O)c1cc(-c2ccc(-c3nn[nH]c3C(=O)O)cc2)ccc1Cl] |
| 77 | 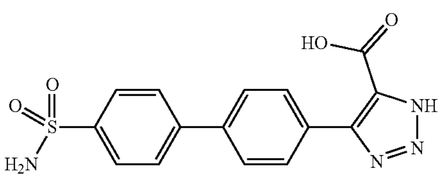 |
| 78 | 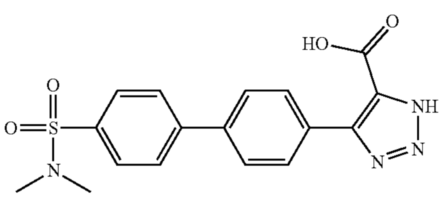 [SMILES: CN(C)S(=O)(=O)c1ccc(-c2ccc(-c3nn[nH]c3C(=O)O)cc2)cc1] |
| 79 | 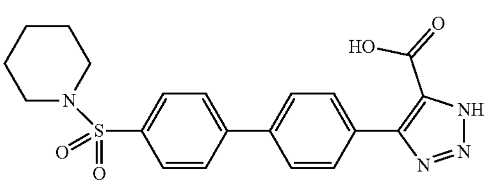 [SMILES: O=C(O)c1[nH]nnc1-c1ccc(-c2ccc(S(=O)(=O)N3CCCCC3)cc2)cc1] |
| 80 | 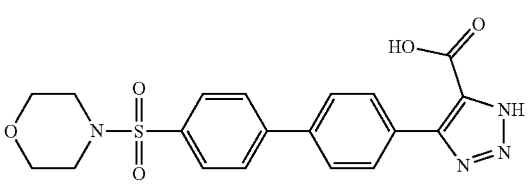 [SMILES: O=C(O)c1[nH]nnc1-c1ccc(-c2ccc(S(=O)(=O)N3CCOCC3)cc2)cc1] |
| 81 | 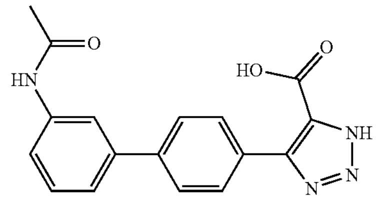 [SMILES: CC(=O)Nc1cccc(-c2ccc(-c3nn[nH]c3C(=O)O)cc2)c1] |
| 82 | 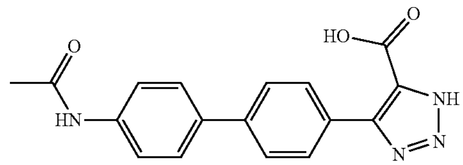 [SMILES: CC(=O)Nc1ccc(-c2ccc(-c3nn[nH]c3C(=O)O)cc2)cc1] |
| 83 | 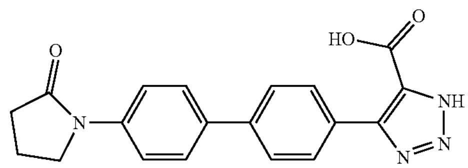 [SMILES: O=C(O)c1[nH]nnc1-c1ccc(-c2ccc(N3CCCC3=O)cc2)cc1] |
| 84 | 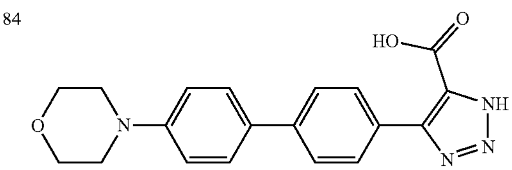 |
| 85 | 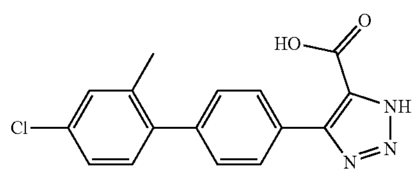 [SMILES: Cc1cc(Cl)ccc1-c1ccc(-c2nn[nH]c2C(=O)O)cc1] |
| 86 | 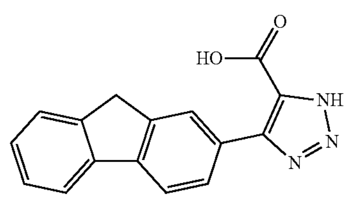 [SMILES: O=C(O)c1[nH]nnc1-c1ccc2c(c1)Cc1ccccc1-2] |
| 87 | 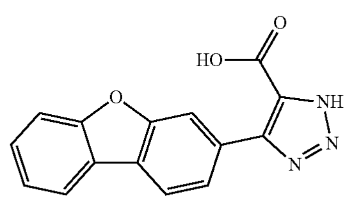 [SMILES: O=C(O)c1[nH]nnc1-c1ccc2c(c1)oc1ccccc12] |
| 88 | 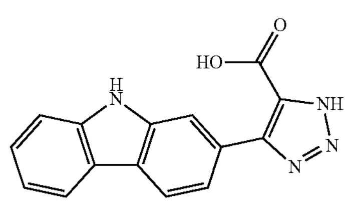 [SMILES: O=C(O)c1[nH]nnc1-c1ccc2c(c1)[nH]c1ccccc12] |

TABLE 1-continued

| No. | Structure |
|---|---|
| 89 | (9-oxofluoren-2-yl)-1H-1,2,3-triazole-4-carboxylic acid |
| 90 | (9,9-dimethylfluoren-2-yl)-1H-1,2,3-triazole-4-carboxylic acid |
| 91 | 5-(4'-chloro-3'-methyl-[1,1'-biphenyl]-4-yl)-1H-1,2,3-triazole-4-carboxylic acid |
| 92 | 5-(4'-carbamoyl-3'-methyl-[1,1'-biphenyl]-4-yl)-1H-1,2,3-triazole-4-carboxylic acid |
| 93 | 5-(4-(1-oxo-1,2,3,4-tetrahydroisoquinolin-6-yl)phenyl)-1H-1,2,3-triazole-4-carboxylic acid |
| 94 | 4-(4-(1-oxo-1,2,3,4-tetrahydroisoquinolin-6-yl)phenyl)-1H-pyrazole-5-carboxylic acid |
| 95 | 5-(4-(3-methyl-1-oxo-1,2,3,4-tetrahydroisoquinolin-7-yl)phenyl)-1H-1,2,3-triazole-4-carboxylic acid |
| 96 | 5-(4-(2-methyl-1-oxo-1,2,3,4-tetrahydroisoquinolin-6-yl)phenyl)-1H-1,2,3-triazole-4-carboxylic acid |
| 97 | 5-(4-(3-oxo-2,3-dihydro-1H-isoindol-5-yl)phenyl)-1H-1,2,3-triazole-4-carboxylic acid |
| 98 | 5-(4-(3,3-dimethyl-1-oxo-2,3-dihydro-1H-isoindol-5-yl)phenyl)-1H-1,2,3-triazole-4-carboxylic acid |
| 99 | 5-([1,1':3',1''-terphenyl]-4-yl)-1H-1,2,3-triazole-4-carboxylic acid |
| 100 | 5-([1,1':4',1''-terphenyl]-4-yl)-1H-1,2,3-triazole-4-carboxylic acid |
| 101 | 5-(4'-(pyridin-2-yl)-[1,1'-biphenyl]-4-yl)-1H-1,2,3-triazole-4-carboxylic acid |
| 102 | 5-(4'-(pyridin-3-yl)-[1,1'-biphenyl]-4-yl)-1H-1,2,3-triazole-4-carboxylic acid |
| 103 | 5-(4'-(pyridin-4-yl)-[1,1'-biphenyl]-4-yl)-1H-1,2,3-triazole-4-carboxylic acid |
| 104 | 5-(4'-(pyrimidin-2-yl)-[1,1'-biphenyl]-4-yl)-1H-1,2,3-triazole-4-carboxylic acid |

TABLE 1-continued
| No. | Structure |
|---|---|
| 105 | 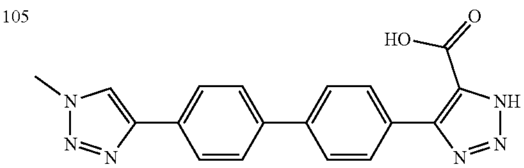 |
| 106 | 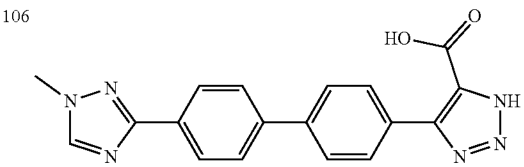 |
| 107 | 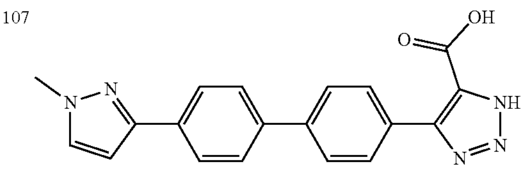 |
| 108 | 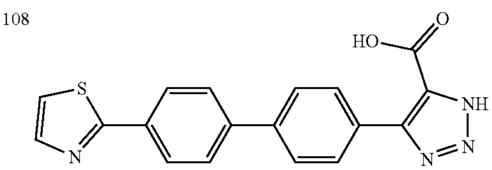 |
| 109 | 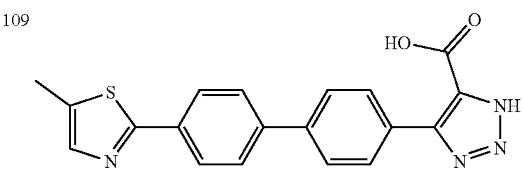 |
| 110 | 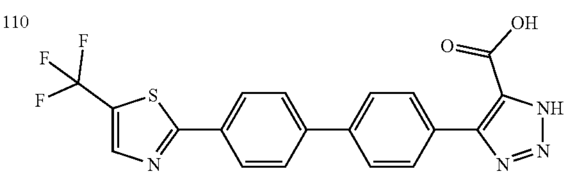 |
| 111 | 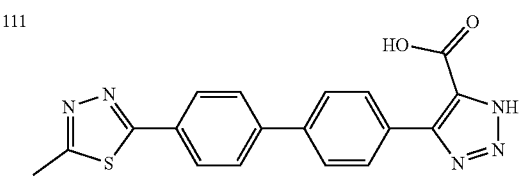 |
| 112 | 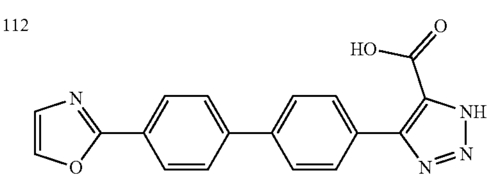 |
| 113 | 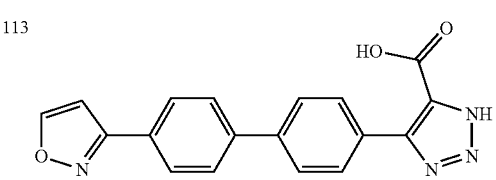 |
| 114 |  |
| 115 | |
| 116 | |
| 117 | |
| 118 | |
| 119 | |
| 120 | |
| 121 | |

TABLE 1-continued
| No. | Structure |
|---|---|
| 122 | 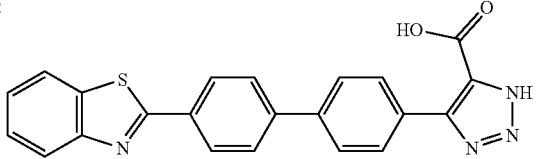 |
| 123 | 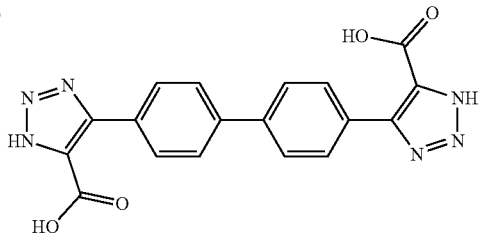 [SMILES: O=C(O)c1[nH]nnc1-c1ccc(-c2ccc(-c3nn[nH]c3C(=O)O)cc2)cc1] |
| 124 | 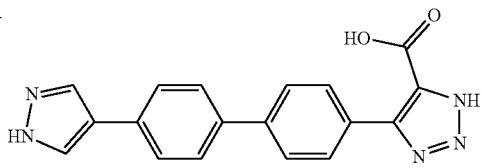 |
| 125 | 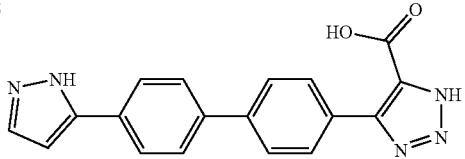 [SMILES: O=C(O)c1[nH]nnc1-c1ccc(-c2ccc(-c3ccn[nH]3)cc2)cc1] |
| 126 | 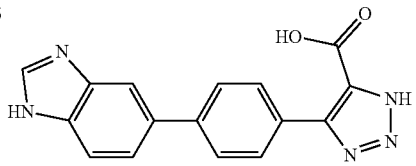 |
| 127 | 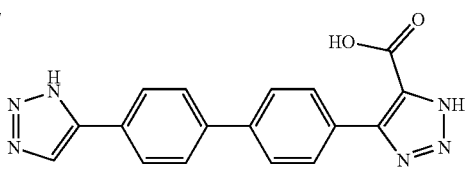 |
| 128 | 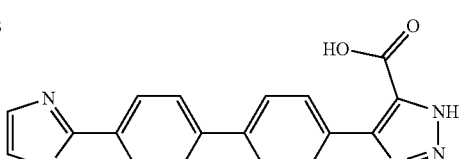 |
| 129 | 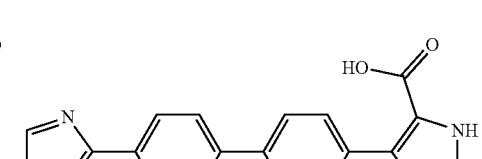 |
| 130 | 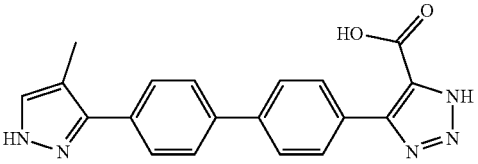 [SMILES: Cc1c[nH]nc1-c1ccc(-c2ccc(-c3nn[nH]c3C(=O)O)cc2)cc1] |
| 131 | 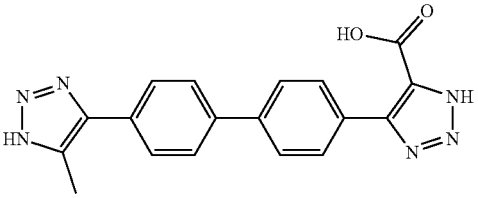 [SMILES: Cc1[nH]nnc1-c1ccc(-c2ccc(-c3nn[nH]c3C(=O)O)cc2)cc1] |
| 132 |  |
| 133 | 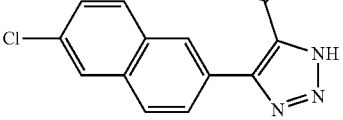 |
| 134 | 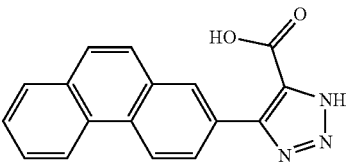 [SMILES: O=C(O)c1[nH]nnc1-c1ccc2c(ccc3ccccc32)c1] |
| 135 |  |
| 136 | 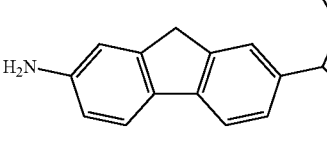 |
| 137 | 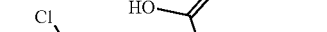 |

TABLE 1-continued
| No. | Structure |
|---|---|
| 138 | 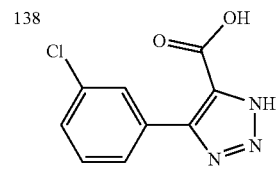 |
| 139 | 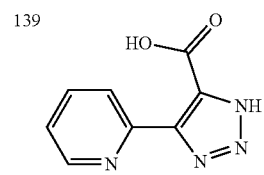 |
| 140 | 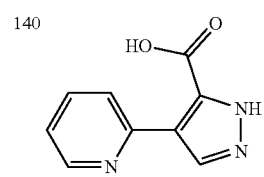 |
| 141 | 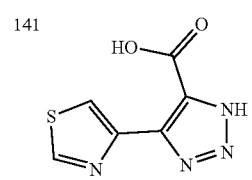 |
| 142 | 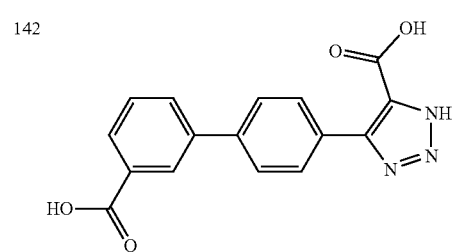 |
| 143 | 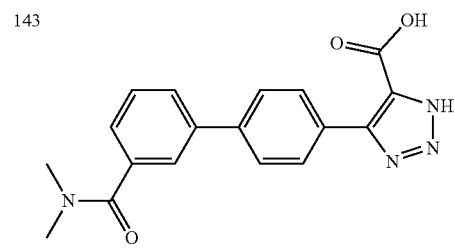 |
| 144 | 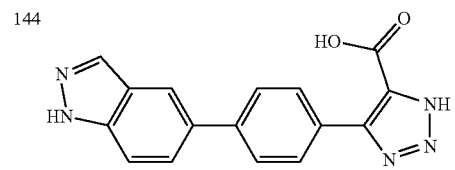 |
| 145 | 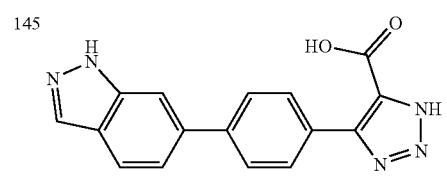 |
| 146 | 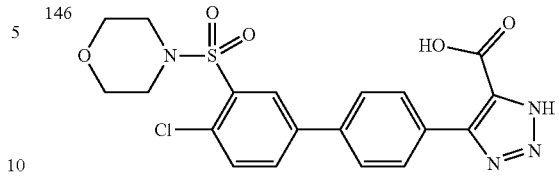 |
| 147 | 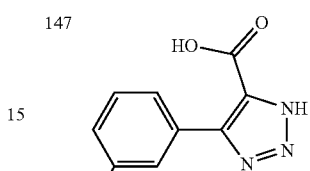 |
| 148 | 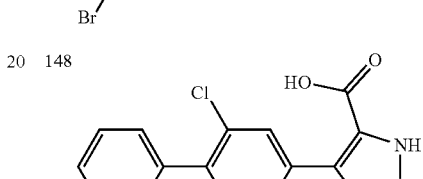 |
| 149 | 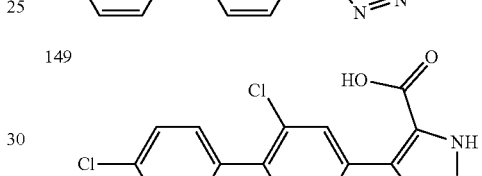 |
| 150 | 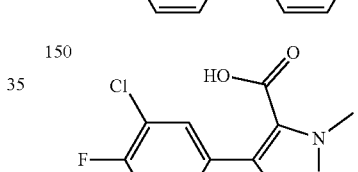 |
| 151 | 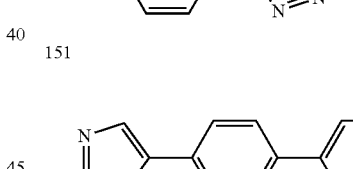 |
| 152 | 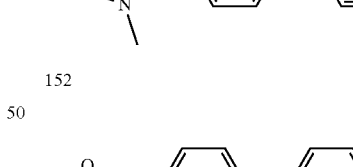 |
| 153 | 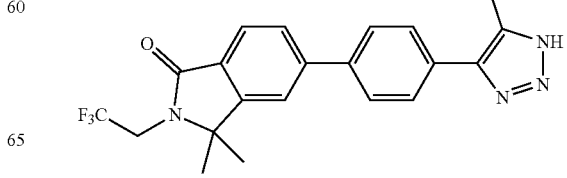 |

TABLE 1-continued

| No. | Structure |
|---|---|
| 154 | 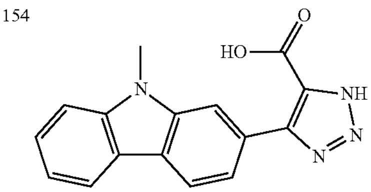 |
| 155 | 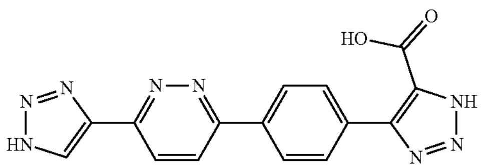 |
| 156 | 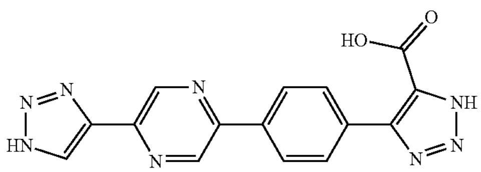 |
| 157 | 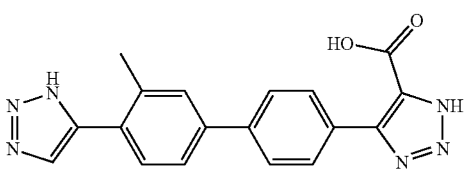 [SMILES: Cc1cc(-c2ccc(-c3nn[nH]c3C(=O)O)cc2)ccc1-c1cnn[nH]1] |
| 158 | 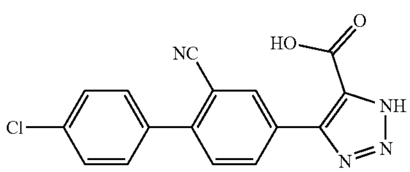 [SMILES: N#Cc1cc(-c2nn[nH]c2C(=O)O)ccc1-c1ccc(Cl)cc1] |
| 159 | 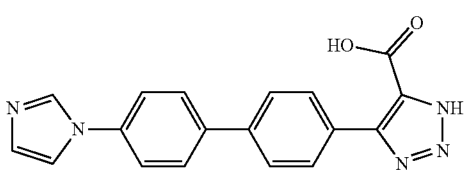 [SMILES: O=C(O)c1[nH]nnc1-c1ccc(-c2ccc(-n3ccnc3)cc2)cc1] |
| 160 | 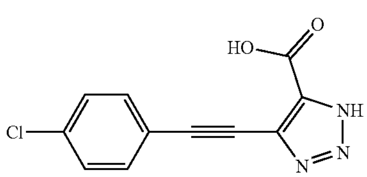 [SMILES: O=C(O)c1[nH]nnc1C#Cc1ccc(Cl)cc1] |
| 161 | 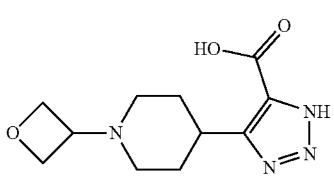 [SMILES: O=C(O)c1[nH]nnc1C1CCN(C2COC2)CC1] |
| 162 | |
| 163 | |
| 164 | |
| 165 | |
| 166 | |
| 167 | |
| 168 | |
| 169 | |

TABLE 1-continued

| No. | Structure |
|---|---|
| 170 | 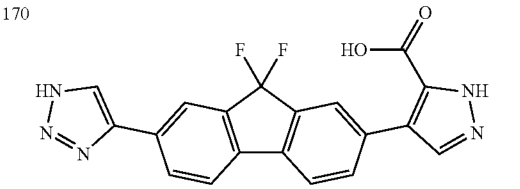 |
| 171 | 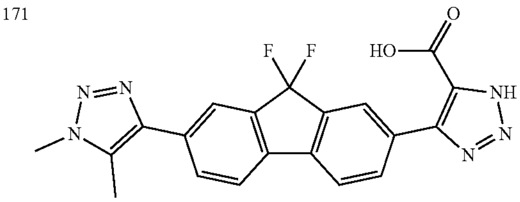 |
| 172 | 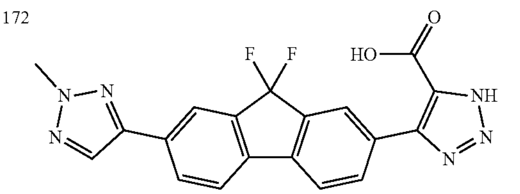 |
| 173 | 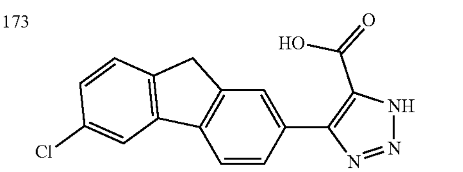 |
| 174 | 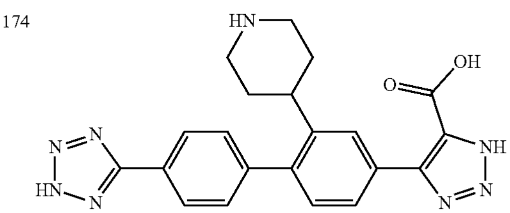 |
| 175 | 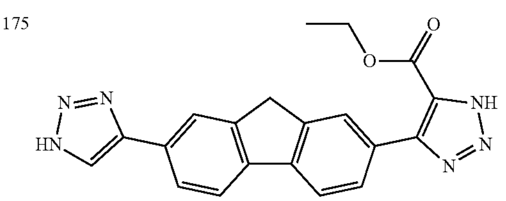 |
| 176 | 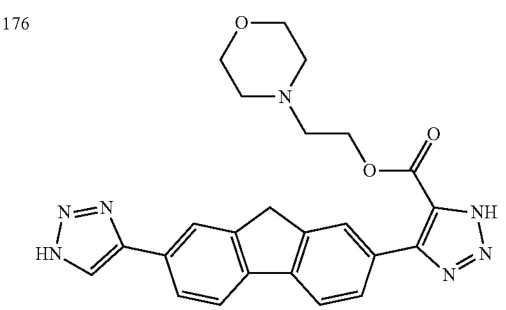 |
| 177 | |
| 178 | |
| 179 | |
| 180 | |
| 181 | |
| 182 | |

TABLE 1-continued

| No. | Structure |
|---|---|
| 183 | [3-(3,5-dichlorophenyl)-1H-pyrazole-4-carboxylic acid] |
| 184 | [5-(3-chloro-4-fluorophenyl)-1H-imidazole-4-carboxylic acid] |
| 185 | [5-(3,5-dichlorophenyl)-1H-imidazole-4-carboxylic acid] |
| 186 | [propyl ester of fluorene-bis-triazole-carboxylate] |
| 187 | [isopropyl ester of fluorene-bis-triazole-carboxylate] |
| 188 | [(S)-1-methoxypropan-2-yl ester of fluorene-bis-triazole-carboxylate] |
| 189 | [(R)-1-methoxypropan-2-yl ester of fluorene-bis-triazole-carboxylate] |
| 190 | [isopentyl ester of fluorene-bis-triazole-carboxylate] |
| 191 | [cyclopentyl ester of fluorene-bis-triazole-carboxylate] |
| 192 | [isobutyl ester of fluorene-bis-triazole-carboxylate] |
| 193 | [2-methoxyethyl ester of fluorene-bis-triazole-carboxylate] |
| 194 | [(S)-sec-butyl ester of fluorene-bis-triazole-carboxylate] |
| 195 | [(R)-sec-butyl ester of fluorene-bis-triazole-carboxylate] |

In certain embodiments, provided is a compound described herein or a pharmaceutically acceptable salt, tautomer, stereoisomer, mixture of stereoisomers, or deuterated analog thereof. In certain embodiments, the compound is selected from:

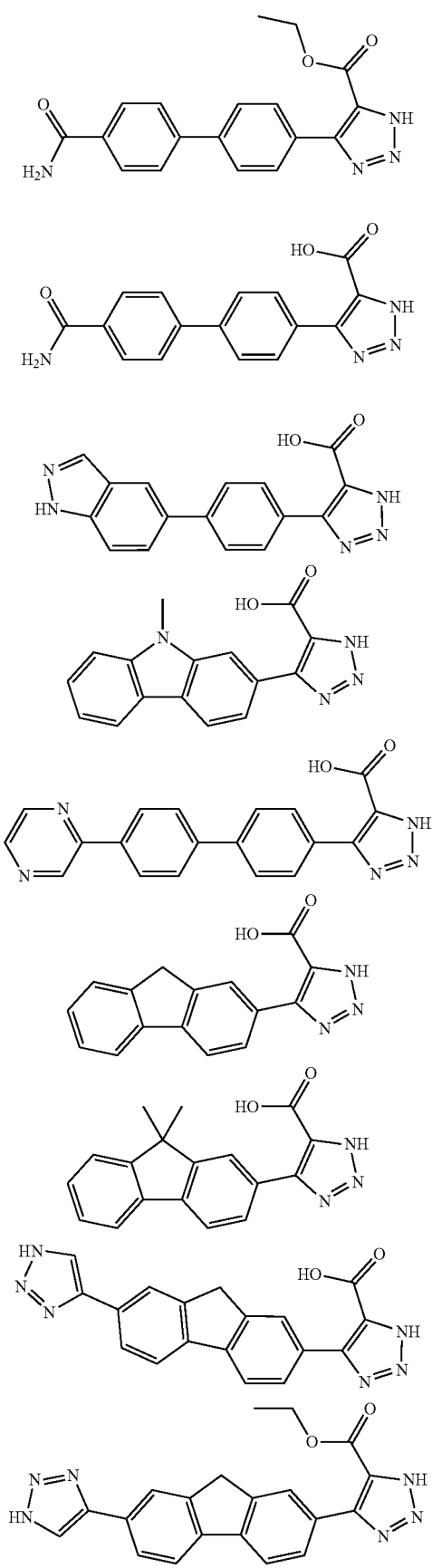
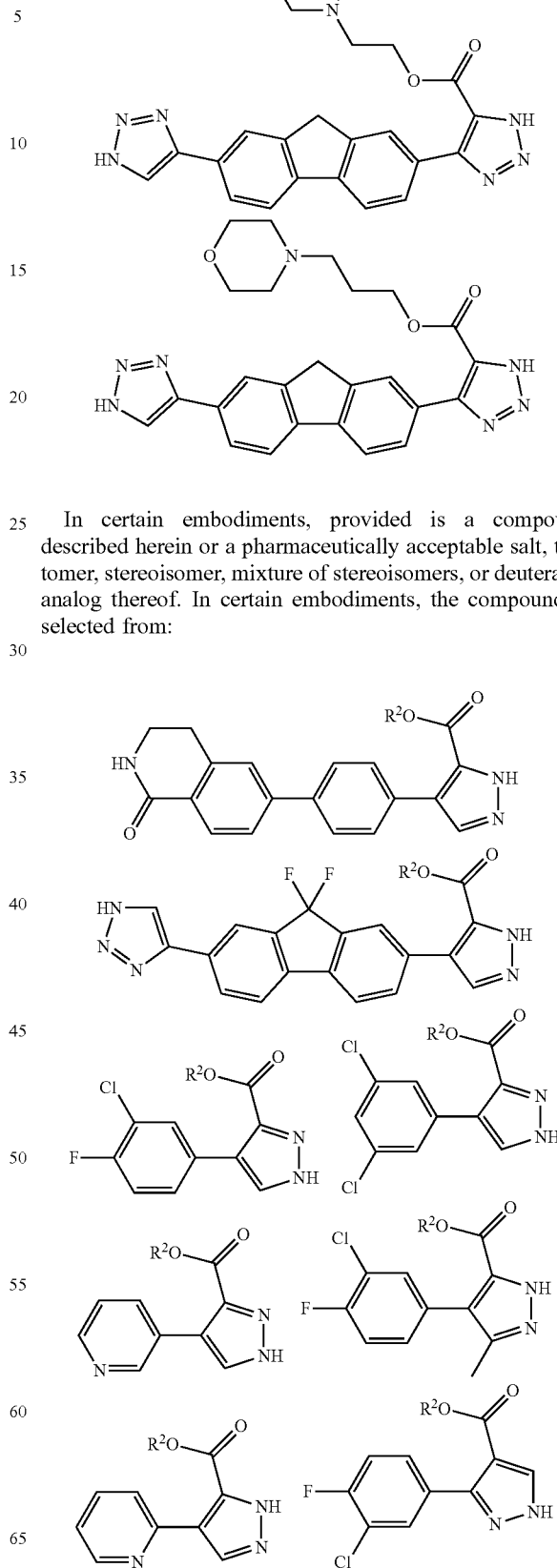
In certain embodiments, provided is a compound described herein or a pharmaceutically acceptable salt, tautomer, stereoisomer, mixture of stereoisomers, or deuterated analog thereof. In certain embodiments, the compound is selected from:
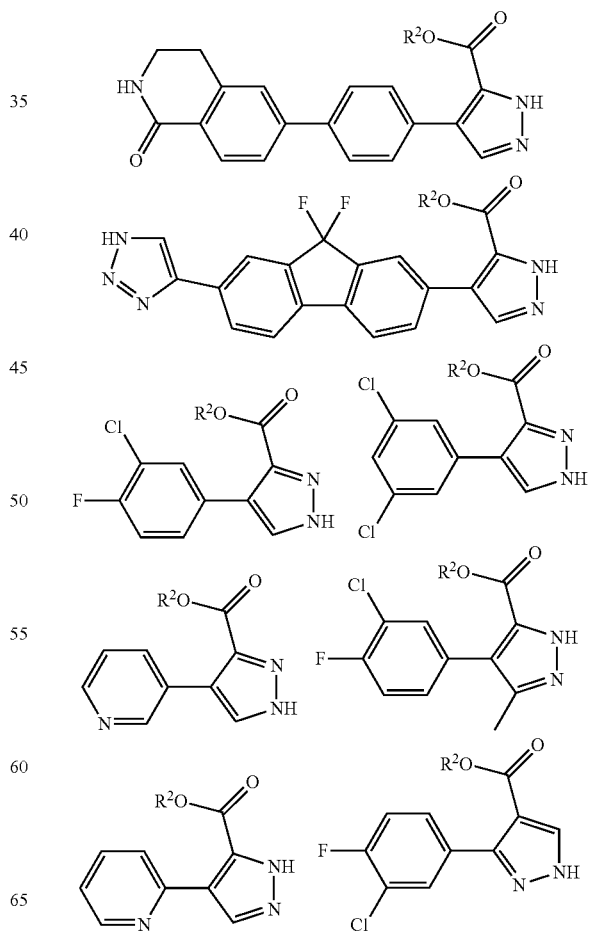

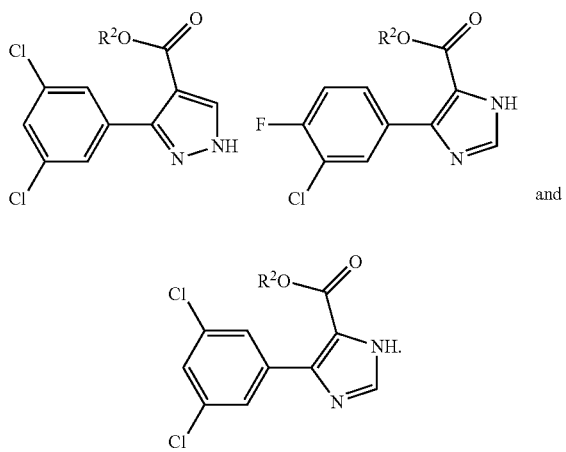

wherein R² is as defined herein.

In certain embodiments, R² is $C_{1-6}$ alkyl optionally substituted with one to three R⁴. In certain embodiments, R² is $C_{1-6}$ alkyl. In certain embodiments, R² is ethyl.

In certain embodiments, the compound is selected from:

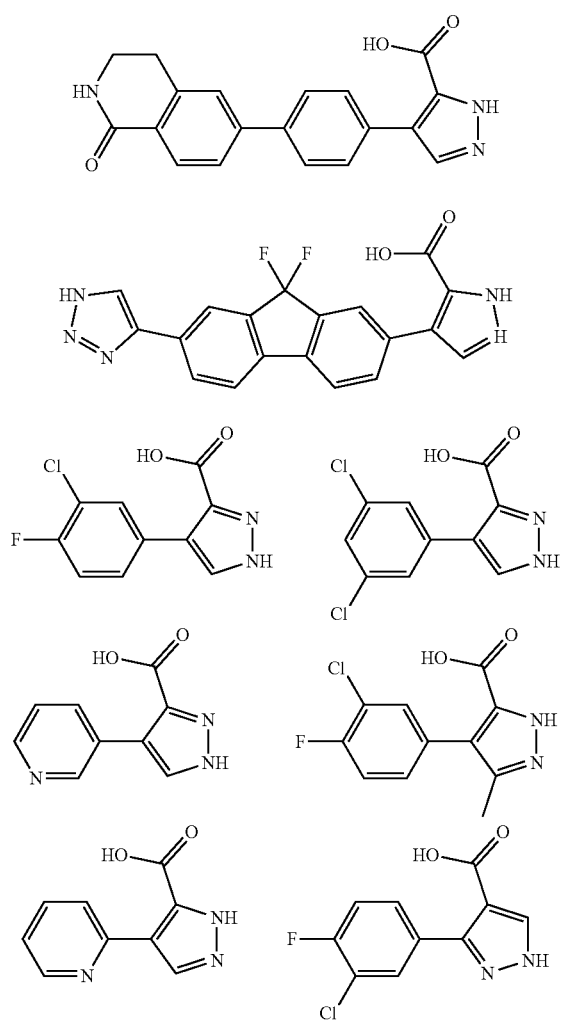

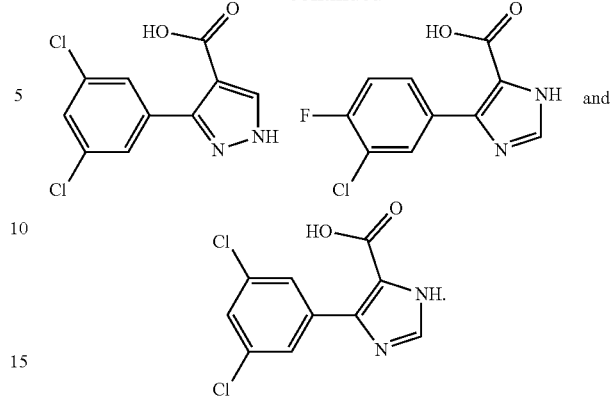

In general, the specific compounds exemplified herein are named using ChemBioDraw Ultra. However, it is understood that other names may be used to identify compounds of the same structure. In particular, the compounds may also be named using other nomenclature systems and symbols that are commonly recognized in the art of chemistry including, for example, Chemical Abstract Service (CAS) and International Union of Pure and Applied Chemistry (IUPAC). Other compounds or radicals may be named with common names, or systematic or non-systematic names.

In certain embodiments, provided are optical isomers, racemates, or other mixtures thereof of the compounds described herein or a pharmaceutically acceptable salt or a mixture thereof. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high pressure liquid chromatography (HPLC) column.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed. In certain embodiments, provided are also chelates, non-covalent complexes, and mixtures thereof, of the compounds described herein or a pharmaceutically acceptable salt, tautomer, stereoisomer, mixture of stereoisomers, prodrug, or deuterated analog thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

In certain embodiments, provided are prodrugs of the compounds described herein. "Prodrug" refers to any compound that when administered to a biological system generates the drug substance, or active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

In certain embodiments, provided is a compound of Formula I or IIa, wherein $R^1$ is

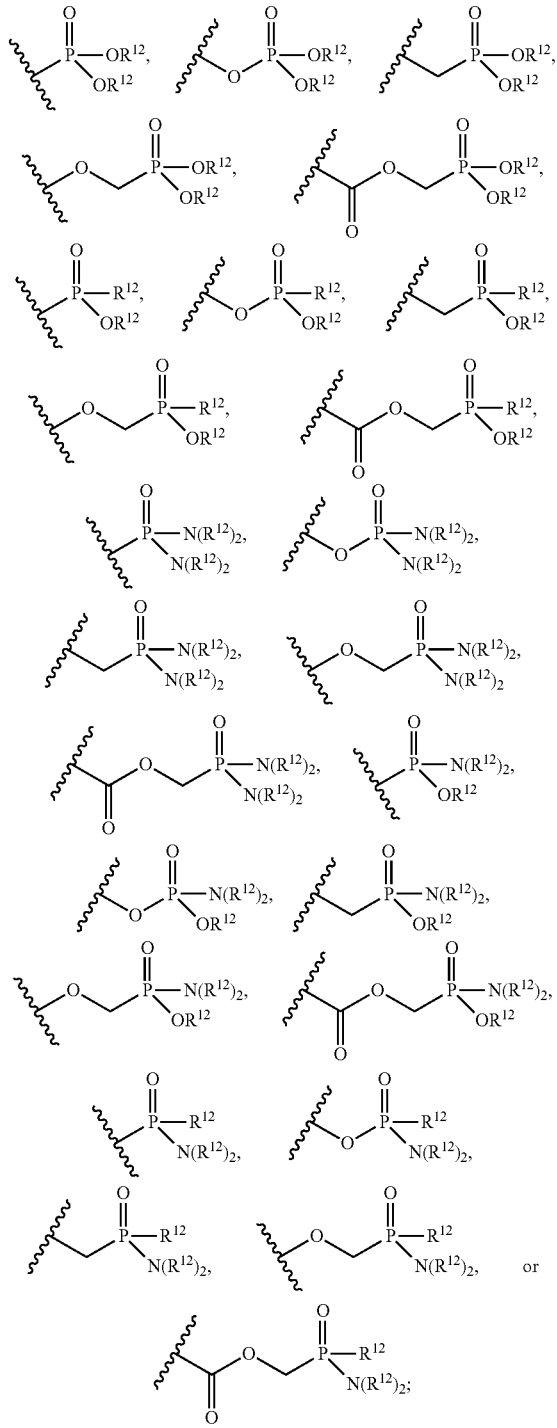

where each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl; wherein any alkyl, alkenyl, alkynyl, cycloalkyl, aryl, heteroaryl or heterocyclyl is optionally substituted with one to four $Z^{1b}$ groups; and each $Z^{1b}$ is independently oxo, thioxo, hydroxy, halo, —$NO_2$, —$N_3$, cyano, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —$O(C_{1-9}$ alkyl), —$O(C_{2-6}$ alkenyl), —$O(C_{2-6}$ alkynyl), —$O(C_{3-15}$ cycloalkyl), —$O(C_{1-8}$ haloalkyl), —$O$(aryl), —$O$(heteroaryl), —$O$(heterocyclyl), —$NH_2$, —$NH(C_{1-9}$ alkyl), —$NH(C_{2-6}$ alkenyl), —$NH(C_{2-6}$ alkynyl), —$NH(C_{3-15}$ cycloalkyl), —$NH(C_{1-8}$ haloalkyl), —$NH$(aryl), —$NH$(heteroaryl), —$NH$(heterocyclyl), —$N(C_{1-9}$ alkyl)$_2$, —$N(C_{3-15}$ cycloalkyl)$_2$, —$N(C_{2-6}$ alkenyl)$_2$, —$N(C_{2-6}$ alkynyl)$_2$, —$N(C_{3-15}$ cycloalkyl)$_2$, —$N(C_{1-8}$ haloalkyl)$_2$, —$N$(aryl)$_2$, —$N$(heteroaryl)$_2$, —$N$(heterocyclyl)$_2$, —$N(C_{1-9}$ alkyl)($C_{3-15}$ cycloalkyl), —$N(C_{1-9}$ alkyl)($C_{2-6}$ alkenyl), —$N(C_{1-9}$ alkyl)($C_{2-6}$ alkynyl), —$N(C_{1-9}$ alkyl)($C_{3-15}$ cycloalkyl), —$N(C_{1-9}$ alkyl)($C_{1-8}$ haloalkyl), —$N(C_{1-9}$ alkyl)(aryl), —$N(C_{1-9}$ alkyl)(heteroaryl), —$N(C_{1-9}$ alkyl)(heterocyclyl), —$C(O)(C_{1-9}$ alkyl), —$C(O)(C_{2-6}$ alkenyl), —$C(O)(C_{2-6}$ alkynyl), —$C(O)(C_{3-15}$ cycloalkyl), —$C(O)(C_{1-8}$ haloalkyl), —$C(O)$(aryl), —$C(O)$(heteroaryl), —$C(O)$(heterocyclyl), —$C(O)O(C_{1-9}$ alkyl), —$C(O)O(C_{2-6}$ alkenyl), —$C(O)O(C_{2-6}$ alkynyl), —$C(O)O(C_{3-15}$ cycloalkyl), —$C(O)O(C_{1-8}$ haloalkyl), —$C(O)O$(aryl), —$C(O)O$(heteroaryl), —$C(O)O$(heterocyclyl), —$C(O)NH_2$, —$C(O)NH(C_{1-9}$ alkyl), —$C(O)NH(C_{2-6}$ alkenyl), —$C(O)NH(C_{2-6}$ alkynyl), —$C(O)NH(C_{3-15}$ cycloalkyl), —$C(O)NH(C_{1-8}$ haloalkyl), —$C(O)NH$(aryl), —$C(O)NH$(heteroaryl), —$C(O)NH$(heterocyclyl), —$C(O)N(C_{1-9}$ alkyl)$_2$, —$C(O)N(C_{3-15}$ cycloalkyl)$_2$, —$C(O)N(C_{2-6}$ alkenyl)$_2$, —$C(O)N(C_{2-6}$ alkynyl)$_2$, —$C(O)N(C_{3-15}$ cycloalkyl)$_2$, —$C(O)N(C_{1-8}$ haloalkyl)$_2$, —$C(O)N$(aryl)$_2$, —$C(O)N$(heteroaryl)$_2$, —$C(O)N$(heterocyclyl)$_2$, —$NHC(O)(C_{1-9}$ alkyl), —$NHC(O)(C_{2-6}$ alkenyl), —$NHC(O)(C_{2-6}$ alkynyl), —$NHC(O)(C_{3-15}$ cycloalkyl), —$NHC(O)(C_{1-8}$ haloalkyl), —$NHC(O)$(aryl), —$NHC(O)$(heteroaryl), —$NHC(O)$(heterocyclyl), —$NHC(O)O(C_{1-9}$ alkyl), —$NHC(O)O(C_{2-6}$ alkenyl), —$NHC(O)O(C_{2-6}$ alkynyl), —$NHC(O)O(C_{3-15}$ cycloalkyl), —$NHC(O)O(C_{1-8}$ haloalkyl), —$NHC(O)O$(aryl), —$NHC(O)O$(heteroaryl), —$NHC(O)O$(heterocyclyl), —$NHC(O)NH(C_{1-9}$ alkyl), —$NHC(O)NH(C_{2-6}$ alkenyl), —$NHC(O)NH(C_{2-6}$ alkynyl), —$NHC(O)NH(C_{3-15}$ cycloalkyl), —$NHC(O)NH(C_{1-8}$ haloalkyl), —$NHC(O)NH$(aryl), —$NHC(O)NH$(heteroaryl), —$NHC(O)NH$(heterocyclyl), —SH, —$S(C_{1-9}$ alkyl), —$S(C_{2-6}$ alkenyl), —$S(C_{2-6}$ alkynyl), —$S(C_{3-15}$ cycloalkyl), —$S(C_{1-8}$ haloalkyl), —$S$(aryl), —$S$(heteroaryl), —$S$(heterocyclyl), —$NHS(O)(C_{1-9}$ alkyl), —$N(C_{1-9}$ alkyl)($S(O)(C_{1-9}$ alkyl), —$S(O)N(C_{1-9}$ alkyl)$_2$, —$S(O)(C_{1-9}$ alkyl), —$S(O)(NH)(C_{1-9}$ alkyl), —$S(O)(C_{2-6}$ alkenyl), —$S(O)(C_{2-6}$ alkynyl), —$S(O)(C_{3-15}$ cycloalkyl), —$S(O)(C_{1-8}$ haloalkyl), —$S(O)$(aryl), —$S(O)$(heteroaryl), —$S(O)$(heterocyclyl), —$S(O)_2(C_{1-9}$ alkyl), —$S(O)_2(C_{2-6}$ alkenyl), —$S(O)_2(C_{2-6}$ alkynyl), —$S(O)_2(C_{3-15}$ cycloalkyl), —$S(O)_2(C_{1-8}$ haloalkyl), —$S(O)_2$(aryl), —$S(O)_2$(heteroaryl), —$S(O)_2$(heterocyclyl), —$S(O)_2NH(C_{1-9}$ alkyl), or —$S(O)_2N(C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —$NH_2$, —$NH(C_{1-9}$ alkyl), —$NH(C_{3-15}$ cycloalkyl), —$NH(C_{1-8}$ haloalkyl), —$NH$(aryl), —$NH$(heteroaryl), —$NH$(heterocyclyl), —$N(C_{1-9}$ alkyl)$_2$, —$N(C_{3-15}$ cycloalkyl)$_2$, —$NHC(O)(C_{3-15}$ cycloalkyl), —$NHC(O)(C_{1-8}$ haloalkyl), —$NHC(O)$(aryl), —$NHC(O)$(heteroaryl), —$NHC(O)$(heterocyclyl), —$NHC(O)O(C_{1-9}$ alkyl), —$NHC(O)O(C_{2-6}$ alkynyl), —$NHC(O)O(C_{3-15}$ cycloalkyl), —$NHC(O)O(C_{1-8}$ haloalkyl), —$NHC(O)O$(aryl), —$NHC(O)O$(heteroaryl), —$NHC(O)O$(heterocyclyl), —$NHC(O)NH(C_{1-9}$ alkyl), —$S(O)(NH)(C_{1-9}$ alkyl), $S(O)_2(C_{1-9}$ alkyl), —$S(O)_2(C_{3-15}$ cycloalkyl), —$S(O)_2(C_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl).

In certain embodiments, provided is a compound of Formula I or any sub-formulas provided herein, wherein R$^2$ is

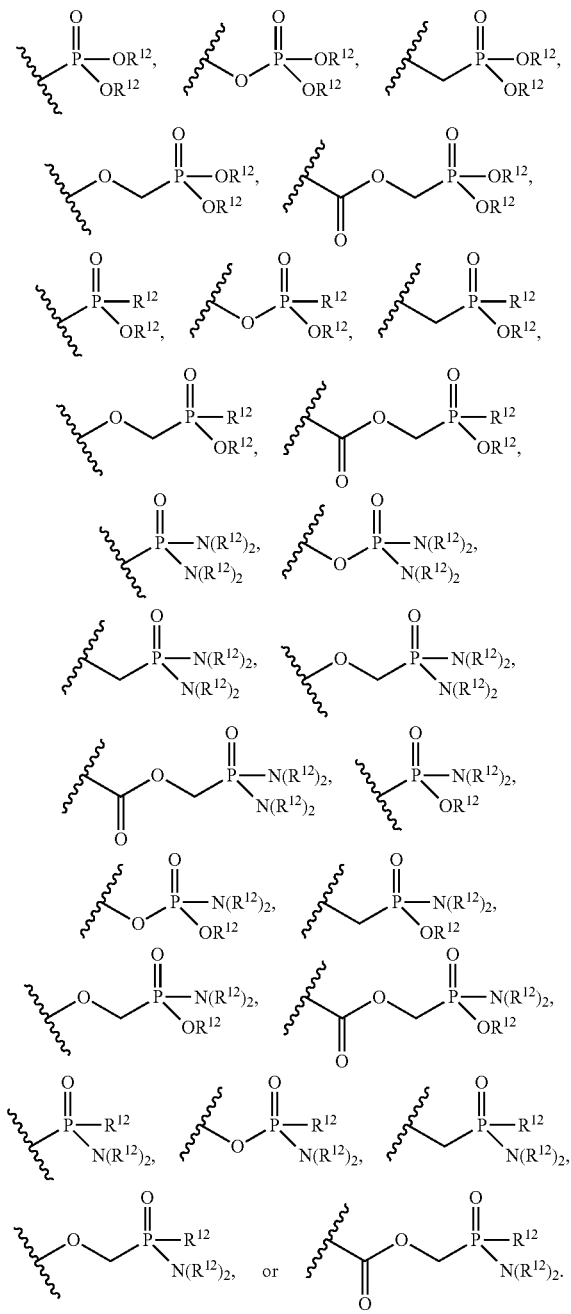

Such substituents also include all individual stereoisomers, and mixtures thereof, including but not limited to, chirality at the phosphorous atom such as in the exemplary moieties shown above.

Also provided herein are the in vivo metabolic products of the compounds described herein. Such products may result, for example, from the oxidation, reduction, hydrolysis, amidation, esterification, and the like, of the administered compound, primarily due to enzymatic processes.

Therapeutic Uses of the Compounds

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition. Primary hyperoxaluria type 1 can result in the need for a kidney transplant. After transplant, remission is very likely. In certain embodiments, the compounds disclosed herein are administered to a patient after transplant for the purpose of preventing remission.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of glycolate oxidase activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of glycolate oxidase" or variants thereof refers to a decrease in activity in the glycolate oxidase enzyme as a direct or indirect response to the presence of a compound of the present application relative to the activity of glycolate oxidase in the absence of the compound of the present application. "Inhibition of glycolate oxidase" refers to a decrease in glycolate oxidase enzyme activity as a direct or indirect response to the presence of a compound described herein relative to the activity of glycolate oxidase in the absence of the compound described herein. In some embodiments, the inhibition of glycolate oxidase enzymatic activity may be compared in the same subject prior to treatment, or other subjects not receiving the treatment.

The methods described herein may be applied to cell populations in vivo or ex vivo. "In vivo" means within a living individual, as within an animal or human. In this context, the methods described herein may be used therapeutically in an individual. "Ax vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the compounds and compositions described herein may be used for a variety of purposes, including therapeutic and experimental purposes. For example, the compounds and compositions described herein may be used ex vivo to determine the optimal schedule and/or dosing of administration of a glycolate oxidase inhibitor for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The compounds disclosed herein are useful for the treatment, prevention, diagnosis, or monitoring of diseases or conditions mediated by glycolate oxidase. Non-limiting examples of diseases or conditions mediated by glycolate oxidase include, without limitation, nephrolithiasis (kidney stones), nephrocalcinosis, bladder stones, hyperoxaluria type 1, Bird's disease, glycolic aciduria, end stage renal disease (ESRD), renal failure, kidney transplant failure, and Type II diabetes.

In certain embodiments, the compounds disclosed herein are useful for the treatment, prevention, diagnosis, or monitoring of diseases or conditions mediated by oxalate or calcium oxalate or glycolate oxidase. In some embodiments, the disease or condition is nephrolithiasis (kidney stones), nephrocalcinosis, bladder stones, hyperoxaluria type 1, Bird's disease, glycolic aciduria, end stage renal disease (ESRD), renal failure, kidney transplant failure, and Type II diabetes.

In further embodiments, the methods are provided for alleviating a symptom of a disease or disorder mediated by glycolate oxidase. In some embodiments, the methods include identifying a mammal having a symptom of a disease or disorder mediated by glycolate oxidase, and providing to the mammal an amount of a compound as described herein effective to ameliorate (i.e., lessen the severity of) the symptom.

In further embodiments, methods are provided for alleviating a symptom of a disease or disorder mediated by oxalate or calcium oxalate or glycolate oxidase. In some embodiments, the methods include identifying a mammal having a symptom of a disease or disorder mediated by oxalate or calcium oxalate or glycolate oxidase, and providing to the mammal an amount of a compound as described herein effective to ameliorate (i.e., lessen the severity of) the symptom.

In some embodiments, the disease or condition mediated by glycolate oxidase is kidney stone formation. In some embodiments, the disease or condition mediated by oxalate or calcium oxalate or glycolate oxidase is kidney stone formation. In particular embodiments, the kidney stone formation is recurrent. In particular embodiments, the kidney stone formation is associated with primary hyperoxaluria type 1.

In some embodiments, the disease or condition mediated by glycolate oxidase is renal failure, which includes failure of a single kidney and of both kidneys. In some embodiments, the disease or condition mediated by oxalate or calcium oxalate or glycolate oxidase is renal failure. In some embodiments, the renal failure is failure of a single kidney or of both kidneys.

In some embodiments, the disease or condition prevented is kidney transplant failure.

In some embodiments, the disease or condition mediated by glycolate oxidase is diabetes, including type 1 and type 2 diabetes, gestational diabetes, prediabetes, insulin resistance, metabolic syndrome, impaired fasting glycaemia and impaired glucose tolerance. In some embodiments, the disease or condition mediated by oxalate or calcium oxalate or glycolate oxidase is diabetes. In some embodiments, the diabetes is type 1 and type 2 diabetes, gestational diabetes, prediabetes, insulin resistance, metabolic syndrome, impaired fasting glycaemia, or impaired glucose tolerance. Type 1 diabetes is also known as Insulin Dependent Diabetes Mellitus (IDDM). Type 2 is also known as Non-Insulin-Dependent Diabetes Mellitus (NIDDM).

In some embodiments, the disease or condition mediated by glycolate oxidase is bladder stone formation. In some embodiments, the disease or condition mediated by oxalate or calcium oxalate or glycolate oxidase is bladder stone formation.

Criteria useful for assessment of disease activity in subjects with primary hyperoxaluria type 1 can be found in, Brooks et. al. (2016) Am. J. Nephrol. 43, 4:293-303. The amount of oxylate and calcium in the urin can be monitored The presently disclosed treatment methods can also be applied at any point in the course of the disease. In certain embodiments, the methods are applied to a subject having primary hyperoxaluria type 1 during a time period of remission (i.e., inactive disease, after kidney transplantation). In such embodiments, the present methods provide benefit by extending the time period of remission (e.g., extending the period of inactive disease) or by preventing, reducing, or delaying the onset of active disease. An example would be in the increase in time between kidney stone incidents. In other embodiments, methods may be applied to a subject having primary hyperoxaluria type 1 during a period of active disease. Such methods provide benefit by reducing the duration of the period of active disease, reducing or ameliorating one or more symptoms of primary hyperoxaluria type 1, or treating primary hyperoxaluria type 1. Such amelioration can be in the reduction of size, number, or frequency of kidney stones.

Measures for determining efficacy of treatment of primary hyperoxaluria type 1 in clinical practice have been described and include, for example, the following: symptom control; calcium oxalate concentration in bodily fluids; renal function assays; and improvement in quality of life.

In certain embodiments, provided herein is a method for the treatment of primary hyperoxaluria type 1, comprising administering a patient in need thereof, a therapeutically effective amount of a compound as described herein, or a pharmaceutical composition as described herein, or a compound of Formula I:

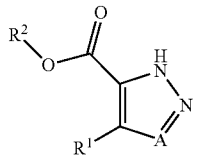

or a pharmaceutically acceptable salt, tautomer, stereoisomer, mixture of stereoisomers, or deuterated analog thereof, wherein A is N or CH;

$R^1$ is alkynyl, cycloalkyl, aryl, heteroaryl or heterocyclyl, wherein each is optionally substituted with one to three $R^3$;

$R^2$ is hydrogen, —(CH$_2$CH$_2$O)$_{1-9}$CH$_2$CH$_2$OCH$_3$, $C_{1-6}$ alkyl optionally substituted with one to three $R^4$, cycloalkyl, or heteroaryl optionally substituted with one to three $R^5$;

each $R^3$ is independently cyano, halo, -L-$C_{1-9}$ alkyl, -L-$C_{1-4}$ haloalkyl, -L-OC$_{1-4}$ haloalkyl, —NR$^7$R$^8$, —C(O)NR$^7$R$^8$, —S(O)$_2$NR$^7$R$^8$, —NR$^7$C(O)R$^8$, —OR$^7$, -L-aryl, -L-heteroaryl or -L-heterocyclyl, wherein each is optionally substituted with one to three $R^6$, and each L is independently —C≡C— or absent;

each $R^4$ is independently halo, hydroxy, —OC$_{1-6}$alkyl, —NH$_2$, —NHC$_{1-6}$ alkyl, —N(C$_{1-6}$alkyl)$_2$, —OC(O)R$^a$, —OC(O)OR$^a$, —OP(O)(OR$^b$)$_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —OC$_{1-4}$alkyl, $C_{1-4}$ haloalkyl, or —OC$_{1-4}$ haloalkyl;

each $R^6$ is independently cyano, halo, —C(O)R$^7$, —C(O)OR$^7$, —C(O)NR$^7$R$^8$, —S(O)$_2$NR$^7$R$^8$, —NR$^7$C(O)R$^8$, —OR$^7$, $C_{1-4}$ alkyl, —OC$_{1-4}$alkyl, $C_{1-4}$ haloalkyl, —OC$_{1-4}$ haloalkyl, phenyl, heterocyclyl, or heteroaryl; wherein each is optionally substituted with one to three $C_{1-4}$ alkyl, —C(O)OH or $C_{1-4}$ haloalkyl;

$R^7$ and $R^8$ are each independently hydrogen, $C_{1-4}$ alkyl or phenyl, pyridyl, or $R^7$ and $R^8$ together with the nitrogen atom to which they are attached form a heterocyclyl;

each $R^a$ is independently $C_{1-6}$ alkyl optionally substituted with —NH$_2$, —NHC$_{1-6}$ alkyl, —N(C$_{1-6}$alkyl)$_2$, or —OP(O)(OR$^b$)$_2$; and each $R^b$ is independently hydrogen or $C_{1-4}$ alkyl.

In certain embodiments, when $R^1$ is phenyl, then $R^3$ is aryl or heteroaryl, each of which is optionally substituted with one to three $R^6$; and when $R^1$ is heteroaryl, then $R^2$ is not unsubstituted $C_{1-6}$ alkyl.

In certain embodiments, provided herein is a method for the treatment of recurrent kidney stone formers, comprising administering a patient in need thereof, a therapeutically effective amount of a compound of as described herein, a pharmaceutical composition as described herein, or a compound of Formula I:

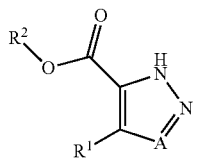

or a pharmaceutically acceptable salt, tautomer, stereoisomer, mixture of stereoisomers, or deuterated analog thereof, wherein A is N or CH;

$R^1$ is alkynyl, cycloalkyl, aryl, heteroaryl or heterocyclyl, wherein each is optionally substituted with one to three $R^3$;

$R^2$ is hydrogen, —(C$_2$CH$_2$O)$_{1-9}$CH$_2$CH$_2$OCH$_3$, $C_{1-6}$ alkyl optionally substituted with one to three $R^4$, cycloalkyl, or heteroaryl optionally substituted with one to three $R^5$;

each $R^3$ is independently cyano, halo, -L-$Ct$-9 alkyl, -L-$C_{1-4}$ haloalkyl, -L-OC$_{1-4}$ haloalkyl, —NR$^7$R$^8$, —C(O)NR$^7$R$^8$, —S(O)$_2$NR$^7$R$^8$, —NR$^7$C(O)R$^8$, —OR$^7$, -L-aryl, -L-heteroaryl or -L-heterocyclyl, wherein each is optionally substituted with one to three $R^6$, and each L is independently —C≡C— or absent;

each $R^4$ is independently halo, hydroxy, —OC$_{1-6}$alkyl, —NH$_2$, —NHC$_{1-6}$ alkyl, —N(C$_{1-6}$alkyl)$_2$, —OC(O)R$^a$, —OC(O)OR$^a$, —OP(O)(OR$^b$)$_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —OC$_{1-4}$alkyl, $C_{1-4}$ haloalkyl, or —OC$_{1-4}$ haloalkyl;

each $R^6$ is independently cyano, halo, —C(O)R$^7$, —C(O)OR$^7$, —C(O)NR$^7$R$^8$, —S(O)$_2$NR$^7$R$^8$, —NR$^7$C(O)R$^8$, —OR$^7$, $C_{1-4}$ alkyl, —OC$_{1-4}$alkyl, $C_{1-4}$ haloalkyl, —OC$_{1-4}$ haloalkyl, phenyl, heterocyclyl, or heteroaryl; wherein each is optionally substituted with one to three $C_{1-4}$ alkyl, —C(O)OH or $C_{1-4}$ haloalkyl;

$R^7$ and $R^8$ are each independently hydrogen, $C_{1-4}$ alkyl or phenyl, pyridyl, or $R^7$ and $R^8$ together with the nitrogen atom to which they are attached form a heterocyclyl;

each $R^a$ is independently $C_{1-6}$ alkyl optionally substituted with —NH$_2$, —NHC$_{1-6}$ alkyl, —N(C$_{1-6}$alkyl)$_2$, or —OP(O)(OR$^b$)$_2$; and each $R^b$ is independently hydrogen or $C_{1-4}$ alkyl.

In certain embodiments, when $R^1$ is phenyl, then $R^3$ is aryl or heteroaryl, each of which is optionally substituted with one to three $R^6$; and when $R^1$ is heteroaryl, then $R^2$ is not unsubstituted $C_{1-6}$ alkyl.

In certain embodiments, provided herein is a method of inhibiting the production of glyoxylate and/or oxalate, and/or inhibiting glycolate oxidase (GO), comprising administering a patient in need thereof, a therapeutically effective amount of a compound as described herein, the pharmaceutical composition as described herein, or a compound of Formula I:

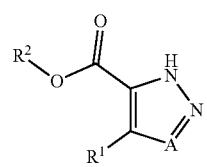

or a pharmaceutically acceptable salt, tautomer, stereoisomer, mixture of stereoisomers, or deuterated analog thereof, wherein A is N or CH;

$R^1$ is alkynyl, cycloalkyl, aryl, heteroaryl or heterocyclyl, wherein each is optionally substituted with one to three $R^3$;

$R^2$ is hydrogen, —(CH$_2$CH$_2$O)$_{1-9}$CH$_2$CH$_2$OCH$_3$, $C_{1-6}$ alkyl optionally substituted with one to three $R^4$, cycloalkyl, or heteroaryl optionally substituted with one to three $R^5$;

each $R^3$ is independently cyano, halo, -L-$C_{1-9}$ alkyl, -L-$C_{1-4}$ haloalkyl, -L-OC$_{1-4}$ haloalkyl, —NR$^7$R$^8$, —C(O)NR$^7$R$^8$, —S(O)$_2$NR$^7$R$^8$, —NR$^7$C(O)R$^8$, —OR$^7$, -L-aryl, -L-heteroaryl or -L-heterocyclyl, wherein each is optionally substituted with one to three $R^6$, and each L is independently —C≡C— or absent;

each $R^4$ is independently halo, hydroxy, —$OC_{1-6}$alkyl, —$NH_2$, —$NHC_{1-6}$ alkyl, —$N(C_{1-6}alkyl)_2$, —$OC(O)R^a$, —$OC(O)OR^a$, —$OP(O)(OR^b)_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —$OC_{1-4}$alkyl, $C_{1-4}$ haloalkyl, or —$OC_{1-4}$ haloalkyl;

each $R^6$ is independently cyano, halo, —$C(O)R^7$, —$C(O)OR^7$, —$C(O)NR^7R^8$, —$S(O)_2NR^7R^8$, —$NR^7C(O)R^8$, —$OR^7$, $C_{1-4}$ alkyl, —$OC_{1-4}$alkyl, $C_{1-4}$ haloalkyl, —$OC_{1-4}$ haloalkyl, phenyl, heterocyclyl, or heteroaryl; wherein each is optionally substituted with one to three $C_{1-4}$ alkyl, —$C(O)OH$ or $C_{1-4}$ haloalkyl;

$R^7$ and $R^8$ are each independently hydrogen, $C_{1-4}$ alkyl or phenyl, pyridyl, or $R^7$ and $R^8$ together with the nitrogen atom to which they are attached form a heterocyclyl;

each $R^a$ is independently $C_{1-6}$ alkyl optionally substituted with —$NH_2$, —$NHC_{1-6}$ alkyl, —$N(C_{1-6}alkyl)_2$, or —$OP(O)(OR^b)_2$; and each $R^b$ is independently hydrogen or $C_{1-4}$ alkyl.

In some embodiments, when $R^1$ is phenyl, then $R^3$ is aryl or heteroaryl, each of which is optionally substituted with one to three $R^6$; and when $R^1$ is heteroaryl, then $R^2$ is not unsubstituted $C_{1-6}$ alkyl.

In certain embodiments, the use of a compound as described herein or a pharmaceutical composition as described herein is for controlling or inhibiting the production of recurrent kidney stone formers, in a patient in need thereof.

In certain embodiments, the use of a compound of Formula I, or a pharmaceutically acceptable salt, tautomer, stereoisomer, mixture of stereoisomers, or deuterated analog thereof, is for controlling or inhibiting the production of recurrent kidney stone formers, in a patient in need thereof, wherein a compound of formula I:

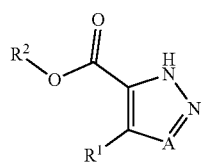

I

A is N or CH;
$R^1$ is alkynyl, cycloalkyl, aryl, heteroaryl or heterocyclyl, wherein each is optionally substituted with one to three $R^3$;
$R^2$ is hydrogen, —$(CH_2CH_2O)_{1-9}CH_2CH_2OCH_3$, $C_{1-6}$ alkyl optionally substituted with one to three $R^4$, cycloalkyl, or heteroaryl optionally substituted with one to three $R^5$;

each $R^3$ is independently cyano, halo, -L-$C_{1-9}$ alkyl, -L-$C_{1-4}$ haloalkyl, -L-$OC_{1-4}$ haloalkyl, —$NR^7R^8$, —$C(O)NR^7R^8$, —$S(O)_2NR^7R^8$, —$NR^7C(O)R^8$, —$OR^7$, -L-aryl, -L-heteroaryl or -L-heterocyclyl, wherein each is optionally substituted with one to three $R^6$, and each L is independently —C≡C— or absent;

each $R^4$ is independently halo, hydroxy, —$OC_{1-6}$alkyl, —$NH_2$, —$NHC_{1-6}$ alkyl, —$N(C_{1-6}alkyl)_2$, —$OC(O)R^a$, —$OC(O)OR^a$, —$OP(O)(OR^b)_2$, or monocyclic heterocyclyl; wherein each is optionally substituted with one to three $R^5$; provided only one $R^4$ is heterocyclyl;

each $R^5$ is independently cyano, halo, $C_{1-4}$ alkyl, hydroxy, —$OC_{1-4}$alkyl, $C_{1-4}$ haloalkyl, or —$OC_{1-4}$ haloalkyl;

each $R^6$ is independently cyano, halo, —$C(O)R^7$, —$C(O)OR^7$, —$C(O)NR^7R^8$, —$S(O)_2NR^7R^8$, —$NR^7C(O)R^8$, —$OR^7$, $C_{1-4}$ alkyl, —$OC_{1-4}$alkyl, $C_{1-4}$ haloalkyl, —$OC_{1-4}$ haloalkyl, phenyl, heterocyclyl, or heteroaryl; wherein each is optionally substituted with one to three $C_{1-4}$ alkyl, —$C(O)OH$ or $C_{1-4}$ haloalkyl;

$R^7$ and $R^8$ are each independently hydrogen, $C_{1-4}$ alkyl or phenyl, pyridyl, or $R^7$ and $R^8$ together with the nitrogen atom to which they are attached form a heterocyclyl;

each $R^a$ is independently $C_{1-6}$ alkyl optionally substituted with —$NH_2$, —$NHC_{1-6}$ alkyl, —$N(C_{1-6}alkyl)_2$, or —$OP(O)(OR^b)_2$; and each $R^b$ is independently hydrogen or $C_{1-4}$ alkyl;

provided that when $R^1$ is phenyl, then $R^3$ is aryl or heteroaryl, each of which is optionally substituted with one to three $R^6$; and when $R^1$ is heteroaryl, then $R^2$ is not unsubstituted $C_{1-6}$ alkyl.

Combination Therapies

In one embodiment, the compounds disclosed herein may be used in combination with one or more additional therapeutic agents or interventions that are being used and/or developed to treat primary hyperoxaluria type 1. Examples of such therapeutic agents are calcium oxalate crystallization inhibitors, oxalate degrading enzyme inhibitors, SiRNA, oxazyme, and lumasiran. Examples of such therapeutic interventions is high fluid intake, dialysis, and kidney transplantation.

In some embodiments, the compounds disclosed herein may be used in combination with a SGLT2 inhibitor. Non-limiting examples of a SGL2 inhibitor include dapagliflozin, ertugliflozin, luseogliflozin, canagliflozin, tofogliflozin, ipragliflozin, ipragliflozin, empagliflozin and potassium citrate.

In some embodiments, methods described herein further comprise administering an additional therapeutic agent. In some embodiments, provided are uses as described herein in combination with an additional therapeutic agent. In some embodiments, the additional therapeutic agent is a calcium oxalate crystallization inhibitor, oxalate degrading enzyme inhibitor, SiRNA, oxazyme, lumasiran, nedosiran, oxabate, or reloxaliase. In some embodiments, the additional therapeutic agent is a SGLT2 inhibitor. In some embodiments, the SGL2 inhibitor is dapagliflozin, ertugliflozin, luseogliflozin, canagliflozin, tofogliflozin, ipragliflozin, ipragliflozin, empagliflozin, or potassium citrate.

Kits

Provided herein are also kits that include a compound of Formula I (or any other Formula described herein), or a pharmaceutically acceptable salt, tautomer, prodrug, or deuterated analog thereof, and suitable packaging. In one embodiment, a kit further includes instructions for use. In one aspect, a kit includes a compound of Formula I (or any other Formula described herein), or a pharmaceutically acceptable salt, tautomer, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, prodrug, or deuterated analog thereof in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds of Formula I

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplemental (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The term "solvent" generally refers to a solvent inert under the conditions of the reaction being described in conjunction therewith (including, for example, benzene, toluene, acetonitrile, tetrahydrofuran (THF), dimethylformamide (DMF), chloroform, methylene chloride (or dichloromethane), diethyl ether, methanol, and the like). Unless specified to the contrary, the solvents are inert organic solvents, and the reactions may carried out under an inert gas, preferably argon or nitrogen.

The term "q.s." means adding a quantity sufficient to achieve a stated function, e.g., to bring a solution to the desired volume (i.e., 100%).

In Scheme 1, A, $R^1$, $R^2$, $R^3$ and $R^6$ are as defined herein, each X is independently halo (e.g., chloro, bromo or iodo), each $R^{50}$ is independently alkyl or two $R^{50}$ together form a ring (e.g., 4,4,5,5-tetramethyl-1,3,2-dioxaborolane), and PG is a protecting group bonded to a heteroatom.

Scheme 1

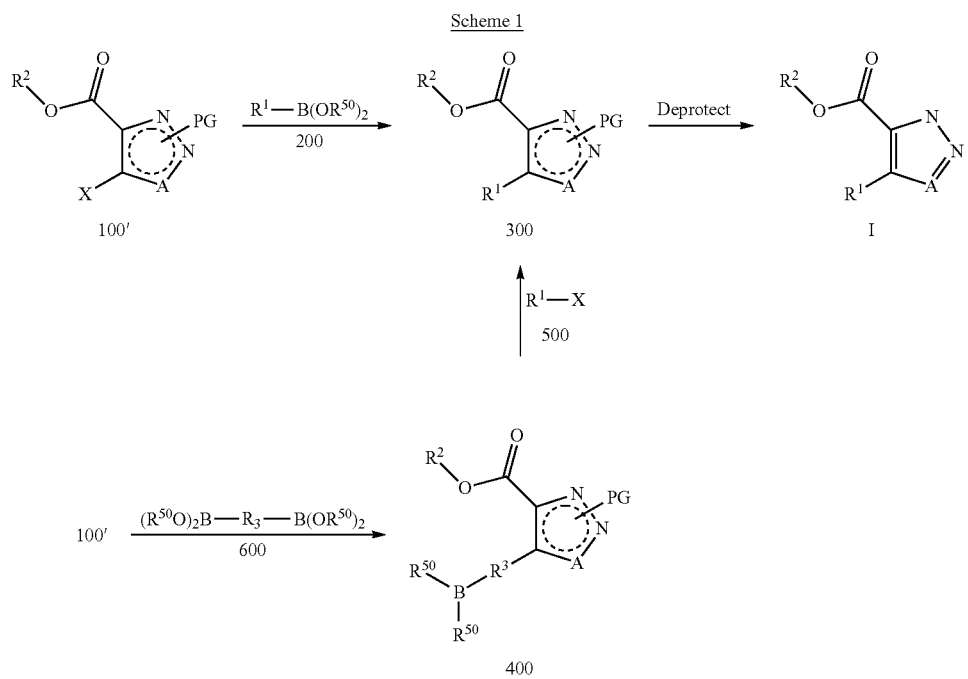

In Scheme 1, the compounds of Formula I are prepared by coupling appropriately protected compound 100' with the corresponding boronic acid or ester 200 in the presence of a catalyst (e.g., palladium, nickel, copper, etc.), followed by deprotection. Compound 300 for use in preparing compounds of Formula I as shown in Scheme 1 is also prepared by coupling appropriately protected compound 400 with the corresponding halo substituted compound 500 in the presence of a catalyst (e.g., palladium, nickel, copper, etc.). Compound 400 is prepared by coupling appropriately protected compound 100' with the corresponding boronic acid or ester 600 in the presence of a catalyst (e.g., palladium, nickel, copper, etc.) Various compounds of formula 100', 200, 500 and 600 for use in the methods provided herein can be purchased from commercial sources or synthesized by known methods.

In some embodiments, compound 300, wherein $R^2$ is hydrogen, may be esterified to form a compound 300, wherein $R^2$ is as defined herein (e.g. —$(CH_2CH_2O)_{1-9}CH_2CH_2OCH_2$. $C_{1-6}$ alkyl optionally substituted with one to three $R^4$, cycloalkyl, or heteroaryl optionally substituted with one to three $R^5$) via standard coupling conditions.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Synthesis of Intermediates 3, 4 and 6 (and their Methyl Esters 3% 4' and 6')

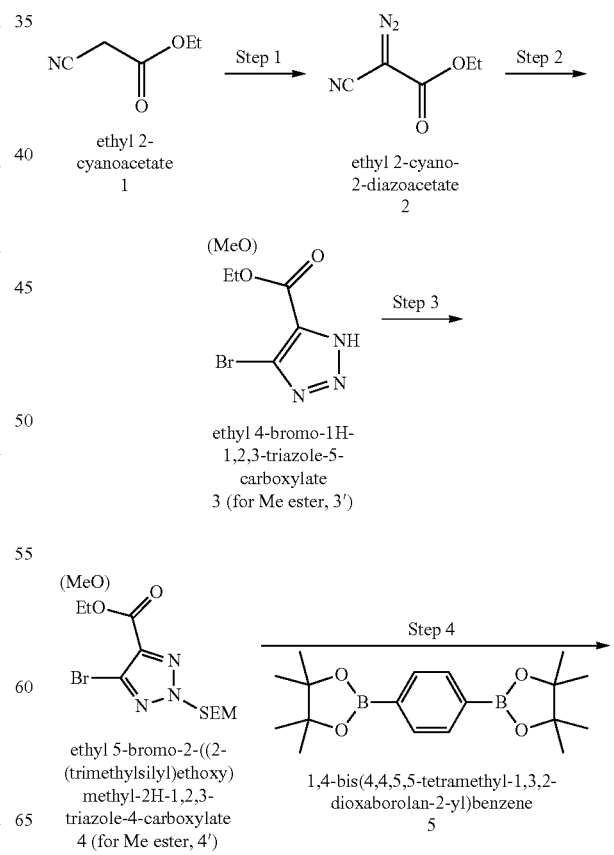

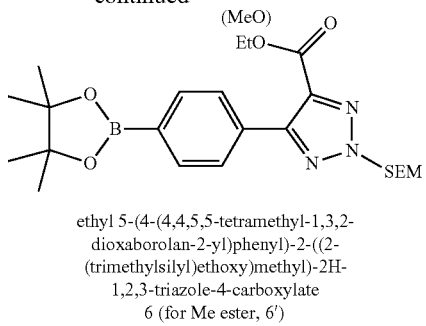

ethyl 5-(4-(4,4,5,5-tetramethyl-1,3,2-
dioxaborolan-2-yl)phenyl)-2-((2-
(trimethylsilyl)ethoxy)methyl)-2H-
1,2,3-triazole-4-carboxylate
6 (for Me ester, 6')

Step 1

To a mixture of sodium azide (150.0 g, 2.25 mol) and tetrabutyl ammonium bisulfate (41.9 g, 123 mmol) in water (2.3 L) was slowly added at 0° C. a solution of triflic anhydride (375 mL, 2.25 mol) in hexane (900 mL). After the resulting mixture was stirred at 0° C. for 1 h, the organic soluble material was extracted with hexane (1.8 L), dried over sodium hydroxide pellets and decanted. To the solution were added ethyl 2-cyanoacetate, 1 (150.0 g, 0.8 mol) in acetonitrile (1.1 L) and pyridine (300 mL, 4.0 mol). The resulting mixture was stirred at room temperature for 2 days, and concentrated under reduced pressure. The residue was purified by column chromatography on silica gel eluting ethyl acetate in petroleum ether (1:6) to give impure ethyl 2-cyano-2-diazoacetate, 2 (111 g, 99%).

Step 2

To a solution of ethyl 2-cyano-2-diazoacetate, 2 (111 g, 795 mmol) in dioxane (7 L) was bubbled with hydrogen bromide gas at 0° C. for 3 h. The reaction mixture was concentrated under reduced pressure to give crude ethyl 4-bromo-1H-1,2,3-triazole-5-carboxylate. 3 (125 g), which was directly used for next step without further purification.

Step 3

To a solution of crude ethyl 4-bromo-1H-1,2,3-triazole-5-carboxylate. 3 (50 g, 227 mmol) in DMF (500 mL) was added sodium hydride (60%, 10.1 g, 275 mmol) at 0° C. and stirred for 30 min under $N_2$ before 2-(trimethylsilyl)ethoxymethyl chloride (40.5 g, 238 mmol) was added at 0° C. After stirring for 1 h at 0° C., the reaction mixture was quenched with 5% aqueous lithium chloride and the product was extracted with ethyl acetate. The organic fraction was dried ($MgSO_4$), filtered, and concentrated under reduced pressure. The residue was purified by column chromatography on silica gel eluting ethyl acetate in hexane (2:5) to give an isomeric mixture of ethyl 5-bromo-2-((2-(trimethylsilyl)ethoxy)methyl)-2H-1,2,3-triazole-4-carboxylate (4, 30 g, 38%) as colorless oil: ES/MS m/z: calculated for $C_{11}H_{20}BrN_3NaO_3Si$ (M+Na$^+$): 372.04, found: 372.15.

Isomeric mixture of methyl 5-bromo-2-((2-(trimethylsilyl)ethoxy)methyl)-2H-1,2,3-triazole-4-carboxylate (4') was also prepared as an oil in a manner similar to the procedure above from the commercially available methyl 4-bromo-1H-1,2,3-triazole-5-carboxylate (3'): ES/MS m/z: calculated for $C_{10}H_{19}BrN_3NaO_3Si$ (M+Na): 337.27, found: 336.53.

Step 4

To a solution of the isomeric mixture of ethyl 5-bromo-2-((2-(trimethylsilyl)ethoxy)methyl)-2H-1,2,3-triazole-4-carboxylate (4, 45 g, 129 mmol) and 1,4-bis(4,4,5,5-tetramethyl-1,3,2-dioxaborolan-2-yl)benzene (5, 85.0 g, 257 mmol) in 1,4-dioxane (800 mL) were added 2.0 M aqueous sodium carbonate (193 mL, 386 mmol) and [1,1'-bis(diphenylphosphino)ferrocene]dichloropalladium(II) (9.45 g, 12.9 mmol). The reaction mixture was stirred under $N_2$ atmosphere at 70° C. for 4 h. After the reaction mixture was cooled to room temperature and diluted with water, the product was extracted with ethyl acetate (3×1 L). The organic fractions were washed with brine, dried ($Na_2SO_4$), and concentrated under reduced pressure. The residue was purified by column chromatography on silica gel eluting with ethyl acetate in petroleum ether (1:30) to give an isomeric mixture of ethyl 5-(4-(4,4,5,5-tetramethyl-1,3,2-dioxaborolan-2-yl)phenyl)-2-((2-(trimethylsilyl)ethoxy)methyl)-2H-1,2,3-triazole-4-carboxylate (6, 25.5 g, 43%) as an oil: ES/MS m/z: calculated for $C_{23}H_{36}BN_3NaO_5Si$ (M+Na): 496.44, found: 496.45.

Synthesis of Intermediate 8

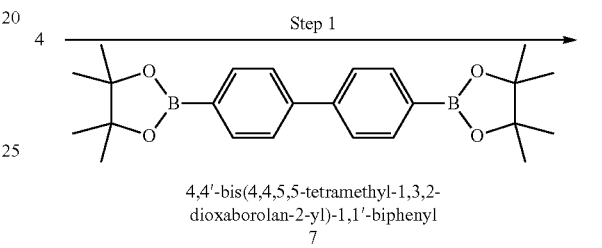

4,4'-bis(4,4,5,5-tetramethyl-1,3,2-
dioxaborolan-2-yl)-1,1'-biphenyl
7

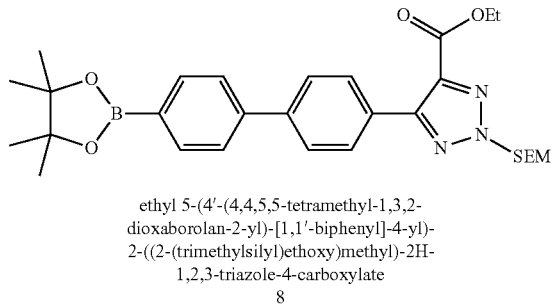

ethyl 5-(4'-(4,4,5,5-tetramethyl-1,3,2-
dioxaborolan-2-yl)-[1,1'-biphenyl]-4-yl)-
2-((2-(trimethylsilyl)ethoxy)methyl)-2H-
1,2,3-triazole-4-carboxylate
8

Step 1

To the isomeric mixture of ethyl 5-bromo-2-((2-(trimethylsilyl)ethoxy)methyl)-2H-1,2,3-triazole-4-carboxylate (4, 25 g, 71.3 mmol) and 4,4'-bis(4,4,5,5-tetramethyl-1,3,2-dioxaborolan-2-yl)-1,1'-biphenyl (7, 45 g, 110.8 mmol) in 1,4-dioxane (500 mL) were added 2.0 M aqueous $Na_2CO_3$ (106 mL, 215.9 mmol) and [1,1'-bis(diphenylphosphino)ferrocene]dichloropalladium(II) (5.2 g, 7.1 mmol). The reaction mixture stirred under $N_2$ atmosphere at 70° C. overnight. After the reaction mixture was cooled to room temperature and diluted with water, the product was extracted with ethyl acetate (3×500 mL). The organic fractions were washed with brine, dried ($Na_2SO_4$), and concentrated under reduced pressure. The residue was purified by column chromatography on silica gel eluting with ethyl acetate in petroleum ether (1:30) to give an isomeric mixture of ethyl 5-(4'-(4,4,5,5-tetramethyl-1,3,2-dioxaborolan-2-yl)-[1,1'-biphenyl]-4-yl)-2-((2-(trimethylsilyl)ethoxy)methyl)-2H-1,2,3-triazole-4-carboxylate (8, 11.5 g, 29%) as an oil: ES/MS m/z: calculated for $C_{29}H_{41}BN_3O_5Si$ (M+H): 550.29, found: 550.45.

Synthesis of Intermediate 10

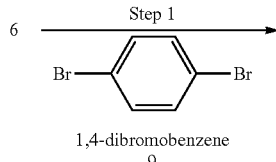

1,4-dibromobenzene
9

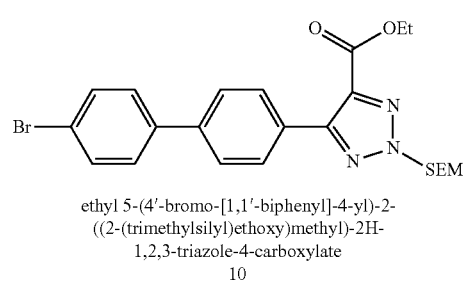

ethyl 5-(4'-bromo-[1,1'-biphenyl]-4-yl)-2-
((2-(trimethylsilyl)ethoxy)methyl)-2H-
1,2,3-triazole-4-carboxylate
10

Step 1

To the isomeric mixture of ethyl 5-(4-(4,4,5,5-tetramethyl-1,3,2-dioxaborolan-2-yl)phenyl)-2-((2-(trimethylsilyl)ethoxy)methyl)-2H-1,2,3-triazole-4-carboxylate (6, 358 mg, 0.76 mmol) and 1,4-dibromobenzene (9, 178 mg, 0.76 mmol) in 1,4-dioxane (3 mL) were added tetrakis(triphenylphosphine)palladium (0) (87 mg, 0.076 mmol) and 2.0 M aqueous Na$_2$CO$_3$ (1.13 mL). After the mixture was purged with argon gas for 10 min, the reaction mixture stirred at 110° C. for 40 min. After the reaction mixture was cooled to room temperature and diluted with saturated NaHCO$_3$, the product was extracted with ethyl acetate, washed, dried (MgSO$_4$), and concentrated under reduced pressure. The residue was purified by column chromatography on silica gel eluting with 1-100% ethyl acetate in hexane to give an isomeric mixture of ethyl 5-(4'-bromo-[1,1'-biphenyl]-4-yl)-2-((2-(trimethylsilyl)ethoxy)methyl)-2H-1,2,3-triazole-4-carboxylate (10, 380 mg, 83%) as an oil.

Synthesis of Intermediates 11 and 12

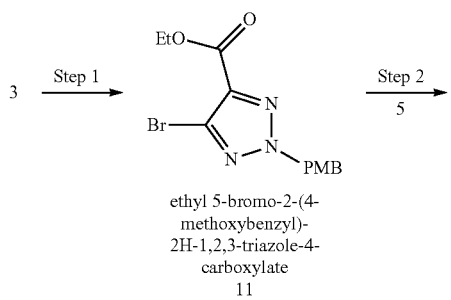

ethyl 5-bromo-2-(4-
methoxybenzyl)-
2H-1,2,3-triazole-4-
carboxylate
11

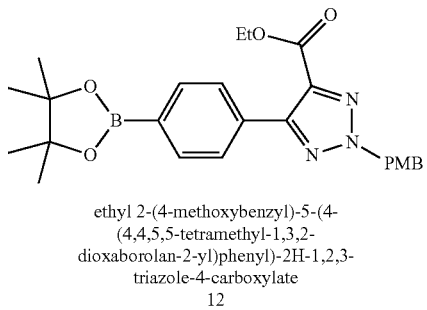

ethyl 2-(4-methoxybenzyl)-5-(4-
(4,4,5,5-tetramethyl-1,3,2-
dioxaborolan-2-yl)phenyl)-2H-1,2,3-
triazole-4-carboxylate
12

Step 1

The isomeric mixture of ethyl 5-bromo-2-(4-methoxybenzyl)-2H-1,2,3-triazole-4-carboxylate (11, 27 g, 49%) was prepared as an oil in a manner similar to the procedure for the isomeric mixture of ethyl 5-bromo-2-((2-(trimethylsilyl)ethoxy)methyl)-2H-1,2,3-triazole-4-carboxylate (3) using para-methoxybenzyl 1 chloride in place of 2-(trimethylsilyl)ethoxymethyl chloride, except the reaction was performed at rt for 8 h: ES/MS m/z: calculated for C$_{13}$H$_{14}$BrN$_3$NaO$_3$ (M+H): 362.01, found: 362.05.

Step 2

An isomeric mixture of ethyl 2-(4-methoxybenzyl)-5-(4-(4,4,5,5-tetramethyl-1,3,2-dioxaborolan-2-yl)phenyl)-2H-1,2,3-triazole-4-carboxylate (12) was prepared as an oil in a manner similar to the procedure for the isomeric mixture of ethyl 5-(4-(4,4,5,5-tetramethyl-1,3,2-dioxaborolan-2-yl)phenyl)-2-((2-(trimethylsilyl)ethoxy)methyl)-2H-1,2,3-triazole-4-carboxylate (6).

Synthesis of Intermediate 13

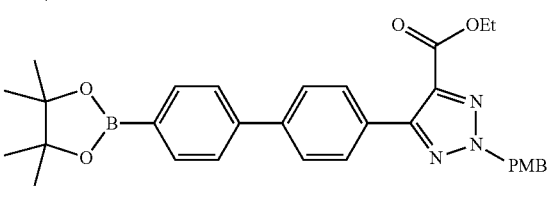

ethyl 2-(4-methoxybenzyl)-5-(4'-
(4,4,5,5-tetramethyl-1,3,2-
dioxaborolan-2-yl)-[1,1'-biphenyl]-4-
yl)-2H-1,2,3-triazole-4-carboxylate
13

Step 1

An isomeric mixture of ethyl 2-(4-methoxybenzyl)-5-(4'-(4,4,5,5-tetramethyl-1,3,2-dioxaborolan-2-yl)-[1,1'-biphenyl]-4-yl)-2H-1,2,3-triazole-4-carboxylate (13, 10.5 g, 26%) was prepared as an oil in a manner similar to the procedure for the isomeric mixture of ethyl 5-(4'-(4,4,5,5-tetramethyl-1,3,2-dioxaborolan-2-yl)-[1,1'-biphenyl]-4-yl)-2-((2-(trimethylsilyl)ethoxy)methyl)-2H-1,2,3-triazole-4-carboxylate (8): ES/MS m/z: calculated for C$_{31}$H$_{35}$BN$_3$O$_5$ (M+H): 540.27, found: 540.55.

Synthesis of Intermediates 15 and 16

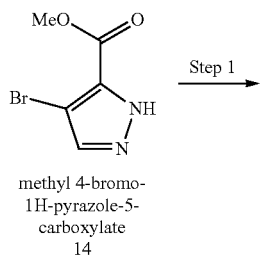

methyl 4-bromo-
1H-pyrazole-5-
carboxylate
14

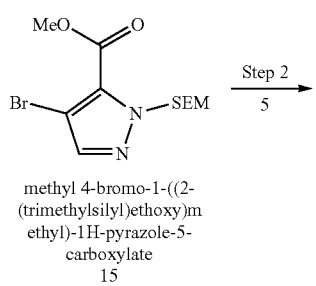

methyl 4-bromo-1-((2-
(trimethylsilyl)ethoxy)m
ethyl)-1H-pyrazole-5-
carboxylate
15

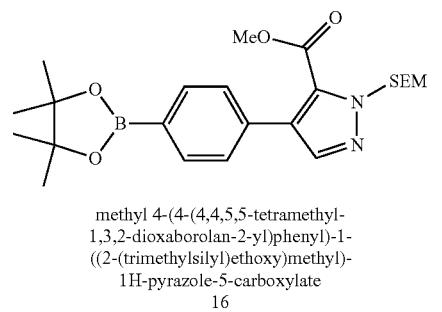

methyl 4-(4-(4,4,5,5-tetramethyl-
1,3,2-dioxaborolan-2-yl)phenyl)-1-
((2-(trimethylsilyl)ethoxy)methyl)-
1H-pyrazole-5-carboxylate
16

Step 1

Methyl 4-bromo-1-((2-(trimethylsilyl)ethoxy)methyl)-1H-pyrazole-5-carboxylate (15, 5.1 g, 59%) was prepared as an oil from methyl-4-bromo-1H-pyrazole-5-carboxylate (14, 5.0 g, 24.5 mmol) in a manner similar to the procedure for the preparation of intermediate 4: $^1$H NMR (400 MHz, Chloroform-d) δ 7.56 (s, 1H), 5.81 (s, 2H), 3.96 (s, 3H), 3.54 (t, J=8.0 Hz, 2H), 0.88 (t, J=8.0 Hz, 2H), 0.04 (s, 9H). ES/MS m/z: calculated for $C_{11}H_{20}BrN_2O_3Si$ (M+H): 335.04, no molecular mass detected.

Step 2

Methyl 4-(4-(4,4,5,5-tetramethyl-1,3,2-dioxaborolan-2-yl)phenyl)-1-((2-(trimethylsilyl)ethoxy)methyl)-1H-pyrazole-5-carboxylate (16, 5.83 g, 38%) was prepared as an oil in a manner similar to the procedure for the preparation of 6 using potassium carbonate in place of sodium carbonate, except the reaction was performed at 110° C. overnight: $^1$H NMR (400 MHz, Chloroform-d) δ 7.82 (d, J=8.4 Hz, 2H), 7.60 (s, 1H), 7.40 (d, J=8.4 Hz, 2H), 5.85 (s, 2H), 3.77 (s, 3H), 3.60 (t, J=7.2 Hz, 2H), 1.32 (s, 12H), 0.89 (t, J=7.2 Hz, 2H), 0.04 (s, 9H). ES/MS m/z: calculated for $C_{23}H_{36}BN_2O_5Si$ (M+H): 459.25, no molecular mass detected.

Synthesis of Intermediate 18

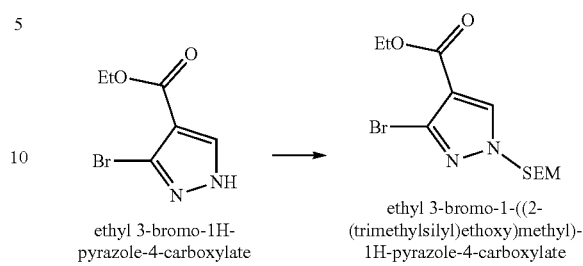

ethyl 3-bromo-1H-
pyrazole-4-carboxylate
17 ethyl 3-bromo-1-((2-
(trimethylsilyl)ethoxy)methyl)-
1H-pyrazole-4-carboxylate
18

Ethyl-3-bromo-1H-pyrazole-4-carboxylate (18, 511 mg, 96%) was prepared as an oil from ethyl 3-bromo-1H-pyrazole-4-carboxylate (17, 335 mg, 1.53 mmol) in a manner similar to the procedure for the preparation of intermediate 15 as a mixture of two regioisomers: ES/MS m/z: calculated for $C_{12}H_{22}BrN_2O_3Si$ (M+H): 349.06, found: 348.46.

Synthesis of Intermediate 20

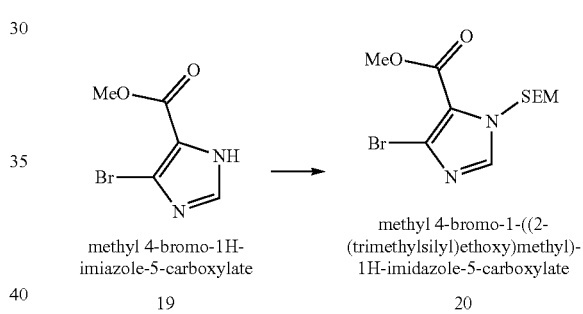

methyl 4-bromo-1H-
imiazole-5-carboxylate
19 methyl 4-bromo-1-((2-
(trimethylsilyl)ethoxy)methyl)-
1H-imidazole-5-carboxylate
20

Methyl 4-bromo-1-((2-(trimethylsilyl)ethoxy)methyl)-1H-imidazole-5-carboxylate (20, 690 mg, 77%) was prepared as an oil from methyl 4-bromo-1H-imidazole-5-carboxylate (19, 335 mg, 1.53 mmol) in a manner similar to the procedure for the preparation of intermediate 15 as a mixture of two region isomers: ES/MS m/z: calculated for $C_{12}H_{22}BrN_2O_3Si$ (M+H): 335.04, found: 334.86.

Representative Procedure of Suzuki Reaction

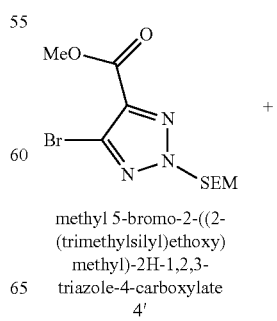

methyl 5-bromo-2-((2-
(trimethylsilyl)ethoxy)
methyl)-2H-1,2,3-
triazole-4-carboxylate
4'

+

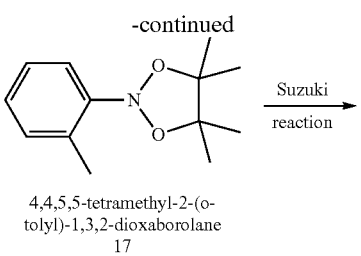

4,4,5,5-tetramethyl-2-(o-tolyl)-1,3,2-dioxaborolane
17

Suzuki reaction →

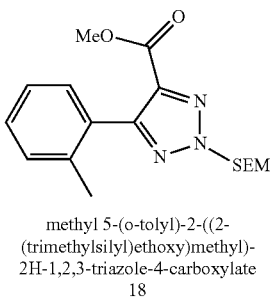

methyl 5-(o-tolyl)-2-((2-(trimethylsilyl)ethoxy)methyl)-2H-1,2,3-triazole-4-carboxylate
18

In a 5 mL microwave vial, the isomeric mixture of methyl 5-bromo-2-((2-(trimethylsilyl)ethoxy)methyl)-2H-1,2,3-triazole-4-carboxylate (4', 46 mg, 0.14 mmol), 4,4,5,5-tetramethyl-2-(o-tolyl)-1,3,2-dioxaborolane (17, 20 mg, 0.15 mmol), tetrakis(triphenylphosphine)palladium (0) (16 mg, 0.014 mmol), 2 N potassium carbonate (0.14 mL), and dioxane (2 mL) were added. After purging with argon gas for 5 minutes, the resulting mixture was stirred at 110° C. for 1 h. After cooling, the reaction mixture was diluted with saturated NaHCO₃ before the product was extracted with ethyl acetate, dried (MgSO₄), concentrated, and purified by column chromatography on silica gel eluting with ethyl acetate in hexane to get methyl 5-(o-tolyl)-2-((2-(trimethylsilyl)ethoxy)methyl)-2H-1,2,3-triazole-4-carboxylate (18): ES/MS m/z: calculated for $C_{17}H_{26}N_3O_3Si$ (M+H): 348.17, found: 347.58.

Representative Procedure of SEM Deprotection by HCl

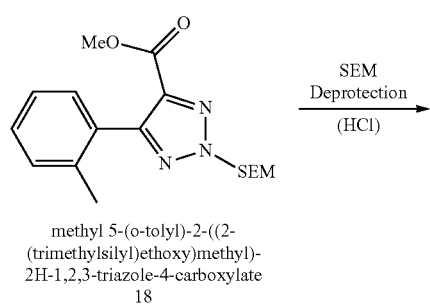

methyl 5-(o-tolyl)-2-((2-(trimethylsilyl)ethoxy)methyl)-2H-1,2,3-triazole-4-carboxylate
18

SEM Deprotection (HCl) →

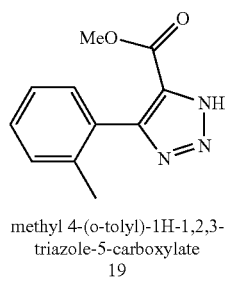

methyl 4-(o-tolyl)-1H-1,2,3-triazole-5-carboxylate
19

To a solution of methyl 5-(o-tolyl)-2-((2-(trimethylsilyl)ethoxy)methyl)-2H-1,2,3-triazole-4-carboxylate (18, 49 mg, 0.14 mmol) in tetrahydrofuran (1 mL) and methanol (1 mL) was added 3 N HCl (0.21 mL) and the resulting mixture was stirred at 80° C. for 2 h and then then 50° C. overnight. The resulting reaction mixture was concentrated down to obtain crude methyl 4-(o-tolyl)-1H-1,2,3-triazole-5-carboxylate (19): ES/MS m/z: calculated for $C_{11}H_{10}N_3O_2$ (M–H): 216.08, found: 216.15.

Representative Procedure of SEM Deprotection by TBAF

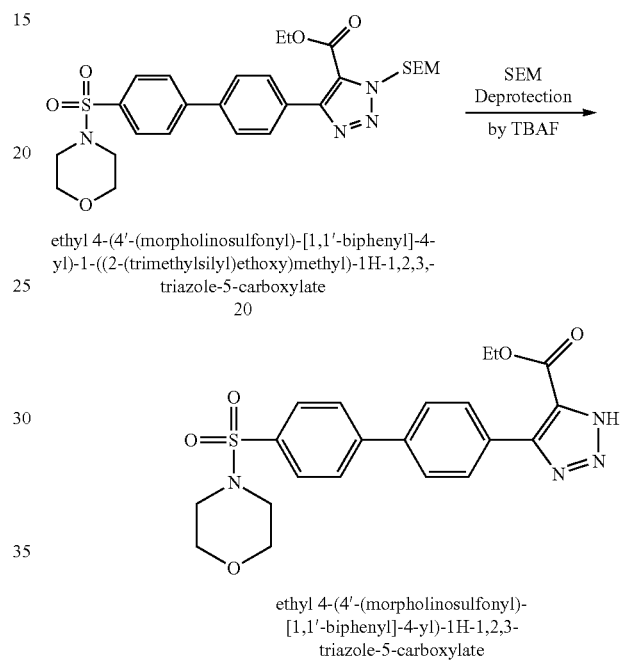

ethyl 4-(4'-(morpholinosulfonyl)-[1,1'-biphenyl]-4-yl)-1-((2-(trimethylsilyl)ethoxy)methyl)-1H-1,2,3,-triazole-5-carboxylate
20

SEM Deprotection by TBAF → ethyl 4-(4'-(morpholinosulfonyl)-[1,1'-biphenyl]-4-yl)-1H-1,2,3-triazole-5-carboxylate
21

Ethyl 4-(4'-(morpholinosulfonyl)-[1,1'-biphenyl]-4-yl)-1-((2-(trimethylsilyl)ethoxy)methyl)-1H-1,2,3-triazole-5-carboxylate (20) was dissolved in 1N TBAF (5 eq.) and the solution was heated to 60° C. for 3 hours. After cooling, the reaction mixture was diluted with saturated NaHCO₃ before the product was extracted with ethyl acetate, dried (MgSO₄), concentrated, and purified by column chromatography on silica gel eluting with ethyl acetate in hexane to get ethyl 4-(4'-(morpholinosulfonyl)-[1,1'-biphenyl]-4-yl)-1H-1,2,3-triazole-5-carboxylate (21): ES/MS m/z: calculated for $C_{21}H_{23}N_4O_5$ (M+H): 443.49, found: 443.16.

Representative Procedure of PMB Deprotection by TFA

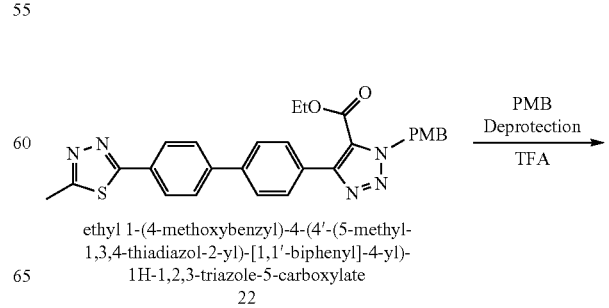

ethyl 1-(4-methoxybenzyl)-4-(4'-(5-methyl-1,3,4-thiadiazol-2-yl)-[1,1'-biphenyl]-4-yl)-1H-1,2,3-triazole-5-carboxylate
22

PMB Deprotection TFA →

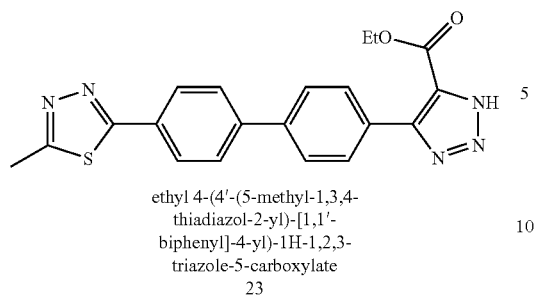

ethyl 4-(4'-(5-methyl-1,3,4-
thiadiazol-2-yl)-[1,1'-
biphenyl]-4-yl)-1H-1,2,3-
triazole-5-carboxylate
23

Ethyl 1-(4-methoxybenzyl)-4-(4'-(5-methyl-1,3,4-thiadiazol-2-yl)-[1,1'-biphenyl]-4-yl)-1H-1,2,3-triazole-5-carboxylate (22) was dissolved in 1 mL TFA and the mixture was heated to 40° C. for 80 minutes. After cooling, the reaction mixture was concentrated and diluted with saturated NaHCO₃ before the product was extracted with ethyl acetate, dried (MgSO₄), concentrated, and purified by column chromatography on silica gel eluting with ethyl acetate in hexane and 10% methanol in ethyl acetate to get ethyl 4-(4'-(5-methyl-1,3,4-thiadiazol-2-yl)-[1,1'-biphenyl]-4-yl)-1H-1,2,3-triazole-5-carboxylate (23): ES/MS m/z: calculated for $C_{20}H_{18}N_5O_2S$ (M+H): 392.45, found: 392.16.

Representative Procedure of Ester Hydrolysis

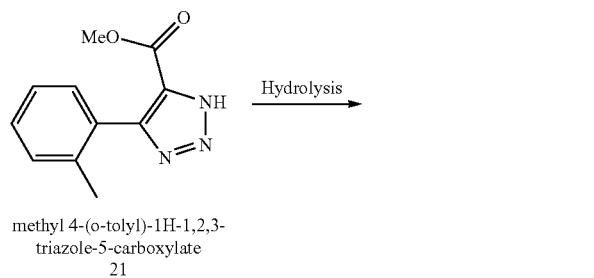

methyl 4-(o-tolyl)-1H-1,2,3-
triazole-5-carboxylate
21

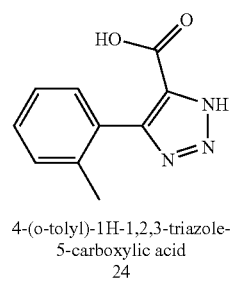

4-(o-tolyl)-1H-1,2,3-triazole-
5-carboxylic acid
24

To the crude methyl 4-(o-tolyl)-1H-1,2,3-triazole-5-carboxylate (21) in tetrahydrofuran (1 mL) and methanol (1 mL) was added 2 N NaOH (1 mL) and the resulting mixture was stirred at 80° C. for 2 h. After the reaction mixture was cooled and neutralized with 1 N HCl, the solids were filtered and the solids were purified by HPLC and freeze-dried to get 4-(o-tolyl)-1H-1,2,3-triazole-5-carboxylic acid (24): ES/MS m/z: ES/MS m/z: calculated for $C_{10}H_8N_3O_2$ (M−H): 202.08, found: 201.97.

Representative Procedure of SEM Protection of Heterocyclic N—H

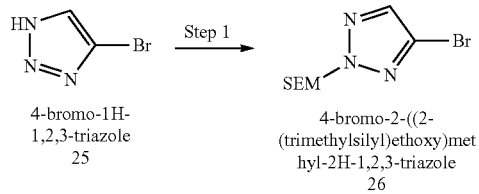 [SMILES: Brc1c[nH]nn1 ; C[Si](C)(C)CCOCn1ncc(Br)n1]

4-bromo-1H-
1,2,3-triazole
25

4-bromo-2-((2-
(trimethylsilyl)ethoxy)met
hyl-2H-1,2,3-triazole
26

A solution of 5-bromo-1H-1,2,3-triazole (25, 996.3 mg, 6.733 mmol) in DMF (20 mL) was stirred at ice bath as 60% sodium hydride in mineral oil (410 mg, 10.25 mmol) was added portionwise. After 30 min, (2-(chloromethoxy)ethyl)trimethylsilane (1.25 mL, 7.063 mmol) was added to the reaction mixture and the resulting mixture was stirred in ice bath for 1 h followed by rt overnight. After 19 h, the reaction mixture was diluted with sat. aq. NH₄Cl (~100 mL) and ethyl acetate (~100 mL) and the two layers were separated. After aqueous fraction was extracted with ethyl acetate (×1), organic fractions were washed with water (~150 mL×1), combined, dried (MgSO₄), and concentrated. The residual oil was purified by column chromatography on silica gel eluting 0-30% ethyl acetate in hexane to obtain 726.0 mg (39%) of 4-bromo-2-((2-(trimethylsilyl)ethoxy)methyl)-2H-1,2,3-triazole (26): ¹H NMR (400 MHz, Chloroform-d) δ 7.63 (s, 1H), 5.63 (s, 2H), 3.72-3.60 (m, 2H), 0.99-0.86 (m, 2H), −0.02 (s, 9H). ES/MS m/z: calculated for $C_{11}H_{20}BrN_2O_3Si$ (M+H): 335.04, no molecular mass detected.

Representative Procedure of Preparation of the Boronate Ester from an Aryl Bromide

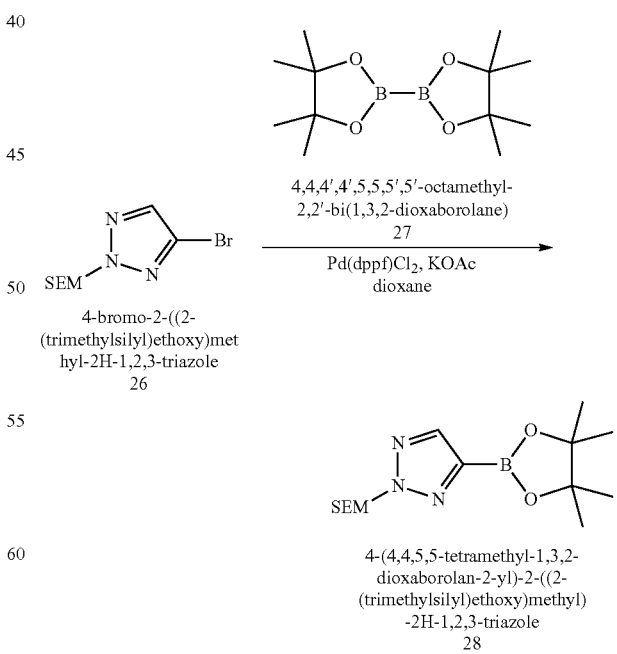

4-bromo-2-((2-
(trimethylsilyl)ethoxy)met
hyl-2H-1,2,3-triazole
26

4,4,4',4',5,5,5',5'-octamethyl-
2,2'-bi(1,3,2-dioxaborolane)
27

Pd(dppf)Cl₂, KOAc
dioxane 4-(4,4,5,5-tetramethyl-1,3,2-
dioxaborolan-2-yl)-2-((2-
(trimethylsilyl)ethoxy)methyl)
-2H-1,2,3-triazole
28

A mixture of 4-bromo-2-((2-(trimethylsilyl)ethoxy)methyl)-2H-1,2,3-triazole (26, 359 mg, 1.29 mmol), bis (pinacolato)diboron (27, 362 mg, 1.43 mmol), dichloro 1,1'-bis(diphenylphosphino)ferrocene palladium (II) dichloromethane (116 mg, 0.14 mmol), and potassium acetate (384 mg, 3.92 mmol) in 1,4-dioxane (6 mL) in a 20 mL μW vial was purged with Ar gas for 15 min before the mixture was heated at 110° C. 1 h. The reaction mixture was diluted with ethyl acetate (60 mL), treated with Na$_2$SO$_4$, and filtered. The filtrate was concentrated and the residue was purified by column chromatography on silica gel eluting 0-40% ethyl acetate in hexane to get 282 mg (67%) of 4-(4,4,5,5-tetramethyl-1,3,2-dioxaborolan-2-yl)-2-((2-(trimethylsilyl)ethoxy)methyl)-2H-1,2,3-triazole (28): $^1$H NMR (400 MHz, Chloroform-d) δ 7.99 (s, 1H), 5.74 (s, 2H), 3.70-3.56 (m, 2H), 1.37 (s, 12H), 0.96-0.85 (m, 2H), −0.04 (s, 9H).

The following compounds were prepared in a manner similar to the representative procedures of Suzuki reaction, SEM or PMB deprotections described above, and ester hydrolysis either using previously mentioned bromide intermediates, 4 (or 4'), 10, or 15 with commercially available boronates, or using previously mentioned boronate intermediates, 6 (or 6'), 8, 12, 13, and 16 with commercially available bromides:

Example 1: ethyl 4-(4'-chloro-[1,1'-biphenyl]-4-yl)-1H-1,2,3-triazole-5-carboxylate

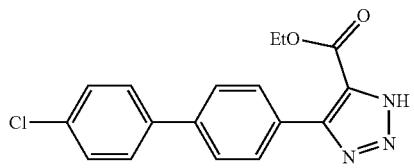 [SMILES: CCOC(=O)c1[nH]nnc1-c1ccc(-c2ccc(Cl)cc2)cc1]

$^1$H NMR (400 MHz, Chloroform-d) δ 7.95 (dd, J=8.3, 6.7 Hz, 2H), 7.65 (dd, J=8.2, 5.5 Hz, 2H), 7.60-7.49 (m, 2H), 7.43 (dd, J=8.5, 1.9 Hz, 2H), 5.90 (s, 1H), 4.45 (qd, J=7.2, 4.8 Hz, 2H), 1.41 (t, J=7.1 Hz, 3H). ES/MS m/z: calculated for C$_{17}$H$_{13}$ClN$_3$O$_2$(M−H): 326.08, found: 326.31.

Example 2: ethyl 4-(4'-carbamoyl-[1,1'-biphenyl]-4-yl)-1H-1,2,3-triazole-5-carboxylate

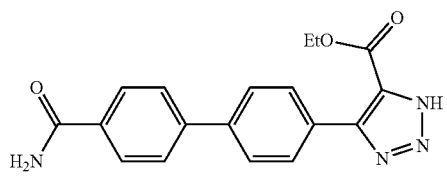

$^1$H NMR (400 MHz, Methanol-d$_4$) δ 7.99-7.91 (m, 2H), 7.88 (d, J=8.1 Hz, 2H), 7.72 (dd, J=8.4, 1.8 Hz, 4H), 4.38 (q, J=7.2 Hz, 2H), 1.35 (t, J=7.1 Hz, 3H). ES/MS m/z: calculated for C$_{18}$H$_{17}$N$_4$O$_3$ (M+H): 337.13, found: 337.03.

Example 3: 4-(o-tolyl)-1H-1,2,3-triazole-5-carboxylic acid

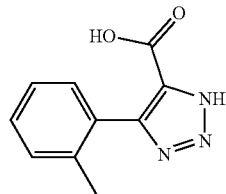

$^1$H NMR (400 MHz, Methanol-d$_4$) δ 7.42-7.31 (m, 2H), 7.31-7.21 (m, 2H), 2.17 (s, 3H). ES/MS m/z: calculated for C$_{10}$H$_{10}$N$_3$O$_2$ (M+H): 204.08, found: 347.58.

Example 4: 4-(m-tolyl)-1H-1,2,3-triazole-5-carboxylic acid

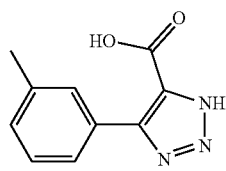

$^1$H NMR (400 MHz, Methanol-d$_4$) δ 7.65-7.55 (m, 2H), 7.34 (t, J=7.6 Hz, 1H), 7.27 (d, J=7.7 Hz, 1H), 2.40 (s, 3H). ES/MS m/z: calculated for C$_{10}$H$_{10}$N$_3$O$_2$ (M+H): 204.20, found: 203.92.

Example 5: 4-(p-tolyl)-1H-1,2,3-triazole-5-carboxylic acid

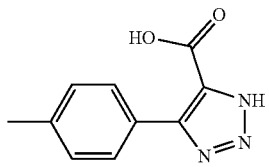

$^1$H NMR (400 MHz, Methanol-d$_4$) δ 7.81 (d, J=7.8 Hz, 2H), 7.23 (d, J=7.9 Hz, 2H), 2.36 (s, 3H). ES/MS m/z: calculated for C$_{10}$H$_{10}$N$_3$O$_2$ (M+H): 204.20, found: 203.92.

Example 6: 4-(3-ethylphenyl)-1H-1,2,3-triazole-5-carboxylic acid

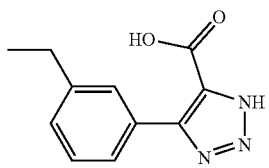 [SMILES: CCc1cccc(-c2nn[nH]c2C(=O)O)c1]

¹H NMR (400 MHz, Methanol-d₄) δ 7.68-7.56 (m, 2H), 7.42-7.28 (m, 2H), 2.71 (q, J=7.6 Hz, 2H), 1.27 (t, J=7.6 Hz, 3H). ES/MS m/z: calculated for $C_{11}H_{12}N_3O_2$ (M+H): 218.09, found: 217.97

Example 7:
4-(2-fluorophenyl)-1H-1,2,3-triazole-5-carboxylic acid

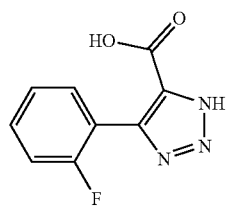 [SMILES: O=C(O)c1[nH]nnc1-c1ccccc1F]

¹H NMR (400 MHz, Methanol-d₄): δ 7.61-7.45 (m, 2H), 7.32-7.17 (m, 2H). ES/MS m/z: calculated for $C_9H_7FN_3O_2$ (M+H): 208.04, found: 207.94.

Example 8:
4-(3-fluorophenyl)-1H-1,2,3-triazole-5-carboxylic acid

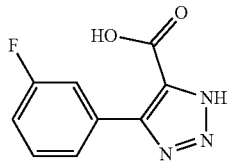

¹H NMR (400 MHz, Methano-d₄) δ 7.74-7.66 (m, 2H), 7.46 (td, J=8.1, 5.9 Hz, 1H), 7.16 (td, J=8.6, 2.5 Hz, 1H). ES/MS m/z: calculated for $C_9H_7FN_3O_2$ (M+H): 208.04, found: 207.91.

Example 9:
4-(4-chlorophenyl)-1H-1,2,3-triazole-5-carboxylic acid

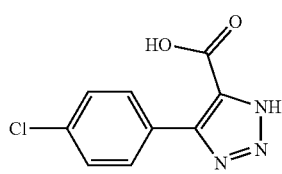 [SMILES: O=C(O)c1[nH]nnc1-c1ccc(Cl)cc1]

¹H NMR (400 MHz, Methanol-d₄): δ 7.89-7.81 (m, 2H). 7.51-7.42 (m, 2H). ES/MS m/z: calculated for $C_9H_7Cl_1N_3O_2$ (M+H): 224.01, found: 223.94.

Example 10:
4-(3-methoxyphenyl)-1H-1,2,3-triazole-5-carboxylic acid

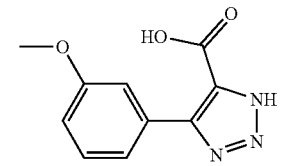 [SMILES: COc1cccc(-c2nn[nH]c2C(=O)O)c1]

¹H NMR (400 MHz, Methanol-d₄) δ 7.45 (d, J=2.5 Hz, 1H), 7.37 (d, J=7.1 Hz, 2H), 7.06-6.98 (m, 1H), 3.84 (s, 3H). ES/MS m/z: calculated for $C_{10}H_8N_3O_3$ (M−H): 218.20, found: 217.98.

Example 11:
4-(4-methoxyphenyl)-1H-1,2,3-triazole-5-carboxylic acid

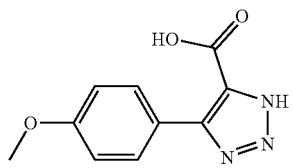 [SMILES: COc1ccc(-c2nn[nH]c2C(=O)O)cc1]

¹H NMR (400 MHz, Methanol-d₄) δ 7.78 (d, J=8.4 Hz, 2H), 7.06-6.98 (m, 2H), 3.85 (s, 3H). ES/MS m/z: calculated for $C_{10}H_{10}N_3O_3$ (M+H): 220.06, found: 219.93.

Example 12: 4-(2,4'-dichloro-[1,1'-biphenyl]-4-yl)-1H-1,2,3-triazole-5-carboxylic acid

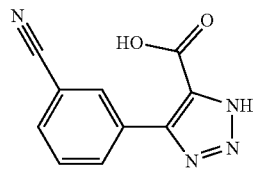

¹H NMR (400 MHz, Methanol-d₄) δ 8.34 (s, 1H), 8.24 (d, J=8.0 Hz, 1H), 7.78 (dt, J=7.8, 1.4 Hz, 1H), 7.64 (t, J=7.9 Hz, 1H). ES/MS m/z: calculated for $C_{10}H_7N_4O_2$ (M+H): 215.05, found: 214.96.

Example 13: 4-(3-(trifluoromethyl)phenyl)-1H-1,2,3-triazole-5-carboxylic acid

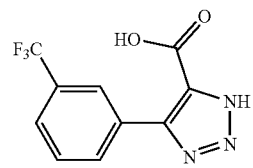 [SMILES: O=C(O)c1[nH]nnc1-c1cccc(C(F)(F)F)c1]

¹H NMR (400 MHz, Methanol-d₄) δ 8.24 (t, J=1.7 Hz, 1H), 8.15 (d, J=7.9 Hz, 1H), 7.74 (d, J=7.8 Hz, 1H), 7.66 (t, J=7.8 Hz, 1H). ES/MS m/z: calculated for C$_{10}$H$_7$F$_3$N$_3$O$_2$ (M+H): 258.07, found: 257.97

Example 14: 4-(3-(tert-butyl)phenyl)-1H-1,2,3-triazole-5-carboxylic acid

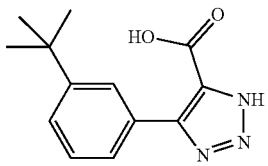 [SMILES: CC(C)(C)c1cccc(-c2nn[nH]c2C(=O)O)c1]

¹H NMR (400 MHz, Methanol-d₄) δ 7.90 (t, J=1.9 Hz, 1H), 7.59 (dt, J=7.6, 1.4 Hz, 1H), 7.51 (ddd, J=7.9, 2.0, 1.1 Hz, 1H), 7.39 (t, J=7.8 Hz, 1H), 1.36 (s, 9H). ES/MS m/z: calculated for C$_{13}$H$_{16}$N$_3$O$_2$ (M+H): 246.12, found: 246.04.

Example 15: 4-(4-(tert-butyl)phenyl)-1H-1,2,3-triazole-5-carboxylic acid

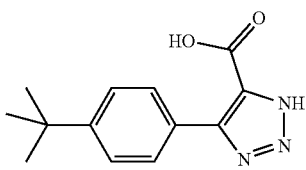 [SMILES: CC(C)(C)c1ccc(-c2nn[nH]c2C(=O)O)cc1]

¹H NMR (400 MHz, Methanol-d₄): δ 7.78-7.70 (m, 2H), 7.55-7.47 (m, 2H), 1.36 (s, 9H). ES/MS m/z: calculated for C$_{13}$H$_{16}$N$_3$O$_2$ (M+H): 246.12, found: 246.01.

Example 16: 4-(3-(trifluoromethoxy)phenyl)-1H-1,2,3-triazole-5-carboxylic acid

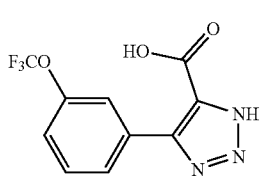 [SMILES: O=C(O)c1[nH]nnc1-c1cccc(OC(F)(F)F)c1]

¹H NMR (400 MHz, Methanol-d₄) δ 7.89 (d, J=7.8 Hz, 2H), 7.55 (td, J=7.9, 7.4, 1.0 Hz, 1H), 7.39-7.31 (m, 1H). ES/MS m/z: calculated for C$_{10}$H$_7$FN$_3$O$_3$ (M+H): 274.04, found: 273.95.

Example 17: 5-(3-chloro-4-fluorophenyl)-1-methyl-1H-1,2,3-triazole-4-carboxylic acid

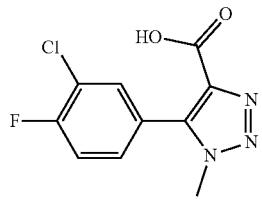 [SMILES: Cn1nnc(C(=O)O)c1-c1ccc(F)c(Cl)c1]

¹H NMR (400 MHz, Chloroform-d) δ 8.00 (dd, J=7.1, 2.2 Hz, 1H), 7.83 (ddd, J=8.7, 4.6, 2.2 Hz, 1H), 7.21 (t, J=8.7 Hz, 1H), 4.32 (s, 3H). ES/MS m/z: calculated for C$_{10}$H$_9$ClFN$_3$O$_2$ (M–H): 254.63, found: 254.04.

Example 18: 4-(3-chloro-4-fluorophenyl)-1H-pyrazole-3-carboxylic acid

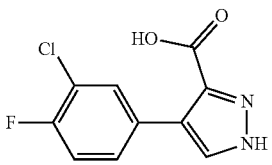 [SMILES: O=C(O)c1n[nH]cc1-c1ccc(F)c(Cl)c1]

1H NMR (400 MHz, Methanol-d₄) δ 7.80 (s, 1H), 7.71 (dd, J=7.2, 2.2 Hz, 1H), 7.50 (ddd, J=8.6, 4.6, 2.2 Hz, 1H), 7.22 (dd, J=9.2, 8.6 Hz, 1H). ES/MS m/z: calculated for C$_{10}$H$_7$ClF$_2$O$_2$ (M+H): 241.01, found: 240.88.

Example 19: 4-(3,4-dichlorophenyl)-1H-1,2,3-triazole-5-carboxylic acid

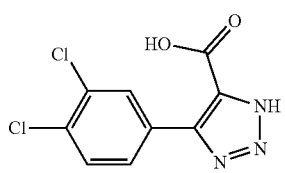 [SMILES: O=C(O)c1[nH]nnc1-c1ccc(Cl)c(Cl)c1]

¹H NMR (400 MHz, Methanol-d₄) δ 8.13 (d, J=2.1 Hz, 1H), 7.85 (dd, J=8.4, 2.1 Hz, 1H), 7.61 (d, J=8.5 Hz, 1H). ES/MS m/z: calculated for C$_9$H$_6$Cl$_2$N$_3$O (M+H): 257.98, found: 257.95.

Example 20: 4-(3,5-dichlorophenyl)-1H-1,2,3-triazole-5-carboxylic acid

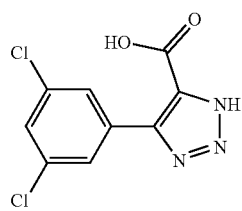 [SMILES: O=C(O)c1[nH]nnc1-c1cc(Cl)cc(Cl)c1]

¹H NMR (400 MHz, Methano-d₄) δ 7.95 (s, 2H), 7.52 (s, 1H). ES/MS m/z: calculated for $C_9H_6Cl_2N_3O_2$ (M+H): 257.98, found: 257.92.

Example 21:
4-(3,5-dichlorophenyl)-1H-pyrazole-3-carboxylic acid

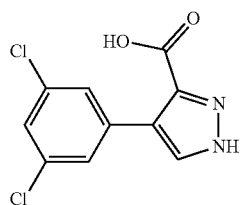 [SMILES: O=C(O)c1n[nH]cc1-c1cc(Cl)cc(Cl)c1]

¹H NMR (400 MHz, DMSO-d₆): δ 8.00 (s, 1H), 7.68 (s, 2H), 7.58-7.44 (m, 1H). ES/MS m/z: calculated for $C_{10}H_5Cl_2N_2O_2$ (M−H): 254.98, found: 255.02.

Example 22: 4-(3-chloro-2-fluorophenyl)-1H-1,2,3-triazole-5-carboxylic acid

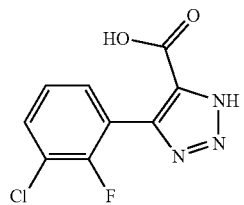 [SMILES: O=C(O)c1[nH]nnc1-c1cccc(Cl)c1F]

¹H NMR (400 MHz, Methanol-d₄) δ 7.59 (ddd, J=8.6, 7.0, 1.7 Hz, 1H), 7.50 (ddd, J=7.9, 6.3, 1.7 Hz, 1H), 7.27 (td, J=7.9, 1.2 Hz, 1H). ES/MS m/z: calculated for $C_9H_6ClFN_3O_2$ (M+H): 242.01, found: 241.94.

Example 23: 5-(4-bromo-3-chlorophenyl)-1H-1,2,3-triazole-4-carboxylic acid

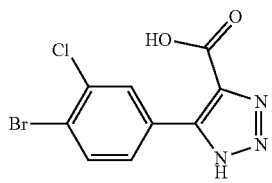 [SMILES: O=C(O)c1nn[nH]c1-c1ccc(Br)c(Cl)c1]

¹H NMR (400 MHz, Methanol-d₄): δ 8.04 (s, 1H), 7.70-7.65 (m, 2H). ES/MS m/z: calculated for $C_9H_4BrClN_3O_2$ (M−H): 299.93, found: 300.02.

Example 24: 4-(3,5-dichloro-4-fluorophenyl)-1H-1,2,3-triazole-5-carboxylic acid

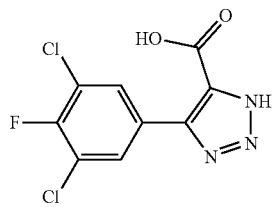 [SMILES: O=C(O)c1[nH]nnc1-c1cc(Cl)c(F)c(Cl)c1]

¹H NMR (400 MHz, Methano-d₄) δ 8.09 (d, J=6.4 Hz, 2H). ES/MS m/z: calculated for $C_9H_4Cl_2FN_3O_2$ (M+H): 275.97, found: 275.96.

Example 25:
4-(3-phenoxyphenyl)-1H-1,2,3-triazole-5-carboxylic acid

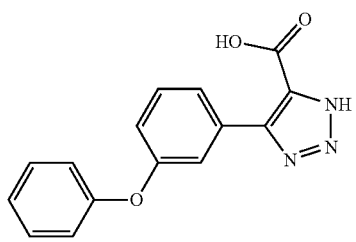 [SMILES: O=C(O)c1[nH]nnc1-c1cccc(Oc2ccccc2)c1]

¹H NMR (400 MHz, Methanol-d₄) δ 7.57 (ddd, J=7.7, 1.6, 1.0 Hz, 1H), 7.52-7.40 (m, 2H), 7.40-7.31 (m, 2H), 7.18-7.08 (m, 1H), 7.08-6.99 (m, 3H). ES/MS m/z: calculated for $C_{15}H_{12}N_3O_3$ (M+H): 282.08, found: 282.01

Example 26:
4-(4-phenoxyphenyl)-1H-1,2,3-triazole-5-carboxylic acid

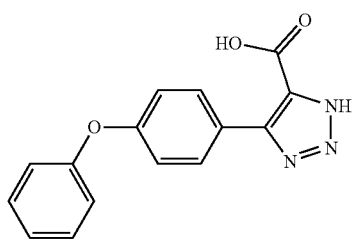 [SMILES: O=C(O)c1[nH]nnc1-c1ccc(Oc2ccccc2)cc1]

¹H NMR (400 MHz, Methanol-d₄) δ 7.83 (d, J=8.4 Hz, 2H), 7.44-7.34 (m, 2H), 7.21-7.12 (m, 1H), 7.10-7.01 (m, 4H). ES/MS m/z: calculated for $C_{15}H_{12}N_3O_3$ (M+H): 282.08, found: 281.98.

Example 27: 4-([1,1'-biphenyl]-3-yl)-1H-1,2,3-triazole-5-carboxylic acid

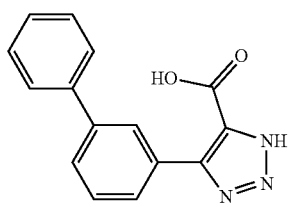 [SMILES: O=C(O)c1[nH]nnc1-c1cccc(-c2ccccc2)c1]

¹H NMR (400 MHz, Methanol-d₄) δ 8.03 (t, J=1.8 Hz, 1H), 7.71 (dt, J=7.7, 1.4 Hz, 1H), 7.67-7.54 (m, 3H), 7.46 (t, J=7.8 Hz, 1H), 7.41-7.32 (m, 2H), 7.31-7.22 (m, 1H). ES/MS m/z: calculated for $C_{15}H_{12}N_3O_2$ (M+H): 266.09, found: 266.01.

Example 28: 4-([1,1'-biphenyl]-4-yl)-1H-1,2,3-triazole-5-carboxylic acid

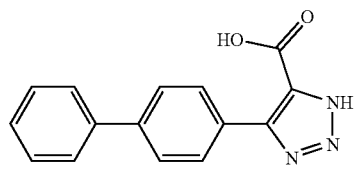 [SMILES: O=C(O)c1[nH]nnc1-c1ccc(-c2ccccc2)cc1]

¹H NMR (400 MHz, Methanol-d₄) δ 7.92 (d, J=8.0 Hz, 2H), 7.77-7.64 (m, 4H), 7.51-7.41 (m, 2H), 7.41-7.32 (m, 1H). ES/MS m/z: calculated for $C_{15}H_{12}N_3O_2$ (M+H): 266.09, found: 265.96.

Example 29: 4-(2,2-difluorobenzo[d][1,3]dioxol-5-yl)-1H-1,2,3-triazole-5-carboxylic acid

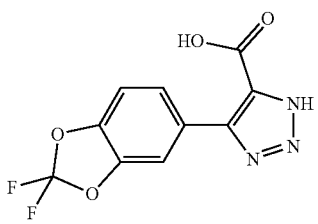 [SMILES: O=C(O)c1[nH]nnc1-c1ccc2c(c1)OC(F)(F)O2]

¹H NMR (400 MHz, Methanol-d₄) δ 7.79 (dd, J=1.7, 0.5 Hz, 1H), 7.72 (dd, J=8.4, 1.7 Hz, 1H), 7.29 (d, J=8.4 Hz, 1H). ES/MS m/z: calculated for $C_{10}H_6CF_2N_3O_4$(M+H): 270.02, found: 269.97.

Example 30: 4-(benzo[d][1,3]dioxol-5-yl)-1H-1,2,3-triazole-5-carboxylic acid

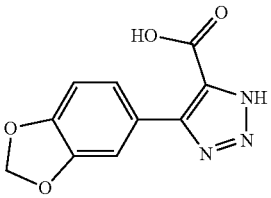 [SMILES: O=C(O)c1[nH]nnc1-c1ccc2c(c1)OCO2]

¹H NMR (400 MHz, Methanol-d₄) δ 7.35 (d, J=1.7 Hz, 2H), 6.95-6.86 (m, 1H), 6.02 (s, 2H). ES/MS m/z: calculated for $C_{10}H_6N_3O_4$ (M–H): 232.04, found: 232.00.

Example 31: 4-(4-(2,2-difluorobenzo[d][1,3]dioxol-5-yl)phenyl)-1H-1,2,3-triazole-5-carboxylic acid

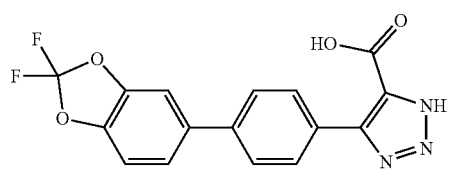 [SMILES: O=C(O)c1[nH]nnc1-c1ccc(-c2ccc3c(c2)OC(F)(F)O3)cc1]

¹H NMR (400 MHz, Methanol-d₄) δ 7.46-7.35 (m, 3H), 7.32 (dt, J=8.4, 1.6 Hz, 1H), 7.19 (dd, J=8.4, 1.3 Hz, 1H), 6.89-6.81 (m, 2H). ES/MS m/z: Calculated for $C_{16}H_8F_2N_3O_4$ (M–H)=344.06; found 344.04

Example 32: 4-(2,3-dihydrobenzo[b][1,4]dioxin-6-yl)-1H-1,2,3-triazole-5-carboxylic acid

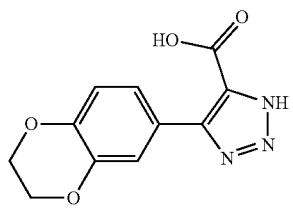 [SMILES: O=C(O)c1[nH]nnc1-c1ccc2c(c1)OCCO2]

¹H NMR (400 MHz, Methanol-d₄) δ 7.39 (s, 1H), 7.31 (d, J=7.1 Hz, 1H), 6.90 (d, J=8.5 Hz, 1H), 4.32-4.24 (s, 4H). ES/MS m/z: calculated for $C_{11}H_{10}N_3O_4$ (M+H): 248.06, found: 248.00.

Example 33: 4-(naphthalen-2-yl)-1H-1,2,3-triazole-5-carboxylic acid

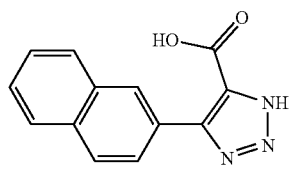 [SMILES: O=C(O)c1[nH]nnc1-c1ccc2ccccc2c1]

¹H NMR (400 MHz, Methanol-d₄): δ 8.39 (s, 1H), 7.98-7.86 (m, 4H), 7.59-7.49 (m, 2H). ES/MS m/z: calculated for C₉H₆ClFN₃O₂ (M+H): 242.01, found: 239.97.

Example 34:
4-(pyridin-3-yl)-1H-1,2,3-triazole-5-carboxylic acid

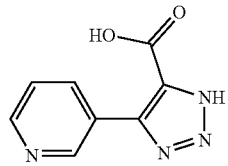 [SMILES: O=C(O)c1[nH]nnc1-c1cccnc1]

¹H NMR (400 MHz, Methanol-d₄) δ 9.61-9.53 (m, 1H), 9.24 (dt, J=8.2, 1.7 Hz, 1H), 8.89 (dt, J=5.7, 1.2 Hz, 1H), 8.18 (ddd, J=8.2, 5.8, 0.8 Hz, 1H). ES/MS m/z: calculated for C₈H₇N₄O₂ (M+H): 191.05, found: 191.01

Example 35:
4-(pyridin-3-yl)-1H-pyrazole-3-carboxylic acid

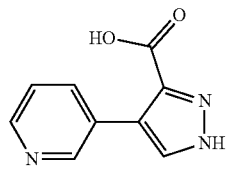 [SMILES: O=C(O)c1n[nH]cc1-c1cccnc1]

¹H NMR (400 MHz, Methanol-d₄) δ 9.40 (d, J=1.9 Hz, 1H), 9.00 (ddd, J=8.2, 2.0, 1.5 Hz, 1H), 8.79 (ddd, J=5.6, 1.4, 0.7 Hz, 1H), 8.35 (s, 1H), 8.03 (ddd, J=8.2, 5.7, 0.8 Hz, 1H). ES/MS m/z: calculated for C₉H₇N₃O₂ (M–H): 190.05, found: 190.02.

Example 36:
4-(quinolin-7-yl)-1H-1,2,3-triazole-5-carboxylic acid

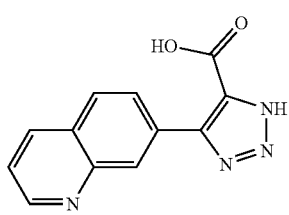

¹H NMR (400 MHz, DMSO-d₆) δ 9.05-8.98 (m, 1H), 8.62-8.52 (m, 1H), 8.11 (d, J=11.3 Hz, 1H), 7.69-7.48 (m, 4H). ES/MS m/z: calculated for C₁₂H₉N₄O₂(M+H): 241.06, found: 241.07.

Example 37: 4-(isoquinolin-7-yl)-1H-1,2,3-triazole-5-carboxylic acid

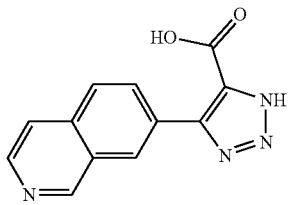 [SMILES: O=C(O)c1[nH]nnc1-c1ccc2ccncc2c1]

¹H NMR (400 MHz, Methanol-d₄) δ 9.80 (s, 1H), 9.11 (s, 1H), 8.74 (d, J=9.3 Hz, 1H), 8.60 (d, J=6.6 Hz, 1H), 8.47 (d, J=6.6 Hz, 1H), 8.36 (d, J=8.8 Hz, 1H). ES/MS m/z: calculated for C₁₂H₈N₄O₂ (M+H): 241.06, found: 241.05.

Example 38: 4-(6-phenylnaphthalen-2-yl)-1H-1,2,3-triazole-5-carboxylic acid

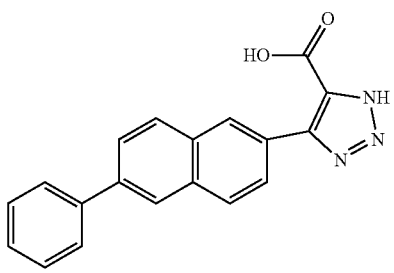 [SMILES: O=C(O)c1[nH]nnc1-c1ccc2cc(-c3ccccc3)ccc2c1]

¹H NMR (400 MHz, Methanol-d₄) δ 8.43 (s, 1H), 8.15 (s, 1H), 8.02 (d, J=8.4 Hz, 2H), 7.95 (s, 1H), 7.89-7.81 (m, 1H), 7.81-7.74 (m, 2H), 7.49 (t, J=7.7 Hz, 2H), 7.43-7.34 (m, 1H). ES/MS m/z: calculated for C₁₉H₁₄N₃O₂ (M+H): 316.10, found: 316.00.

Example 39: 4-(3-chloroisoquinolin-7-yl)-1H-1,2,3-triazole-5-carboxylic acid

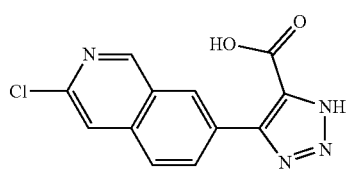 [SMILES: O=C(O)c1[nH]nnc1-c1ccc2cc(Cl)ncc2c1]

¹H NMR (400 MHz, Methanol-d₄) δ 9.17 (s, 1H), 8.70 (s, 1H), 8.29 (dd, J=8.6, 1.7 Hz, 1H), 8.12-7.86 (m, 2H). ES/MS m/z: Calculated for C₁₂H₈ClN₄O₂ (M+H)=275.03; Found 275.05.

Example 40: 4-(3-methoxyisoquinolin-7-yl)-1H-1,2,3-triazole-5-carboxylic acid

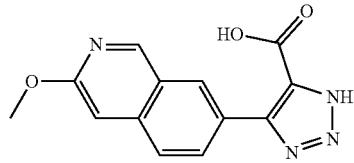 [SMILES: COc1cc2ccc(-c3nn[nH]c3C(=O)O)cc2cn1]

¹H NMR (400 MHz, Methanol-d₄) δ 9.06 (d, J=0.9 Hz, 1H), 8.40-8.35 (m, 1H), 8.12 (dd, J=8.7, 1.9 Hz, 1H), 7.94 (d, J=8.8 Hz, 1H), 7.19 (s, 1H), 4.04 (s, 3H).

Example 41: 4-(3-phenylisoquinolin-7-yl)-1H-1,2,3-triazole-5-carboxylic acid

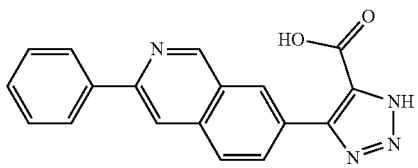 [SMILES: O=C(O)c1[nH]nnc1-c1ccc2cc(-c3ccccc3)ncc2c1]

¹H NMR (400 MHz, Methanol-d₄) δ 9.55 (s, 1H), 8.86 (s, 1H), 8.45 (d, J=15.6 Hz, 2H), 8.20 (d, J=8.5 Hz, 1H), 8.07 (d, J=7.7 Hz, 2H), 7.64-7.51 (m, 3H). ES/MS m/z: Calculated for $C_{18}H_{13}N_4O_2$ (M+H)=317.10; Found 317.09.

Example 42: 4-(4-(naphthalen-1-yl)phenyl)-1H-1,2,3-triazole-5-carboxylic acid

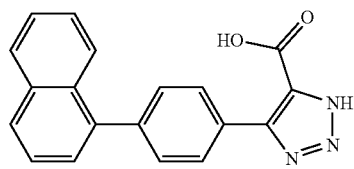 [SMILES: O=C(O)c1[nH]nnc1-c1ccc(-c2cccc3ccccc23)cc1]

¹H NMR (400 MHz, Methanol-d₄) δ 8.02-7.85 (m, 5H), 7.61-7.40 (m, 6H). ES/MS m/z: Calculated for $C_{19}H_{14}N_3O_2$ (M+H)=316.11; Found 316.03.

Example 43: 4-(4-(pyridin-2-yl)phenyl)-1H-1,2,3-triazole-5-carboxylic acid

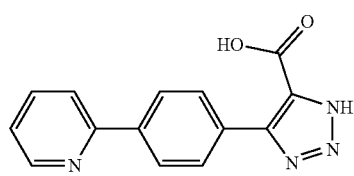 [SMILES: O=C(O)c1[nH]nnc1-c1ccc(-c2ccccn2)cc1]

¹H NMR (400 MHz, DMSO-d₆) δ 8.69 (dt, J=4.7, 1.5 Hz, 1H), 8.19 (d, J=12.8 Hz, 2H), 8.03 (d, J=8.0 Hz, 1H), 7.90 (td, J=7.7, 1.9 Hz, 3H), 7.38 (dd, J=7.6, 4.9 Hz, 1H). ES/MS m/z: calculated for $C_{14}H_{11}N_4O_2$ (M+H): 267.08, found: 267.10.

Example 44: 4-(4-(pyridin-3-yl)phenyl)-1H-1,2,3-triazole-5-carboxylic acid

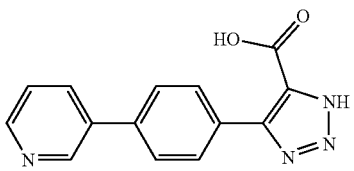 [SMILES: O=C(O)c1[nH]nnc1-c1ccc(-c2cccnc2)cc1]

¹H NMR (400 MHz, Methanol-d₄) δ 9.17 (d, J=2.1 Hz, 1H), 8.88-8.76 (m, 2H), 8.11 (d, J=8.4 Hz, 2H), 8.06 (dd, J=8.2, 5.6 Hz, 1H), 7.91 (d, J=8.5 Hz, 2H). ES/MS m/z: calculated for $C_{14}H_{11}N_4O_2$ (M+H): 267.09, found: 267.04.

Example 45: 4-(4-(naphthalen-2-yl)phenyl)-1H-1,2,3-triazole-5-carboxylic acid

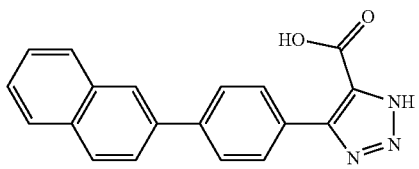 [SMILES: O=C(O)c1[nH]nnc1-c1ccc(-c2ccc3ccccc3c2)cc1]

¹H NMR (400 MHz, DMSO-d₆) δ 8.31 (s, 1H), 8.09-7.99 (m, 2H), 7.93 (tt, J=8.6, 4.4 Hz, 6H), 7.54 (tt, J=6.9, 5.4 Hz, 2H). ES/MS m/z: calculated for $C_{19}H_{12}N_3O_2$(M−H): 314.10, found: 314.14.

Example 46: 4-(4-(6-chloronaphthalen-2-yl)phenyl)-1H-1,2,3-triazole-5-carboxylic acid

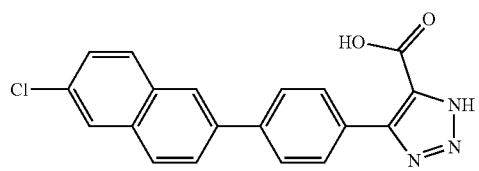

¹H NMR (400 MHz, DMSO-d₆) δ 8.31 (s, 1H), 8.07-7.91 (m, 6H), 7.89 (s, 2H), 7.51 (dd, J=8.7, 2.2 Hz, 1H). ES/MS m/z: calculated for $C_{19}H_{13}ClN_3O_2$ (M+H): 350.06, found: 350.00.

Example 47: 4-(4-(isoquinolin-6-yl)phenyl)-1H-1,2,3-triazole-5-carboxylic acid

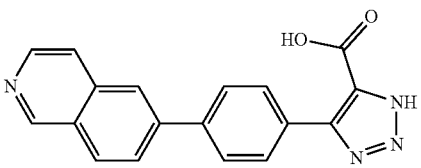 [SMILES: O=C(O)c1[nH]nnc1-c1ccc(-c2ccc3cnccc3c2)cc1]

¹H NMR (400 MHz, Methanol-d₄) δ 9.51 (s, 1H), 8.59 (d, J=6.0 Hz, 1H), 8.48 (d, J=2.1 Hz, 1H), 8.36 (d, J=8.5 Hz, 1H), 8.21 (d, J=8.7 Hz, 1H), 8.08 (s, 1H), 8.02 (s, 4H). ES/MS m/z: calculated for $C_{14}H_{11}N_4O_2$ (M+H): 267.09, found: 267.04.

Example 48: 4-(4-(1-methyl-1H-benzo[d]imidazol-5-yl)phenyl)-1H-1,2,3-triazole-5-carboxylic acid

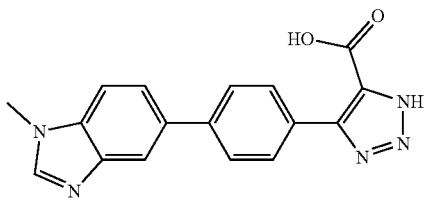

¹H NMR (400 MHz, DMSO-d₆) δ 8.36 (s, 1H), 8.00 (s, 1H), 7.85 (t, J=15.5 Hz, 4H), 7.70 (s, 2H), 3.88 (s, 3H). ES/MS m/z: calculated for $C_{17}H_{14}N_5O_2$ (M+H): 320.11, found: 320.14.

Example 49: 4-(4'-chloro-[1,1'-biphenyl]-4-yl)-1H-1,2,3-triazole-5-carboxylic acid

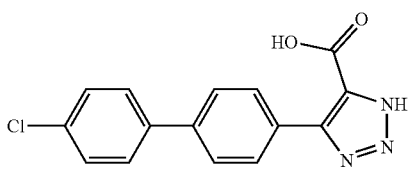 [SMILES: O=C(O)c1[nH]nnc1-c1ccc(-c2ccc(Cl)cc2)cc1]

¹H NMR (400 MHz, Methanol-d₄) δ 7.94 (d, J=8.0 Hz, 1H), 7.76-7.71 (m, 1H), 7.71-7.65 (m, 2H), 7.65-7.55 (m, 1H), 7.61-7.58 (m, 1H), 7.55-7.42 (m, 2H). ES/MS m/z: calculated for $C_{15}H_{11}ClN_3O_2$ (M+H): 300.05, found: 299.97.

Example 50: 4-(3'-chloro-[1,1'-biphenyl]-4-yl)-1H-1,2,3-triazole-5-carboxylic acid

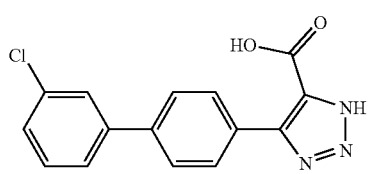 [SMILES: O=C(O)c1[nH]nnc1-c1ccc(-c2cccc(Cl)c2)cc1]

¹H NMR (400 MHz, Methanol-d₄) δ 8.02-7.90 (m, 2H), 7.76-7.66 (m, 3H), 7.65-7.59 (m, 1H), 7.45 (t, J=7.9 Hz, 1H), 7.38 (ddd, J=8.0, 2.1, 1.1 Hz, 1H). ES/MS m/z: calculated for $C_{15}H_{11}ClN_3O_2$ (M+H): 300.05, found: 299.98.

Example 51: 4-(4'-bromo-[1,1'-biphenyl]-4-yl)-1H-1,2,3-triazole-5-carboxylic acid

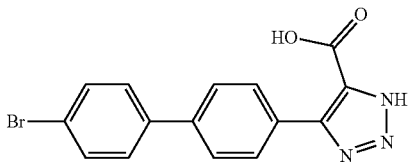

¹H NMR (400 MHz, DMSO-d₆) δ 7.88 (s, 2H), 7.77 (d, J=7.9 Hz, 2H), 7.72-7.60 (m, 4H). ES/MS m/z: calculated for $C_{15}H_{11}BrN_3O_2$ (M+H): 344.00, found: 344.06.

Example 52: 4-(2,4'-dichloro-[1,1'-biphenyl]-4-yl)-1H-1,2,3-triazole-5-carboxylic acid

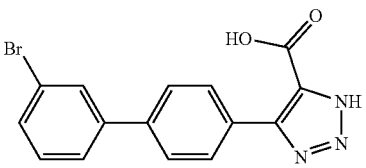

¹H NMR (400 MHz, DMSO-d₆) δ 7.92 (t, J=1.9 Hz, 2H), 7.84-7.69 (m, 3H), 7.58 (dt, J=7.9, 1.4 Hz, 1H), 7.44 (t, J=7.9 Hz, 2H). ES/MS m/z: calculated for $C_{15}H_{11}BrN_3O_2$ (M+H): 344.00, found: 343.95.

Example 53: 4-(4'-methyl-[1,1'-biphenyl]-4-yl)-1H-1,2,3-triazole-5-carboxylic acid

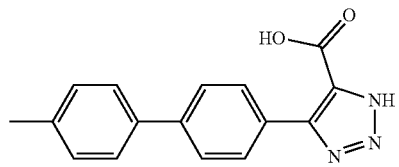

¹H NMR (400 MHz, Methanol-d₄) δ 7.90 (d, J=8.0 Hz, 2H), 7.71 (d, J=8.1 Hz, 2H), 7.61-7.53 (m, 2H), 7.31-7.24 (m, 2H), 2.38 (s, 3H). ES/MS m/z: calculated for $C_{16}H_{14}N_3O_2$ (M+H): 280.10, found: 279.96.

Example 54: 4-(4'-(tert-butyl)-[1,1'-biphenyl]-4-yl)-1H-1,2,3-triazole-5-carboxylic acid

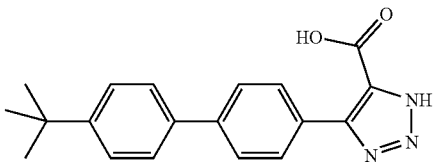 [SMILES: CC(C)(C)c1ccc(-c2ccc(-c3nn[nH]c3C(=O)O)cc2)cc1]

¹H NMR (400 MHz, Methanol-d₄) δ 7.90 (d, J=8.1 Hz, 2H), 7.73 (d, J=8.1 Hz, 2H), 7.66-7.58 (m, 2H), 7.55-7.46

(m, 2H), 1.36 (s, 9H). ES/MS m/z: calculated for $C_{19}H_{20}N_3O_2$ (M+H): 322.15, found: 322.06.

Example 55: 4-(4'-(trifluoromethoxy)-[1,1'-biphenyl]-4-yl)-1H-1,2,3-triazole-5-carboxylic acid

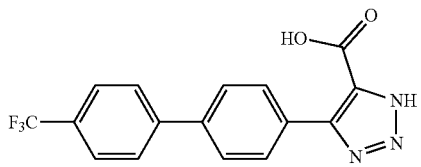

$^1$H NMR (400 MHz, Methanol-$d_4$) δ 7.95 (d, J=8.1 Hz, 2H), 7.78 (d, J=8.8 Hz, 2H), 7.75 (d, J=8.0 Hz, 2H), 7.41-7.34 (m, 2H). ES/MS m/z: calculated for $C_{16}H_{11}F_3N_3O_3$ (M+H): 350.08, found: 350.00.

Example 56: 4-(4'-methoxy-[1,1'-biphenyl]-4-yl)-1H-1,2,3-triazole-5-carboxylic acid

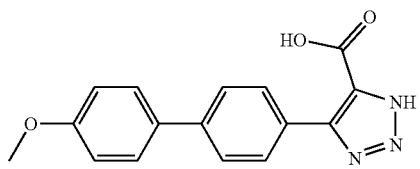

$^1$H NMR (400 MHz, Methanol-$d_4$) δ 7.89 (d, J=8.0 Hz, 2H), 7.69 (d, J=8.1 Hz, 2H), 7.62 (d, J=8.8 Hz, 2H), 7.02 (d, J=8.8 Hz, 2H), 3.84 (s, 3H). ES/MS m/z: calculated for $C_{16}H_{14}N_3O_3$ (M+H): 296.10, found: 296.03.

Example 57: 4-(4'-fluoro-[1,1'-biphenyl]-4-yl)-1H-1,2,3-triazole-5-carboxylic acid

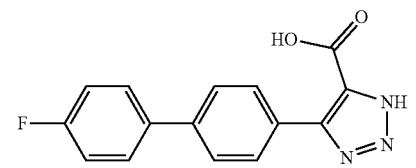

$^1$H NMR (400 MHz, Methanol-$d_4$) δ 7.57-7.48 (m, 2H), 7.43-7.36 (m, 2H), 7.14-7.05 (m, 2H), 6.87-6.80 (m, 2H). ES/MS m/z: Calculated for $C_{15}H_{11}FN_3O_2$ (M+H)=284.08; Found 284.31.

Example 58: 4-(3',4'-dichloro-[1,1'-biphenyl]-4-yl)-1H-1,2,3-triazole-5-carboxylic acid

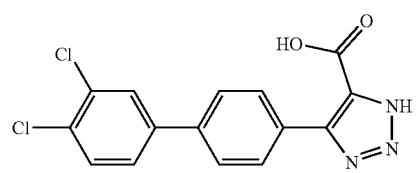

$^1$H NMR (400 MHz, Methanol-$d_4$) δ 7.96 (d, J=7.9 Hz, 2H), 7.87 (d, J=1.7 Hz, 1H), 7.75 (d, J=8.0 Hz, 2H), 7.68-7.58 (m, 2H). ES/MS m/z: calculated for $C_{15}H_{10}Cl_2N_3O_2$ (M+H): 334.02, found: 334.08.

Example 59: 4-(4'-cyano-[1,1'-biphenyl]-4-yl)-1H-1,2,3-triazole-5-carboxylic acid

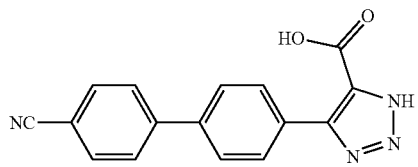

$^1$H NMR (400 MHz, Methanol-$d_4$) δ 8.00 (d, J=7.9 Hz, 2H), 7.93-7.77 (m, 6H). ES/MS m/z: calculated for $C_{16}H_9N_4O_2$ (M−H)=289.07; Found: 289.01.

Example 60: 4-(4'-chloro-3'-fluoro-[1,1'-biphenyl]-4-yl)-1H-1,2,3-triazole-5-carboxylic acid

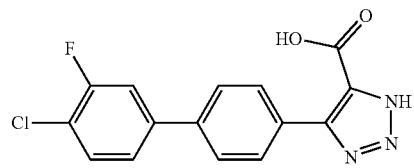 [SMILES: O=C(O)c1[nH]nnc1-c1ccc(-c2ccc(Cl)c(F)c2)cc1]

$^1$H NMR (400 MHz, Methanol-$d_4$) δ 7.96 (d, J=8.1 Hz, 1H), 7.75 (d, J=8.2 Hz, 1H), 7.69-7.48 (m, 5H). ES/MS m/z: calculated for $C_{15}H_8ClFN_3O_2$ (M−H): 316.04, found: 316.09.

Example 61: 4-(3'-chloro-4'-fluoro-[1,1'-biphenyl]-4-yl)-1H-1,2,3-triazole-5-carboxylic acid

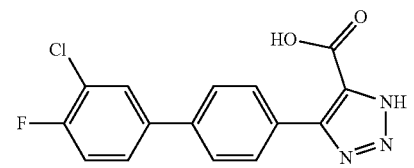 [SMILES: O=C(O)c1[nH]nnc1-c1ccc(-c2ccc(F)c(Cl)c2)cc1]

$^1$H NMR (400 MHz, Methanol-$d_4$) δ 7.95 (d, J=8.3 Hz, 2H), 7.81 (dd, J=7.0, 2.3 Hz, 1H), 7.72 (d, J=8.2 Hz, 2H), 7.65 (ddd, J=8.6, 4.5, 2.3 Hz, 1H), 7.34 (t, J=8.9 Hz, 1H). ES/MS m/z: calculated for $C_{15}H_{10}ClFN_3O_2$ (M+H): 318.04, found: 317.97.

Example 62: 4-(3'-phenoxy-[1,1'-biphenyl]-4-yl)-1H-1,2,3-triazole-5-carboxylic acid

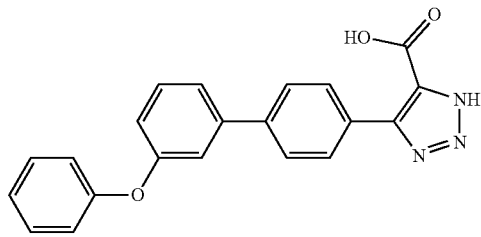 [SMILES: O=C(O)c1[nH]nnc1-c1ccc(-c2cccc(Oc3ccccc3)c2)cc1]

$^1$H NMR (400 MHz, Methanol-$d_4$) δ 7.91 (d, J=7.9 Hz, 2H), 7.68 (d, J=8.2 Hz, 2H), 7.49-7.42 (m, 2H), 7.41-7.31 (m, 2H), 7.29 (dt, J=2.4, 1.0 Hz, 1H), 7.17-7.08 (m, 1H), δ 7.06-7.00 (m, 2H), 7.00-6.95 (m, 1H). ES/MS m/z: calculated for $C_{21}H_{16}N_3O_3$ (M+H): 358.11, found: 358.01.

Example 63: 4-(4'-phenoxy-[1,1'-biphenyl]-4-yl)-1H-1,2,3-triazole-5-carboxylic acid

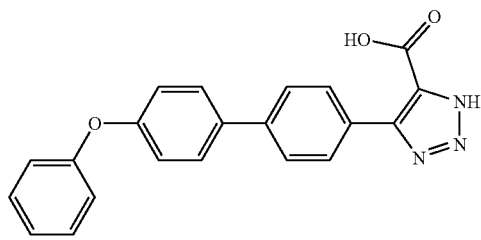

$^1$H NMR (400 MHz, Methanol-$d_4$) δ 7.91 (d, J=8.0 Hz, 2H), 7.78-7.63 (m, 4H), 7.37 (dd, J=8.5, 7.3 Hz, 2H), 7.12 (d, J=7.4 Hz, 1H), 7.09-6.97 (m, 4H). ES/MS m/z: calculated for $C_{21}H_{16}N_3O_3$ (M+H): 358.11, found: 357.98.

Example 64: 4-(4'-(pyridin-2-yloxy)-[1,1'-biphenyl]-4-yl)-1H-1,2,3-triazole-5-carboxylic acid

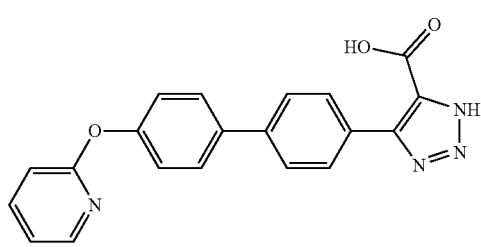

$^1$H NMR (400 MHz, Methanol-$d_4$) δ 8.16 (ddd, J=5.0, 2.0, 0.9 Hz, 1H), 7.93 (d, J=7.8 Hz, 2H), 7.84 (ddd, J=8.3, 7.2, 2.0 Hz, 1H), 7.77-7.68 (m, 4H), 7.27-7.19 (m, 2H), 7.14 (ddd, J=7.2, 5.0, 1.0 Hz, 1H), 6.99 (dt, J=8.3, 0.9 Hz, 1H). ES/MS m/z: calculated for $C_{20}H_{15}N_4O_3$ (M+H): 359.11, found: 359.14.

Example 65: 4-(4'-acetyl-[1,1'-biphenyl]-4-yl)-1H-1,2,3-triazole-5-carboxylic acid

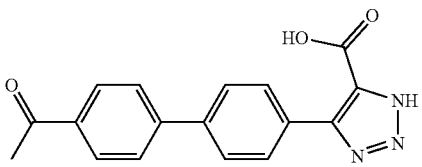 [SMILES: CC(=O)c1ccc(-c2ccc(-c3nn[nH]c3C(=O)O)cc2)cc1]

$^1$H NMR (400 MHz, Methanol-$d_4$) δ 8.14-8.07 (m, 2H), 7.98 (d, J=8.2 Hz, 2H), 7.83 (dd, J=11.8, 8.3 Hz, 4H), 2.65 (s, 3H). ES/MS m/z: Calculated for $C_{17}H_{14}N_3O_3$ (M+H) =308.10; Found 308.00.

Example 66: 4-(3'-carbamoyl-[1,1'-biphenyl]-4-yl)-1H-1,2,3-triazole-5-carboxylic acid

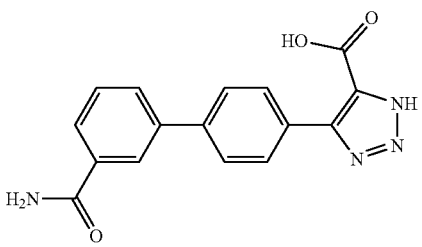 [SMILES: NC(=O)c1cccc(-c2ccc(-c3nn[nH]c3C(=O)O)cc2)c1]

$^1$H NMR (400 MHz, Methanol-$d_4$) δ 8.21 (t, J=1.9 Hz, 1H), 8.01-7.93 (m, 2H), 7.89 (dd, J=7.8, 1.9 Hz, 2H), 7.83-7.74 (m, 2H), 7.58 (t, J=7.8 Hz, 1H). ES/MS m/z: calculated for $C_{16}H_{13}N_4O_3$ (M+H): 309.09, found: 309.09.

Example 67: 4-(3'-(methylcarbamoyl)-[1,1'-biphenyl]-4-yl)-1H-1,2,3-triazole-5-carboxylic acid

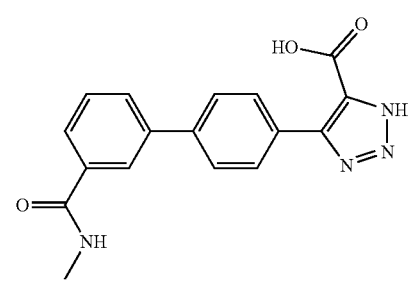 [SMILES: CNC(=O)c1cccc(-c2ccc(-c3nn[nH]c3C(=O)O)cc2)c1]

$^1$H NMR (400 MHz, Methanol-$d_4$) δ 8.14 (t, J=1.8 Hz, 1H), 8.01-7.91 (m, 2H), 7.91-7.74 (m, 4H), 7.56 (t, J=7.8 Hz, 1H), 2.95 (s, 3H). ES/MS m/z: calculated for $C_{17}H_{15}N_4O_3$ (M+H): 323.11, found: 323.12.

Example 68: 4-(4'-carbamoyl-[1,1'-biphenyl]-4-yl)-1H-1,2,3-triazole-5-carboxylic acid

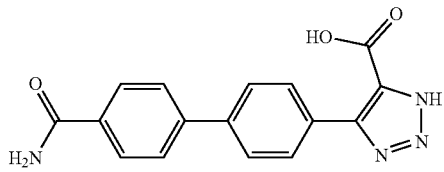

$^1$H NMR (400 MHz, Methanol-d$_4$): δ 7.98 (d, 4H), 7.77 (d, 4H). ES/MS m/z: calculated for C$_{16}$H$_{13}$N$_4$O$_3$ (M+H): 309.09, found: 309.05.

Example 69: 4-(4'-(methylcarbamoyl)-[1,1'-biphenyl]-4-yl)-1H-1,2,3-triazole-5-carboxylic acid

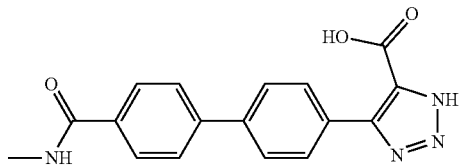 [SMILES: CNC(=O)c1ccc(-c2ccc(-c3nn[nH]c3C(=O)O)cc2)cc1]

$^1$H NMR (400 MHz, Methanol-d$_4$): δ 7.97 (d, J=8.0 Hz, 2H), 7.95-7.87 (m, 2H), 7.84-7.72 (m, 4H), 2.95 (s, 3H). ES/MS m/z: calculated for C$_{17}$H$_{15}$N$_4$O$_3$ (M+H): 323.11, found: 323.16.

Example 70: 4-(4'-(dimethylcarbamoyl)-[1,1'-biphenyl]-4-yl)-1H-1,2,3-triazole-5-carboxylic acid

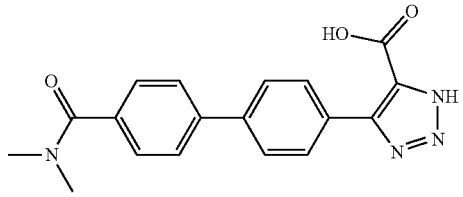 [SMILES: CN(C)C(=O)c1ccc(-c2ccc(-c3nn[nH]c3C(=O)O)cc2)cc1]

$^1$H NMR (400 MHz, Methanol-d$_4$): δ 8.03-7.92 (m, 2H), 7.87-7.74 (m, 4H), 7.60-7.47 (m, 2H), 3.13 (s, 3H), 3.06 (s, 3H). ES/MS m/z: calculated for C$_{18}$H$_{17}$N$_4$O$_3$ (M+H): 337.35, found: 338.06.

Example 71: 4-(4'-carbamoyl-3'-chloro-[1,1'-biphenyl]-4-yl)-1H-1,2,3-triazole-5-carboxylic acid

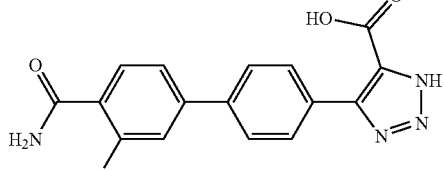

$^1$H NMR (400 MHz, Methanol-d$_4$) δ 7.97 (d, J=8.0 Hz, 2H), 7.86-7.74 (m, 3H), 7.70 (dd, J=8.1, 1.7 Hz, 1H), 7.62 (d, J=8.1 Hz, 1H). ES/MS m/z: calculated for C$_{16}$H$_{12}$ClN$_4$O$_3$ (M+H): 343.05, found: 343.13.

Example 72: 4-(3'-sulfamoyl-[1,1'-biphenyl]-4-yl)-1H-1,2,3-triazole-5-carboxylic acid

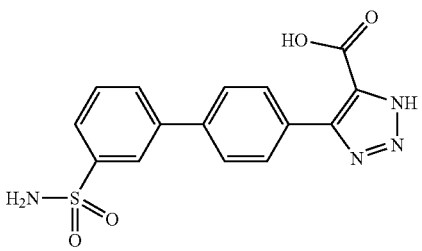 [SMILES: NS(=O)(=O)c1cccc(-c2ccc(-c3nn[nH]c3C(=O)O)cc2)c1]

$^1$H NMR (400 MHz, Methanol-d$_4$) δ 8.22 (t, J=1.8 Hz, 1H), 7.99 (d, J=8.0 Hz, 2H), 7.91 (dtt, J=8.5, 3.6, 1.8 Hz, 2H), 7.84-7.73 (m, 2H), 7.65 (t, J=7.9 Hz, 1H). ES/MS m/z: calculated for C$_{15}$H$_{13}$N$_4$O$_4$S (M−H): 345.06, found: 345.03.

Example 73: 4-(3'-(N,N-dimethylsulfamoyl)-[1,1'-biphenyl]-4-yl)-1H-1,2,3-triazole-5-carboxylic acid

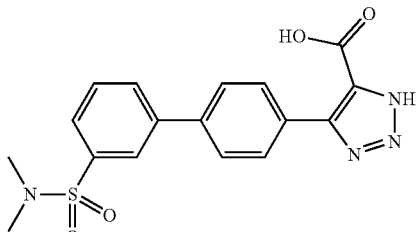

$^1$H NMR (400 MHz, Methanol-d$_4$): δ 8.06-7.97 (m, 4H), 7.85-7.69 (m, 4H), 2.74 (s, 6H). ES/MS m/z: calculated for C$_{17}$H$_{17}$N$_4$O$_4$S (M+H): 373.09, found: 373.11.

Example 74: 4-(3'-(piperidin-1-ylsulfonyl)-[1,1'-biphenyl]-4-yl)-1H-1,2,3-triazole-5-carboxylic acid

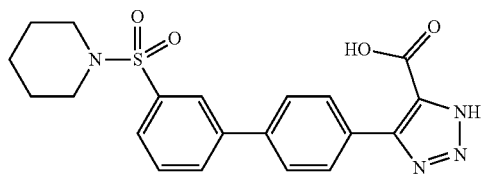 [SMILES: O=C(O)c1[nH]nnc1-c1ccc(-c2cccc(S(=O)(=O)N3CCCCC3)c2)cc1]

$^1$H NMR (400 MHz, DMSO-d$_6$) δ 8.09 (d, J=6.6 Hz, 1H), 7.96 (s, 2H), 7.93-7.79 (m, 3H), 7.77 (d, J=6.6 Hz, 2H), 2.95 (t, J=5.5 Hz, 4H), 1.56 (dt, J=10.7, 5.9 Hz, 4H), 1.42-1.30 (m, 2H). ES/MS m/z: calculated for C$_{20}$H$_{21}$N$_4$O$_4$S (M+H): 413.13, found: 413.17.

Example 75: 4-(3'-(morpholinosulfonyl)-[1,1'-biphenyl]-4-yl)-1H-1,2,3-triazole-5-carboxylic acid

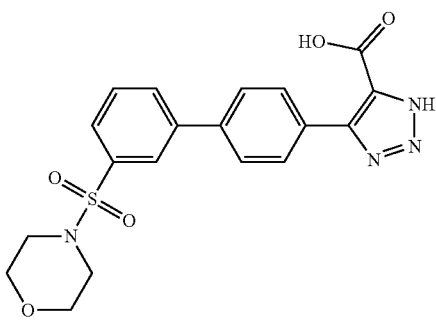 [SMILES: O=C(O)c1[nH]nnc1-c1ccc(-c2cccc(S(=O)(=O)N3CCOCC3)c2)cc1]

$^1$H NMR (400 MHz, Methanol-d$_4$): δ 8.08-7.96 (m, 4H), 7.86-7.65 (m, 4H), 3.78-3.65 (m, 4H), 3.07-2.95 (m, 4H). ES/MS m/z: calculated for C$_{19}$H$_{19}$N$_4$O$_5$S (M+H): 415.10, found: 415.11.

Example 76: 4-(4'-chloro-3'-sulfamoyl-[1,1'-biphenyl]-4-yl)-1H-1,2,3-triazole-5-carboxylic acid

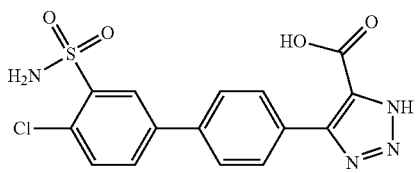 [SMILES: NS(=O)(=O)c1cc(-c2ccc(-c3nn[nH]c3C(=O)O)cc2)ccc1Cl]

10 $^1$H NMR (400 MHz, Methanol-d$_4$) δ 8.35 (d, J=2.3 Hz, 1H), 7.98 (d, J=8.1 Hz, 2H), 7.90-7.83 (m, 1H), 7.82-7.72 (m, 2H), 7.71-7.62 (m, 1H). ES/MS m/z: calculated for C$_{15}$H$_{12}$ClN$_4$O$_3$S (M+H): 379.02, found: 379.07.

Example 77: 4-(4'-sulfamoyl-[1,1'-biphenyl]-4-yl)-1H-1,2,3-triazole-5-carboxylic acid

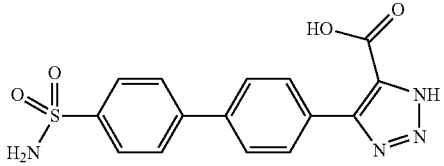

$^1$H NMR (400 MHz, Methanol-d$_4$) δ 7.99 (d, J=8.2 Hz, 4H), 7.86 (d, J=8.2 Hz, 2H), 7.80 (d, J=8.1 Hz, 2H). ES/MS m/z: calculated for C$_{15}$H$_{11}$N$_4$O$_4$S (M−H): 343.06, found: 342.31.

Example 78: 4-(4'-(N,N-dimethylsulfamoyl)-[1,1'-biphenyl]-4-yl)-1H-1,2,3-triazole-5-carboxylic acid

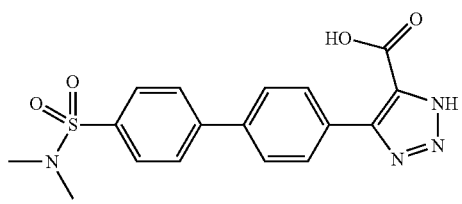 [SMILES: CN(C)S(=O)(=O)c1ccc(-c2ccc(-c3nn[nH]c3C(=O)O)cc2)cc1]

$^1$H NMR (400 MHz, Methanol-d$_4$) δ 8.01 (d, J=8.2 Hz, 2H), 7.96-7.93 (m, 2H), 7.91-7.86 (m, 2H), 7.83 (dd, J=7.6, 5.6 Hz, 2H), 2.73 (s, 6H). ES/MS m/z: calculated for C$_{17}$H$_{17}$N$_4$O$_4$S (M+H): 373.09, found: 373.06.

Example 79: 4-(4'-(piperidin-1-ylsulfonyl)-[1,1'-biphenyl]-4-yl)-1H-1,2,3-triazole-5-carboxylic acid

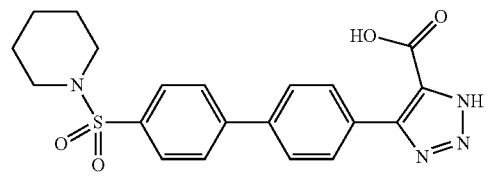 [SMILES: O=C(O)c1[nH]nnc1-c1ccc(-c2ccc(S(=O)(=O)N3CCCCC3)cc2)cc1]

$^1$H NMR (400 MHz, DMSO-d$_6$) δ 8.01 (d, J=8.2 Hz, 2H), 7.97-7.85 (m, 4H), 7.82 (d, J=8.3 Hz, 2H), 2.94 (t, J=5.5 Hz, 4H), 1.56 (p, J=6.2, 5.4 Hz, 4H), 1.45-1.32 (m, 2H). ES/MS m/z: calculated for C$_{20}$H$_{21}$N$_4$O$_4$S (M+H): 413.13, found: 413.10.

Example 80: 4-(4'-(morpholinosulfonyl)-[1,1'-biphenyl]-4-yl)-1H-1,2,3-triazole-5-carboxylic acid

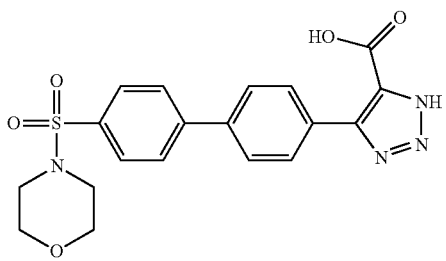 [SMILES: O=C(O)c1[nH]nnc1-c1ccc(-c2ccc(S(=O)(=O)N3CCOCC3)cc2)cc1]

$^1$H NMR (400 MHz, Methanol-d$_4$) δ 8.05-7.93 (m, 4H), 7.93-7.76 (m, 4H), 3.78-3.65 (m, 4H), 3.07-2.96 (m, 4H). ES/MS m/z: calculated for C$_{19}$H$_{19}$N$_4$O$_5$S (M+H): 415.11, found: 415.07.

Example 81: 4-(3'-acetamido-[1,1'-biphenyl]-4-yl)-1H-1,2,3-triazole-5-carboxylic acid

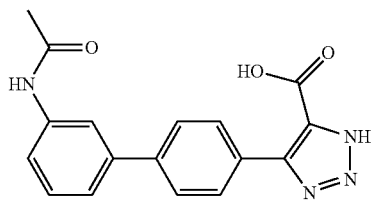 [SMILES: CC(=O)Nc1cccc(-c2ccc(-c3nn[nH]c3C(=O)O)cc2)c1]

¹H NMR (400 MHz, Methanol-d₄): δ 8.06-7.85 (m, 3H), 7.77-7.68 (m, 2H), 7.60-7.51 (m, 1H), 7.47-7.32 (m, 2H), 2.15 (s, 3H). ES/MS m/z: calculated for $C_{17}H_{15}N_4O_3$ (M+H): 323.11, found: 323.13.

Example 82: 4-(4'-acetamido-[1,1'-biphenyl]-4-yl)-1H-1,2,3-triazole-5-carboxylic acid

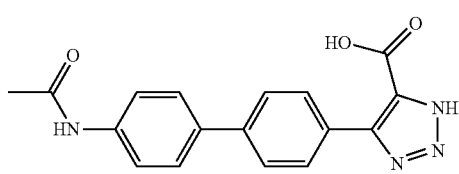 [SMILES: CC(=O)Nc1ccc(-c2ccc(-c3nn[nH]c3C(=O)O)cc2)cc1]

¹H NMR (400 MHz, DMSO-d₆) δ 10.03 (s, 1H), 7.85 (s, 2H), 7.73 (d, J=8.1 Hz, 2H), 7.68 (s, 4H), 2.05 (s, 3H). ES/MS m/z: calculated for $C_{17}H_{15}N_4O_3$ (M+H): 323.11, found: 323.12.

Example 83: 4-(4'-(2-oxopyrrolidin-1-yl)-[1,1'-biphenyl]-4-yl)-1H-1,2,3-triazole-5-carboxylic acid

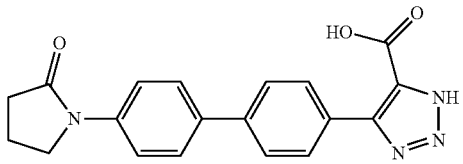 [SMILES: O=C(O)c1[nH]nnc1-c1ccc(-c2ccc(N3CCCC3=O)cc2)cc1]

¹H NMR (400 MHz, DMSO-d₆) δ 7.76 (m, 8H), 3.87 (t, J=7.0 Hz, 2H), 2.52 (d, J=8.0 Hz, 2H), 2.07 (p, J=7.6 Hz, 2H). ES/MS m/z: calculated for $C_{19}H_{17}N_4O_3$ (M+H): 349.12, found: 349.13.

Example 84: 4-(2,4'-dichloro-[1,1'-biphenyl]-4-yl)-1H-1,2,3-triazole-5-carboxylic acid

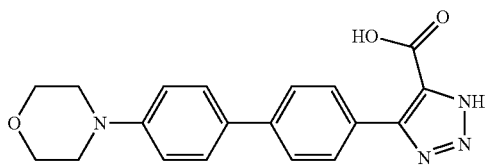 [SMILES: O=C(O)c1[nH]nnc1-c1ccc(-c2ccc(N3CCOCC3)cc2)cc1]

¹H NMR (400 MHz, Methanol-d₄) δ 7.88 (d, J=8.0 Hz, 2H), 7.69 (d, J=8.1 Hz, 2H), 7.61 (d, J=8.7 Hz, 2H), 7.06 (d, J=8.8 Hz, 2H), 3.93-3.81 (m, 4H), 3.23-3.16 (m, 4H). ES/MS m/z: calculated for $C_{19}H_{19}N_4O_2$ (M+H): 351.14, found: 350.01.

Example 85: 4-(4'-chloro-2'-methyl-[1,1'-biphenyl]-4-yl)-1H-1,2,3-triazole-5-carboxylic acid

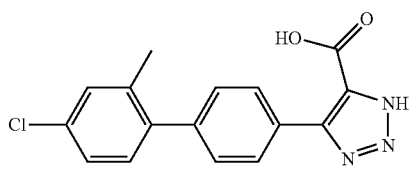 [SMILES: Cc1cc(Cl)ccc1-c1ccc(-c2nn[nH]c2C(=O)O)cc1]

1H NMR (400 MHz, Methanol-d₄) δ 7.94-7.87 (m, 2H), 7.44-7.37 (m, 2H), 7.32 (d, J=2.0 Hz, 1H), 7.29-7.18 (m, 2H), 2.27 (s, 3H). ES/MS m/z: Calculated for $C_{16}H_{13}ClN_3O_2$ (M+H)=314.07; Found 314.01.

Example 86: 4-(9H-fluoren-2-yl)-1H-1,2,3-triazole-5-carboxylic acid

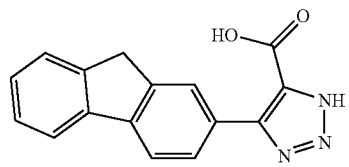 [SMILES: O=C(O)c1[nH]nnc1-c1ccc2c(c1)Cc1ccccc1-2]

¹H NMR (400 MHz, Methanol-d₄) δ 8.02 (s, 1H), 7.94-7.80 (m, 3H), 7.58 (dt, J=7.3, 1.0 Hz, 1H), 7.43-7.29 (m, 2H), 3.97 (s, 2H). ES/MS m/z: calculated for $C_{16}H_{12}N_3O_2$ (M+H): 278.09, found: 278.02.

Example 87: 4-(dibenzo[b,d]furan-3-yl)-1H-1,2,3-triazole-5-carboxylic acid

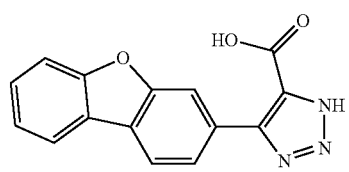 [SMILES: O=C(O)c1[nH]nnc1-c1ccc2c(c1)oc1ccccc12]

¹H NMR (400 MHz, Methanol-d₄) δ 8.16 (dd, J=1.3, 0.6 Hz, 1H), 8.14-8.04 (m, 2H), 7.87 (d, J=8.0 Hz, 1H), 7.61 (dt, J=8.3, 0.9 Hz, 1H), 7.52 (ddd, J=8.4, 7.3, 1.3 Hz, 1H), 7.39 (ddd, J=7.7, 7.2, 1.0 Hz, 1H). ES/MS m/z: calculated for $C_{15}H_{10}N_3O_3$ (M+H): 280.06, found: 280.00.

Example 88: 4-(9H-carbazol-2-yl)-1H-1,2,3-triazole-5-carboxylic acid

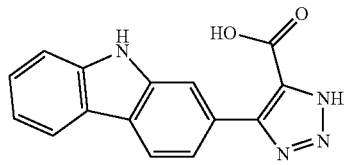 [SMILES: O=C(O)c1[nH]nnc1-c1ccc2c(c1)[nH]c1ccccc12]

¹H NMR (400 MHz, Acetonitrile-d₃) δ 6.77 (dd, J=18.7, 8.0 Hz, 2H), 6.64 (s, 1H), 6.23 (s, 1H), 6.12 (d, J=8.1 Hz, 1H), 6.05 (t, J=7.6 Hz, 1H), 5.83 (t, J=7.4 Hz, 1H). ES/MS m/z: Calculated for $C_{15}H_{11}N_4O_2$ (M+H)=279.09; Found, 279.01.

Example 89: 4-(9-oxo-9H-fluoren-2-yl)-1H-1,2,3-triazole-5-carboxylic acid

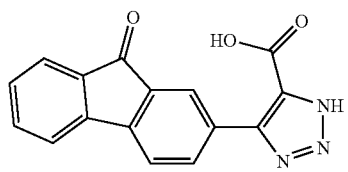 [SMILES: O=C1c2ccccc2-c2ccc(-c3nn[nH]c3C(=O)O)cc21]

¹H NMR (400 MHz, Methanol-d₄) δ 8.11 (d, J=13.5 Hz, 2H), 7.77 (dd, J=14.9, 7.6 Hz, 2H), 7.69-7.53 (m, 2H), 7.39 (t, J=7.3 Hz, 1H). ES/MS m/z: calculated for $C_{16}H_{10}N_3O_3$ (M+H): 292.06, found: 292.08.

Example 90: 4-(9,9-dimethyl-9H-fluoren-2-yl)-1H-1,2,3-triazole-5-carboxylic acid

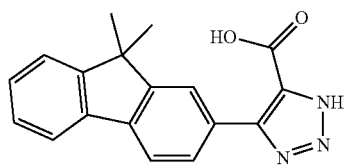 [SMILES: CC1(C)c2ccccc2-c2ccc(-c3nn[nH]c3C(=O)O)cc21]

¹H NMR (400 MHz, Methanol-d₄) δ 7.96 (d, J=1.5 Hz, 1H), 7.88-7.76 (m, 3H), 7.50 (dd, J=5.8, 2.9 Hz, 1H), 7.39-7.29 (m, 2H), 1.51 (s, 6H). ES/MS m/z: Calculated for $C_{18}H_{16}N_3O_2$ (M+H)=306.12; Found 306.06.

Example 91: 4-(4'-chloro-3'-methyl-[1,1'-biphenyl]-4-yl)-1H-1,2,3-triazole-5-carboxylic acid

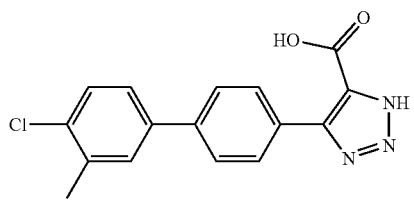 [SMILES: Cc1cc(-c2ccc(-c3nn[nH]c3C(=O)O)cc2)ccc1Cl]

¹H NMR (400 MHz, DMSO-d₆) δ 7.12 (d, J=7.9 Hz, 2H), 6.91 (d, J=8.2 Hz, 2H), 6.81 (d, J=2.3 Hz, 1H), 6.72-6.52 (m, 3H), 1.64 (s, 3H). ES/MS m/z: calculated for $C_{16}H_{11}ClN_3O_2$ (M−H): 312.06, found: 312.08.

Example 92: 4-(4'-carbamoyl-3'-methyl-[1,1'-biphenyl]-4-yl)-1H-1,2,3-triazole-5-carboxylic acid

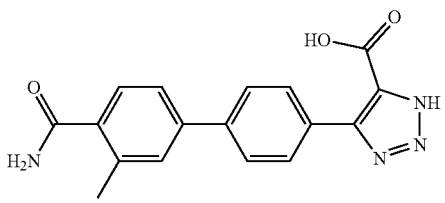 [SMILES: Cc1cc(-c2ccc(-c3nn[nH]c3C(=O)O)cc2)ccc1C(N)=O]

¹H NMR (400 MHz, Methanol-d₄) δ 7.95 (d, J=7.7 Hz, 2H), 7.75 (d, J=8.1 Hz, 2H), 7.62-7.45 (m, 3H), 2.53 (s, 3H). ES/MS m/z: calculated for $C_{17}H_{15}N_4O_3$ (M+H): 323.11, found: 323.10.

Example 93: 4-(4-(1-oxo-1,2,3,4-tetrahydroisoquinolin-6-yl)phenyl)-1H-1,2,3-triazole-5-carboxylic acid

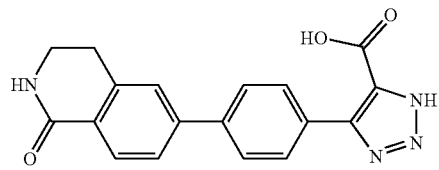 [SMILES: O=C1NCCc2cc(-c3ccc(-c4nn[nH]c4C(=O)O)cc3)ccc21]

¹H NMR (400 MHz, Methanol-d₄) δ 8.01 (t, J=7.3 Hz, 2H), 7.79 (d, J=8.0 Hz, 3H), 7.74-7.63 (m, 2H), 3.55 (t, J=6.7 Hz, 2H), 3.08 (t, J=6.6 Hz, 2H). ES/MS m/z: calculated for $C_{18}H_{15}N_4O_3$ (M+H): 335.11, found: 335.16.

Example 94: 4-(4-(1-oxo-1,2,3,4-tetrahydroisoquinolin-6-yl)phenyl)-1H-pyrazole-5-carboxylic acid

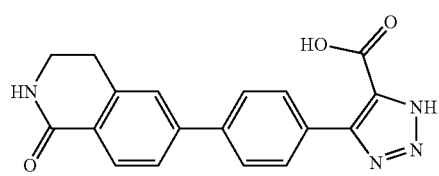

¹H NMR (400 MHz, DMSO-d₆) δ 7.89 (d, J=8.1 Hz, 2H), 7.77-7.56 (m, 5H), 3.40 (dt, J=7.2, 3.6 Hz, 2H), 2.97 (t, J=6.6 Hz, 2H). ES/MS m/z: calculated for $C_{19}H_{16}N_3O_3$ (M+H): 334.11, found: 334.13.

Example 95: 4-(4-(3-methyl-1-oxo-1,2,3,4-tetrahydroisoquinolin-6-yl)phenyl)-1H-1,2,3-triazole-5-carboxylic acid

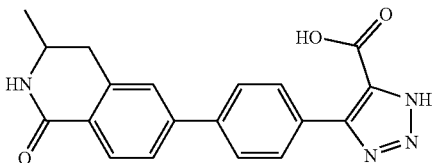 [SMILES: CC1Cc2cc(-c3ccc(-c4nn[nH]c4C(=O)O)cc3)ccc2C(=O)N1]

¹H NMR (400 MHz, Methano-d₄) δ 8.01 (d, J=8.1 Hz, 1H), 7.99-7.93 (m, 2H), 7.82-7.75 (m, 2H), 7.69 (dd, J=8.1, 1.8 Hz, 1H), 7.62 (d, J=1.7 Hz, 1H), 3.84 (dqd, J=12.9, 6.5, 4.6 Hz, 1H), 3.11 (dd, J=15.8, 4.5 Hz, 1H), 2.84 (dd, J=15.7, 10.1 Hz, 1H), 1.33 (d, J=6.5 Hz, 3H). ES/MS m/z: calculated for $C_{19}H_{17}O_3$ (M+H): 349.13, found: 349.10.

Example 96: 4-(4-(2-methyl-1-oxo-1,2,3,4-tetrahydroisoquinolin-6-yl)phenyl)-1H-1,2,3-triazole-5-carboxylic acid

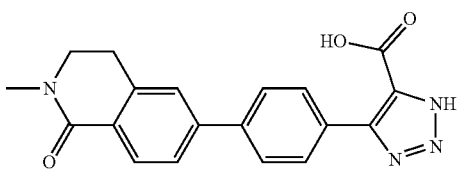 [SMILES: CN1CCc2cc(-c3ccc(-c4nn[nH]c4C(=O)O)cc3)ccc2C1=O]

¹H NMR (400 MHz, DMSO-d₆) δ 13.14 (s, 1H), 7.96 (d, J=8.1 Hz, 1H), 7.85 (m, 4H), 7.72 (dd, J=8.2, 1.8 Hz, 1H), 7.69 (s, 2H), 3.59 (t, J=6.6 Hz, 2H), 3.07 (t, J=6.6 Hz, 2H), 3.05 (s, 3H). ES/MS m/z: calculated for $C_{19}H_{17}N_4O_3$ (M+H): 349.13, found: 349.09.

Example 97: 4-(4-(1-oxoisoindolin-5-yl)phenyl)-1H-1,214,3-triazole-5-carboxylic acid

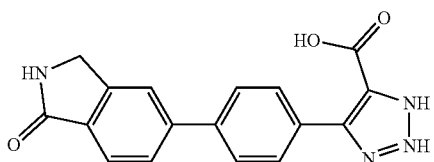

¹H NMR (400 MHz, Methanol-d₄): δ 8.00 (m, 3H), 7.94-7.77 (m, 4H), 4.55 (s, 2H). ES/MS m/z: calculated for $C_{17}H_{13}N_4O_3$ (M+H): 321.09, found: 321.07.

Example 98: 4-(4-(3,3-dimethyl-1-oxoisoindolin-5-yl)phenyl)-1H-1,214,3-triazole-5-carboxylic acid

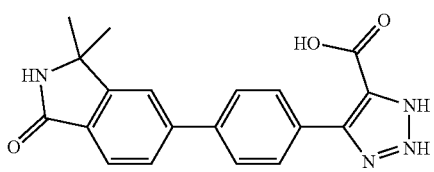 [SMILES: CC1(C)NC(=O)c2ccc(-c3ccc(-c4nn[nH]c4C(=O)O)cc3)cc21]

¹H NMR (400 MHz, Methanol-d₄) δ 7.98 (d, J=8.0 Hz, 2H), 7.90-7.76 (m, 5H), 1.60 (s, 6H). ES/MS m/z: Calculated for $C_{19}H_{18}N_4O_3$ (M+H)=349.13; Found 349.13

Example 99: 4-([1,1'3',1''-terphenyl]-4-yl)-1H-1,2,3-triazole-5-carboxylic acid

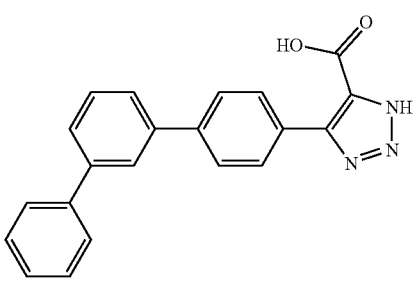 [SMILES: O=C(O)c1[nH]nnc1-c1ccc(-c2cccc(-c3ccccc3)c2)cc1]

¹H NMR (400 MHz, DMSO-d₆) δ 8.06-7.83 (m, 5H), 7.81-7.76 (m, 2H), 7.73-7.62 (m, 2H), 7.57 (t, J=7.7 Hz, 1H), 7.48 (dd, J=8.4, 6.9 Hz, 2H), 7.43-7.30 (m, 1H). ES/MS m/z: calculated for $C_{21}H_{16}N_3O_2$ (M+H): 342.12, found: 342.01.

Example 100: 4-([1,1':4',1''-terphenyl]-4-yl)-1H-1,2,3-triazole-5-carboxylic acid

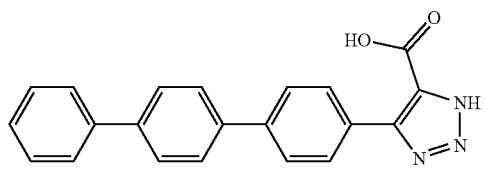 [SMILES: O=C(O)c1[nH]nnc1-c1ccc(-c2ccc(-c3ccccc3)cc2)cc1]

¹H NMR (400 MHz, DMSO-d₆) δ 7.97-7.63 (m, 10H), 7.48 (t, J=7.6 Hz, 2H), 7.46-7.25 (m, 2H). ES/MS m/z: calculated for $C_{21}H_{14}N_3O_2$ (M−H): 340.12, found: 339.95.

Example 101: 4-(4'-(pyridin-2-yl)-[1,1'-biphenyl]-4-yl)-1H-1,2,3-triazole-5-carboxylic acid

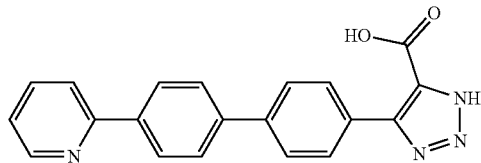 [SMILES: O=C(O)c1[nH]nnc1-c1ccc(-c2ccc(-c3ccccn3)cc2)cc1]

¹H NMR (400 MHz, Methanol-d₄) δ 8.83 (d, J=5.3 Hz, 1H), 8.62 (s, 2H), 8.41 (d, J=9.3 Hz, 1H), 8.17-7.93 (m, 6H), 7.87 (d, J=9.7 Hz, 2H). ES/MS m/z: calculated for $C_{20}H_{15}N_4O_2$ (M+H): 343.11, found: 343.15.

Example 102: 4-(4'-(pyridin-3-yl)-[1,1'-biphenyl]-4-yl)-1H-1,2,3-triazole-5-carboxylic acid

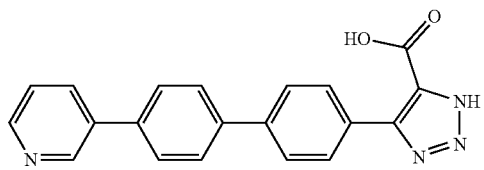

¹H NMR (400 MHz, Methanol-d₄) δ 9.04 (s, 1H), 8.67 (d, J=5.0 Hz, 1H), 8.56-8.50 (m, 1H), 7.99 (d, J=8.1 Hz, 2H), 7.94-7.86 (m, 4H), 7.83 (d, J=8.1 Hz, 3H). ES/MS m/z: calculated for $C_{20}H_{15}N_4O_2$ (M+H): 343.12, found: 343.13.

Example 103: 4-(4'-(pyridin-4-yl)-[1,1'-biphenyl]-4-yl)-1H-1,2,3-triazole-5-carboxylic acid

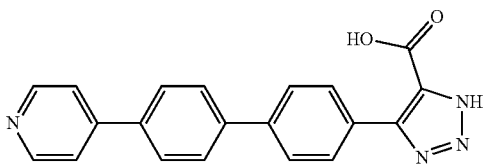 [SMILES: O=C(O)c1[nH]nnc1-c1ccc(-c2ccc(-c3ccncc3)cc2)cc1]

¹H NMR (400 MHz, Methanol-d₄) δ 8.79 (d, J=6.1 Hz, 2H), 8.30-8.23 (m, 2H), 8.07 (d, J=8.2 Hz, 2H), 8.02 (d, J=8.0 Hz, 2H), 7.97 (d, J=8.3 Hz, 2H), 7.86 (d, J=8.3 Hz, 2H). ES/MS m/z: calculated for $C_{20}H_{15}N_4O_2$ (M+H): 343.12, found: 343.13.

Example 104: 4-(4'-(pyrimidin-2-yl)-[1,1'-biphenyl]-4-yl)-1H-1,2,3-triazole-5-carboxylic acid

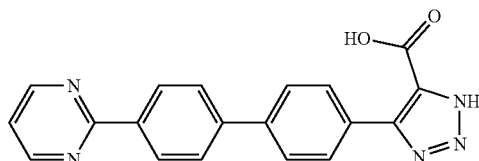

¹H NMR (400 MHz, Methanol-d₄) δ 8.87 (d, J=4.8 Hz, 2H), 8.52 (d, J=8.5 Hz, 2H), 7.98 (s, 2H), 7.85 (dd, J=8.2, 6.4 Hz, 4H), 7.37 (t, J=4.9 Hz, 1H). ES/MS m/z: Calculated for $C_{19}H_{14}N_5O_2$ (M+H)=344.11; Found 344.03

Example 105: 4-(4'-(1-methyl-1H-1,2,3-triazol-4-yl)-[1,1'-biphenyl]-4-yl)-1H-1,2,3-triazole-5-carboxylic acid

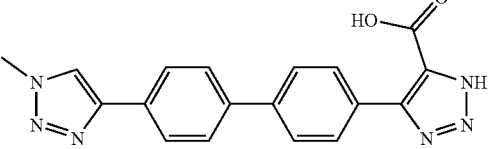

¹H NMR (400 MHz, Methanol-d₄) δ 8.33 (s, 1H), 7.95 (dd, J=14.0, 8.3 Hz, 4H), 7.79 (d, J=8.2 Hz, 4H), 4.18 (s, 3H). ES/MS m/z: Calculated for $C_{18}H_{15}N_6O_2$ (M+H)= 347.13; Found 347.14.

Example 106: 4-(4'-(1-methyl-1H-1,2,4-triazol-3-yl)-[1,1'-biphenyl]-4-yl)-1H-1,2,3-triazole-5-carboxylic acid

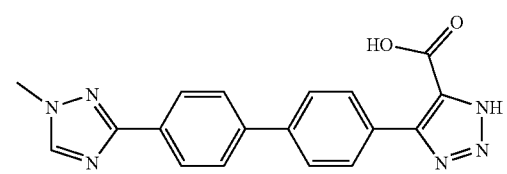 [SMILES: Cn1cnc(-c2ccc(-c3ccc(-c4nn[nH]c4C(=O)O)cc3)cc2)n1]

¹H NMR (400 MHz, DMSO-d₆) δ 8.53 (s, 1H), 8.14-8.04 (m, 2H), 7.84 (d, J=8.7 Hz, 6H), 3.93 (s, 3H). ES/MS m/z: calculated for $C_{18}H_{15}N_6O_2$ (M+H): 347.12, found: 347.10.

Example 107: 4-(4'-(1-methyl-1H-pyrazol-3-yl)-[1,1'-biphenyl]-4-yl)-1H-1,2,3-triazole-5-carboxylic acid

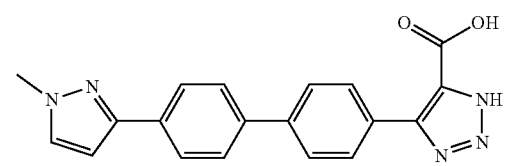 [SMILES: Cn1ccc(-c2ccc(-c3ccc(-c4nn[nH]c4C(=O)O)cc3)cc2)n1]

¹H NMR (400 MHz, DMSO-d₆) δ 7.96-7.87 (m, 4H), 7.83 (d, J=8.0 Hz, 2H), 7.78 (d, J=8.3 Hz, 2H), 7.76 (d, J=2.2 Hz, 1H), 6.76 (d, J=2.3 Hz, 1H), 3.91 (s, 3H). ES/MS m/z: calculated for $C_{19}H_{16}N_5O_2$ (M+H): 346.13, found: 346.15.

Example 108: 4-(4'-(thiazol-2-yl)-[1,1'-biphenyl]-4-yl)-1H-1,2,3-triazole-5-carboxylic acid

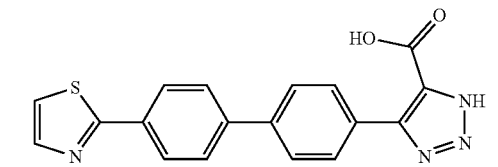 [SMILES: O=C(O)c1[nH]nnc1-c1ccc(-c2ccc(-c3nccs3)cc2)cc1]

¹H NMR (400 MHz, Methanol-d₄) δ 8.07 (d, J=8.4 Hz, 2H), 7.97 (d, J=7.7 Hz, 2H), 7.89 (d, J=3.3 Hz, 1H), 7.83 (t, J=8.7 Hz, 4H), 7.63 (d, J=3.3 Hz, 1H). ES/MS m/z: calculated for $C_{18}H_{13}N_4O_2S$ (M+H): 349.07, found: 349.03.

Example 109: 4-(4'-(5-methylthiazol-2-yl)-[1,1'-biphenyl]-4-yl)-1H-1,2,3-triazole-5-carboxylic acid

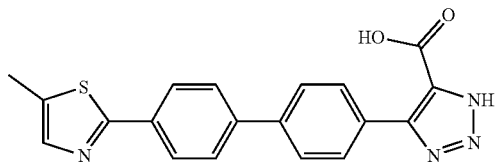 [SMILES: Cc1cnc(-c2ccc(-c3ccc(-c4nn[nH]c4C(=O)O)cc3)cc2)s1]

$^1$H NMR (400 MHz, DMSO-d$_6$): δ 8.03-7.74 (m, 8H), 7.62 (s, 1H), 2.50 (s, 3H). ES/MS m/z: calculated for C$_{19}$H$_{15}$N$_4$O$_2$S (M+H): 362.08, found: 362.11.

Example 110: 4-(4'-(5-(trifluoromethyl)thiazol-2-yl)-[1,1'-biphenyl]-4-yl)-1H-1,2,3-triazole-5-carboxylic acid

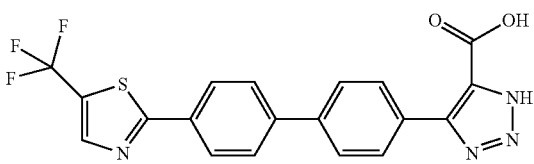

$^1$H NMR (400 MHz, DMSO-d$_6$) δ 8.58 (s, 1H), 8.15 (d, J=8.0 Hz, 2H), 7.97 (d, J=8.0 Hz, 2H), 7.94-7.85 (m, 4H). ES/MS m/z: calculated for C$_{19}$H$_{12}$F$_3$N$_4$O$_2$S (M+H): 417.06, found: 417.00.

Example 111: 4-(4'-(5-methyl-1,3,4-thiadiazol-2-yl)-[1,1'-biphenyl]-4-yl)-1H-1,2,3-triazole-5-carboxylic acid

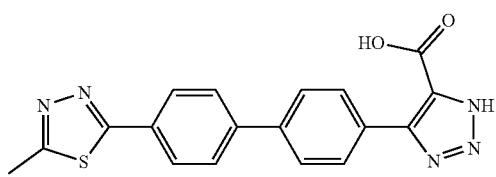 [SMILES: Cc1nnc(-c2ccc(-c3ccc(-c4nn[nH]c4C(=O)O)cc3)cc2)s1]

$^1$H NMR (400 MHz, DMSO-d$_6$) δ 8.03 (d, J=6.5 Hz, 1H), 8.00 (d, J=16.3 Hz, 2H), 7.96-7.89 (m, 3H), 7.85 (d, J=8.3 Hz, 2H), 2.78 (s, 3H). ES/MS m/z: calculated for C$_{18}$H$_{12}$N$_5$O$_2$S (M−H): 362.07, found: 362.03.

Example 112: 4-(4'-(oxazol-2-yl)-[1,1'-biphenyl]-4-yl)-1H-1,2,3-triazole-5-carboxylic acid

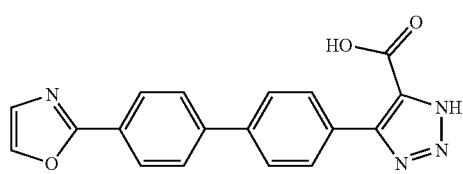 [SMILES: O=C(O)c1[nH]nnc1-c1ccc(-c2ccc(-c3ncco3)cc2)cc1]

$^1$H NMR (400 MHz, Methanol-d$_4$) δ 8.13 (s, 1H), δ 8.09-7.91 (m, 4H), δ 7.91-7.77 (m, 3H), δ 7.39-7.28 (s, 2H). ES/MS m/z: Calculated for C$_{18}$H$_{13}$N$_4$O$_3$ (M+H)=333.10; Found 333.00.

Example 113: 4-(4'-(isoxazol-3-yl)-[1,1'-biphenyl]-4-yl)-1H-1,2,3-triazole-5-carboxylic acid

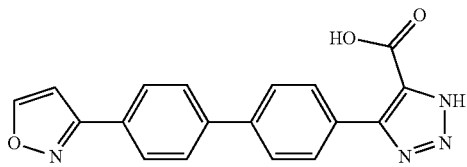 [SMILES: O=C(O)c1[nH]nnc1-c1ccc(-c2ccc(-c3ccon3)cc2)cc1]

$^1$H NMR (400 MHz, DMSO-d$_6$) δ 9.02 (d, J=1.7 Hz, 1H), 8.07-7.97 (m, 3H), 7.93-7.86 (m, 5H), 7.24-7.19 (m, 1H). ES/MS m/z: Calculated for C$_{18}$H$_{13}$N$_4$O$_3$ (M+H)=333.10; Found 333.05.

Example 114: 4-(4'-(4-methylthiazol-2-yl)-[1,1'-biphenyl]-4-yl)-1H-1,2,3-triazole-5-carboxylic acid

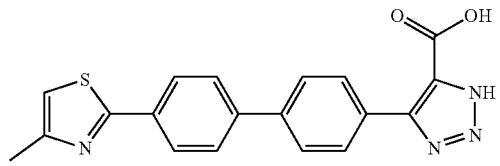 [SMILES: Cc1csc(-c2ccc(-c3ccc(-c4nn[nH]c4C(=O)O)cc3)cc2)n1]

$^1$H NMR (400 MHz, DMSO-d$_6$) δ 8.03 (d, J=8.4 Hz, 2H), 7.95 (d, J=8.0 Hz, 2H), 7.87 (t, J=7.9 Hz, 4H), 7.36 (d, J=1.2 Hz, 1H), 3.33 (s, 3H). ES/MS m/z: calculated for C$_{19}$H$_{15}$N$_4$O$_2$S (M+H): 363.09, found: 363.08.

Example 115: 4-(4'-(2-methyl-2H-1,2,3-triazol-4-yl)-[1,1'-biphenyl]-4-yl)-1H-1,2,3-triazole-5-carboxylic acid

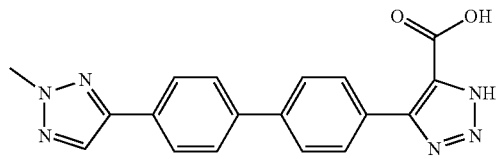

$^1$H NMR (400 MHz, DMSO-d$_6$) δ 8.30 (s, 1H), 7.95 (t, J=7.0 Hz, 4H), 7.90-7.80 (m, 4H), 4.22 (s, 3H). ES/MS m/z: calculated for C$_{18}$H$_{15}$N$_6$O$_2$ (M+H): 347.13, found: 347.02.

Example 116: 4-(4'-(thiazol-5-yl)-[1,1'-biphenyl]-4-yl)-1H-1,2,3-triazole-5-carboxylic acid

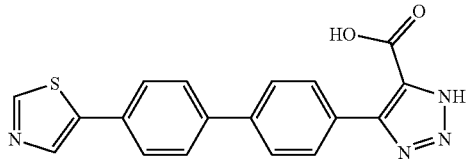 [SMILES: O=C(O)c1[nH]nnc1-c1ccc(-c2ccc(-c3cncs3)cc2)cc1]

¹H NMR (400 MHz, DMSO-d₆) δ 9.10 (s, 1H), 8.39 (s, 1H), 7.81 (q, J=8.4 Hz, 8H). ES/MS m/z: calculated for C₁₈H₁₃N₄O₂S (M+H): 349.07, found: 348.96.

Example 117: 4-(4'-(1,5-dimethyl-1H-pyrazol-3-yl)-[1,1'-biphenyl]-4-yl)-1H-1,2,3-triazole-5-carboxylic acid

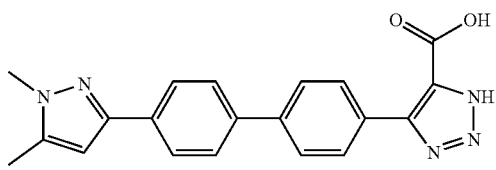 [SMILES: Cc1cc(-c2ccc(-c3ccc(-c4nn[nH]c4C(=O)O)cc3)cc2)nn1C]

¹H NMR (400 MHz, DMSO-d₆) δ 7.92 (d, J=8.1 Hz, 2H), 7.88-7.79 (m, 4H), 7.76 (d, J=8.2 Hz, 2H), 6.54 (s, 1H), 3.78 (s, 3H), 2.30 (s, 3H). ES/MS m/z: calculated for C₂₀H₁₈N₅O₂ (M+H): 360.15, found: 360.16.

Example 118: 4-(4'-(1,5-dimethyl-1H-1,2,3-triazol-4-yl)-[1,1'-biphenyl]-4-yl)-1H-1,2,3-triazole-5-carboxylic acid

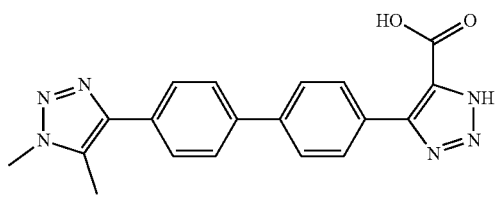 [SMILES: Cc1c(-c2ccc(-c3ccc(-c4nn[nH]c4C(=O)O)cc3)cc2)nnn1C]

10 ¹H NMR (400 MHz, DMSO-d₆) δ 13.13 (s, 1H), 7.95-7.90 (m, 1H), 7.89-7.75 (m, 8H), 4.00 (s, 3H), 2.51 (s, 3H). ES/MS m/z: calculated for C₁₉H₁₇N₆O₂ (M+H): 361.14, found: 361.13.

Example 119: 4-(4'-(1H-pyrazol-1-yl)-[1,1'-biphenyl]-4-yl)-1H-1,2,3-triazole-5-carboxylic acid

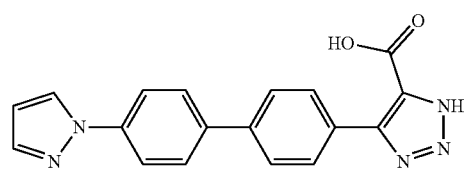 [SMILES: O=C(O)c1[nH]nnc1-c1ccc(-c2ccc(-n3cccn3)cc2)cc1]

¹H NMR (400 MHz, Methanol-d₄) δ 8.28 (d, J=2.4 Hz, 1H), 7.96 (d, J=7.8 Hz, 2H), 7.91-7.62 (m, 6H), 6.56 (d, J=2.4 Hz, 2H). ES/MS m/z: Calculated for C₁₈H₁₄N₅O₂ (M+H): 332.11; Found 332.14.

Example 120: 4-(4'-(1H-1,2,3-triazol-1-yl)-[1,1'-biphenyl]-4-yl)-1H-1,2,3-triazole-5-carboxylic acid

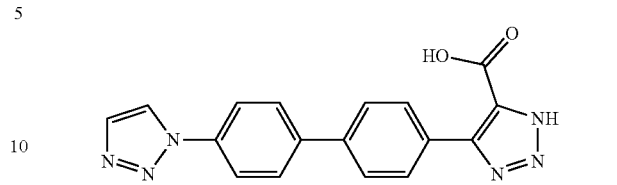

¹H NMR (400 MHz, Methanol-d₄) δ 8.59 (s, 1H), 8.07 (s, 2H), 8.01-7.85 (m, 5H), 7.79 (d, J=8.2 Hz, 2H). ES/MS m/z: Calculated for C₁₇H₁₃N₆O₂ (M+H)=333.11; Found 333.11.

Example 121: 4-(4'-(5-methyl-1H-1,2,3-triazol-1-yl)-[1,1'-biphenyl]-4-yl)-1H-1,2,3-triazole-5-carboxylic acid

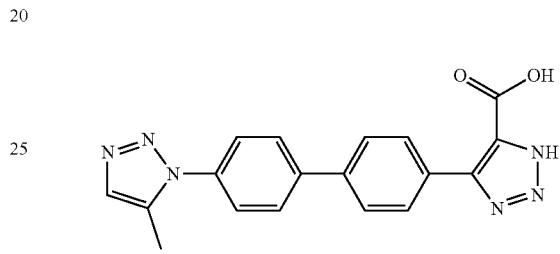

¹H NMR (400 MHz, Methanol-d₄) δ 8.01 (d, J=8.0 Hz, 2H), 7.97-7.90 (m, 2H), 7.83 (d, J=8.2 Hz, 2H), 7.70-7.61 (m, 3H), 2.42 (d, J=0.9 Hz, 3H). ES/MS m/z: calculated for C₁₈H₁₅N₆O₂ (M+H): 347.13, found: 347.09.

Example 122: 4-(4'-(benzo[d]thiazol-2-yl)-[1,1'-biphenyl]-4-yl)-1H-1,2,3-triazole-5-carboxylic acid

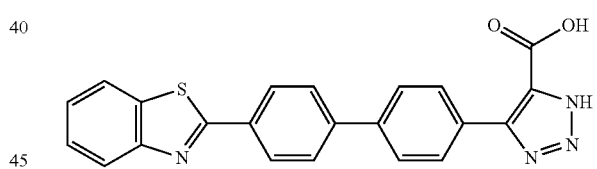

¹H NMR (400 MHz, DMSO-d₆) δ 8.20 (d, J=8.2 Hz, 2H), 8.16 (d, J=8.0 Hz, 1H), 8.08 (d, J=8.1 Hz, 1H), 7.96 (d, J=8.2 Hz, 5H), 7.88 (d, J=8.3 Hz, 2H), 7.55 (t, J=7.6 Hz, 1H), 7.47 (t, J=7.6 Hz, 1H). ES/MS m/z: calculated for C₂₂H₁₅N₄O₂S (M+H): 399.09, found: 399.08.

Example 123: 4,4'-([1,1'-biphenyl]-4,4'-diyl)bis(1H-1,2,3-triazole-5-carboxylic acid)

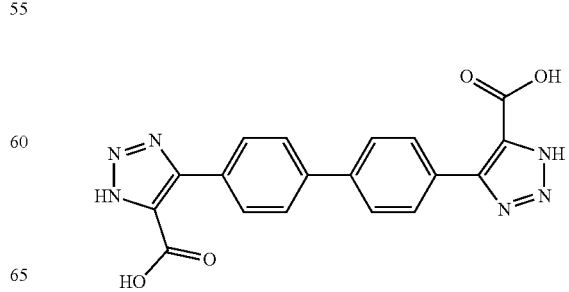

4,4'-([1,1'-biphenyl]-4,4'-diyl)bis(1H-1,2,3-triazole-5-carboxylic acid) was prepared from ethyl 5-bromo-2-(4-methoxybenzyl)-2H-1,2,3-triazole-4-carboxylate (11) and ethyl 2-(4-methoxybenzyl)-5-(4'-(4,4,5,5-tetramethyl-1,3,2-dioxaborolan-2-yl)-[1,1'-biphenyl]-4-yl)-2H-1,2,3-triazole-4-carboxylate (13) in a manner similar to the general procedures of Suzuki reaction, followed by PMB deprotection and ester hydrolysis: $^1$H NMR (400 MHz, DMSO-$d_6$) δ 7.95 (s, 4H), 7.86 (d, J=8.1 Hz, 4H). ES/MS m/z: calculated for $C_{18}H_{13}N_6O_4$ (M+H): 377.10, found: 377.03.

Example 181: 4-(4'-(5,6-dihydro-4H-cyclopenta[d]thiazol-2-yl)-[1,1'-biphenyl]-4-yl)-1H-1,2,3-triazole-5-carboxylic acid

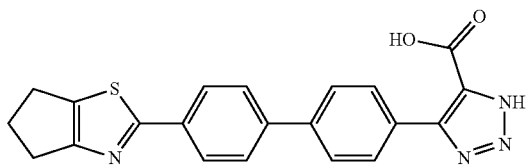 [SMILES: O=C(O)c1[nH]nnc1-c1ccc(-c2ccc(-c3nc4c(s3)CCC4)cc2)cc1]

$^1$H NMR (400 MHz, DMSO-$d_6$) δ 7.99 (d, J=8.1 Hz, 2H), 7.86 (m, 6H), 3.17 (s, 2H), 2.96 (s, 2H), 2.89-2.78 (m, 2H). ES/MS m/z: calculated for $C_{21}H_{17}N_4O_2S$ (M+H): 389.11, found: 389.11.

The following compounds were prepared in a manner similar to the representative procedures of Suzuki reaction and SEM or PMB deprotections described above, followed by ester hydrolysis using previously mentioned boronate intermediates, 6 or 8, with commercially available bromides containing heterocycle after SEM protection of the heterocyclic N—H:

Example 124: 4-(4'-(1H-pyrazol-4-yl)-[1,1'-biphenyl]-4-yl)-1H-1,2,3-triazole-5-carboxylic acid

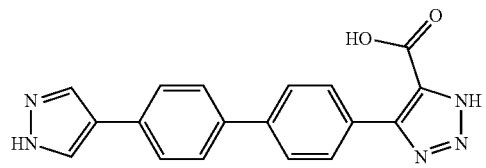 [SMILES: O=C(O)c1[nH]nnc1-c1ccc(-c2ccc(-c3cn[nH]c3)cc2)cc1]

$^1$H NMR (400 MHz, DMSO-$d_6$) δ 8.11 (s, 2H), 7.79 (d, J=14.4 Hz, 4H), 7.72 (s, 4H). ES/MS m/z: calculated for $C_{18}H_{14}N_5O_2$ (M+H): 332.11, found: 332.07.

Example 125: 4-(4'-(1H-pyrazol-5-yl)-[1,1'-biphenyl]-4-yl)-1H-1,2,3-triazole-5-carboxylic acid

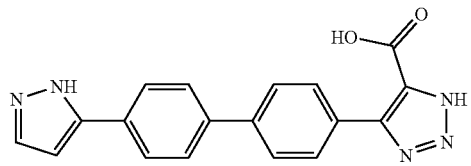 [SMILES: O=C(O)c1[nH]nnc1-c1ccc(-c2ccc(-c3ccn[nH]3)cc2)cc1]

$^1$H NMR (400 MHz, DMSO-$d_6$) δ 7.99-7.86 (m, 4H), 7.88-7.74 (m, 4H), 7.72 (d, J=2.2 Hz, 1H), 6.76 (t, J=2.3 Hz, 1H). ES/MS m/z: calculated for $C_{18}H_{14}N_5O_2$ (M+H): 332.11, found: 332.11.

Example 126: 4-(4-(1H-benzo[d]imidazol-5-yl)phenyl)-1H-1,2,3-triazole-5-carboxylic acid

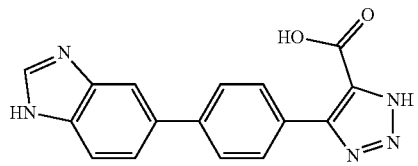 [SMILES: O=C(O)c1[nH]nnc1-c1ccc(-c2ccc3[nH]cnc3c2)cc1]

$^1$H NMR (400 MHz, Methanol-$d_4$) δ 9.31 (s, 1H), 8.09 (dd, J=1.6, 0.8 Hz, 1H), 8.03 (d, J=1.8 Hz, 1H), 8.02-7.89 (m, 3H), 7.88-7.79 (m, 2H). ES/MS m/z: calculated for $C_{16}H_{12}N_5O_3$ (M+H): 306.09, found: 306.14.

Example 127: 4-(4'-(1H-1,2,3-triazol-5-yl)-[1,1'-biphenyl]-4-yl)-1H-1,2,3-triazole-5-carboxylic acid

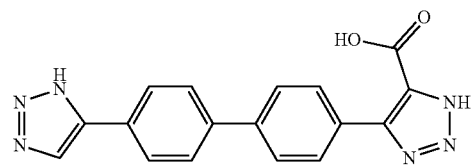 [SMILES: O=C(O)c1[nH]nnc1-c1ccc(-c2ccc(-c3cnn[nH]3)cc2)cc1]

$^1$H NMR (400 MHz, Methanol-$d_4$) δ 7.96 (d, J=7.6 Hz, 4H), 7.80 (d, J=7.9 Hz, 5H). ES/MS m/z: calculated for $C_{16}H_{12}N_5O_3$ (M+H): 333.10, found: 333.07.

Example 128: 4-(4'-(1H-imidazol-2-yl)-[1,1'-biphenyl]-4-yl)-1H-1,2,3-triazole-5-carboxylic acid

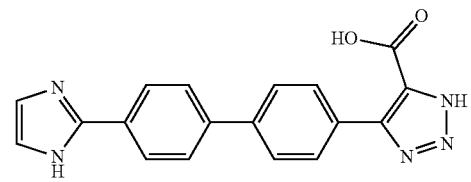 [SMILES: O=C(O)c1[nH]nnc1-c1ccc(-c2ccc(-c3ncc[nH]3)cc2)cc1]

$^1$H NMR (400 MHz, Methanol-$d_4$) δ 7.29-7.05 (m, 4H), 6.95-6.62 (m, 6H). ES/MS m/z: Calculated for $C_{18}H_{14}N_5O_2$ (M+H)=332.11; Found 332.12.

Example 129: 4-(4'-(1H-imidazol-4-yl)-[1,1'-biphenyl]-4-yl)-1H-1,2,3-triazole-5-carboxylic acid

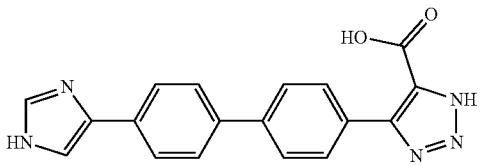 [SMILES: O=C(O)c1[nH]nnc1-c1ccc(-c2ccc(-c3c[nH]cn3)cc2)cc1]

¹H NMR (400 MHz, Methanol-d₄): δ 9.02 (d, J=1.4 Hz, 1H), 8.10-7.95 (m, 3H), 7.85 (dt, J=24.3, 8.3 Hz, 6H). ES/MS m/z: Calculated for $C_{18}H_{14}N_5O_2$ (M+H)=332.11; Found 332.12

Example 130: 4-(4'-(4-methyl-1H-pyrazol-3-yl)-[1,1'-biphenyl]-4-yl)-1H-1,2,3-triazole-5-carboxylic acid

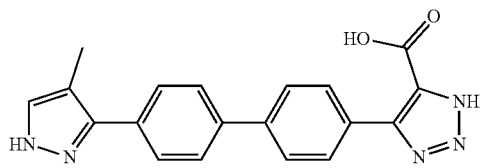 [SMILES: Cc1c[nH]nc1-c1ccc(-c2ccc(-c3nn[nH]c3C(=O)O)cc2)cc1]

¹H NMR (400 MHz, DMSO-d₆) δ 12.98 (s, 2H), 7.82 (d, J=8.1 Hz, 4H), 7.75 (d, J=8.1 Hz, 2H), 7.51 (s, 1H), 2.23 (d, J=0.7 Hz, 3H). ES/MS m/z: Calculated for $C_{19}H_{16}N_5O_2$ (M+H)=346.13; Found 346.18.

The following compounds were prepared in a manner similar to the representative procedures of Suzuki reaction and SEM deprotection by HCl, followed by ester hydrolysis either using previously mentioned bromide intermediates, 4 or 10, with commercially available bromides after conversion to pinacol boronates:

Example 131: 4-(4'-(5-methyl-1H-1,2,3-triazol-4-yl)-[1,1'-biphenyl]-4-yl)-1H-1,2,3-triazole-5-carboxylic acid

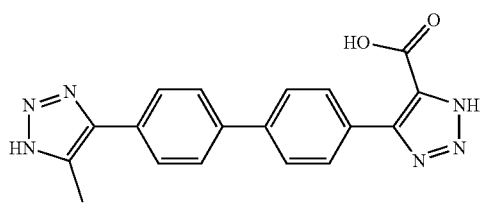 [SMILES: Cc1[nH]nnc1-c1ccc(-c2ccc(-c3nn[nH]c3C(=O)O)cc2)cc1]

¹H NMR (400 MHz, D₂O+NaHCO₃) δ 7.5-8.0 (m, 8H), 2.48 (s, 3H). ES/MS m/z: calculated for $C_{18}H_{15}N_6O_2$ (M+H): 347.13, found: 347.12.

Example 132: 4-(6-chloronaphthalen-2-yl)-1H-1,2,3-triazole-5-carboxylic acid

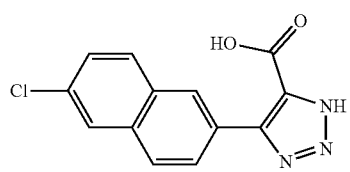 [SMILES: O=C(O)c1[nH]nnc1-c1ccc2cc(Cl)ccc2c1]

¹H NMR (400 MHz, Methanol-d₄) δ 8.45 (m, 1H) 7.92 (dd, J=13.0, 8.2 Hz, 4H), 7.50 (d, J=8.7 Hz, 1H). ES/MS m/z: calculated for $C_{13}H_9ClN_3O_2$ (M+H): 274.04, found: 273.96.

Example 133: 4-(phenanthren-2-yl)-1H-1,2,3-triazole-5-carboxylic acid

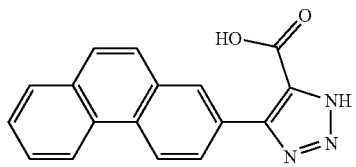 [SMILES: O=C(O)c1[nH]nnc1-c1ccc2c(ccc3ccccc32)c1]

¹H NMR (400 MHz, DMSO-d₆) δ 8.88 (s, 2H), 8.43 (s, 1H), 8.22-7.82 (m, 4H), 7.80-7.59 (m, 3H). ES/MS m/z: Calculated for $C_{17}H_{12}N_3O_2$ (M+H)=290.09; Found, 290.03.

Example 134: 4-(7-amino-9H-fluoren-2-yl)-1H-1,2,3-triazole-5-carboxylic acid

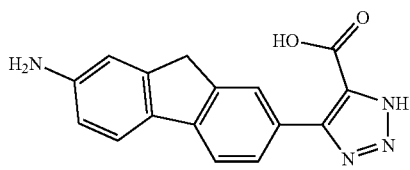 [SMILES: Nc1ccc2c(c1)Cc1cc(-c3nn[nH]c3C(=O)O)ccc1-2]

¹H NMR (400 MHz, Methanol-d₄) δ 8.07 (s, 1H), 7.97 (dd, J=14.0, 8.1 Hz, 2H), 7.88 (d, J=7.9 Hz, 1H), 7.55 (s, 1H), 7.36 (d, J=8.3 Hz, 1H), 4.05 (s, 2H). ES/MS m/z: calculated for $C_{16}H_{13}N_4O_2$ (M+H): 293.10, found: 293.05.

Example 135: 5-(3-chloro-4-fluorophenyl)-1H-1,2,3-triazole-4-carboxylic acid

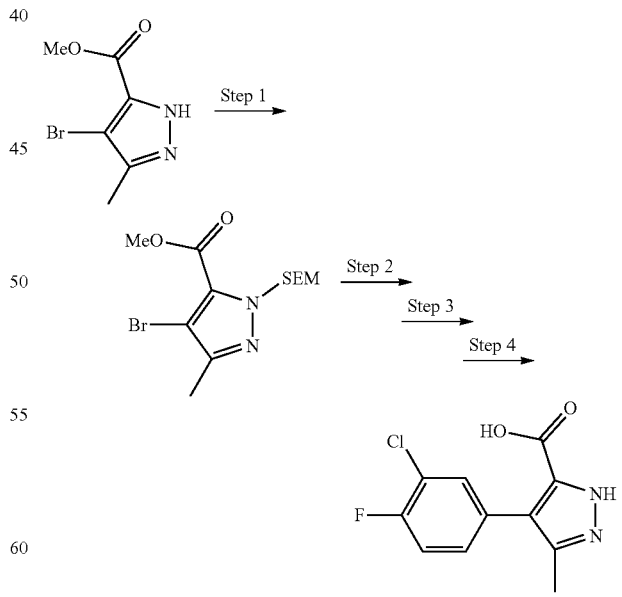

Step 1

To a solution of methyl 4-bromo-3-methyl-1H-pyrazole-5-carboxylate (275 mg. 1.255 mmol) in DMF was added sodium hydride (60% suspension, 1.38 mmol) at 0° C., followed by SEM-Cl (0.233 mL, 1.31 mmol). After 10 min, the reaction mixture was diluted with saturated NaHCO$_3$ before the product was extracted with ethyl acetate, dried (MgSO$_4$), concentrated, and purified by column chromatography on silica gel eluting with ethyl acetate in hexane to get an isomeric mixture of methyl 4-bromo-3-methyl-1-((2-(trimethylsilyl)ethoxy)methyl)-1H-pyrazole-5-carboxylate: ES/MS m/z: calculated for C$_{12}$H$_{22}$BrN$_2$O$_3$Si (M+H): 349.05, found: 348.93.

Step 2, Step 3, and Step 4

4-(3-chloro-4-fluorophenyl)-3-methyl-1H-pyrazole-5-carboxylic acid was prepared in a manner similar to the general procedures of Suzuki reaction using (3-chloro-4-fluorophenyl)boronic acid, followed by SEM deprotection by HCl and ester hydrolysis: $^1$H NMR (400 MHz, Methanol-d$_4$) δ 7.43 (ddd, J=7.2, 1.9, 0.5 Hz, 1H), 7.31-7.19 (m, 2H), 2.22 (s, 3H). ES/MS m/z: calculated for C$_{11}$H$_9$ClFN$_2$O$_2$ (M+H): 255.03, found: 254.94.

Example 136: 4-(3-chloro-4-fluorophenyl)-3-methyl-1H-pyrazole-5-carboxylic acid

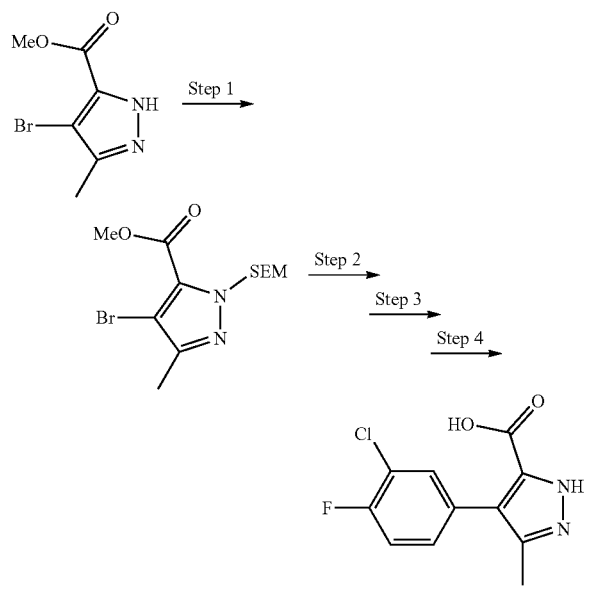

Step 1

A solution of 1-(3-chloro-4-fluorophenyl)ethan-1-one (301, 5.00 g, 29.0 mmol) in dimethyl carbonate (4.9 mL, 58 mmol) was added dropwise to a stirred solution of potassium tert-butoxide (6.50 g, 57.9 mmol) in THF (30 mL) under N$_2$ and cooled in a water bath. After 90 min, the reaction mixture was cooled in an ice bath then quenched with 2 M HCl. The mixture was then extracted with ethyl acetate, and the organic extract was dried (MgSO$_4$) and concentrated under vacuum. The resulting crude residue was purified by column chromatography on silica gel eluting 0-40% ethyl acetate in hexanes to get methyl 3-(3-chloro-4-fluorophenyl)-3-oxopropanoate (2.97 g, 44%). LC/MS m/z: calculated for C$_{10}$H$_9$ClFO$_3$ (M+H): 231.02, found: 231.0.

Step 2

A mixture of methyl 3-(3-chloro-4-fluorophenyl)-3-oxopropanoate (537 mg, 2.33 mmol), p-methoxybenzyl azide (400 mg, 2.45 mmol), and potassium carbonate (1.36 g, 9.80 mmol) in dimethylsulfoxide (5 mL) were stirred vigorously at 80° C. overnight. After the reaction mixture was then cooled and diluted with water, resulting solids were isolated by filtration, then further purified by column chromatography on silica gel eluting 0-50% ethyl acetate in hexanes to get methyl 5-(3-chloro-4-fluorophenyl)-1-(4-methoxybenzyl)-1H-1,2,3-triazole-4-carboxylate (400 mg, 43%) as a white solid: ES/MS m/z: calculated for C$_{18}$H$_{16}$ClFN$_3$O$_3$ (M+H): 376.09, found 376.1.

Step 3 and Step 4

To a solution of methyl 5-(3-chloro-4-fluorophenyl)-1-(4-methoxybenzyl)-1H-1,2,3-triazole-4-carboxylate (75 mg, 0.20 mmol) in 1:1 THF/methanol (2 mL) was added 1M LiOH (1.0 mL, 1.0 mmol) at rt. After stirring for 1 h, the reaction mixture was acidified with 2N HCl and the product was extracted with ethyl acetate (×3). The combined organic extracts were dried (MgSO$_4$), and concentrated under vacuum. The resulting residue was then dissolved in TFA and stirred at 65° C. for 2 h. After the reaction mixture was concentrated under vacuum, the residue was purified by reverse phase preparative HPLC to afford 5-(3-chloro-4-fluorophenyl)-1H-1,2,3-triazole-4-carboxylic acid: $^1$H NMR (400 MHz, DMSO-d$_6$) δ 13.33 (br s, 1H), 8.07 (br s, 1H), 7.84 (br s, 1H), 7.54 (br t, J=8.0 Hz, 1H). ES/MS m/z: calculated for C$_9$H$_6$ClFN$_3$O$_2$ (M+H): 242.01, found 242.0.

Example 137: 4-phenyl-1H-1,2,3-triazole-5-carboxylic acid

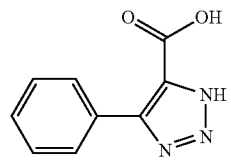 [SMILES: O=C(O)c1[nH]nnc1-c1ccccc1]

4-phenyl-1H-1,2,3-triazole-5-carboxylic acid was prepared in a manner similar to the procedures in Example 136 from acetophenone: $^1$H NMR (400 MHz, DMSO-d$_6$) δ 13.14 (br s, 1H), 7.79 (br s, 2H), 7.51-7.42 (m, 3H). ES/MS m/z: calculated for C$_9$H$_8$N$_3$O$_2$ (m+H): 190.06, found 190.0.

Example 138: 4-(3-chlorophenyl)-1H-1,2,3-triazole-5-carboxylic acid

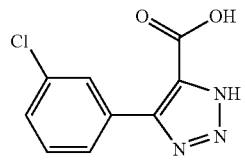 [SMILES: O=C(O)c1[nH]nnc1-c1cccc(Cl)c1]

4-(3-chlorophenyl)-1H-1,2,3-triazole-5-carboxylic acid was prepared in a manner similar to the procedures in Example 136 from 3-chloroacetophenone: $^1$H NMR (400 MHz, DMSO-d$_6$) 7.92 (s, 1H), 7.80 (br s, 1H), 7.54-7.48 (m, 2H). ES/MS m/z: calculated for C$_9$H$_7$ClN$_3$O$_2$ (M+H): 224.02, found 224.0.

Example 139:
4-(pyridin-2-yl)-1H-1,2,3-triazole-5-carboxylic acid

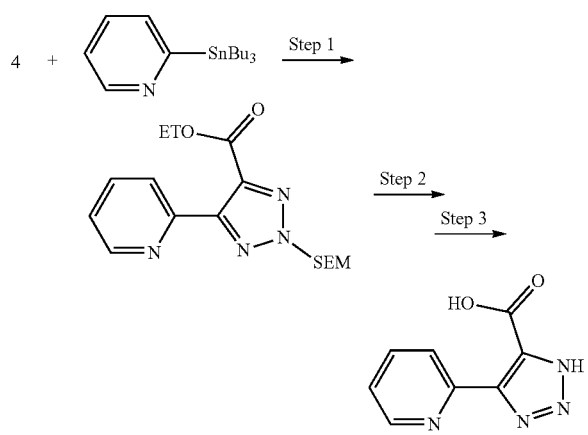

In a 5 mL microwave vial, the isomeric mixture of methyl 5-bromo-2-((2-(trimethylsilyl)ethoxy)methyl)-2H-1,2,3-triazole-4-carboxylate (192 mg, 0.55 mmol), 2-(tributylstannyl)pyridine (222 mg, 0.193 mL, 0.60 mmol), tetrakis(triphenylphosphine)palladium (0) (63 mg, 0.055 mmol), and toluene (2 mL) were added. After purging with argon gas for 5 minutes, the resulting mixture was stirred at 110° C. for 2 hours. After cooling, the reaction mixture was diluted with saturated NaHCO$_3$ before the product was extracted with ethyl acetate, dried (MgSO$_4$), concentrated, and purified by column chromatography on silica gel eluting with ethyl acetate in hexane to get ethyl 5-(pyridin-2-yl)-2-((2-(trimethylsilyl)ethoxy)methyl)-2H-1,2,3-triazole-4-carboxylate: ES/MS m/z: calculated for C$_{16}$H$_{25}$N$_4$O$_3$Si (M+H): 349.16, found: 349.05.

Step 2 and Step 3

4-(pyridin-2-yl)-1H-1,2,3-triazole-5-carboxylic acid was prepared in a manner similar to the general procedures of SEM deprotection by HCl followed by and ester hydrolysis: $^1$H NMR (400 MHz, DMSO-d$_6$) δ 8.78 (d, J=5.2 Hz, 1H), 8.41 (d, J=8.0 Hz, 1H), 8.25 (t, J=8.0 Hz, 1H), 7.69 (dd, J=7.4, 5.4 Hz, 1H). ES/MS m/z: calculated for C$_8$H$_7$N$_4$O$_2$ (M+H): 191.05, found: 190.99.

Example 140:
4-(pyridin-2-yl)-1H-pyrazole-5-carboxylic acid

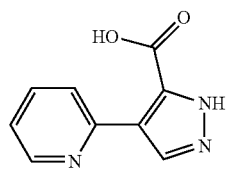 [SMILES: O=C(O)c1[nH]ncc1-c1ccccn1]

4-(pyridin-2-yl)-1H-pyrazole-5-carboxylic acid was prepared in a manner similar to the procedure of Example 141 from 4-(tributylstannyl)pyridine: $^1$H NMR (400 MHz, Methanol-d$_4$) δ 8.85-8.78 (m, 1H), 8.70 (s, 1H), 8.54 (td, J=8.0, 1.6 Hz, 1H), 8.43 (dt, J=8.4, 1.0 Hz, 1H), 7.89 (ddd, J=7.3, 5.9, 1.2 Hz, 1H). ES/MS m/z: calculated for C$_9$H$_8$N$_3$O$_2$ (M+H): 190.05, found: 190.00.

Example 141:
4-(thiazol-4-yl)-1H-1,2,3-triazole-5-carboxylic acid

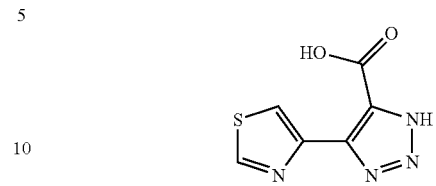

4-(thiazol-4-yl)-1H-1,2,3-triazole-5-carboxylic acid was prepared in a manner similar to the procedure of Example 141 from 4-(tributylstannyl)thiazole: $^1$H NMR (400 MHz, DMSO-d$_6$): δ 9.32 (s, 1H), 8.65 (s, 1H), 3.15 (s, 1H). ES/MS m/z: calculated for C$_6$H$_3$N$_4$O$_2$S (M–H): 191.05, found: 194.95.

Examples 142 and 143: 4-(3'-(dimethylcarbamoyl)-[1,1'-biphenyl]-4-yl)-1H-1,2,3-triazole-5-carboxylic acid and 4-(3'-carboxy-[1,1'-biphenyl]-4-yl)-1H-1,2,3-triazole-5-carboxylic acid

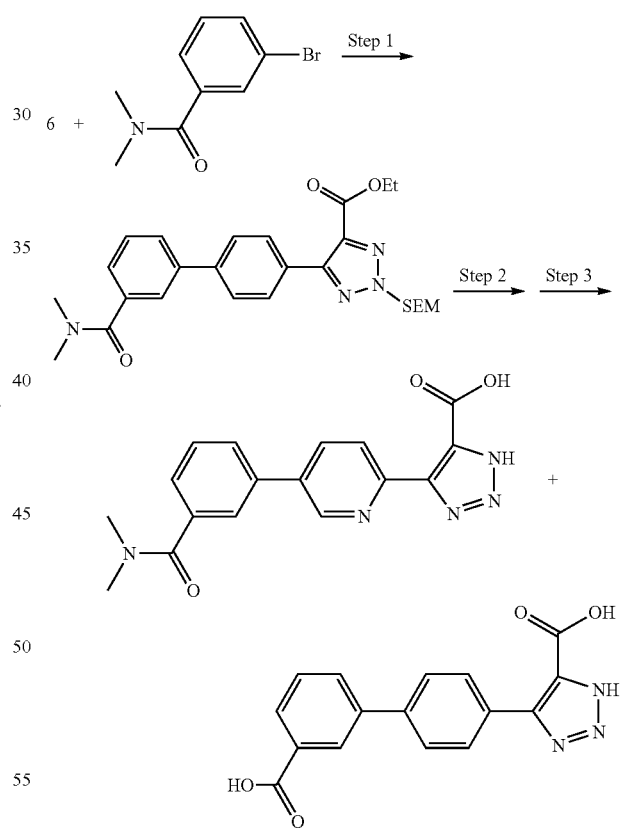

Step 1

An isomeric mixture of ethyl 5-(3'-(dimethylcarbamoyl)-[1,1'-biphenyl]-4-yl)-2-((2-(trimethylsilyl)ethoxy)methyl)-2H-1,2,3-triazole-4-carboxylate was prepared in a manner similar to the general procedure of Suzuki reaction from 3-bromo-N,N-dimethylbenzamide:

Step 2 and Step 3

4-(3'-(dimethylcarbamoyl)-[1,1'-biphenyl]-4-yl)-1H-1,2,3-triazole-5-carboxylic acid and 4-(3'-carboxy-[1,1'-biphenyl]-4-yl)-1H-1,2,3-triazole-5-carboxylic acid were prepared in a manner similar to t the general procedure of SEM deprotection by HCl followed by ester hydrolysis. Two compounds were separated by precipitation followed by preparative HPLC purifications:

Example 142: 4-(3'-(dimethylcarbamoyl)-[1,1'-biphenyl]-4-yl)-1H-1,2,3-triazole-5-carboxylic acid

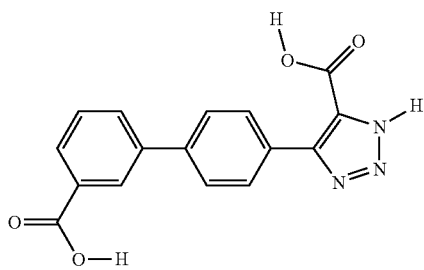 [SMILES: O=C(O)c1cccc(-c2ccc(-c3nn[nH]c3C(=O)O)cc2)c1]

$^1$H NMR (400 MHz, Methanol-d$_4$) δ 8.33 (t, J=1.7 Hz, 1H), 8.10-7.87 (m, 3H), 7.87-7.71 (m, 2H), 7.59 (t, J=7.9 Hz, 2H). ES/MS m/z: calculated for C$_{16}$H$_{12}$N$_3$O$_4$ (M+H): 310.07, found: 310.05.

Example 143: 4-(3'-carboxy-[1,1'-biphenyl]-4-yl)-1H-1,2,3-triazole-5-carboxylic acid

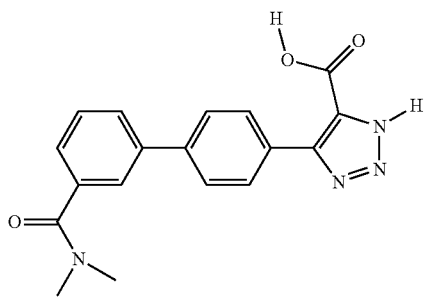 [SMILES: CN(C)C(=O)c1cccc(-c2ccc(-c3nn[nH]c3C(=O)O)cc2)c1]

$^1$H NMR (400 MHz, Methanol-d$_4$) δ 7.96 (d, J=8.4 Hz, 2H), 7.86-7.72 (m, 4H), 7.57 (td, J=7.7, 0.6 Hz, 1H), 7.44 (dt, J=7.6, 1.3 Hz, 1H), 3.14 (s, 3H), 3.06 (s, 3H). ES/MS m/z: calculated for C$_{18}$H$_{17}$N$_4$O$_3$ (M+H): 337.12, found: 337.17.

Example 144: 4-(4-(1H-indazol-5-yl)phenyl)-1H-1,2,3-triazole-5-carboxylic acid

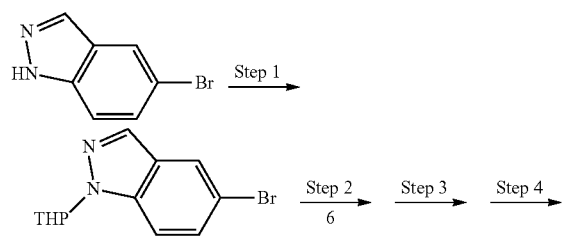

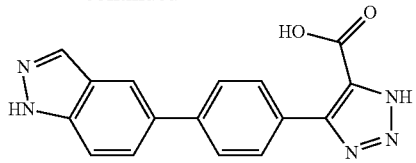

Step 1

To a solution of 5-bromo-1H-indazole (100 mg, 0.49 mmol) in dichloromethane (2.0 mL) was added p-toluenesulfonic acid (9.0 mg, 0.049 mmol) and 3,4-dihydropyran (0.089 mL, 0.97 mmol). After the mixture was heated to 35° C. overnight, the reaction mixture was diluted with aqueous saturated NaHCO$_3$ before the product was extracted with ethyl acetate (×2). The combined organic layers were washed with water (×1), dried (Na$_2$SO$_4$), and concentrated. The residue was purified by column chromatography on silica gel eluting ethyl acetate in hexane to afford 5-bromo-1-(tetrahydro-2H-pyran-2-yl)-1H-indazole: $^1$H NMR (400 MHz, Acetonitrile-d$_3$) 8.03-7.93 (m, 2H), 7.62 (dt, J=8.9, 0.8 Hz, 1H), 7.52 (dd, J=8.9, 1.9 Hz, 1H), 5.77 (dd, J=9.8, 2.6 Hz, 1H), 4.89 (t, J=3.8 Hz, 0H), 4.01-3.91 (m, 1H), 3.86-3.72 (m, 1H), 3.48 (dd, J=11.0, 6.0 Hz, 0H), 2.47 (dddd, J=13.7, 12.2, 9.7, 4.0 Hz, 1H), 2.17-1.97 (m, 2H), 1.87-1.60 (m, 3H), 1.64-1.48 (m, 1H). ES/MS m/z: Calculated for C$_{12}$H$_{14}$BrN$_2$O (M+H)=281.03; Found 280.75.

Step 2, 3 and 4

4-(4-(1H-Indazol-5-yl)phenyl)-1H-1,2,3-triazole-5-carboxylic acid was prepared in a manner similar to the general procedures of Suzuki reaction with intermediate 6 and 5-bromo-1-(tetrahydro-2H-pyran-2-yl)-1H-indazole, and PMB and THP deprotection by TFA, followed by ester hydrolysis: $^1$H NMR (400 MHz, Methanol-d$_4$) δ 8.10-8.05 (m, 1H), 7.89 (d, J=8.0 Hz, 1H), 7.50-7.35 (m, 6H). ES/MS m/z: calculated for C$_{15}$H$_{11}$ClN$_3$O$_2$ (M+H): 300.05, found: 300.00.

Example 145: 4-(4-(1H-indazol-6-yl)phenyl)-1H-1,2,3-triazole-5-carboxylic acid

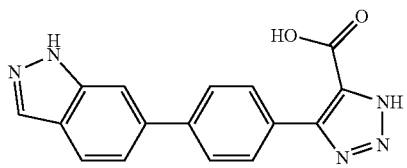 [SMILES: O=C(O)c1[nH]nnc1-c1ccc(-c2ccc3cn[nH]c3c2)cc1]

4-(4-(1H-indazol-6-yl)phenyl)-1H-1,2,3-triazole-5-carboxylic acid was prepared from 6-bromo-1H-indazole in a manner similar to the procedures in Example 146: $^1$H NMR (400 MHz, Methanol-d$_4$) δ 8.10-7.92 (m, 3H), 7.81 (d, J=8.4 Hz, 1H), 7.75 (s, 1H), 7.65 (d, J=8.2 Hz, 2H), 7.46 (d, J=8.7 Hz, 2H). ES/MS m/z: Calculated for C$_{16}$H$_{12}$N$_5$O$_2$ (M+H)=306.10; Found 306.15

Example 146: 4-(4'-chloro-3'-(morpholinosulfonyl)-[1,1'-biphenyl]-4-yl)-1H-1,2,3-triazole-5-carboxylic acid

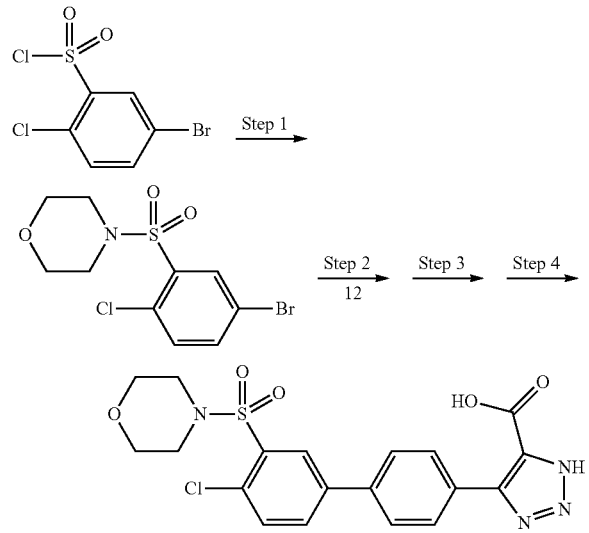

Step 1

To a solution of 5-bromo-2-chlorobenzenesulfonyl chloride (366 mg, 10 mmol) in THF (3 mL) were added morpholine (220 mg, 3 mmol) at 0° C. After 10 minutes, the reaction mixture was diluted with ethyl acetate, washed with 1 N HCl (×2), water (×1), and saturated NaHCO$_3$ (×1). The resulting organic fraction was dried (MgSO$_4$) and concentrated. The residue was purified by column chromatography on silica gel eluting 0-100% ethyl acetate in hexane to get 4-((5-bromo-2-chlorophenyl)sulfonyl)morpholine: $^1$H NMR (400 MHz, chloroform-d): δ 7.60 (s, 1H), 7.60 (d, 1H), 7.29 (d, 1H), 3.70 (m, 4H), 3.28 (m, 4H).

Step 2, 3 and 4

4-(4'-chloro-3'-(morpholinosulfonyl)-[1,1'-biphenyl]-4-yl)-1H-1,2,3-triazole-5-carboxylic acid was prepared in a manner similar to the general procedures of Suzuki reaction with intermediate 6 and 4-((5-bromo-2-chlorophenyl)sulfonyl)morpholine, and PMB deprotection, followed by ester hydrolysis: $^1$H NMR (400 MHz, Methanol-d$_4$) δ 8.30 (d, J=2.3 Hz, 1H), 8.07-7.91 (m, 3H), 7.76 (dd, J=16.0, 8.2 Hz, 3H), 3.75-3.65 (m, 4H), 3.29 (m, 4H): ES/MS m/z: calculated for C$_{19}$H$_{18}$ClN$_4$O$_5$S (M+H): 449.06, found: 449.16.

Example 147: 4-(3-bromophenyl)-1H-1,2,3-triazole-5-carboxylic acid

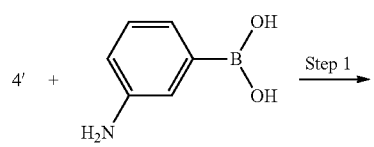

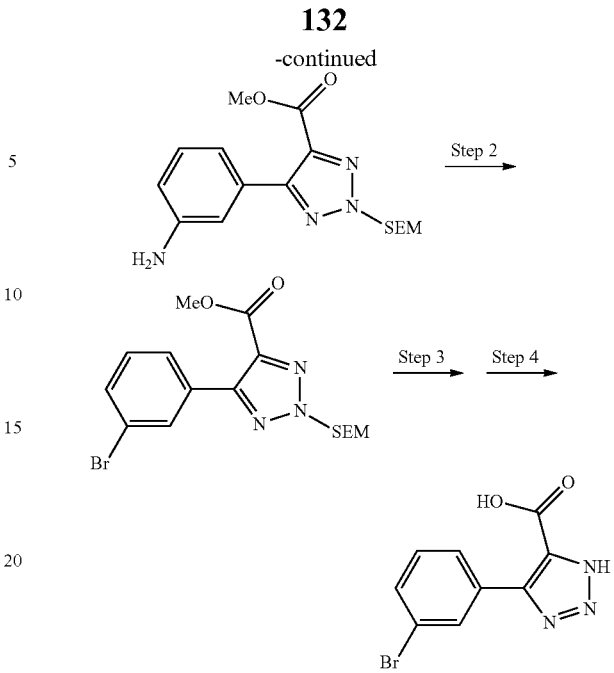

Step 1

The isomeric mixture of methyl 5-(3-aminophenyl)-2-((2-(trimethylsilyl)ethoxy)methyl)-2H-1,2,3-triazole-4-carboxylate was prepared in a manner similar to the general procedures of Suzuki reaction using intermediate 4' and (3-aminophenyl)boronic acid: ES/MS m/z: calculated for C$_{16}$H$_{25}$N$_4$O$_3$Si (M+H): 347.17, found: 348.96.

Step 2:

To a solution of methyl 4-(3-aminophenyl)-1-((2-(trimethylsilyl)ethoxy)methyl)-1H-1,2,3-triazole-5-carboxylate (102 mg, 0.29 mmol) in 3 mL acetonitrile were added tert-butyl nitrite (0.042 mL, 0.35 mmol) and copper(II) bromide (78 mg, 0.35 mmol) at 0° C. After 30 minutes, the reaction mixture was diluted with saturated NaHCO$_3$ before the product was extracted with ethyl acetate, dried (MgSO$_4$), concentrated, and purified by column chromatography on silica gel eluting with ethyl acetate in hexane to get the isomeric mixture of methyl 5-(3-bromophenyl)-2-((2-(trimethylsilyl)ethoxy)methyl)-2H-1,2,3-triazole-4-carboxylate: $^1$H NMR (400 MHz, Chloroform-d): δ 8.12-7.30 (m, 4H), 6.18-5.76 (m, 2H), 3.98 (d, 3H), 3.78-3.684 (m, 2H), 0.95 (m, 2H), 0.00 (d, 9H).

Step 3 and Step 4

5-(4-bromophenyl)-1H-1,2,3-triazole-4-carboxylic acid was prepared in a manner similar to the general procedures of SEM deprotection by HCl, followed by ester hydrolysis: $^1$H NMR (400 MHz, Methanol-d$_4$) δ 8.07 (s, 1H), 7.85 (d, J=7.8 Hz, 1H), 7.63-7.56 (m, 1H), 7.38 (t, J 5=7.9 Hz, 1H). ES/MS m/z: calculated for C$_9$H$_7$BrN$_3$O$_2$ (M+H): 267.96, found: 267.90.

Example 148: 4-(2-chloro-[1,1'-biphenyl]-4-yl)-1H-1,2,3-triazole-5-carboxylic acid

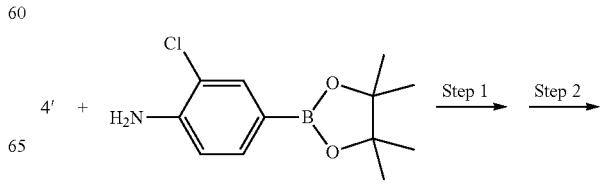

133

-continued

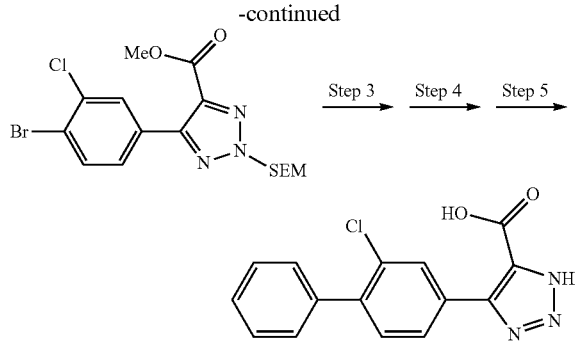

Step 1 and 2

The isomeric mixture of methyl 5-(4-bromo-3-chlorophenyl)-2-((2-(trimethylsilyl)ethoxy)methyl)-2H-1,2,3-triazole-4-carboxylate was prepared in a manner similar to the procedures in Example 149, Step 1 and 2 using 2-chloro-4-(4,4,5,5-tetramethyl-1,3,2-dioxaborolan-2-yl)aniline: ES/MS m/z: calculated for $C_{16}H_{22}BrClN_3O_3Si$ (M+H): 446.03, found: 445.69.

Step 3, Step 4, and Step 5

4-(2-chloro-[1,1'-biphenyl]-4-yl)-1H-1,2,3-triazole-5-carboxylic acid was prepared in a manner similar to the general procedures of Suzuki reaction using phenylboronic acid, SEM deprotection by HCl, and ester hydrolysis: $^1$H NMR (400 MHz, Methanol-$d_4$) δ 8.10-8.05 (m, 1H), 7.89 (d, J=8.0 Hz, 1H), 7.50-7.35 (m, 6H). ES/MS m/z: calculated for $C_{15}H_{11}ClN_3O_2$ (M+H): 300.05, found: 300.00.

Example 149: 4-(2,4'-dichloro-[1,1'-biphenyl]-4-yl)-1H-1,2,3-triazole-5-carboxylic acid

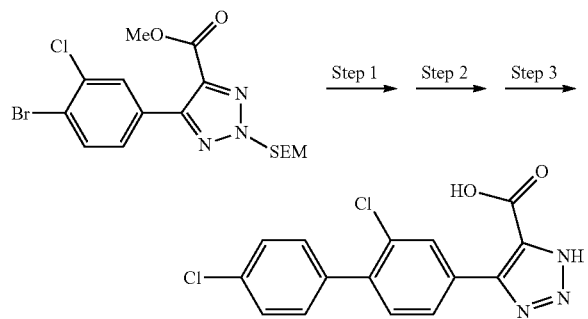

4-(2,4'-dichloro-[1,1'-biphenyl]-4-yl)-1H-1,2,3-triazole-5-carboxylic acid was prepared in a manner similar to the general procedure of Suzuki reaction from the isomeric mixture of methyl 5-(4-bromo-3-chlorophenyl)-2-((2-(trimethylsilyl)ethoxy)methyl)-2H-1,2,3-triazole-4-carboxylate and 4-chlorophenylboronic acid, followed by the general procedures of SEM deprotection by HCl and ester hydrolysis: $^1$H NMR (400 MHz, Methanol-$d_4$) δ 8.00 (d, J=1.7 Hz, 1H), 7.81 (dd, J=8.0, 1.8 Hz, 1H), 7.37 (m, 5H). ES/MS m/z: calculated for $C_{15}H_{10}Cl_2N_3O_2$ (M+H): 334.01, found: 333.97.

134

Example 150: 4-(3-chloro-4-fluorophenyl)-1-methyl-1H-1,2,3-triazole-5-carboxylic acid

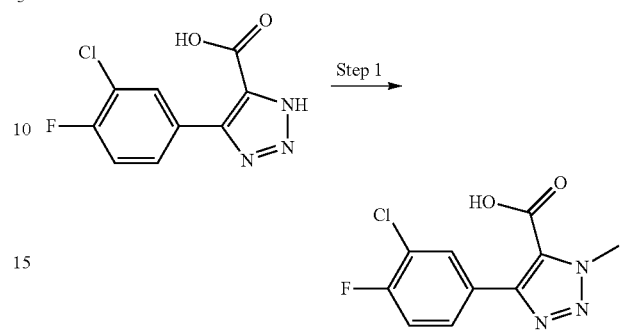

To a solution of 5-(3-chloro-4-fluorophenyl)-1H-1,2,3-triazole-4-carboxylic acid (10 mg, 0.038 mmol) in 0.5 mL DMF was added NaH (60% oil suspension, 6 mg) at 0° C. After 10 min at 0° C., iodomethane (7 μL, 0.11 mmol) was added and the resulting mixture was stirred at 0° C. for 10 minutes. After the reaction was quenched by addition of methanol, the product was purified by HPLC purification to give 5-(3-chloro-4-fluorophenyl)-1-methyl-1H-1,2,3-triazole-4-carboxylic acid: $^1$H NMR (400 MHz, Chloroform-d) δ 7.99 (dd, J=7.1, 2.2 Hz, 1H), 7.82 (ddd, J=8.6, 4.6, 2.2 Hz, 1H), 7.20 (t, J=8.7 Hz, 1H), 4.31 (s, 3H). ES/MS m/z: calculated for $C_{10}H_6ClFN_3O_2$ (M−H): 254.01, found: 253.96.

Example 151: 4-(4'-(1-methyl-1H-1,2,3-triazol-5-yl)-[1,1'-biphenyl]-4-yl)-1H-1,2,3-triazole-5-carboxylic acid

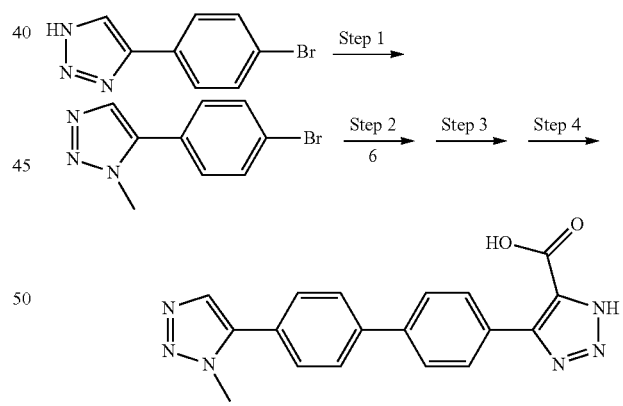

Step 1

To a solution of 4-(4-bromophenyl)-1H-1,2,3-triazole (242 mg, 1.05 mmol) in 2 mL DMF was added 60% NaH in oil suspension (48 mg, 1.2 mmol) at 0° C. After 10 min at 0° C., iodomethane (71 μL, 1.1 mmol) was added and the resulting mixture was stirred at 0° C. for 10 minutes. The reaction mixture was extracted using ethyl acetate with brine, the organic layer was concentrated and purified by column chromatography on silica gel eluting ethyl acetate and hexane to give 5-(4-bromophenyl)-1-methyl-1H-1,2,3-triazole: ES/MS m/z: calculated for $C_9H_9BrN_3$ (M+H): 237.99, found: 238.09.

Step 2, Step 3, and Step 4

4-(4'-(1-methyl-1H-1,2,3-triazol-5-yl)-[1,1'-biphenyl]-4-yl)-1H-1,2,3-triazole-5-carboxylic acid was prepared in a manner similar to the general procedures of Suzuki reaction with compound 28, followed by SEM deprotection by HCl and ester hydrolysis: $^1$H NMR (400 MHz, DMSO-d$_6$) δ 8.27 (s, 1H), 8.09 (s, 2H), 7.97-7.88 (m, 2H), 7.81 (dt, J=13.6, 5.3 Hz, 4H), 4.20 (s, 3H). ES/MS m/z: calculated for C$_{18}$H$_{15}$N$_6$O$_2$ (M+H): 347.12, found: 347.04.

Example 152: 4-(4-(2,3,3-trimethyl-1-oxoisoindolin-5-yl)phenyl)-1H-1,2,3-triazole-5-carboxylic acid

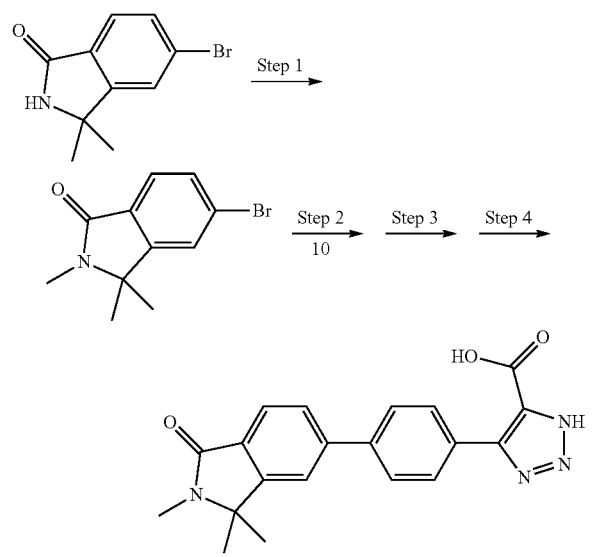

Step 1

To a solution of 5-bromo-3,3-di methylisoindolin-1-one (205 mg, 0.85 mmol) in N,N-dimethylformamide (2 mL) was added 60% sodium hydride in mineral oil (43 mg, 1.08 mmol) at 0° C. After 15 min, iodomethane (0.1 mL, 1.61 mmol) was added to the reaction mixture. The resulting solution was stirred at 0° C. for 1 h. The reaction mixture was diluted with ethyl acetate (25 mL) before washed with ~50% saturated NH$_4$Cl solution. After the aqueous fraction was extracted with ethyl acetate (25 mL×1), the organic fractions were combined, dried (MgSO$_4$), and concentrated. The residue was purified by column chromatography on silica gel eluting 0-100% EA in hexane to get 5-bromo-2,3,3-trimethylisoindolin-1-one: ES/MS m/z: calculated for C$_{11}$H$_{13}$BrNO (M+H): 254.02, found: 254.12.

Step 2, Step 3, and Step 4

4-(4-(2,3,3-trimethyl-1-oxoisoindolin-5-yl)phenyl)-1H-1,2,3-triazole-5-carboxylic acid was prepared in a manner similar to the procedure for the general procedures of Suzuki reaction with intermediate 6 and 5-bromo-2,3,3-trimethylisoindolin-1-one, and PMB deprotection, followed by ester hydrolysis: $^1$H NMR (400 MHz, DMSO-d$_6$) δ 8.10 (d, J=1.5 Hz, 1H), 8.00 (s, 2H), 7.89 (dd, J=7.7, 5.6 Hz, 2H), 7.83 (dd, J=7.9, 1.6 Hz, 1H), 7.73 (d, J=7.9 Hz, 1H), 2.95 (s, 3H), 1.50 (s, 6H). ES/MS m/z: calculated for C$_{20}$H$_{19}$N$_4$O$_3$ (M+H): 363.15, found: 363.12.

Example 153: 4-(4-(3,3-dimethyl-1-oxo-2-(2,2,2-trifluoroethyl)isoindolin-5-yl)phenyl)-1H-1,2,3-triazole-5-carboxylic acid

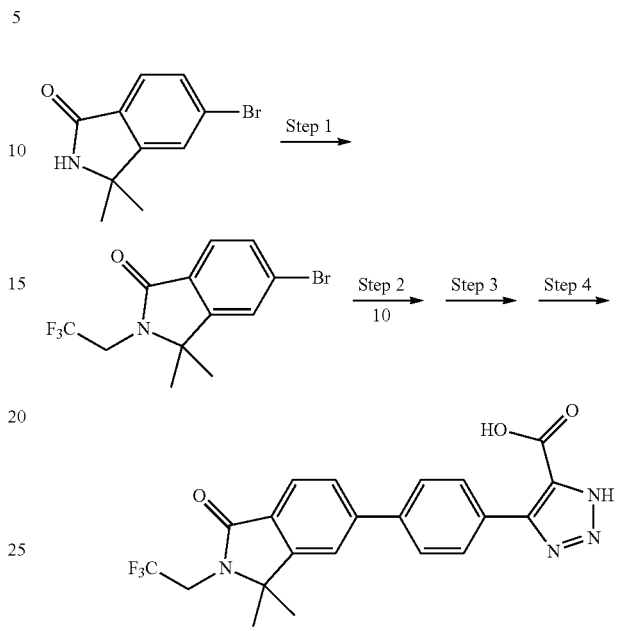

4-(4-(3,3-Dimethyl-1-oxo-2-(2,2,2-trifluoroethyl)isoindolin-5-yl)phenyl)-1H-1,2,3-triazole-5-carboxylic acid was prepared from 5-bromo-3,3-dimeth ylisoindolin-1-one in a manner similar procedures in Example 154 using 2,2,2-trifluoroethyl trifluoromethanesulfonate: $^1$H NMR (400 MHz, DMSO-d$_6$) δ 8.11 (d, J=19.7 Hz, 3H), 8.00-7.83 (m, 3H), 7.79 (d, J=7.9 Hz, 1H), 4.34 (q, J=9.6 Hz, 2H), 1.58 (s, 6H). ES/MS m/z: calculated for C$_{21}$H$_{18}$F$_3$N$_4$O$_3$ (M+H): 431.13, found: 431.15.

Example 154: 4-(9-methyl-9H-carbazol-2-yl)-1H-1,2,3-triazole-5-carboxylic acid

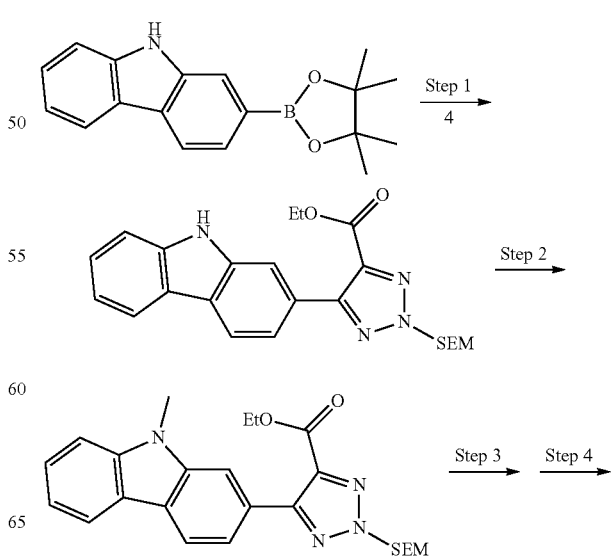

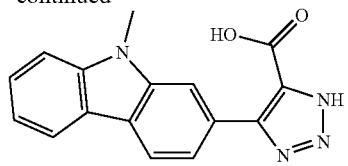

Step 1

Ethyl 5-(9H-carbazol-2-yl)-2-((2-(trimethylsilyl)ethoxy)methyl)-2H-1,2,3-triazole-4-carboxylate was prepared in a manner similar to the procedure for the general procedures of Suzuki reaction with intermediate 4 and 2-(4,4,5,5-tetramethyl-1,3,2-dioxaborolan-2-yl)-9H-carbazole.

Step 2

To a solution of ethyl 5-(9H-carbazol-2-yl)-1-((2-(trimethylsilyl)ethoxy)methyl)-1H-1,2,3-triazole-4-carboxylate (0.060 g; 0.068 mmol) in dimethylformamide (1 mL) was added 60% sodium hydride in mineral oil (0.008 g; 0.21 mmol) and stirred for 30 min prior to addition of MeI (0.009 mL; 0.13 mmol). The solution was allowed to stir at rt overnight. Once complete, the mixture was diluted with ethyl acetate (10 mL) and washed with saturated NH$_4$Cl (1 mL). After the aqueous fraction was extracted with ethyl acetate (2×10 mL), organic fractions were combined and washed with 5% LiCl (3×5 mL). Finally, the organic fraction was washed with water (5 mL), dried (Na$_2$SO$_4$), and concentrated to dryness before purification by column chromatography on silica gel eluting ethyl acetate in hexanes to afford ethyl 5-(9-methyl-9H-carbazol-2-yl)-2-((2-(trimethylsilyl)ethoxy)methyl)-2H-1,2,3-triazole-4-carboxylate: ES/MS m/z Calculated for C$_{24}$H$_{31}$N$_4$O$_3$Si (M+H)=451.22, Found 450.90.

Step 3

4-(9-Methyl-9H-carbazol-2-yl)-1H-1,2,3-triazole-5-carboxylic acid was prepared in a manner similar to the procedure for the general procedures of SEM deprotection by TBAF, followed by ester hydrolysis: $^1$H NMR (400 MHz, Methanol-d$_4$) δ 8.21-8.09 (m, 2H), 8.06 (d, J=1.3 Hz, 1H), 7.65 (d, J=8.0 Hz, 1H), 7.56-7.45 (m, 2H), 7.23 (ddd, J=7.9, 6.6, 1.6 Hz, 1H), 3.92 (s, 3H). ES/MS m/z: Calculated for C$_{16}$H$_{11}$N$_4$O$_2$ (M−H)=291.09; Found 291.11.

Example 155: 4-(4-(6-(1H-1,2,3-triazol-4-yl)pyridazin-3-yl)phenyl)-1H-1,2,3-triazole-5-carboxylic acid

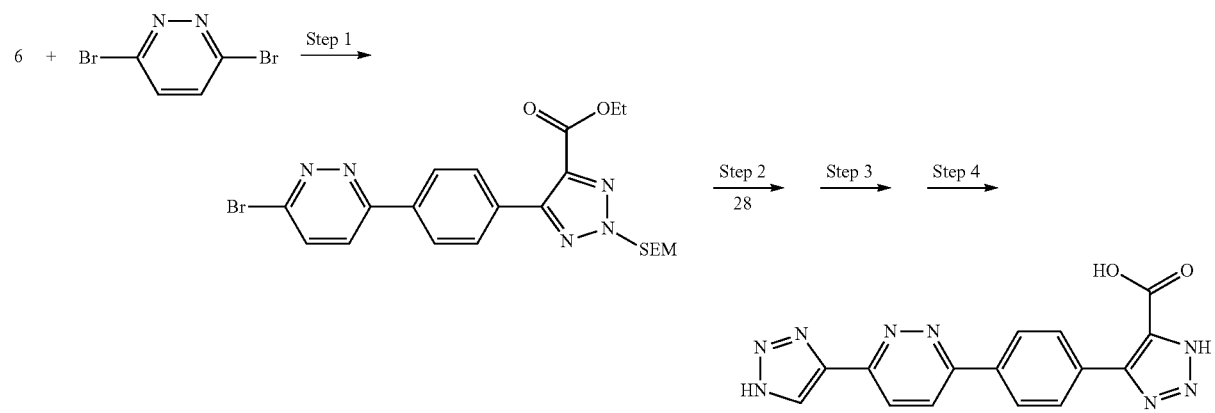

Step 1

An isomeric mixture of ethyl 5-(4-(6-bromopyridazin-3-yl)phenyl)-2-((2-(trimethylsilyl)ethoxy)methyl)-2H-1,2,3-triazole-4-carboxylate was prepared from intermediate 6 and 3,6-dibromopyridazine in a manner similar to the procedure for the preparation of intermediate 10: ES/MS m/z: calculated for C$_{21}$H$_{27}$BrN$_5$O$_3$Si (M+H): 504.11, found: 504.14 and 504.18.

Step 2, Step 3, and Step 4

4-(4-(6-(1H-1,2,3-triazol-4-yl)pyridazin-3-yl)phenyl)-1H-1,2,3-triazole-5-carboxylic acid was prepared in a manner similar to the general procedures of Suzuki reaction with compound 28, followed by SEM deprotection by HCl and ester hydrolysis: $^1$H NMR (400 MHz, Methanol-d$_4$) δ 8.53 (s, 1H), 8.43 (d, J=9.0 Hz, 1H), 8.28 (d, J=8.9 Hz, 1H), 8.24-8.15 (m, 2H), 8.12-8.03 (m, 2H). ES/MS m/z: calculated for C$_{15}$H$_{11}$N$_8$O$_2$ (M+H): 335.10, found: 335.11.

Example 156: 4-(4-(5-(1H-1,2,3-triazol-4-yl)pyrazin-2-yl)phenyl)-1H-1,2,3-triazole-5-carboxylic acid

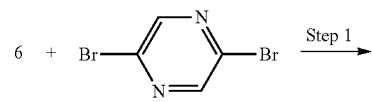

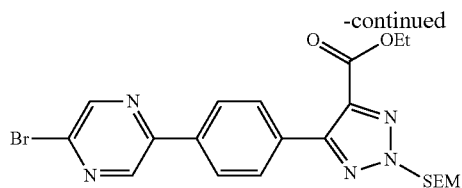

Step 2 → Step 3 → Step 4
28

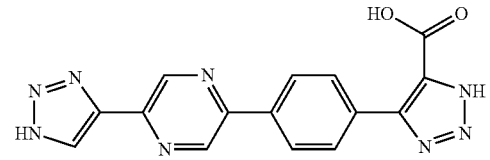

4-(4-(5-(1H-1,2,3-triazol-4-yl)pyrazin-2-yl)phenyl)-1H-1,2,3-triazole-5-carboxylic acid was prepared from 2,5-dibromopyrazine in a manner similar to the procedures in Example 157: ¹H NMR (400 MHz, Methanol-d₄) δ 9.30 (s, 1H), 9.22 (d, J=1.5 Hz, 1H), 8.26 (d, J=8.2 Hz, 2H), 8.06 (d, J=7.7 Hz, 3H). ES/MS m/z: calculated for $C_{15}H_{11}N_8O_2$ (M+H): 335.10, found: 335.10.

Example 157: 4-(3'-methyl-4'-(1H-1,2,3-triazol-5-yl)-[1,1'-biphenyl]-4-yl)-1H-1,2,3-triazole-5-carboxylic acid

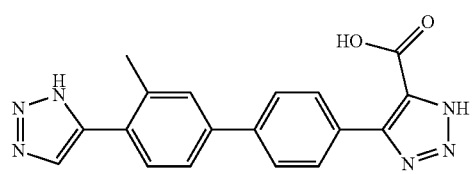 [SMILES: Cc1cc(-c2ccc(-c3nn[nH]c3C(=O)O)cc2)ccc1-c1cnn[nH]1]

Step 1

An isomeric mixture of ethyl 5-(4-(6-bromopyridazin-3-yl)phenyl)-2-((2-(trimethylsilyl)ethoxy)methyl)-2H-1,2,3-triazole-4-carboxylate was prepared from intermediate 6 and 1-bromo-4-iodo-2-methylbenzene in a manner similar to the procedure for the preparation of intermediate 10: ES/MS m/z: calculated for $C_{24}H_{31}BrN_3O_3Si$ (M+H): 516.11, found: 516.02.

Step 2, Step 3, and Step 4

4-(3'-methyl-4'-(1H-1,2,3-triazol-4-yl)-[1,1'-biphenyl]-4-yl)-1H-1,2,3-triazole-5-carboxylic acid was prepared in a manner similar to the general procedures of Suzuki reaction with compound 28, followed by SEM deprotection by HCl and ester hydrolysis: ¹H NMR (400 MHz, Methanol-d₄) δ 7.97 (d, J=8.0 Hz, 3H), 7.77 (d, J=8.3 Hz, 2H), 7.73-7.53 (m, 3H), 2.54 (s, 3H). ES/MS m/z: calculated for $C_{18}H_{15}N_6O_2S$ (M+H): 347.12, found: 347.15.

Example 158: 4-(4'-chloro-2-cyano-[1,1'-biphenyl]-4-yl)-1H-1,2,3-triazole-5-carboxylic acid

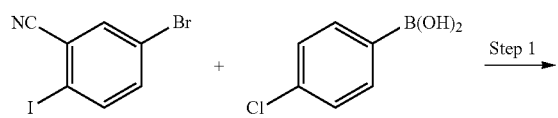

Step 1

5-Bromo-2-iodobenzonitrile (1000 mg; 3.25 mmol), (4-chlorophenyl)boronic acid (559 mg; 3.57 mmol), triphenylphosphine (26 mg; 0.097 mmol), palladium acetate (36 mg; 0.162 mmol), potassium phosphate (1347 mg; 9.74 mmol), toluene (4 mL) and water (2 mL) were combined into a flask and purged with Ar for 5 minutes. The reaction was then heated to 60° C. for 70 minutes. The reaction mixture was then diluted with water and extracted with ethyl acetate before filtering through diatomaceous earth/celite before concentrating to dryness under reduced pressure. The crude reaction mixture was purified by flash chromatography (0 to 100% Ethyl Acetate/hexanes) to afford 4-Bromo-4'-chloro-[1,1'-biphenyl]-2-carbonitrile: 1H NMR (400 MHz, Chloroform-d) δ 7.89 (d, J=2.1 Hz, 1H), 7.77 (dd, J=8.4, 2.1 Hz, 1H), 7.47 (s, 4H), 7.36 (d, J=8.4 Hz, 1H).

Step 2

4'-chloro-4-(4,4,5,5-tetramethyl-1,3,2-dioxaborolan-2-yl)-[1,1'-biphenyl]-2-carbonitrile was prepared from 4-bromo-4'-chloro-[1,1'-biphenyl]-2-carbonitrile in a manner similar to the representative procedure of the boronate ester preparation.

Steps 3, 4, and 5

4-(4'-chloro-2-cyano-[1,1'-biphenyl]-4-yl)-1H-1,2,3-triazole-5-carboxylic acid was prepared in a manner similar to the general procedures of Suzuki reaction with compound 4 and 4'-chloro-4-(4,4,5,5-tetramethyl-1,3,2-dioxaborolan-2-yl)-[1,1'-biphenyl]-2-carbonitrile, followed by SEM deprotection by TBAF and ester hydrolysis: ¹H NMR (400 MHz, Methanol-d₄) δ 8.46 (s, 1H), 8.30 (d, J=8.2 Hz, 1H), 7.72-7.59 (m, 3H), 7.58-7.50 (m, 2H). ES/MS m/z: Calculated for $C_{16}H_{10}ClN_4O_2$ (M+H)=325.05; Found 325.03.

Example 159: 4-(4'-(1H-imidazol-1-yl)-[1,1'-biphenyl]-4-yl)-1H-1,2,3-triazole-5-carboxylic acid

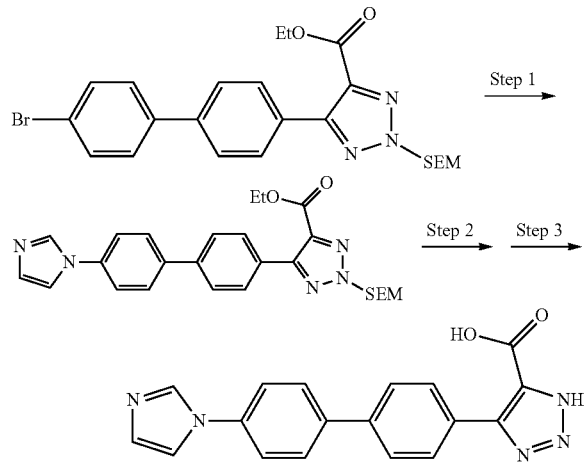

Step 1

Tris(Benzylideneacetone) dipalladium (20 mg; 0.0039 mmol), 2-di-tert-butylphosphino-3,4,5,6-tetramethyl-2',4',6'-triisopropyl-1,1'-biphenyl (8 mg; 0.016 mmol), and potassium phosphate tribasic (83 mg, 0.39 mmol) were charged into reaction vessel and the head space was purged with nitrogen gas for 10 minutes. Separately, Imidazole (16 mg; 0.23 mmol) and ethyl 5-(4'-bromo-[1,1'-biphenyl]-4-yl)-2-((2-(trimethylsilyl)ethoxy)methyl)-2H-1,2,3-tri azole-4-carboxylate (98 mg; 0.2 mmol) were dissolved in 5:1 (v/v) toluene-dioxane (3.0 mL) and purged with nitrogen gas for 10 minutes. The imidazole solution was added to the reaction vessel and the reaction was heated to 110° C. until the reaction was completed. The reaction mixture was diluted with ethyl acetate (10 mL) and washed with saturated NH$_4$Cl (3×5 mL). The aqueous layer was extracted with ethyl acetate (2×5 mL) and the combined organic fractions were washed with water (2×5 mL). Finally, the organic fraction was dried (Na$_2$SO$_4$), and concentrated to dryness before purification by column chromatography on silica gel eluting ethyl acetate in hexanes to get ethyl 5-(4'-(1H-imidazol-1-yl)-[1,1'-biphenyl]-4-yl)-2-((2-(trimethylsilyl)ethoxy)methyl)-2H-1,2,3-triazole-4-carboxylate: ES/MS m/z: Calculated for C$_{26}$H$_{32}$N$_5$O$_3$Si (M+H)=490.23; Found 490.39.

Steps 2 and 3

4-(4'-(1H-Imidazol-1-yl)-[1,1'-biphenyl]-4-yl)-1H-1,2,3-triazole-5-carboxylic acid was prepared in a manner similar to the general procedures SEM deprotection by TBAF followed by ester hydrolysis: $^1$H NMR (400 MHz, Methanol-d$_4$) δ 9.48 (s, 3H), 8.145 (t, 1H) 8.00 (dd, J=12.2, 8.5 Hz, 3H), 7.83 (dd, J=8.4, 6.2 Hz, 4H). ES/MS m/z: Calculated for C$_{18}$H$_{14}$N$_5$O$_2$ (M+H)=332.11; Found 332.14.

Example 160: 4-((4-chlorophenyl)ethynyl)-1H-1,2,3-triazole-5-carboxylic acid

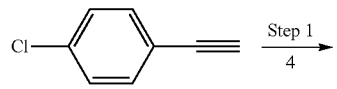

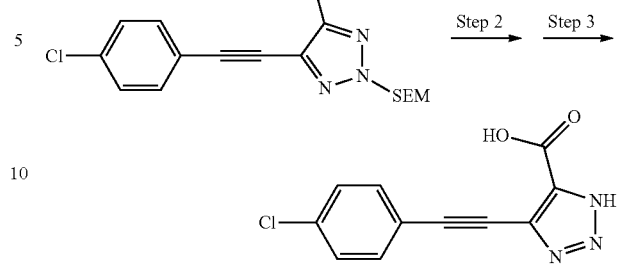

Step 1

A mixture of ethyl 5-bromo-2-((2-(trimethylsilyl)ethoxy)methyl)-2H-1,2,3-triazole-4-carboxylate (114 mg, 0.033 mmol), copper(I) iodide (19 mg, 0.0098 mmol), 1-chloro-4-ethynylbenzene (55 mg, 0.40 mmol), triethylamine (0.363 mL, 3 mmol), and dichlorobis(triphenyl-phosphine)palladium(II) (41 mg; 0.0065 mmol) in acetonitrile (3 mL) was purged with N$_2$ for 10 min and heated to 60° C. overnight. More copper (I) Iodide and dichlorobis(triphenyl-phosphine)palladium(II) were added as necessary to improve conversion to desired product. Once judged sufficiently complete LC/MS, the reaction was diluted with ethyl acetate (10 mL) and filtered through celite. The filtrate was washed satd. NH$_4$Cl (2×9 mL) and NaHCO$_3$ (aq). The aqueous layers were extracted with ethyl acetate (1×10 mL). The combined organics were wash water (1×10 mL), dried (Na$_2$SO$_4$), and concentrated before purification by column chromatography on silica gel eluting 0-100% ethyl acetate in hexanes to afford ethyl 5-((4-chlorophenyl)ethynyl)-2-((2-(trimethylsilyl)ethoxy)methyl)-2H-1,2,3-triazole-4-carboxylate: $^1$H NMR (400 MHz, Acetonitrile-d$_3$) δ 7.64-7.56 (m, 1H), 7.52-7.45 (m, 1H), 5.98 (d, J=9.7 Hz, 1H), 5.72 (s, OH), 4.51-4.37 (m, 1H), 3.75-3.58 (m, 1H), 2.14 (s, 2H), 2.11 (d, J=1.2 Hz, 0H), 1.45-1.34 (m, 2H), 1.29 (s, OH), 0.97-0.83 (m, 1H). ES/MS m/z Calculated for C$_{19}$H$_{25}$ClN$_3$O$_3$Si (M+H)=406.14; Found 406.86.

Steps 2 and 3

4-((4-chlorophenyl)ethynyl)-1H-1,2,3-triazole-5-carboxylic acid was prepared using the general procedures for SEM deprotection by TBAF followed by ester hydrolysis: $^1$H NMR (400 MHz, Methanol-d$_4$) δ 7.57 (d, J=8.4 Hz, 2H), 7.43 (d, J=8.4 Hz, 2H). ES/MS m/z: calculated for C$_{11}$H$_7$ClN$_3$O$_2$ (M+H)=248.02; Found: 247.96.

Example 161: 4-(1-(oxetan-3-yl)piperidin-4-yl)-1H-1,2,3-triazole-5-carboxylic acid

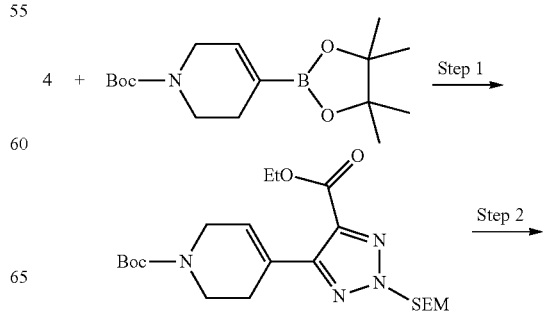

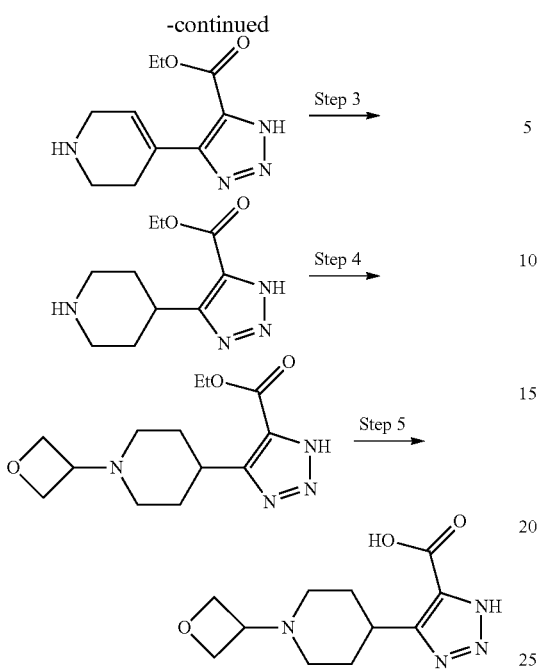

Step 1

In a microwave reaction vial, the isomeric mixture of ethyl 5-bromo-2-((2-(trimethylsilyl)ethoxy)methyl)-2H-1,2,3-triazole-4-carboxylate (4, 285 mg, 0.814 mmol), tert-butyl 4-(4,4,5,5-tetramethyl-1,3,2-dioxaborolan-2-yl)-3,6-dihydropyridine-1(2H)-carboxylate (277 mg, 0.89 mmol), tetrakis(triphenylphosphine)palladium (0) (94 mg, 0.081 mmol), 2N potassium carbonate (1022 mL, 2 mmol) and 1,4-dioxane (4 mL) were added. After purging with argon gas for 5 minutes, the resulting mixture was stirred at 110° C. for 2 hours. After cooling, the reaction mixture was diluted with saturated NaHCO$_3$ before the product was extracted with ethyl acetate, dried (MgSO$_4$), concentrated, and purified by column chromatography on silica gel eluting with ethyl acetate in hexane to get tert-butyl 4-(5-(ethoxycarbonyl)-2-((2-(trimethylsilyl)ethoxy)methyl)-2H-1,2,3-triazol-4-yl)-3,6-dihydropyridine-1 (2H)-carboxylate: ES/MS m/z: calculated for C$_{21}$H$_{36}$N$_4$O$_5$Si (M+H): 453.25, found: 452.68.

Step 2

A solution of tert-butyl 4-(5-(ethoxycarbonyl)-2-((2-(trimethylsilyl)ethoxy)methyl)-2H-1,2,3-triazol-4-yl)-3,6-dihydropyridine-1 (2H)-carboxylate (120 mg, 0.27 mmol) in 4 N HCl in 1,4-dioxane (2 mL) was stirred at rt overnight. After the reaction mixture was concentrated, the residue was purified by column chromatography on silica gel eluting with methanol in ethyl acetate to get impure ethyl 4-(1,2,3,6-tetrahydropyridin-4-yl)-1H-1,2,3-triazole-5-carboxylate: ES/MS m/z: calculated for C$_{10}$H$_{15}$N$_4$O$_2$ (M+H): 223.11, found: 223.01.

Step 3

A mixture of ethyl 4-(1,2,3,6-tetrahydropyridin-4-yl)-1H-1,2,3-triazole-5-carboxylate (22 mg, 0.01 mmol) and 10% palladium on carbon (20 mg) in ethanol (1 mL) was stirred under hydrogen atmosphere for 2 h. The reaction mixture was filtered and the filtrate was concentrated. The residue was purified via preparative HPLC to get ethyl 4-(piperidin-4-yl)-1H-1,2,3-triazole-5-carboxylate: ES/MS m/z: calculated for C$_{10}$H$_{17}$N$_4$O$_2$ (M+H): 225.13, found: 225.17.

Step 4

To a suspension of ethyl 4-(piperidin-4-yl)-1H-1,2,3-triazole-5-carboxylate (22 mg, 0.01 mmol) and 3-oxetanone (35 mg, 0.05 mmol) in THF (1 mL) was added sodium triacetoxyborohydride (104 mg, 0.05 mmol) followed by a drop of acetic acid. The reaction mixture was stirred at rt overnight. After the reaction mixture was concentrated, the residue was purified by preparative HPLC to get ethyl 4-(1-(oxetan-3-yl)piperidin-4-yl)-1H-1,2,3-triazole-5-carboxylate: ES/MS m/z: calculated for C$_{13}$H$_{21}$N$_4$O$_3$ (M+H): 281.15, found: 281.18.

Step 5:

4-(1-(oxetan-3-yl)piperidin-4-yl)-1H-1,2,3-triazole-5-carboxylic acid was prepared from ethyl 4-(1-(oxetan-3-yl)piperidin-4-yl)-1H-1,2,3-triazole-5-carboxylate in a manner similar for the general procedures of ester hydrolysis: $^1$H NMR (400 MHz, Methanol-d$_4$): δ 4.89 (m, 4H), 4.17-4.01 (m, 1H), 3.80 (m, 1H), 3.72-3.42 (m, 3H), 3.26-3.05 (m, 1H), 2.37-2.02 (m, 4H). ES/MS m/z: calculated for C$_{11}$H$_{17}$N$_4$O$_3$ (M+H): 253.12, found: 253.13.

Example 162: 4-(4-(1-acetyl-1,2,3,6-tetrahydropyridin-4-yl)phenyl)-1H-1,2,3-triazole-5-carboxylic acid

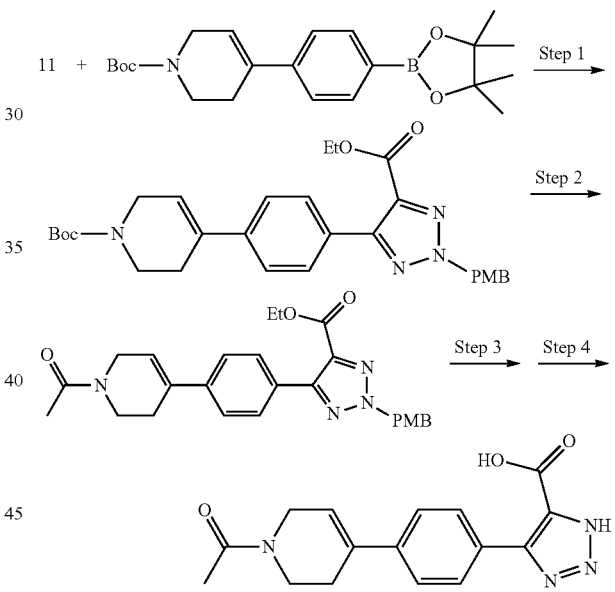

Step 1

The isomeric mixture of tert-butyl 4-(4-(5-(ethoxycarbonyl)-2-(4-methoxybenzyl)-2H-1,2,3-triazol-4-yl)phenyl)-3,6-dihydropyridine-1(2H)-carboxylate was prepared from intermediate 11 and tert-butyl 4-(4-(4,4,5,5-tetramethyl-1,3,2-dioxaborolan-2-yl)phenyl)-3,6-dihydropyridine-1(2H)-carboxylate in a manner similar to the general procedures of Suzuki reaction: ES/MS m/z: calculated for C$_{29}$H$_{35}$N$_4$O$_5$ (M+H): 519.26, found: 518.98 and 518.96.

Step 2

To a flask containing the isomeric mixture of tert-butyl 4-(4-(5-(ethoxycarbonyl)-2-(4-methoxybenzyl)-2H-1,2,3-triazol-4-yl)phenyl)-3,6-dihydropyridine-1(2H)-carboxylate (128 mg, 0.25 mmol) was added 4 N HCl in 1,4-dioxane (3 mL) and the resulting mixture was stirred at rt for 15 min. After the solution was concentrated completely, the residue and pyridine (0.05 mL, 0.62 mmol) in dichloromethane (3 mL) was added acetic anhydride (0.05 mL, 0.53 mmol) at 0°

C. After 30 min at 0° C. and 30 min at room temperature, the reaction mixture was diluted with ethyl acetate (25 mL) and washed with saturated aqueous ammonium chloride (×1), saturated aqueous sodium bicarbonate (×1), and brine (×1). After the aqueous fractions were extracted with ethyl acetate (20 mL×1), the organic fractions were combined, dried (MgSO$_4$), and concentrated. The residue was purified by column chromatography on silica gel eluting 50-100% ethyl acetate in hexane followed by 0-20% methanol in ethyl acetate to get the isomeric mixture of ethyl 5-(4-(1-acetyl-1,2,3,6-tetrahydropyridin-4-yl)phenyl)-2-(4-methoxybenzyl)-2H-1,2,3-triazole-4-carboxylate: ES/MS m/z: calculated for C$_{26}$H$_{29}$N$_4$O$_4$ (M+H): 461.22, found: 460.94 and 461.17.

Step 3 and Step 4

4-(4-(1-acetyl-1,2,3,6-tetrahydropyridin-4-yl)phenyl)-1H-1,2,3-triazole-5-carboxylic acid was prepared in a manner similar to the general procedures of PMB deprotection followed by ester hydrolysis: $^1$H NMR (400 MHz, Methanol-d$_4$) δ 7.82 (d, J=8.2 Hz, 2H), 7.54 (d, J=8.1 Hz, 2H), 6.24 (s, 1H), 4.23 (dq, J=5.8, 2.6 Hz, 2H), 3.81 (t, J=5.8 Hz, 0.83H), 3.76 (t, J=5.7 Hz, 1.17H), 2.66 (d, J=6.6 Hz, 1.17H), 2.59 (s, 0.83H), 2.18 (s, 1.755H), 2.15 (s, 1.245H). ES/MS m/z: calculated for C$_{16}$H$_{17}$N$_4$O$_3$ (M+H): 313.13, found: 313.10.

Example 163: 4-(4-(1-acetylpiperidin-4-yl)phenyl)-1H-1,2,3-triazole-5-carboxylic acid

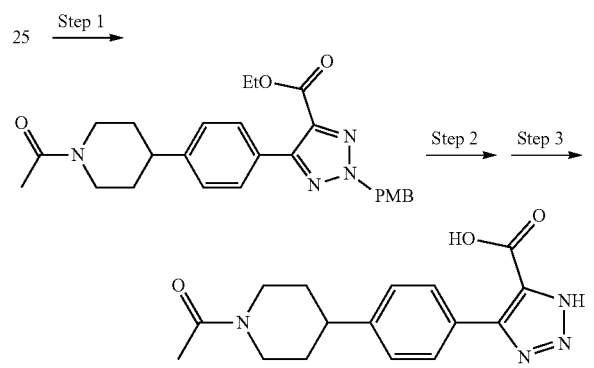

Step 1

To a flask containing the isomeric mixture of ethyl 4-(4-(1-acetyl-1,2,3,6-tetrahydropyridin-4-yl)phenyl)-1-(4-methoxybenzyl)-1H-1,2,3-triazole-5-carboxylate (the product of Example 164 Step 2, 55 mg, 0.12 mmol) were added 20% palladium hydroxide on carbon (6.6 mg) and ethanol (4 mL), and the resulting mixture was stirred under H$_2$ atmosphere for 3.5 h at room temperature. The reaction mixture was diluted with methanol and dichloromethane before filtering through celite pad. After the celite pad was washed with ethanol, the filtrate was concentrated completely, co-evaporated with toluene (×1), to obtain a crude isomeric mixture of ethyl 5-(4-(1-acetylpiperidin-4-yl)phenyl)-2-(4-methoxybenzyl)-2H-1,2,3-triazole-4-carboxylate: ES/MS m/z: calculated for C$_{26}$H$_{31}$N$_4$O$_4$ (M+H): 463.23, found: 463.04 and 463.06.

Step 2 and Step 3

4-(4-(1-acetylpiperidin-4-yl)phenyl)-1H-1,2,3-triazole-5-carboxylic acid was prepared in a manner similar to the general procedures of PMB deprotection followed by ester hydrolysis: $^1$H NMR (400 MHz, Methanol-d$_4$) δ 7.80-7.70 (m, 2H), 7.41-7.30 (m, 2H), 4.68 (ddt, J=13.2, 4.4, 2.2 Hz, 1H), 4.15-3.95 (m, 1H), 3.25 (dt, J=13.0, 2.9 Hz, 1H), 2.89 (tt, J=12.1, 3.6 Hz, 1H), 2.73 (td, J=13.0, 2.7 Hz, 1H), 2.14 (s, 3H), 1.92 (ddt, J=17.2, 14.8, 2.9 Hz, 2H), 1.73 and 1.62 (two qd, J=12.5, 4.1 Hz, 2H). ES/MS m/z: calculated for C$_{16}$H$_{19}$N$_4$O$_3$ (M+H): 315.15, found: 315.14.

Example 164: 4-(4'-(pyrazin-2-yl)-[1,1'-biphenyl]-4-yl)-1H-1,2,3-triazole-5-carboxylic acid

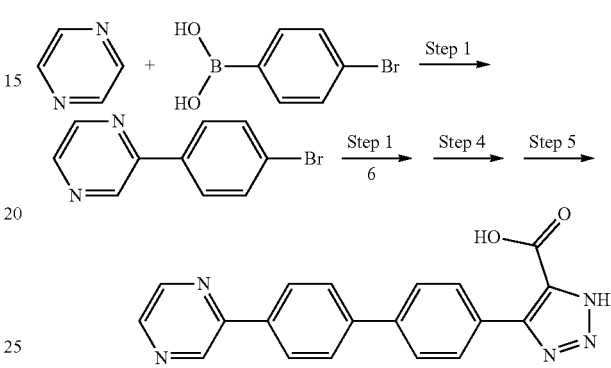

Step 1

A mixture of pyrazine (200 mg; 2 mmol), 4-bromophenylboronic acid (552 mg; 3 mmol), trifluoroacetic acid (0.191 mL; 2 mmol), tetrabutylammonium bromide (40 mg; 0.125 mmol), potassium persulfate (2.0 g; 7 mmol), and iron (iii) acetylacetonate (440 mg, 1 mmol) in CH$_2$Cl$_2$ (10 ml) and water (10 ml) was stirred at ambient temperature overnight. The reaction mixture was diluted with duck (10 ml) and water (10 ml), and solid potassium carbonate was added until the pH>8. After two layers were separated, the aqueous fraction was extracted with dichloromethane (2×10 mL), and the combined organic fractions were dried (Na$_2$SO$_4$), concentrated, and purified by column chromatography on silica gel eluting 0-100% ethyl acetate in hexanes) to afford 2-(4-bromophenyl)pyrazine: $^1$H NMR (400 MHz, chloroform-d) δ 9.01 (d, J=1.5 Hz, 1H), 8.63 (dd, 0.7=2.5, 1.5 Hz, 1H), 8.53 (d, 0.7=2.5 Hz, 1H), 7.94-7.86 (m, 2H), 7.69-7.61 (m, 2H). ES/MS m/z calculated for C$_{10}$H$_8$BrN$_2$ (m+H)=234.99; found, 235.05.

Steps 2, 3, and 4

4-(4'-(pyrazin-2-yl)-[1,1'-biphenyl]-4-yl)-1H-1,2,3-triazole-5-carboxylic acid was synthesized from 2-(4-Bromophenyl)pyrazine using representative procedures for Suzuki reaction with intermediate 6, SEM deprotection with HCl, and ester hydrolysis. $^1$H NMR (400 MHz, DMSO-d$_6$) δ 13.21 (s, 1H), 9.32 (d, J=1.6 Hz, 1H), 8.73 (dd, J=2.5, 1.5 Hz, 1H), 8.62 (d, J=2.5 Hz, 1H), 8.30-8.23 (m, 2H), 7.96-7.86 (m, 6H). ES/MS m/z: Calculated for C$_{19}$H$_{14}$N$_5$O$_2$ (M+H)=344.11; Found 344.04.

Example 165: 4-(4'-(1H-1,2,4-triazol-5-yl)-[1,1'-biphenyl]-4-yl)-1H-1,2,3-triazole-5-carboxylic acid

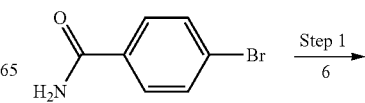

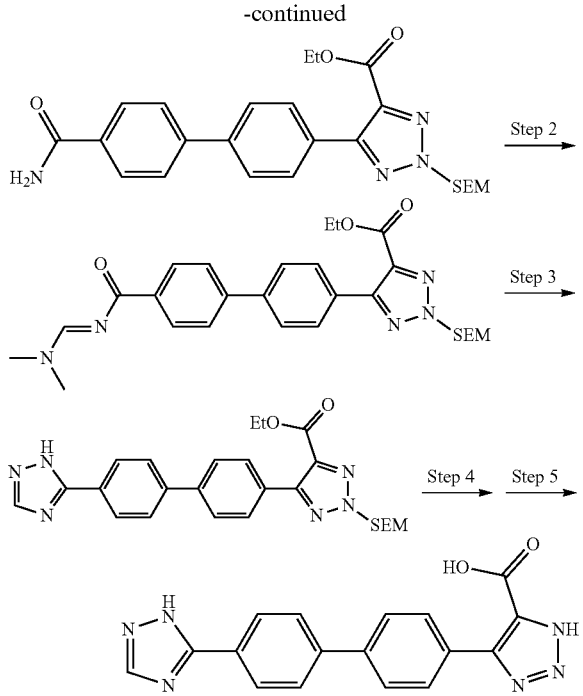

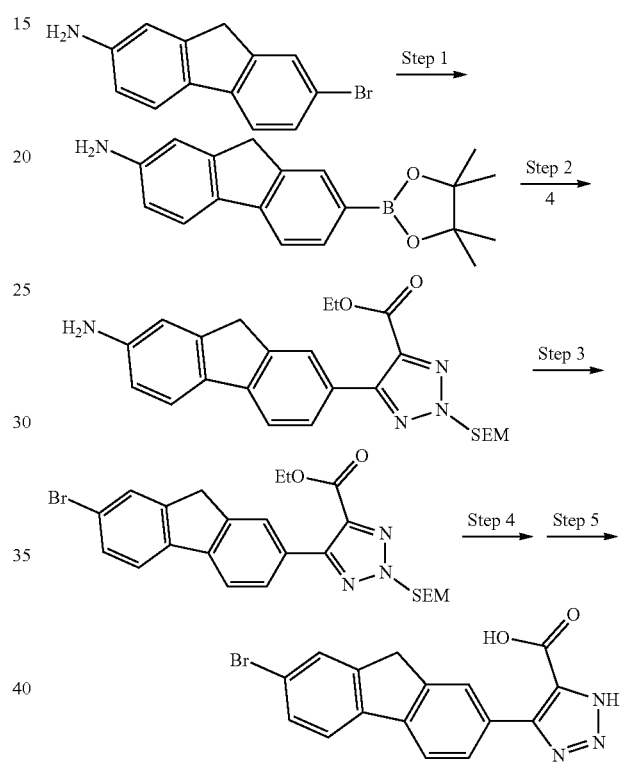

Step 1

An isomeric mixture of ethyl 5-(4'-carbamoyl-[1,1'-biphenyl]-4-yl)-2-((2-(trimethylsilyl)ethoxy)methyl)-2H-1,2,3-triazole-4-carboxylate was prepared in a manner similar to the general procedure of Suzuki reaction from 4-bromobenzamide and intermediate 6: ES/MS m/z: calculated for $C_{24}H_{30}N_4O_4Si$ (M+H)=467.2; Found 467.16.

Step 2

To a solution of ethyl 5-(4'-carbamoyl-[1,1'-biphenyl]-4-yl)-2-((2-(trimethylsilyl)ethoxy)methyl)-2H-1,2,3-triazole-4-carboxylate (117 mg; 0.25 mmol) in THF (1 mL) was added t-butoxybis(dimethylamino)methane (Bredereck's Reagent; 62 µL; 0.30 mmol). The mixture was then heated to 60° C. until starting material was consumed and ethyl (E)-5-(4'-(((dimethylamino)methylene)carbamoyl)-[1,1'-biphenyl]-4-yl)-2-((2-(trimethylsilyl)ethoxy)methyl)-2H-1,2,3-triazole-4-carboxylate appeared. The material from this reaction was used directly in step 3: ES/MS m/z: calculated for $C_{27}H_{35}N_5O_4Si$ (M+H)=522.25; Found 522.11.

Step 3

To the reaction mixture from step 2 was added hydrazine (39 µL; 1 mmol) and acetic acid (109 µL; 2.0 mmol) and heated to 60° C. Once complete by LC/MS, the reaction mixture was diluted with ethyl acetate (10 mL) and washed with saturated $NaHCO_3$ (2×5 mL). After the aqueous fraction was extracted with ethyl acetate (2×10 mL), the organic fractions were combined, washed with 1N HCl (5 mL) and water (5 mL), dried ($Na_2SO_4$), and concentrated to dryness. The crude product, ethyl 5-(4'-(1H-1,2,4-triazol-5-yl)-[1,1'-biphenyl]-4-yl)-2-((2-(trimethylsilyl)ethoxy)methyl)-2H-1,2,3-triazole-4-carboxylate, was used directly in step 4 without further purification: $^1$H NMR (400 MHz, Chloroform-d) δ 8.36 (s, 1H), 8.18 (d, J=8.0 Hz, 1H), 7.94 (dd, 0.7=26.9, 8.1 Hz, 1H), 7.70 (ddd, J=21.3, 12.8, 7.8 Hz, 3H), 7.58 (t, J=12 Hz, 0H), 7.53-7.45 (m, 0H), 6.05 (s, 0H), 5.77 (s, 1H), 4.50-4.36 (m, 1H), 4.12 (q, J=7.1 Hz, 2H), 3.81-3.72 (m, 1H), 3.70-3.61 (m, OH), 2.11 (s, 1H), 2.04 (s, 3H), 1.45-1.31 (m, 2H), 1.25 (t, J=7.1 Hz, 4H), 0.95 (dt, J=15.9, 8.3 Hz, 1H). ES/MS m/z: calculated for $C_{25}H_{30}N_6O_3Si$ (M+H)= 491.21; Found 491.25.

Steps 4 and 5

4-(4'-(1H-1,2,4-triazol-5-yl)-[1,1'-biphenyl]-4-yl)-1H-1,2,3-triazole-5-carboxylic acid was prepared in a manner similar to the general procedures of sem deprotection by HCl, followed by ester hydrolysis: $^1$H NMR (400 MHz, DMSO-$d_6$) δ 8.49 (s, 1H), 8.15-8.08 (m, 2H), 7.96-7.81 (m, 6H). ES/MS m/z calculated for $C_{17}H_{13}N_6O_2$ (m+H) 333.10; found 333.11.

Example 166: 4-(7-bromo-9H-fluoren-2-yl)-1H-1,2, 3-triazole-5-carboxylic acid

Step 1

7-(4,4,5,5-tetramethyl-1,3,2-dioxaborolan-2-yl)-9H-fluoren-2-amine was prepared in a manner similar to the representative procedure of the boronate synthesis from the aromatic bromide using bis(pinacolato)diboron (27):

Step 2

The isomeric mixture of ethyl 5-(7-amino-9H-fluoren-2-yl)-2-((2-(trimethylsilyl)ethoxy)methyl)-2H-1,2,3-triazole-4-carboxylate was prepared from intermediate 4 and 7-(4, 4,5,5-tetramethyl-1,3,2-dioxaborolan-2-yl)-9H-fluoren-2-amine in a manner similar to the general procedures of Suzuki reaction: ES/MS m/z: calculated for $C_{24}H_{31}N_4O_3Si$ (M+H): 451.22, found: 451.33.

Step 3

To a solution of ethyl 5-(7-amino-9H-fluoren-2-yl)-2-((2-(trimethylsilyl)ethoxy)methyl)-2H-1,2,3-triazole-4-carboxylate (1.00 g, 2.22 mmol) in acetonitrile (12 mL) were added t-butyl nitrite (0.32 mL, 2.69 mmol) and cupric bromide (595 mg, 2.66 mmol) at 0° C. After 45 min, the reaction mixture was quenched with 1 M $Na_2S_2O_3$ solution and the product was extracted with ethyl acetate. The extract was dried ($MgSO_4$), concentrated, and purified by column chromatography on silica gel eluting 0-100% ethyl acetate in hexane to get a mixture of the desired ethyl 5-(7-bromo-9H-fluoren-2-yl)-2-((2-(trimethylsilyl)ethoxy)methyl)-2H-1,2,3-triazole-4-carboxylate with deaminated by-product. The mixture was used for the next reaction without further purification.

Steps 4 and 5

4-(7-bromo-9H-fluoren-2-yl)-1H-1,2,3-triazole-5-carboxylic acid was prepared in a manner similar to the general procedures of SEM deprotection by HCl, and ester hydrolysis: $^1$H NMR (400 MHz, Methanol-d$_4$) δ 8.03 (s, 1H), 7.94-7.82 (m, 2H), 7.81-7.71 (m, 2H), 7.54 (dd, J=8.1, 1.8 Hz, 1H), 3.98 (s, 2H). ES/MS m/z: calculated for $C_{16}H_{11}BrClN_3O_2$ (M+H): 355.92, found: 356.00.

Example 167: 4-(7-chloro-9H-fluoren-2-yl)-1H-1,2,3-triazole-5-carboxylic acid

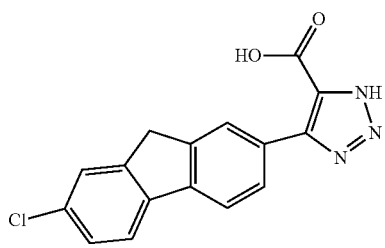 [SMILES: O=C(O)c1[nH]nnc1-c1ccc2c(c1)Cc1cc(Cl)ccc1-2]

4-(7-chloro-9H-fluoren-2-yl)-1H-1,2,3-triazole-5-carboxylic acid (56) was prepared in a manner similar to the procedure of Example 168 Step 3 using copper(II) chloride instead of copper(II) bromide, followed by the general procedures of SEM deprotection by HCl and ester hydrolysis: $^1$H NMR (400 MHz, Methanol-d$_4$) δ 8.03 (s, 1H), 7.94-7.81 (m, 3H), 7.60 (s, 1H), 7.39 (dd, J=8.1, 1.9 Hz, 1H), 3.99 (s, 2H). ES/MS m/z: calculated for $C_{16}H_{11}ClN_3O_2$(M+H): 312.05, found: 311.93

Example 168: 4-(7-(1H-1,2,3-triazol-4-yl)-9H-fluoren-2-yl)-1H-1,2,3-triazole-5-carboxylic acid

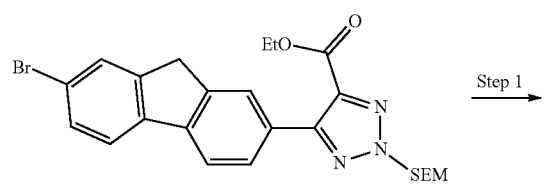

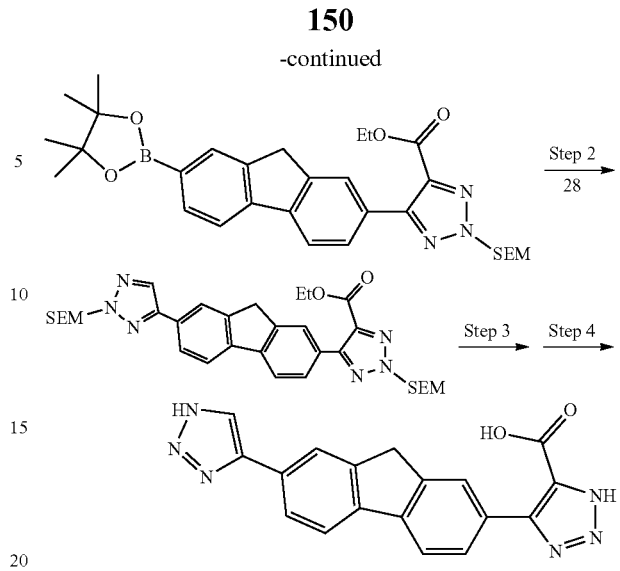

Step 1 ethyl 5-(7-(4,4,5,5-tetramethyl-1,3,2-dioxaborolan-2-yl)-9H-fluoren-2-yl)-2-((2-(trimethylsilyl)ethoxy)methyl)-2H-1,2,3-triazole-4-carboxylate was prepared in a manner similar to the representative procedure of the boronate synthesis from the aromatic bromide using bis(pinacolato)diboron (27).

Steps 2, 3, and 4

4-(7-(1H-1,2,3-triazol-4-yl)-9H-fluoren-2-yl)-1H-1,2,3-triazole-5-carboxylic acid was prepared in a manner similar to the general procedures of Suzuki reaction from ethyl 5-(7-(4,4,5,5-tetramethyl-1,3,2-dioxaborolan-2-yl)-9H-fluoren-2-yl)-2-((2-(trimethylsilyl)ethoxy)methyl)-2H-1,2,3-triazole-4-carboxylate and the boronate 28, followed by SEM deprotection by HCl and ester hydrolysis: $^1$H NMR (400 MHz, Methanol-d$_4$) δ 7.80-7.70 (m, 2H), 7.41-7.30 (m, 2H), 4.68 (ddt, J=13.2, 4.4, 2.2 Hz, 1H), 4.15-3.95 (m, 1H), 3.25 (dt, J=13.0, 2.9 Hz, 1H), 2.89 (tt, J=12.1, 3.6 Hz, 1H), 2.73 (td, J=13.0, 2.7 Hz, 1H), 2.14 (s, 3H), 1.92 (ddt, J=17.2, 14.8, 2.9 Hz, 2H), 1.73 and 1.62 (two qd, J=12.5, 4.1 Hz, 2H). ES/MS m/z: calculated for $C_{18}H_{13}N_6O_2$ (M+H): 345.10, found: 345.11.

Example 169: 4-(9,9-difluoro-7-(1H-1,2,3-triazol-4-yl)-9H-fluoren-2-yl)-1H-1,2,3-triazole-5-carboxylic acid

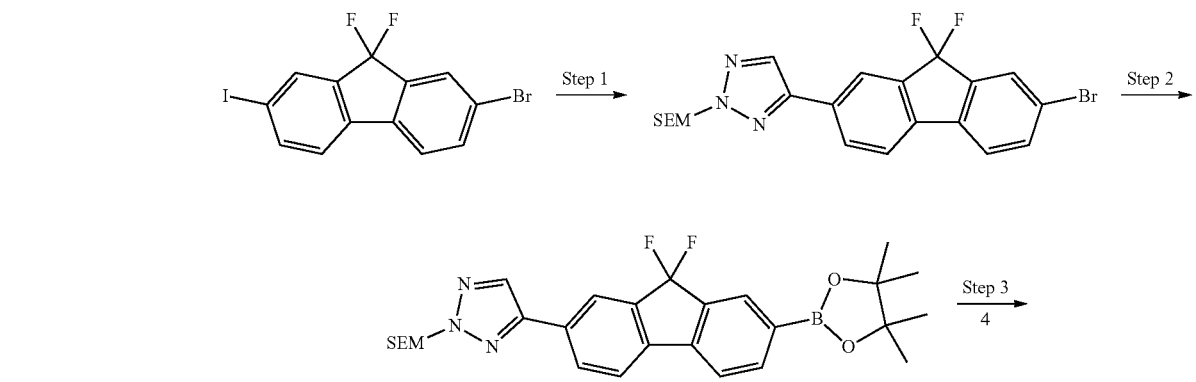

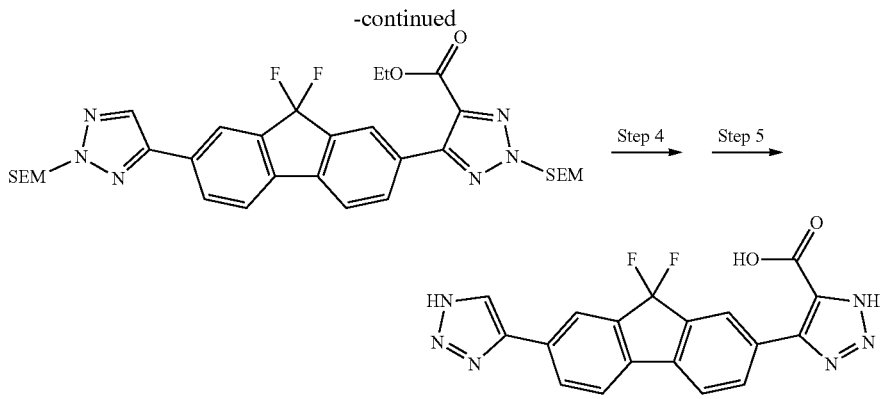

Step 1

4-(7-bromo-9,9-difluoro-9H-fluoren-2-yl)-2-((2-(trimethylsilyl)ethoxy)methyl)-2H-1,2,3-triazole was prepared in a manner similar to the general procedures of Suzuki reaction from 2-bromo-9,9-difluoro-7-iodo-9H-fluorene and the boronate 28: ES/MS m/z: calculated for $C_{21}H_{23}BrF_2N_3OSi$ (M+H): 478.08, found: 477.76.

Step 2

4-(9,9-difluoro-7-(4,4,5,5-tetramethyl-1,3,2-dioxaborolan-2-yl)-9H-fluoren-2-yl)-2-((2-(trimethylsilyl)ethoxy)methyl)-2H-1,2,3-triazole was prepared from 4-(7-bromo-9,9-difluoro-9H-fluoren-2-yl)-2-((2-(trimethylsilyl)ethoxy)methyl)-2H-1,2,3-triazole in a manner similar to the representative procedure of the boronate synthesis from the aromatic bromide using bis(pinacolato)diboron (27): ES/MS m/z: calculated for $C_{27}H_{35}BF_2N_3O_3Si$ (M+H): 526.25, found: 525.96.

Step 5, Step 6, and Step 7

4-(9,9-Difluoro-7-(1H-1,2,3-triazol-4-yl)-9H-fluoren-2-yl)-1H-1,2,3-triazole-5-carboxylic acid was prepared in a manner similar to the general procedures of Suzuki reaction using intermediate 4 and 4-(9,9-difluoro-7-(4,4,5,5-tetramethyl-1,3,2-dioxaborolan-2-yl)-9H-fluoren-2-yl)-2-((2-(trimethylsilyl)ethoxy)methyl)-2H-1,2,3-triazole, followed by SEM deprotection by HCl and ester hydrolysis: $^1$H NMR (400 MHz, Methanol-$d_4$) δ 8.45-8.01 (m, 1H), 8.19 (s, 1H), 8.15 (s, 1H), 8.13-8.01 (m, 2H), 7.85 (t, J=7.0 Hz, 2H). ES/MS m/z: calculated for $C_{18}H_{11}F_2N_6O_2$ (M+H): 381.09, found: 381.06.

Example 170: 4-(9,9-difluoro-7-(1H-1,2,3-triazol-4-yl)-9H-fluoren-2-yl)-1H-pyrazole-5-carboxylic acid

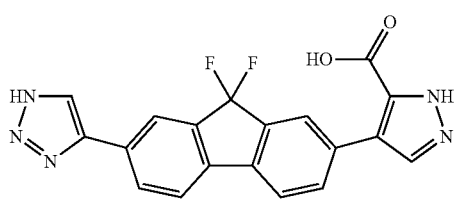 [SMILES: O=C(O)c1[nH]ncc1-c1ccc2c(c1)C(F)(F)c1cc(-c3c[nH]nn3)ccc1-2]

4-(9,9-difluoro-7-(1H-1,2,3-triazol-4-yl)-9H-fluoren-2-yl)-1H-pyrazole-5-carboxylic acid was prepared in a manner similar to the general procedures of Suzuki reaction from intermediate 15 and 4-(9,9-difluoro-7-(1H-1,2,3-triazol-4-yl)-9H-fluoren-2-yl)-1H-1,2,3-triazole-5-carboxylic acid, followed by SEM deprotection by HCl and ester hydrolysis:

$^1$H NMR (400 MHz, Methanol-$d_4$) δ 8.27 (s, 1H), 8.11 (d, J=1.7 Hz, 1H), 8.03 (dd, J=7.9, 1.5 Hz, 1H), 7.89 (s, 1H), 7.88-7.84 (m, 1H), 7.79 (d, J=7.9 Hz, 1H), 7.77-7.70 (m, 2H). ES/MS m/z: calculated for $C_{19}H_{12}F_2N_5O_2$ (M+H): 380.10, found: 380.11.

Example 171: 4-(7-(1,5-dimethyl-1H-1,2,3-triazol-4-yl)-9,9-difluoro-9H-fluoren-2-yl)-1H-1,2,3-triazole-5-carboxylic acid

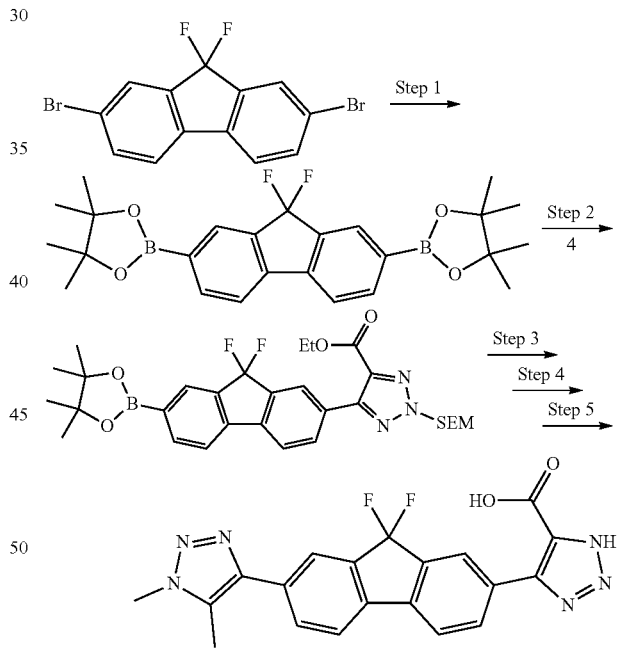

Step 1

A mixture of 2,7-dibromo-9,9-difluoro-9H-fluorene (2000 mg, 5.56 mmol), bis(pinacolato)diboron (5646 mg, 22.2 mmol), dichloro 1,1'-bis(diphenylphosphino)ferrocene palladium (II) dichloromethane (679 mg, 0.83 mmol), and potassium acetate (2903 mg, 29.6 mmol) in 1,4-dioxane (50 mL) was purged with argon gas for 15 min and before stirred at 80° C. for 16 h. The reaction mixture was concentrated completely and the residue was dissolved in ethyl acetate (~300 mL) and washed with water (~250 mL×2). After the aq. fractions were extracted with ethyl acetate (~100 mL×1), the organic fractions were combined, dried (Na$_2$SO$_4$), and concentrated. The residue was purified by column chromatography on silica gel eluting 0-20% ethyl acetate in hexanes to get 2,2'-(9,9-difluoro-9H-fluorene-2,7-diyl)bis(4,4,5,5-tetramethyl-1,3,2-dioxaborolane): $^1$H NMR (400 MHz, Chloroform-d) δ 8.08 (dt, J=2.0, 0.9 Hz, 2H), 7.95-7.89 (m, 2H), 7.60 (dd, J=7.5, 0.9 Hz, 2H), 1.36 (s, 24H), no mass.

Step 2

An isomeric mixture of ethyl 5-(9,9-difluoro-7-(4,4,5,5-tetramethyl-1,3,2-dioxaborolan-2-yl)-9H-fluoren-2-yl)-2-((2-(trimethylsilyl)ethoxy)methyl)-2H-1,2,3-triazole-4-carboxylate was prepared in a manner similar to the general procedures of Suzuki reaction from intermediate 4 and 2,2'-(9,9-difluoro-9H-fluorene-2,7-diyl)bis(4,4,5,5-tetramethyl-1,3,2-dioxaborolane): ES/MS m/z: calculated for $C_{30}H_{39}BF_2N_3O_5Si$ (M+H): 598.27, found: 597.81 and 597.67.

Step 3, Step 4, and Step 5

4-(7-(1,5-dimethyl-1H-1,2,3-triazol-4-yl)-9,9-difluoro-9H-fluoren-2-yl)-1H-1,2,3-triazole-5-carboxylic acid was prepared in a manner similar to the general procedures of Suzuki reaction using 4-bromo-1,5-dimethyl-1H-1,2,3-triazole and the isomeric mixture of ethyl 5-(9,9-difluoro-7-(4,4,5,5-tetramethyl-1,3,2-dioxaborolan-2-yl)-9H-fluoren-2-yl)-2-((2-(trimethylsilyl)ethoxy)methyl)-2H-1,2,3-triazole-4-carboxylate, followed by SEM deprotection by HCl and ester hydrolysis: $^1$H NMR (400 MHz, Methanol-d$_4$) δ 8.20 (s, 1H), 8.11 (d, J=7.8 Hz, 1H), 7.94 (s, 1H), 7.88 (d, J=8.1 Hz, 1H), 7.85 (d, J=8.6 Hz, 2H), 4.06 (s, 3H), 2.54 (s, 3H). ES/MS m/z: calculated for $C_{20}H_{15}F_2N_6O_2$ (M+H): 409.12, found: 409.14.

Example 172: 4-(9,9-difluoro-7-(2-methyl-2H-1,2,3-triazol-4-yl)-9H-fluoren-2-yl)-1H-1,2,3-triazole-5-carboxylic acid

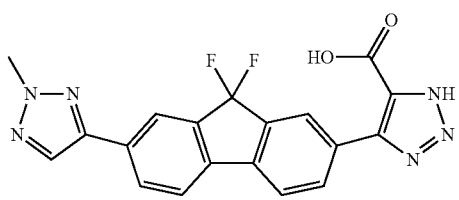 [SMILES: Cn1ncc(-c2ccc3c(c2)C(F)(F)c2cc(-c4nn[nH]c4C(=O)O)ccc2-3)n1]

4-(9,9-difluoro-7-(2-methyl-2H-1,2,3-triazol-4-yl)-9H-fluoren-2-yl)-1H-1,2,3-triazole-5-carboxylic acid was prepared in a manner similar to the general procedures of Suzuki reaction using 4-bromo-2-methyl-2H-1,2,3-triazole and the isomeric mixture of ethyl 5-(9,9-difluoro-7-(4,4,5,5-tetramethyl-1,3,2-dioxaborolan-2-yl)-9H-fluoren-2-yl)-2-((2-(trimethylsilyl)ethoxy)methyl)-2H-1,2,3-triazole-4-carboxylate, followed by SEM deprotection by HCl and ester hydrolysis: $^1$H NMR (400 MHz, Methanol-d$_4$) δ 8.19 (s, 1H), 8.11 (s, 3H), 8.03 (d, J=7.9 Hz, 1H), 7.83 (d, J=8.0 Hz, 2H), 4.24 (s, 3H). ES/MS m/z: calculated for $C_{19}H_{13}F_2N_6O_2$ (M+H): 395.11, found: 395.03.

Example 173: 4-(6-chloro-9H-fluoren-2-yl)-1H-1,2,3-triazole-5-carboxylic acid

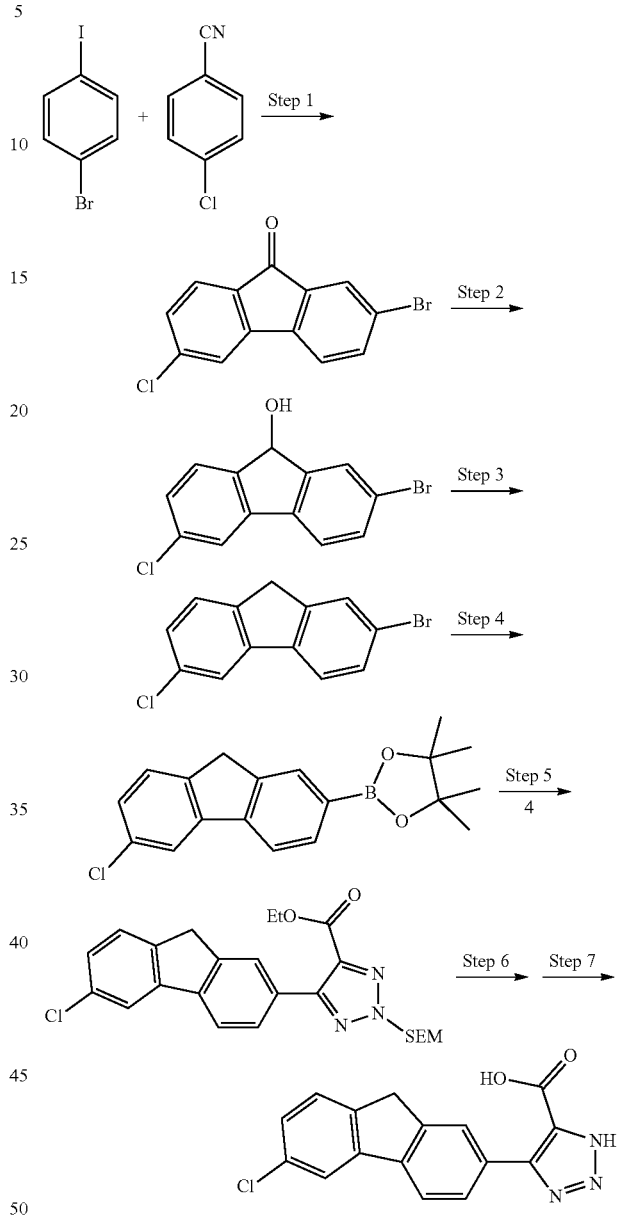

Step 1

A mixture of 1-bromo-4-iodobenzene (1.00 g, 3.5 mmol), 4-chlorobenzonitrile (973 mg, 7.1 mmol), bis(acetonitrile) palladium (II) chloride (92 mg, 0.35 mmol), and silver (I) oxide (901 mg, 3.9 mmol) in trifluoroacetic acid (35 mL) and dimethylacetamide (1.75 mL) was purged with argon gas. After 15 min, water (64 μL) was slowly added dropwise to the mixture while argon purging. After 1 min, the flask was kept tightly and heated to 140° C. for 90 h. After cooling, the reaction mixture was diluted with dichloromethane, filtered through celite pad, and the resulting filtrate was concentrated. After the residue was dissolved in dichloromethane and aq. HCl, insoluble material was filtered off through celite pad again, and the two layers of the filtrate were separated. The organic fraction was dried (MgSO$_4$), concentrated, and purified by column chromatography on silica gel eluting 0-100% ethyl acetate in hexane to get 2-bromo-6-chloro-9H-fluoren-9-one.

Step 2

To a solution of 2-bromo-6-chloro-9H-fluoren-9-one (33 mg, 0.11 mmol) in tetrahydrofuran (1 mL) was added 1 M lithium triethylborohydride (0.34 mL) at −78° C. After 25 min, the reaction mixture was quenched with saturated aq. NH$_4$Cl. After the product was extracted with ethyl acetate (×4), the organic extracts were combined, washed with brine (×1), dried (MgSO$_4$), and concentrated to get crude 2-bromo-6-chloro-9H-fluoren-9-ol, which was used for the next step.

Step 3

To the crude 2-bromo-6-chloro-9H-fluoren-9-ol were added triethylsiline (0.3 mL) and trifluoroacetic acid (0.3 mL), and the resulting mixture was stirred at rt for 1.7 h. After the concentration, the residue was purified by column chromatography on silica gel eluting 0-100% ethyl acetate in hexane to get 2-bromo-6-chloro-9H-fluorene.

Step 4

A mixture of 2-bromo-6-chloro-9H-fluorene (27 mg, 0.095 mmol), bis(pinacolato)diboron (29 mg, 0.11 mmol), [1,1'-bis(diphenylphosphino)ferrocene]dichloropalladium (II) (7.8 mg, 9.5 μmol), and potassium acetate (28 mg, 0.29 mmol) in dioxane (1.5 mL) was placed in microwave reaction vial and purged with argon gas. After the resulting mixture was stirred at 95° C. for 2.25 h and cooled, the mixture was diluted with water, and the product was extracted with ethyl acetate (×4). The combined organic extracts were dried (MgSO$_4$), concentrated, and purified by column chromatography on silica gel eluting 0-100% ethyl acetate in hexane to get 2-(6-chloro-9H-fluoren-2-yl)-4,4,5,5-tetramethyl-1,3,2-dioxaborolane.

Step 5, Step 6 and Step 7

4-(6-chloro-9-oxo-9H-fluoren-2-yl)-1H-1,2,3-triazole-5-carboxylic acid was prepared in a manner similar to the general procedures of Suzuki reaction using intermediate 4 and 2-(6-chloro-9H-fluoren-2-yl)-4,4,5,5-tetramethyl-1,3,2-dioxaborolane, followed by SEM deprotection by HCl and ester hydrolysis: $^1$H NMR (400 MHz, Methanol-d$_4$) δ 8.05 (s, 1H), 7.94 (d, J=8.0 Hz, 1H), 7.92-7.84 (m, 2H), 7.57 (d, J=8.0 Hz, 1H), 7.33 (dd, J=8.0, 2.0 Hz, 1H), 3.98 (s, 2H). ES/MS m/z: calculated for C$_{16}$H$_{11}$ClN$_3$O$_2$ (M+H): 312.05, found: 311.96.

Example 174: 4-(2-(piperidin-4-yl)-4'-(1H-1,2,3-triazol-4-yl)-[1,1'-biphenyl]-4-yl)-1H-1,2,3-triazole-5-carboxylic acid

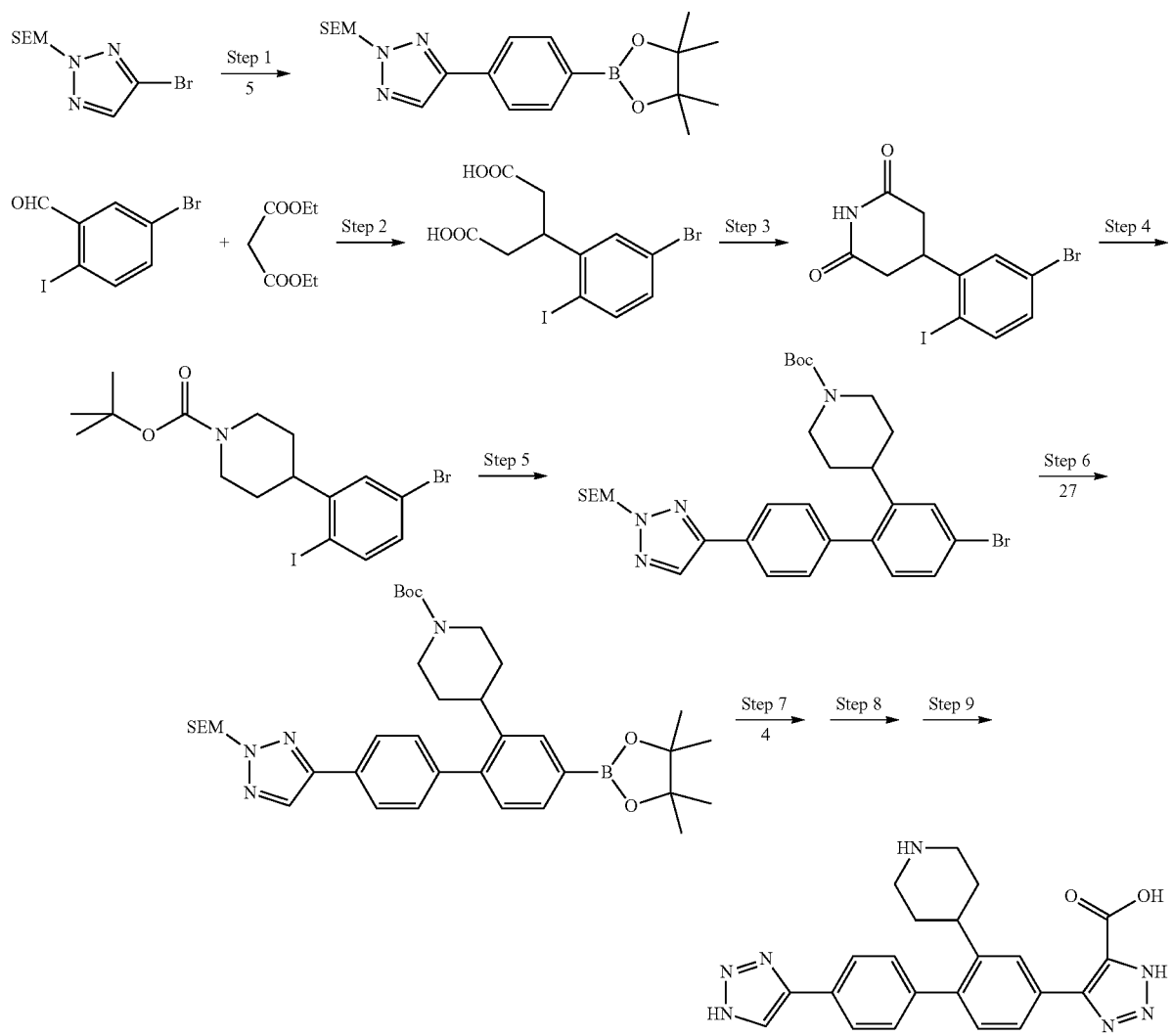

Step 1

A mixture of 4-bromo-2-((2-(trimethylsilyl)ethoxy)methyl)-2H-1,2,3-triazole (28, 403 mg, 1.45 mmol), 1,4-bis(4,4,5,5-tetramethyl-1,3,2-dioxaborolan-2-yl)benzene (5, 1.93 g, 5.84 mmol), and palladium (0) tetrakis(triphenylphosphine) (168 mg, 0.15 mmol) in 2 M potassium carbonate (2.9 mL) and 1,4-dioxane (15 mL) in a 20 mL microwave reaction vial was purge with Ar for 10 minutes and then stirred at 110° C. bath for 1.25 hour. The reaction mixture was dissolved in ethyl acetate (~100 mL) and washed with ~50% saturated NaHCO$_3$ (×1) and water (×1). After the aq. fractions were extracted with ethyl acetate (~50 mL×1) the organic fractions were combined, dried (MgSO$_4$), and concentrated. The residue was purified by column chromatography on silica gel eluting 0-100% ethyl acetate in hexane. The partially purified product was further purified by column chromatography on silica gel eluting 0-20% ethyl acetate in hexane to get 4-(4-(4,4,5,5-tetramethyl-1,3,2-dioxaborolan-2-yl)phenyl)-2-((2-(trimethylsilyl)ethoxy)methyl)-2H-1,2,3-triazole: ES/MS m/z: calculated for $C_{20}H_{33}BN_3O_3Si$ (M+H): 402.24, found: 401.96.

Step 2

A mixture of 5-bromo-2-iodobenzaldehyde (3.11 g, 10.00 mmol), diethyl malonate (6.45 g, 40.27 mmol), and potassium carbonate (5.57 g, 40.30 mmol) in DMF (20 mL) was stirred at 85° C. bath for 18 h. After the reaction mixture was cooled and diluted with water (100 mL), the product was extracted with ethyl acetate (100 mL×4). After the extracts were washed with water (100 mL×1), the combined extracts were dried (Na$_2$SO$_4$) and concentrated. After the residue was treated with concentrated HCl (25 mL) the mixture was refluxed for 36 h. After the resulting mixture was cooled in refrigerator, the insoluble material was filtered, and washed with water. The solids were dissolved in ethyl acetate (~100 mL), dried (MgSO$_4$), and concentrated to get crude 3-(5-bromo-2-iodophenyl)pentanedioic acid: ES/MS m/z: calculated for $C_{11}H_{11}BrIO_4$ (M+H): 412.89, found: 412.58.

Step 3

A mixture of the above crude 3-(5-bromo-2-iodophenyl)pentanedioic acid in acetic anhydride (~10 mL) was refluxed in 155° C. bath for 3 h. After the resulting solution was concentrated, the remained syrup was co-evaporated with toluene (×2) and dried in vacuum. The residue was dissolved in THF (50 mL) and stirred at rt as 28% aq. NH$_3$ solution (0.65 mL each) were added three times about 15 min interval. The resulting mixture was stirred at rt for 7 h. The resulting suspension was concentrated completely, co-evaporated with toluene (×2), and dried. The residue was refluxed with acetic anhydride (15 mL) at 155° C. bath for 4 h and cooled. The solution was concentrated and the residue was purified by column chromatography on silica gel eluting 0-60% ethyl acetate in hexanes to get 4-(5-bromo-2-iodophenyl)piperidine-2,6-dione: $^1$H NMR (400 MHz, DMSO-d$_6$) δ 10.98 (s, 1H), 7.82 (d, J=8.4 Hz, 1H), 7.55 (d, J=2.4 Hz, 1H), 7.25 (dd, J=8.4, 2.4 Hz, 1H), 3.52 (tt, J=12.0, 4.1 Hz, 1H), 2.90-2.78 (m, 2H), 2.63 (dd, J=16.7, 4.1 Hz, 2H).

Step 4

4-(5-bromo-2-iodophenyl)piperidine-2,6-dione (1.60 g, 4.06 mmol) in THF (5 mL) was stirred at 0° C. as 1.0 M borane tetrahydrofuran complex solution in THF (10.2 mL) was added dropwise. After the resulting mixture was refluxed for 20 h, c. HCl (16 mL) was added to the mixture and the resulting solution was refluxed at 105° C. bath for 4.5 h. The solution was stirred at ice bath while NaOH (solid) was added to neutralize the mixture. The resulting basic solution was diluted with some NaHCO$_3$ solution, and the product was extracted with ethyl acetate (60 mL×2). The extracts were washed with brine (×1), combined, dried (Na$_2$SO$_4$), and concentrated to get 4-(5-bromo-2-iodophenyl)piperidine as oil.

A solution of the crude 4-(5-bromo-2-iodophenyl)piperidine in methanol (25 mL) was stirred at 0° C. as BoC$_2$O (1078 mg, 4.939 mmol) and triethylamine (0.8 mL, 5.740 mmol) were added. After 2 h at 0° C. and at rt overnight. The reaction mixture was concentrated and the residue was dissolved in ethyl acetate before washing with water (×2). The resulting organic fraction was dried (MgSO$_4$), concentrated, and purified by column chromatography on silica gel eluting 0-10% EA in hexane to get tert-butyl 4-(5-bromo-2-iodophenyl)piperidine-1-carboxylate: $^1$H NMR (400 MHz, Chloroform-d) δ 7.68 (d, J=8.4 Hz, 1H), 7.27 (d, J=2.4 Hz, 1H), 7.05 (dd, J=8.4, 2.4 Hz, 1H), 4.27 (s, 2H), 2.94-2.85 (tt, J=3.4, 12.9 Hz, 1H), 2.82 (s, 2H), 1.84 (d, J=12.9 Hz, 2H), 1.51 (dd, J=3.8, 12.9 Hz, 2H), 1.48 (s, 9H).

Step 5

A mixture of tert-butyl 4-(5-bromo-2-iodophenyl)piperidine-1-carboxylate (250 mg, 0.63 mmol), 4-(4-(4,4,5,5-tetramethyl-1,3,2-dioxaborolan-2-yl)phenyl)-2-((2-(trimethylsilyl)ethoxy)methyl)-2H-1,2,3-triazole (273 mg, 0.68 mmol), tetrakis(triphenylphosphine)palladium (0) (75 mg, 0.06 mmol), and 2 N potassium carbonate (0.6 mL) in dioxane (6 mL) was purged with Ar gas for 10 min and the stirred at 110° C. bath for 1.5 h. After cooling, the mixture was diluted with ethyl acetate, dried (MgSO$_4$), concentrated, and purified by column chromatography on silica gel eluting 0-50% ethyl acetate in hexane to get tert-Butyl 4-(4-bromo-4'-(2-((2-(trimethylsilyl)ethoxy)methyl)-2H-1,2,3-triazol-4-yl)-[1,1'-biphenyl]-2-yl)piperidine-1-carboxylate: ES/MS m/z: calculated for $C_{30}H_{41}BrN_4NaO_3Si$ (M+Na): 635.20, found: 635.14.

Step 6

A mixture of tert-butyl 4-(4-bromo-4'-(2-((2-(trimethylsilyl)ethoxy)methyl)-2H-1,2,3-triazol-4-yl)-[1,1'-biphenyl]-2-yl)piperidine-1-carboxylate (201 mg, 0.33 mmol), bis(pinacolato)diboron (27, 27 mg, 0.66 mmol), dichloro 1,1'-bis(diphenylphosphino)ferrocene palladium (II) dichloromethane (116 mg, 0.03 mmol), and potassium acetate (102 mg, 1.04 mmol) in 1,4-dioxane (3 mL) in a microwave reaction vial was purged with Ar gas for 15 min before the mixture was heated at 120° C. for 1.5 h. After cooling, the reaction mixture was diluted with ethyl acetate, dried (MgSO$_4$), and concentrated. The residue was purified by column chromatography on silica gel eluting 0-35% ethyl acetate in hexane to provide tert-butyl 4-(4-(4,4,5,5-tetramethyl-1,3,2-dioxaborolan-2-yl)-4'-(2-((2-(trimethylsilyl)ethoxy)methyl)-2H-1.2.3-triazol-4-yl)-[1,1'-biphenyl]-2-yl)piperidine-1-carboxylate: ES/MS m/z: calculated for $C_{36}H_{53}BN_4NaO_5Si$ (M+Na): 683.38, found: 683.35.

Step 7, Step 8, and Step 9

4-(2-(piperidin-4-yl)-4'-(1H-1,2,3-triazol-4-yl)-[1,1'-biphenyl]-4-yl)-1H-1,2,3-triazole-5-carboxylic acid was prepared in a manner similar to the general procedures of Suzuki reaction using intermediate 4 and tert-butyl 4-(4-(4,4,5,5-tetramethyl-1,3,2-dioxaborolan-2-yl)-4'-(2-((2-(trimethylsilyl)ethoxy)methyl)-2H-1,2,3-triazol-4-yl)-[1,1'-biphenyl]-2-yl)piperidine-1-carboxylate, followed by SEM deprotection by HCl and ester hydrolysis: $^1$H NMR (400 MHz, Methanol-d$_4$) δ 8.23 (s, 1H), 7.99 (d, J=1.8 Hz, 1H), 7.98-7.91 (m, 2H), 7.78 (dd, J=8.0, 1.7 Hz, 1H), 7.49-7.41 (m, 2H), 7.36 (d, J=7.9 Hz, 1H), 3.41 (dd, J=12.8, 3.2 Hz, 2H), 3.21-3.03 (m, 1H), 2.93 (ddd, J=16.6, 8.6, 5.2 Hz, 2H), 2.03 (tt, J=8.6, 3.4 Hz, 4H). ES/MS m/z: calculated for $C_{22}H_{22}N_7O_2$ (M+H): 416.18, found: 416.14.

Example 175: Ethyl 4-(7-(1H-1,2,3-triazol-4-yl)-9H-fluoren-2-yl)-1H-1,2,3-triazole-5-carboxylate

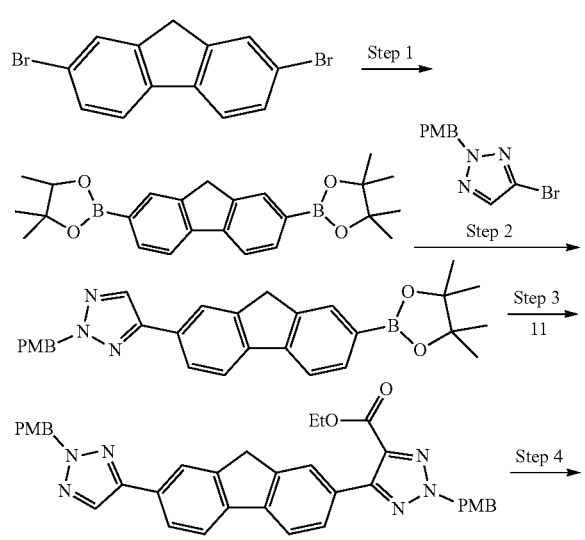

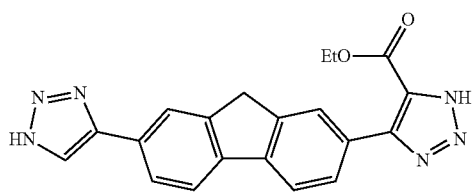

Step 1, Step 2, Step 3, and Step 4

Ethyl 4-(7-(1H-1,2,3-triazol-4-yl)-9H-fluoren-2-yl)-1H-1,2,3-triazole-5-carboxylate was prepared in a manner similar to the procedures described herein using intermediate 11 and 2,7-dibromo-9H-fluorene, followed by a manner similar to the general procedures of PMB deprotection: $^1$H NMR (400 MHz, DMSO-$d_6$) δ 8.39 (s, 1H), 8.14 (s, 1H), 8.07-8.02 (m, 3H), 7.95 (d, J=8.0 Hz, 1H), 7.82 (m, 1H), 4.32 (q, J=7.0 Hz, 2H), 4.08 (s, 2H), 1.28 (t, J=7.0 Hz, 3H). ES/MS m/z: calculated for $C_{20}H_{17}N_6O_2$ (M+H): 373.14, found: 373.30.

Example 176: 2-morpholinoethyl 4-(7-(1H-1,2,3-triazol-4-yl)-9H-fluoren-2-yl)-1H-1,2,3-triazole-5-carboxylate

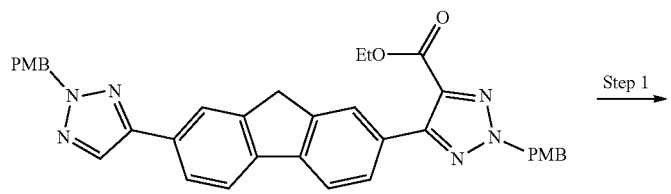

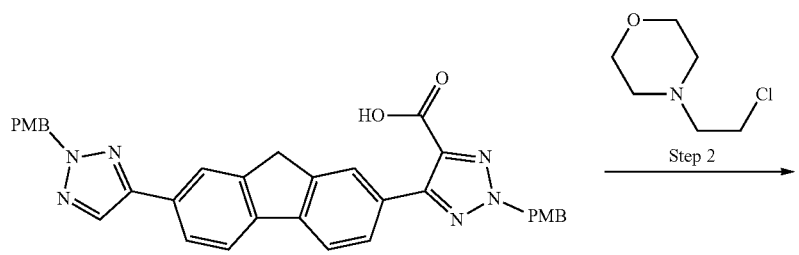

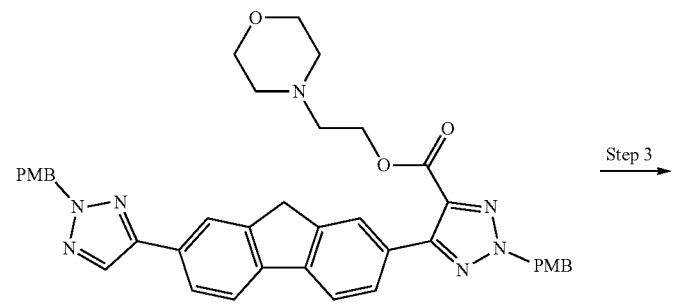

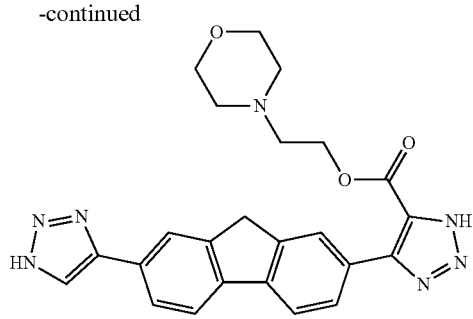

Step 1

To a stirred solution of ethyl 2-(4-methoxybenzyl)-5-(7-(2-(4-methoxybenzyl)-2H-1,2,3-triazol-4-yl)-9H-fluoren-2-yl)-2H-1,2,3-triazole-4-carboxylate (18 g, 29.4 mmol) in MeOH (36 mL), THF (108 mL), and water (36 mL) at rt under argon was added lithium hydroxide monohydrate (3.7 g, 88.18 mmol). The reaction mixture was heated to 60° C. and stirred for 5 h. The reaction mixture was concentrated under reduced pressure to obtain crude product, which was diluted with water and acidified with 1 N HCl solution and stirred for 10 min. The precipitated solid was filtered and washed the solid with water and dried under vacuum to obtain 2-(4-methoxybenzyl)-5-(7-(2-(4-methoxybenzyl)-2H-1,2,3-triazol-4-yl)-9H-fluoren-2-yl)-2H-1,2,3-triazole-4-carboxylic acid: ES/MS m/z: calculated for $C_{34}H_{29}N_6O_4$ (M+H): 585.23, found: 585.41.

Step 2

To a stirred solution of 2-(4-methoxybenzyl)-5-(7-(2-(4-methoxybenzyl)-2H-1,2,3-triazol-4-yl)-9H-fluoren-2-yl)-2H-1,2,3-triazole-4-carboxylic acid (3.0 g, 5.14 mmol) in DMF (30 mL) at rt under argon was added potassium carbonate (1.41 g, 10.3 mmol), followed by 4-(2-chloroethyl)morpholine (1.53 g, 10.3 mmol). The mixture was heated to 50° C. and stirred for 6 h. The reaction mixture was diluted with ethyl acetate and washed with water. The organic layer was dried ($Na_2SO_4$) and concentrated under reduced pressure. The residue was purified by column chromatography on silica gel eluting 80-100% ethyl acetate in pet-ether to obtain 2-morpholinoethyl 2-(4-methoxybenzyl)-5-(7-(2-(4-methoxybenzyl)-2H-1,2,3-triazol-4-yl)-9H-fluoren-2-yl)-2H-1,2,3-triazole-4-carboxylate: ES/MS m/z: calculated for $C_{40}H_{40}N_7O_5$ (M+H): 683.31, found: 698.52.

Step 3

A mixture of 2-morpholinoethyl 2-(4-methoxybenzyl)-5-(7-(2-(4-methoxybenzyl)-2H-1,2,3-triazol-4-yl)-9H-fluoren-2-yl)-2H-1,2,3-triazole-4-carboxylate (3.0 g, 4.3 mmol) in TFA (30 mL) was heated at 80° C. for 16 h. After the reaction mixture was concentrated under reduced pressure, and the crude residue was neutralized with sat.$NaHCO_3$ solution; the product was extracted with ethyl acetate. The organic layer was dried ($Na_2SO_4$) and concentrated under reduced pressure. The crude compound was purified by Prep-HPLC (Neutral method), and the pure fraction was lyophilized to obtain 2-morpholinoethyl 4-(7-(1H-1,2,3-triazol-4-yl)-9H-fluoren-2-yl)-1H-1,2,3-triazole-5-carboxylate: $^1$H NMR (400 MHz, DMSO-$d_6$) δ 8.41 (s, 1H), 8.14 (s, 1H), 8.05 (t, J=8.4 Hz, 2H), 8.00 (s, 1H), 7.95 (d, J=8.4 Hz, 1H), 7.81 (d, J=8.4 Hz, 1H), 4.38 (t, J=5.6 Hz, 2H), 4.08 (s, 2H), 3.49 (t, J=4.6 Hz, 4H), 2.61 (t, J=5.6 Hz, 2H), 2.49-2.33 (m, 4H). ES/MS m/z: calculated for $C_{24}H_{24}N_7O_3$ (M+H): 458.19, found: 458.32.

Example 177: 3-morpholinopropyl 4-(7-(1H-1,2,3-triazol-4-yl)-9H-fluoren-2-yl)-1H-1,2,3-triazole-5-carboxylate

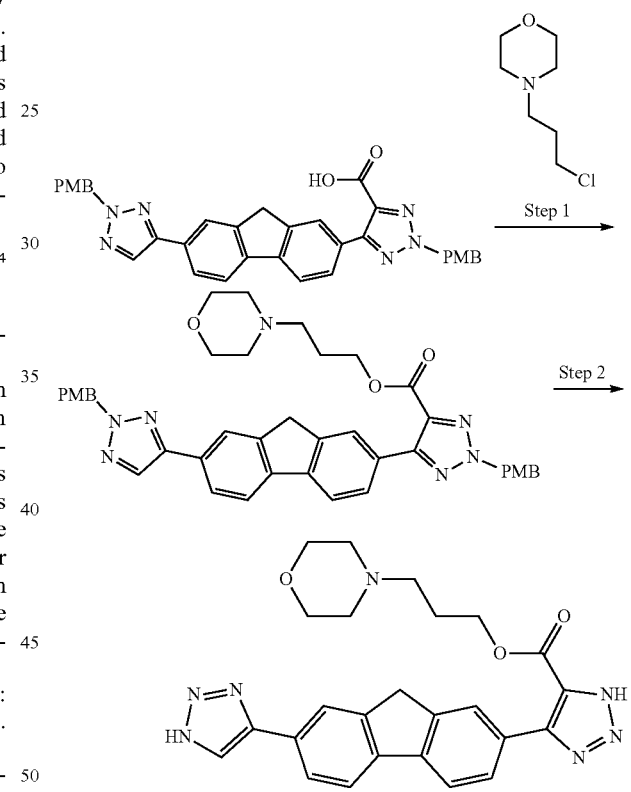

Step 1 and Step 2

3-morpholinopropyl 4-(7-(1H-1,2,3-triazol-4-yl)-9H-fluoren-2-yl)-1H-1,2,3-triazole-5-carboxylate was prepared in a manner similar to the procedures of Example 175, step 2 and step 3, using 4-(3-chloropropyl)morpholine and 2-(4-methoxybenzyl)-5-(7-(2-(4-methoxybenzyl)-2H-1,2,3-triazol-4-yl)-9H-fluoren-2-yl)-2H-1,2,3-triazole-4-carboxylic acid, followed by a manner similar to the general procedures of PMB deprotection: $^1$H NMR (400 MHz, DMSO-$d_6$) δ 15.18 (s, 1H), 8.42 (s, 1H), 8.14 (s, 1H), 8.04 (m, 2H), 7.98 (s, 1H), 7.95 (d, J=8.0 Hz, 1H), 7.77 (d, J=8.0 Hz, 1H), 4.27 (t, J=6.2 Hz, 2H), 4.08 (s, 2H), 3.42 (t, J=4.4 Hz, 4H), 2.22-2.18 (m, 6H), 1.77 (qn, J=6.7 Hz, 2H). ES/MS m/z: calculated for $C_{25}H_{26}N_7O_3$ (M+H): 472.21, found: 472.50.

Example 178: 2-((L-valyl)oxy)ethyl 4-(7-(1H-1,2,3-triazol-4-yl)-9H-fluoren-2-yl)-1H-1,2,3-triazole-5-carboxylate

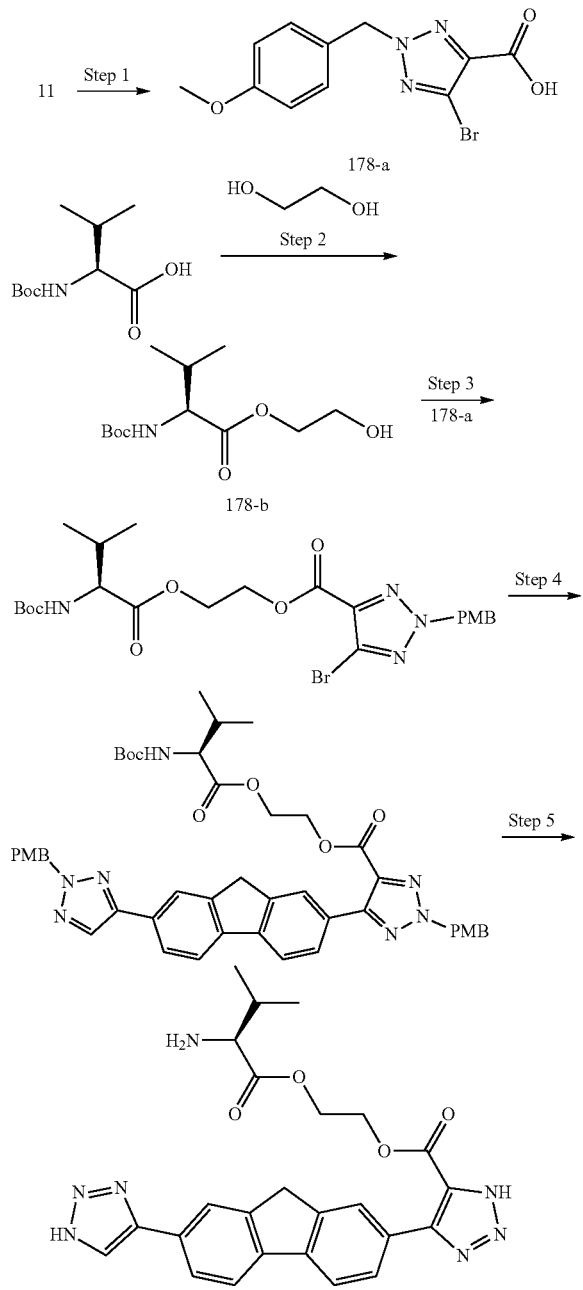

Step 1
To a stirred solution of ethyl 5-bromo-2-(4-methoxybenzyl)-2H-1,2,3-triazole-4-carboxylate (11, 5.0 g, 14.74 mmol) in MeOH (10 mL), THF (30 mL), and water (10 mL) at rt under argon was added lithium hydroxide monohydrate (1.85 g, 44.24 mmol). After the reaction mixture was stirred at rt for 5 h, the reaction mixture was concentrated under reduced pressure. The residue was diluted with water and acidified with 1N HCl solution before stirring for 10 min. The precipitated solid was filtered, washed with water, and dried under vacuum to obtain 5-bromo-2-(4-methoxybenzyl)-2H-1,2,3-triazole-4-carboxylic acid (178-a): ES/MS m/z: calculated for $C_{11}H_{10}BrN_3NaO_3$ (M+H): 333.98, found: 334.10.

Step 2
To a stirred solution of Boc-L-valine (3.0 g, 13.82 mmol), ethane-1,2-diol (1.11 g, 17.96 mmol) in dichloromethane (45 mL) at 0° C. under argon was added 4-dimethylaminopyridine (0.33 g, 2.76 mmol) followed by a solution of dicyclohexylcarbodiimide (3.69 g, 17.96 mmol) in dichloromethane (15 mL). The resulting mixture was stirred at rt for 16 h. The reaction mixture was concentrated under reduced pressure, and the resulting crude residue was purified by column chromatography on silica gel eluting 0-30% ethyl acetate in pet-ether to obtain 2-hydroxyethyl (tert-butoxycarbonyl)-L-valinate (178-b): $^1$H NMR (400 MHz, DMSO-$d_6$) δ 7.11 (d, 2ZH), 4.77 (t, J=5.4 Hz, 1H), 4.06 (m, 2H), 3.87 (dd, J=7.8 and 6.0 Hz, 1H), 3.56 (appt q, J=5.2 Hz, 2H), 2.50 (m, 1H), 2.01 (m, 1H), 1.39 (s, 9H), 0.87 (d, J=6.6 Hz, 6H).

Step 3
To a stirred solution of 5-bromo-2-(4-methoxybenzyl)-2H-1,2,3-triazole-4-carboxylic acid (178-a, 2.55 g, 8.17 mmol), 2-hydroxyethyl (tert-butoxycarbonyl)-L-valinate (178-b, 2.77 g, 10.62 mmol) in dichloromethane (37.5 mL) at 0° C. under argon was added 4-dimethylaminopyridine (0.2 g, 1.63 mmol) followed by a solution of dicyclohexylcarbodiimide (2.18 g, 10.62 mmol) in dichloromethane (12.5 mL). The mixture was stirred at rt for 16 h. After the reaction mixture was concentrated under reduced pressure, the residue was purified by column chromatography on silica gel eluting 0-60% ethyl acetate in pet-ether to obtain 2-(((tert-butoxycarbonyl)-L-valyl)oxy)ethyl 5-bromo-2-(4-methoxybenzyl)-2H-1,2,3-triazole-4-carboxylate: ES/MS m/z: calculated for $C_{23}H_{32}BrN_4O_7$ (M+H): 555.15, found: 555.34.

Step 4
2-(((tert-butoxycarbonyl)-L-valyl)oxy)ethyl 2-(4-methoxybenzyl)-5-(7-(2-(4-methoxybenzyl)-2H-1,2,3-triazol-4-yl)-9H-fluoren-2-yl)-2H-1,2,3-triazole-4-carboxylate was prepared in a manner similar to the general procedures of Suzuki reaction using 2-(4-methoxybenzyl)-4-(7-(4,4,5,5-tetramethyl-1,3,2-dioxaborolan-2-yl)-9H-fluoren-2-yl)-2H-1,2,3-triazole and 2-(((tert-butoxycarbonyl)-L-valyl)oxy)ethyl 5-bromo-2-(4-methoxybenzyl)-2H-1,2,3-triazole-4-carboxylate. ES/MS m/z: calculated for $C_{46}H_{49}N_7NaO_8$ (M+Na): 850.35, found: 850.86.

Step 5
A mixture of 2-(((tert-butoxycarbonyl)-L-valyl)oxy)ethyl 2-(4-methoxybenzyl)-5-(7-(2-(4-methoxybenzyl)-2H-1,2,3-triazol-4-yl)-9H-fluoren-2-yl)-2H-1,2,3-triazole-4-carboxylate (4.5 g, 5.44 mmol) in trifluoroacetic acid (45 mL) was stirred at 70° C. for 48 h. After the reaction mixture was concentrated under reduced pressure, the residue was purified by Prep-HPLC and combined pure fractions were lyophilised to obtain 2-((L-valyl)oxy)ethyl 4-(7-(1H-1,2,3-triazol-4-yl)-9H-fluoren-2-yl)-1H-1,2,3-triazole-5-carboxylate: $^1$H NMR (400 MHz, DMSO-$d_6$) δ 8.42 (s, 1H), 8.28 (s, 3H), 8.14 (s, 1H), 8.07-8.03 (m, 3H), 7.96 (d, J=8.0 Hz, 1H), 7.83 (d, J=6.0 Hz, 1H), 4.56 (m, 1H), 4.55 (m, 2H), 4.43 (m, 1H), 4.08 (s, 2H), 3.92 (m, 1H), 2.05 (h, J=6.8 Hz, 1H), 0.86 (d, J=6.8 Hz, 3H), 0.83 (d, J=6.8 Hz, 3H). ES/MS m/z: calculated for $C_{25}H_{26}N_7O_4$ (M+H): 488.20, found: 488.39.

Example 179: 2-(phosphonooxy)ethyl 4-(7-(1H-1,2,3-triazol-4-yl)-9H-fluoren-2-yl)-1H-1,2,3-triazole-5-carboxylate

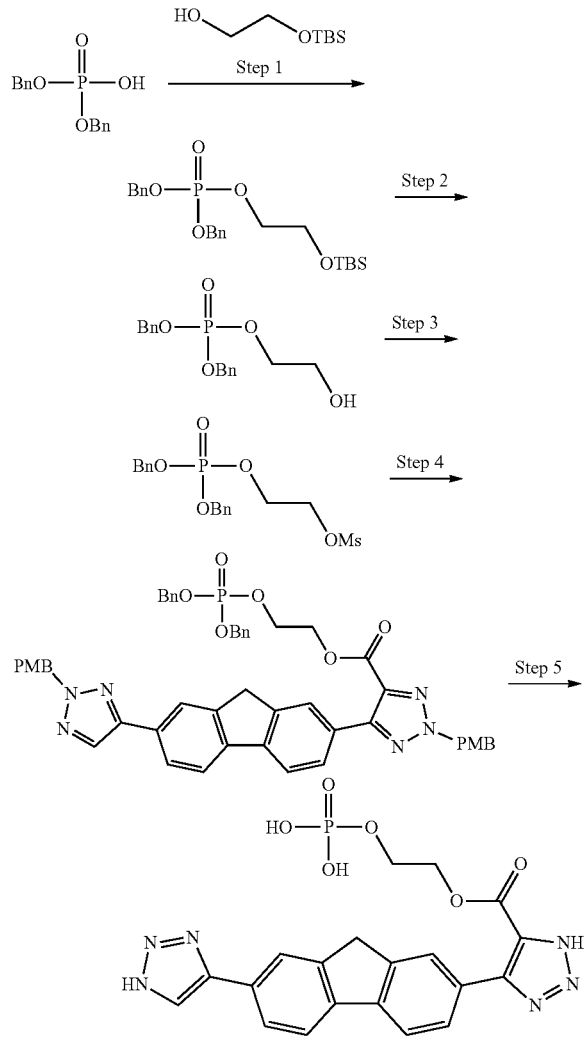

Step 1
To a stirred solution of dibenzyl hydrogen phosphate (117, 20 g, 71.94 mmol), 2-((tert-butyldimethylsilyl)oxy)ethan-1-ol (15.22 g, 86.33 mmol) in THF (200 mL) at 0° C. under argon was added triphenylphosphine (28.27 g, 107.91 mmol), followed by diethyl azodicarboxylate (18.83 g, 107.91 mmol). The resulting mixture was stirred at rt for 5 h. After the reaction mixture was concentrated under reduced pressure, the residue was purified by column chromatography on silica gel eluting 0-10% ethyl acetate in pet-ether to obtain dibenzyl (2-((tert-butyldimethylsilyl)oxy)ethyl) phosphate: ES/MS m/z: calculated for $C_{22}H_{34}O_5PSi$ (M+H): 437.19, found: 437.34.

Step 2
To a stirred solution of dibenzyl (2-((tert-butyldimethylsilyl)oxy)ethyl) phosphate (23 g, 52.75 mmol) in MeOH (230 mL) at rt under argon was added Dowex-50W. The mixture was stirred for 16 h. The reaction mixture was filtered, and the filtrate was concentrated under reduced pressure to obtain crude compound. The crude compound was purified by column chromatography on silica gel eluting 0-2% MeOH in dichloromethane to obtain dibenzyl (2-hydroxyethyl) phosphate: ES/MS m/z: calculated for $C_{16}H_{20}O_5P$ (M+H): 323.10, found: 323.24.

Step 3
To a stirred solution of dibenzyl (2-hydroxyethyl) phosphate (5 g, 15.52 mmol) in dichloromethane (50 mL) at 0° C. under argon was added $NEt_3$ (3.23 mL, 23.28 mmol), followed by MsCl (2.13 g, 18.63 mmol). After the mixture was stirred at rt for 5 h, the reaction mixture was diluted with dichloromethane and washed with water. The organic layer was dried ($Na_2SO_4$), and concentrated under reduced pressure to obtain crude 2-((bis(benzyloxy)phosphoryl)oxy)ethyl methanesulfonate, which was used directly to next step without any further purification: ES/MS m/z: calculated for $C_{17}H_{22}O_7PS$ (M+H): 401.08, found: 401.27.

Step 4
To a stirred mixture of 2-(4-methoxybenzyl)-5-(7-(2-(4-methoxybenzyl)-2H-1,2,3-triazol-4-yl)-9H-fluoren-2-yl)-2H-1,2,3-triazole-4-carboxylic acid (4 g, 6.84 mmol) and potassium carbonate (1.41 g, 10.26 mmol) in DMF (40 mL) at 0° C. under argon was added 2-((bis(benzyloxy)phosphoryl)oxy)ethyl methanesulfonate (3.28 g 8.21 mmol). After the mixture was stirred for 14 h at 50° C., the reaction mixture was diluted with ice water, and the product was extracted with ethyl acetate. The organic extract was dried ($Na_2SO_4$) and concentrated under reduced pressure. The crude residue was purified by column chromatography on silica gel eluting 0-60% ethyl acetate in pet-ether to obtain 2-((bis(benzyloxy)phosphoryl)oxy)ethyl 2-(4-methoxybenzyl)-5-(7-(2-(4-methoxybenzyl)-2H-1,2,3-triazol-4-yl)-9H-fluoren-2-yl)-2H-1,2,3-triazole-4-carboxylate: ES/MS m/z: calculated for $C_{50}H_{46}N_6O_8P$ (M+H): 889.31, found: 889.77.

Step 5
A mixture of 2-((bis(benzyloxy)phosphoryl)oxy)ethyl 2-(4-methoxybenzyl)-5-(7-(2-(4-methoxybenzyl)-2H-1,2,3-triazol-4-yl)-9H-fluoren-2-yl)-2H-1,2,3-triazole-4-carboxylate (11.5 g, 12.94 mmol) in trifluoroacetic acid (45 mL) was stirred at 70° C. for 20 h. After the reaction mixture was concentrated under reduced pressure, the crude residue was purified by Prep-HPLC to obtain 2-(phosphonooxy)ethyl 4-(7-(1H-1,2,3-triazol-4-yl)-9H-fluoren-2-yl)-1H-1,2,3-triazole-5-carboxylate: $^1$H NMR (400 MHz, DMSO-$d_6$) δ 8.39 (s, 1H), 8.19 (s, 1H), 8.11 (s, 1H), 8.01-7.97 (m, 3H), 7.92 (d, J=7.3 Hz, 1H), 4.36 (m, 2H), 4.06 (s, 2H), 4.03 (m, 2H) ES/MS m/z: calculated for $C_{20}H_{18}N_6O_6P$ (M+H): 469.10, found: 469.16.

Example 180: (((2-(phosphonooxy)ethoxy)carbonyl)oxy)methyl 4-(7-(1H-1,2,3-triazol-4-yl)-9H-fluoren-2-yl)-1H-1,2,3-triazole-5-carboxylate

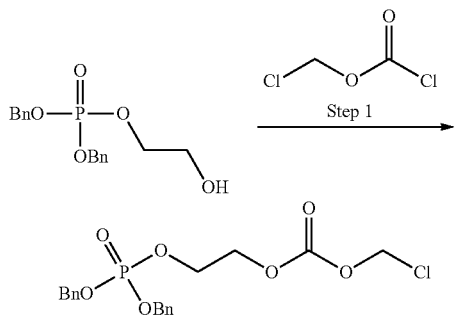

-continued

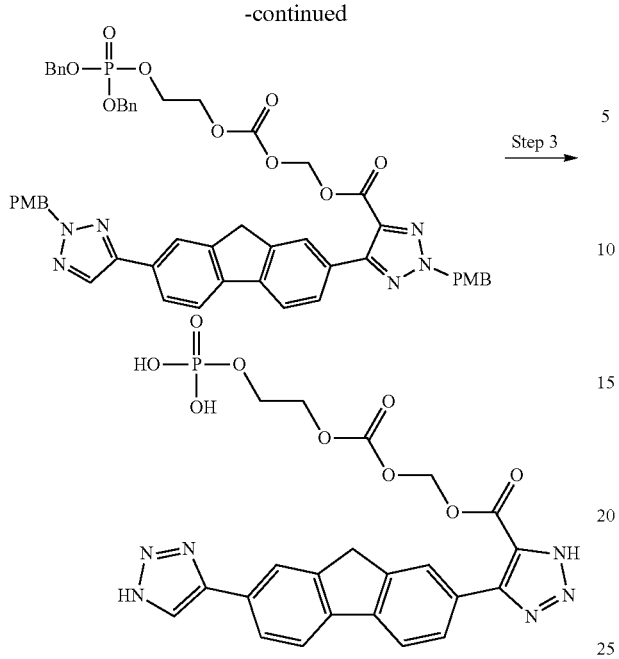

Step 1

To a stirred solution of dibenzyl (2-hydroxyethyl) phosphate (5 g, 15.52 mmol) and pyridine (2.5 mL, 31.04 mmol) in dichloromethane (100 mL) at 0° C. under argon was added chloromethyl carbonochloridate (2.97 g, 23.29 mmol). After the mixture was stirred at rt for 6 h, the reaction mixture was diluted with dichloromethane and washed with water. The organic layer was dried (Na$_2$SO$_4$) and concentrated under reduced pressure to obtain crude 2-((bis(benzyloxy)phosphoryl)oxy)ethyl (chloromethyl) carbonate, which was used directly to next step without any further purification: ES/MS m/z: calculated for C$_{18}$H$_{21}$ClO$_7$P (M+H): 415.07, found: 415.31.

Step 2

To a stirred solution of 2-(4-methoxybenzyl)-5-(7-(2-(4-methoxybenzyl)-2H-1,2,3-triazol-4-yl)-9H-fluoren-2-yl)-2H-1,2,3-triazole-4-carboxylic acid (5.0 g, 8.56 mmol) and potassium carbonate (1.77 g, 12.84 mmol) in DMF (50 mL) at 0° C. under argon was added 2-((bis(benzyloxy)phosphoryl)oxy)ethyl (chloromethyl) carbonate (0.25 g, 10.27 mmol). The mixture was stirred at 50° C. for 18 h. After the reaction mixture was diluted with ice water, the product was extracted with ethyl acetate. The organic extract was dried (Na$_2$SO$_4$) and concentrated under reduced pressure. The residue was purified by column chromatography on silica gel eluting 0-1% MeOH in dichloromethane to obtain (((2-((bis(benzyloxy)phosphoryl)oxy)ethoxy)carbonyl)oxy)methyl 2-(4-methoxybenzyl)-5-(7-(2-(4-methoxybenzyl)-2H-1,2,3-triazol-4-yl)-9H-fluoren-2-yl)-2H-1,2,3-triazole-4-carboxylate: ES/MS m/z: calculated for C$_{52}$H$_{48}$N$_6$O$_{11}$P (M+H): 963.31, found: 963.39.

Step 3

A mixture of (((2-((bis(benzyloxy)phosphoryl)oxy)ethoxy)carbonyl)oxy)methyl 2-(4-methoxybenzyl)-5-(7-(2-(4-methoxybenzyl)-2H-1,2,3-triazol-4-yl)-9H-fluoren-2-yl)-2H-1,2,3-triazole-4-carboxylate (5.5 g, 5.71 mmol) in trifluoroacetic acid (55 mL) was stirred at 70° C. for h. After the reaction mixture was concentrated under reduced pressure, the crude residue was purified by Prep-HPLC to obtain (((2-(phosphonooxy)ethoxy)carbonyl)oxy)methyl 4-(7-(1H-1,2,3-triazol-4-yl)-9H-fluoren-2-yl)-1H-1,2,3-triazole-5-carboxylate: $^1$H NMR (400 MHz, Methanol-d$_4$) δ 8.42 (s, 1H), 8.15 (s, 1H), 8.06 (t, J=8.0 Hz, 2H), 8.00 (s, 1H), 7.95 (d, J=8.0 Hz, 1H), 7.80 (d, J=8.0 Hz, 1H), 5.94 (s, 2H), 4.32 (m, 2H), 4.08 (s, 2H), 4.01 (m, 2H). ES/MS m/z: calculated for C$_{22}$H$_{20}$N$_6$O$_9$P (M+H): 543.10, found: 543.40.

The following compounds were prepared in a manner similar to the representative procedures of Suzuki reaction, SEM or PMB deprotections described above, and ester hydrolysis either using previously mentioned bromide intermediates, 18 or 20 with commercially available boronates:

Example 182: 3-(3-chloro-4-fluorophenyl)-1H-pyrazole-4-carboxylic acid

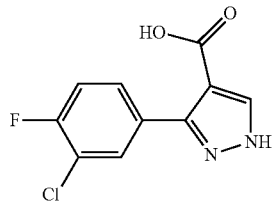 [SMILES: O=C(O)c1c[nH]nc1-c1ccc(F)c(Cl)c1]

$^1$H NMR (400 MHz, Methanol-d$_4$) δ 8.17 (s, 1H), 7.90 (dd, J=7.2, 2.2 Hz, 1H), 7.71 (ddd, J=8.6, 4.6, 2.2 Hz, 1H), 7.29 (t, J=8.9 Hz, 1H). ES/MS m/z: calculated for C$_{10}$H$_7$ClFN$_2$O$_2$ (M+H): 241.02, found: 241.02.

Example 183: 3-(3,5-dichlorophenyl)-1H-pyrazole-4-carboxylic acid

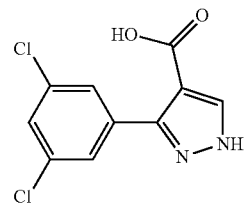 [SMILES: O=C(O)c1c[nH]nc1-c1cc(Cl)cc(Cl)c1]

$^1$H NMR (400 MHz, Methanol-d$_4$) δ 8.21 (s, 1H), 7.77 (d, J=2.0 Hz, 2H), 7.47 (t, J=2.0 Hz, 1H). ES/MS m/z: calculated for C$_{10}$H$_7$Cl$_2$N$_2$O$_2$ (M+H): 256.99, found: 257.03.

Example 184: 4-(3-chloro-4-fluorophenyl)-1H-imidazole-5-carboxylic acid

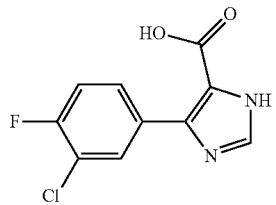 [SMILES: O=C(O)c1[nH]cnc1-c1ccc(F)c(Cl)c1]

$^1$H NMR (400 MHz, Methanol-d$_4$) 8.12 (dd, J=7.4, 2.2 Hz, 1H), 7.90 (ddd, J=8.6, 4.7, 2.2 Hz, 1H), 7.68 (s, 1H), 7.20 (dd, J=9.2, 8.7 Hz, 1H). ES/MS m/z: calculated for $C_{10}H_7ClFN_2O_2$ (M+H): 241.02, found: 240.94.

Example 185:
4-(3,5-dichlorophenyl)-1H-imidazole-5-carboxylic acid

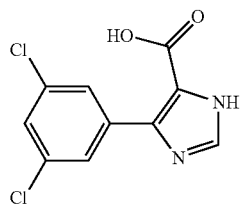 [SMILES: O=C(O)c1[nH]cnc1-c1cc(Cl)cc(Cl)c1]

$^1$H NMR (400 MHz, Methanol-$d_4$) δ 8.03 (s, 2H), 7.67 (s, 1H), 7.31 (s, 1H). ES/MS m/z: calculated for $C_{10}H_7Cl_2N_2O_2$ (M+H): 256.99, found: 257.03.

Biological Assays

Biological Assay 1: Biochemical Cellular Assays
Materials

Glycolate oxidase (GO) was generated at Gilead using HAO1 sequence by Jones et al., 2000 (J. Biol. Chem. 275: 12590-12597). Amplex® Red Hydrogen Peroxide/Peroxidase Assay Kit (Catalog no. A22188) was purchased from Thermo Fisher (Waltham, Mass.). Glycolic acid (Catlog No. 124737) and Tris 1M, pH 7.8 (Catalog no. T2569-1L) were from Sigma (St. Louis, Mo.), 10% Tween-20 (Catalog no. 51-12-02) was from SeraCare (Milford, Mass.), 2% BSA (Catalog no. BSA-1000) was from Rockland Immunochemicals (Pottstown. Pa.), and black 384-well low binding plate (Catalog no. 3860) was from Corning (Sunnyvale, Calif.).

Methods

1. GO Biochemical Assay

GO biochemical enzymatic reaction was performed in black 384-well low binding plate in a total volume of 25 µL. The reaction mixture contained 5 nM GO, 100 µM glycolate, 0.1 U/mL HRP, 50 µM Amplex Red, and 1:3 serial diluted test compounds in a buffer containing 50 mM Tris pH 7.8, 0.0025% Tween-20, and 0.02% BSA. Twenty five nanoliter of 1000× test compounds were pre-spotted onto 384-well low binding plate by Echo 555 Liquid Handler (Labcyte Inc., San Jose, Calif.) with starting final concentration of 10 µM, followed by addition of µL/well of 25 nM GO (5× of 5 nM final concentration) and incubated for 15 min. Ten microliter of 2.5× of 0.1 U/mL final concentration HRP was added to each well, followed by addition of 10 µL 2.5×100 µM final concentration of glycolate substrate and of 2.5×50 µM final concentration of Amplex Red. The reaction was mixed and incubated at room temperature for 20 min followed by reading the plates by EnVision plate reader (Perkin Elmer, San Jose, Calif.) with excitation at 570 nm and emission 585 nm. The wells with DMSO were used as negative controls (as 0% inhibition) whereas wells without GO enzymes were used as positive controls (as 100% inhibition). The % inhibition as calculated as 100%×(Well-Negative)/(Positive-Negative)

2. HRP Counter Screen Assay

HRP counter screen assay was performed in parallel with GO biochemical assay to exclude compounds that might inhibit HRP directly but had no effect on inhibiting GO. Twenty five nanoliter of the same set of 1000× test compounds were pre-spotted onto 384-well low binding plate as described above in GO biochemical assay, followed by addition of 10 µL 2.5×0.1 U/mL final concentration HRP in a buffer containing 50 mM Tris pH 7.8, 0.0025% Tween, 0.02% BSA, and incubated for 15 min. Then 15 µL of 1.67×50 µM final concentration of Amplex Red and 1.67×10 µM final concentration of $H_2O_2$ were added to each well. The reaction was mixed and incubated at room temperature for 20 min. At the end of the incubation, the plates were read by Envision with excitation at 570 nm and emission 585 nm. The wells with DMSO were used as negative controls (as 0% inhibition) whereas wells without HR enzymes were used as positive controls (as 100% inhibition). The % inhibition was calculated as described above.

GO Cell Based Assays

1. GO Transient Transfection Cell Based Assay
Materials

HAO1 plasmid DNA was generated by PCR cloning of HAO1 cDNA (Jones et al., 2000) into pcDNA3.1 (+)-neomycin vector by LakePharma (Belmont, Calif.). FuGENE 6 transfection reagents (Catalog no. E2692) were purchased from Promega (Madison, Wis.). CHO-K1 cell line (Catalog no. ATCC CCL-61) and F-12K medium (Catalog No. 30-2004) were obtained from ATCC (Manassas, Va.). OptiMEM I Reduced Serum Medium (Catalog No. 31985-070) was from Gibco/Life Technologies (Grand Island, N.Y.). Fetal Bovine Serum (FBS) (Catalog no. SH30071.03) was from HyClone (Logan, Utanh), and 100× Penicillin/Streptomycin/L-Glutamine (Catalog no. 30-009-Cl) was from Corning (Fremont, Calif.). 384-well black tissue culture plates (Catalog No. 781086) were purchased from Greiner Bio-One (Monroe, N.C.).

Methods

Transient transfection was performed by mixing 3 parts of FuGENE 6 reagent in pi to one part of HAO1 plasmid DNA or vector control DNA in µg in OptiMEM I Reduced Serum Medium and incubated at room temperature for 15 min. The mixture was mixed with CHO-K1 cells and dispended at 45 µL/well containing 0.025 µg HAO1 plasmid DNA, 0.075 µL FuGENE 6, and 4000 cells in F-12K medium plus 10% FBS. The cells were incubated for 48 hours at 37° C. incubator for GO to be expressed. Then cell culture media were removed and replaced with 25 µL of 1:3 serial diluted test compounds with starting concentration at 1 µM, and incubated for 1 hour at room temperature. Then 25 µl reaction buffer (50 mM Tris pH 7.8, 0.0025% Tween, and 0.02% BSA) containing HRP (final concentration of 0.1 U/mL), 300 µM glycolate, and 50 µM Amplex Red was added to each well. The reaction was mixed and incubated at room temperature for 20 min followed by reading the plates by EnVision plate reader as described above. The wells with DMSO were used as negative control (0% inhibition) whereas the wells with vector control DNA transfection were used as positive controls (as 100% inhibition). The % inhibition was calculated as described above.

2. GO Stable Clone Cell Based Assay
Materials

The reagents and tissue culture media for transient transfection were described in transient transfection assay section. Rabbit anti-HAO1 antibody (Catalog No, ab93137) was purchased from Abeam (Cambridge, Mass.) and anti-rabbit IgG (H+L), F(ab')$_2$ fragment, Alexa Fluor® 555 Conjugate (Catalog No. #4413) was obtained from Cell Signaling Technology (Danvers, Mass.).

Methods

1) Generation of CHO-K1-HAO1 Stable Clones

GO stable clones were generated in house by performing bulk transient transfection of GO plasmid DNA into CHO-K1 cells and incubated for 48 hours as described above. Then the cells were trypsined and 2000 cells/200 µl were added to well A1 followed by 1:2 serial dilutions to A2 and all the way to A12 for 10 96-well tissue culture plates. Cells in A1-A12 were further 1:2 serial diluted down to H1-H12 and incubated for two weeks in F-12K medium with 10% FBS supplemented with G418 at 500 µg/mL. Each plate was monitored for colony formations under the microscope. Twenty eight single colonies were picked and expanded for testing GO expression.

Immunocytochemistry for Intracellular GO Staining

Intracellular GO staining was performed by fixing cells first in with 50 µl/well 4% formaldehyde in PBS in a 384-well plate for 30 min at room temperature, followed by washing 3 times with 80 µL/well washing buffer (PBS with 0.05% Tween-20). The cells were then permeabilized with 50 µL/well 0.1% Triton in PBS for 30 min, washed 3 times, and blocked for 1 hour with 50 µL/well 3% BSA in PBS with 0.05% Tween-20. The cells were washed again for 3 times, and 50 µL of rabbit anti-human GO at 1:100 dilutions in PBS with 1% BSA and 0.05% Tween-20 were added to each well and incubated overnight at 4° C. The cells were washed for 4 times with 15 min incubation in between each wash, followed by addition of 40 µL Alexa Fluor 555 conjugated anti-rabbit IgG (H+L) F(ab')$_2$ fragments at 1:250 dilution and Hoechst at 1:500 dilution in 1% BSA and 0.05% Tween-20 to each well. The plates were incubated for 160 min at room temperature and washed four times at the end of the incubation. Sixty microliter of PBS was added to each well and cell images were examined by Arrayscan XTI HCS reader from Thermo Fisher Scientific (Waltham, Mass.).

2) Stable Clone 2D2 GO Enzymatic Activity Cell Based Assay 384-well tissue culture plates were pre-spotted with 25 nL test compound per well followed by dispensing 5000 cells/well/25 µL of clone 2D2 in reaction buffer (50 mM Tris pH 7.8, 0.0025% Tween, and 0.02% BSA) to all the wells except column 22, where 5000 cells/well/25 µL of clone 1A1 vector control were added. The test compounds were incubated with the cells for 1 hour at room temperature, followed by adding 25 µL reaction buffer (50 mM Tris pH 7.8, 0.0025% Tween, and 0.02% BSA) containing HRP (final concentration of 0.1 U/mL), 160 µM glycolate, and 50 µM Amplex Red. The reaction was mixed and incubated for 20 min at room temperature and the fluorescence of the product resorufin was measured described above. The wells with 2D2 and DMSO were used as negative control (0% inhibition) whereas the wells with 1A1 vector control clone were used as positive controls (as 100% inhibition). Percent inhibition was calculated as described above (Table 2).

TABLE 2

| Ex. | IC$_{50}$ GO AR-384 | EC$_{50}$ GO CHO K1 AR | EC$_{50}$ GO CHO K1 STABLE |
|---|---|---|---|
| 1 | 1000 | 1000 | 1000 |
| 2 | 1000 | 1000 | 1000 |
| 3 | 10000 | | |
| 4 | 616.16 | | |
| 5 | 10000 | | |
| 6 | 666.77 | | |
| 7 | 3772.2 | | |
| 8 | 1311.7 | | |
| 9 | 348.49 | | |
| 10 | 677.77 | | |
| 11 | 4725.8 | | |
| 12 | 130.04 | | |
| 13 | 210.52 | | |
| 14 | 1196.6 | | |
| 15 | 1603.9 | | |
| 16 | 452.59 | | |
| 17 | 10000 | | |
| 18 | 250.27 | | |
| 19 | 196.34 | | |
| 20 | 293.95 | | |
| 21 | 173.23 | | |
| 22 | 158.54 | | |
| 23 | 298.91 | | |
| 24 | 239.81 | | |
| 25 | 730.69 | | |
| 26 | 250.73 | | |
| 27 | 362.7 | | |
| 28 | 101.96 | | |
| 29 | 329.78 | | |
| 30 | 845.14 | | |
| 31 | 1000 | 10000 | |
| 32 | 1254.9 | | |
| 33 | 338.57 | | |
| 34 | 7499.4 | | |
| 35 | 10000 | | |
| 36 | 345.81 | 852.16 | |
| 37 | 91.823 | | |
| 38 | 230.25 | 1003.9 | |
| 39 | 30.686 | 106.34 | |
| 40 | 1000 | 10000 | 1000 |
| 41 | 71.628 | 306.82 | |
| 42 | 96.619 | 840.3 | 240.81 |
| 43 | 268.41 | | |
| 44 | 510.18 | 1000 | 1000 |
| 45 | 316.55 | 1024.4 | |
| 46 | 437.21 | 2210.4 | |
| 47 | 46.556 | 262.95 | 96.174 |
| 48 | 159.94 | 950.06 | 508.67 |
| 49 | 24.817 | 109.17 | 47.096 |
| 50 | 123.55 | 250 | |
| 51 | 35.923 | 100.27 | 49.044 |
| 52 | 174.38 | 485.77 | |
| 53 | 377.06 | | |
| 54 | 4298.1 | | |
| 55 | 562.63 | 1000 | 942.08 |
| 56 | 178.64 | 869.54 | 312.6 |
| 57 | 731.16 | 5013 | |
| 58 | 192.17 | 703.93 | |
| 59 | 26.737 | | |
| 60 | 29.699 | 170.35 | |
| 61 | 97.918 | 575.96 | |
| 62 | 392.22 | 1000 | 572.94 |
| 63 | 34.621 | 115.78 | 77.353 |
| 64 | 29.115 | 162.16 | 83.25 |
| 65 | 23.651 | 214.06 | 60.122 |
| 66 | 125.9 | 505.14 | |
| 67 | 164.4 | 569.68 | |
| 68 | 7.656 | 23.288 | 25.251 |
| 69 | 21.44 | 117.07 | |
| 70 | 109.51 | 448.23 | |
| 71 | 47.717 | 264.27 | 174.01 |
| 72 | 342.59 | 1161.7 | 857.3 |
| 73 | 357.95 | 1000 | 599.85 |
| 74 | 31.797 | 157.85 | 57.913 |
| 75 | 18.638 | 137.34 | 60.402 |
| 76 | 399.49 | 978.17 | |
| 77 | 94.591 | 531.48 | 267.24 |
| 78 | 228.07 | 851.35 | 434.21 |
| 79 | 243.65 | 877.5 | 420.34 |
| 80 | 174.11 | 847.9 | 419.5 |
| 81 | 187.24 | 428.73 | |
| 82 | 113.91 | 305.12 | |
| 83 | 135.5 | 738.62 | 297.65 |
| 84 | 1000 | 1000 | |
| 85 | 47.901 | 209.46 | 119.22 |

TABLE 2-continued

| Ex. | IC$_{50}$ GO AR-384 | EC$_{50}$ GO CHO K1 AR | EC$_{50}$ GO CHO K1 STABLE |
|---|---|---|---|
| 86 | 29.151 | 79.666 | |
| 87 | 23.836 | 83.049 | 50.715 |
| 88 | 77.555 | 127.24 | |
| 89 | 13.554 | 37.294 | |
| 90 | 32.184 | 153.65 | |
| 91 | 64.456 | 632.02 | 141.26 |
| 92 | 57.012 | 412.33 | 208.79 |
| 93 | 8.411 | 68.469 | 27.488 |
| 94 | 57.171 | 307.15 | 142.79 |
| 95 | 12.091 | | 23.553 |
| 96 | 33.951 | 199.44 | 44.832 |
| 97 | 13.504 | 41.277 | 28.132 |
| 98 | 18.959 | 66.126 | 46.147 |
| 99 | 408.36 | 1331.3 | |
| 100 | 195.53 | 1109.3 | |
| 101 | 11.122 | 89.987 | 27.577 |
| 102 | 223.5 | 1000 | 443.36 |
| 103 | 93.231 | 283.25 | 130.53 |
| 104 | 125.41 | 651.91 | 232.61 |
| 105 | 37.445 | 252.33 | 84.69 |
| 106 | 9.662 | 78.035 | 49.673 |
| 107 | 10.322 | 32.526 | 27.695 |
| 108 | 7.911 | 44.339 | 22.084 |
| 109 | 22.687 | 124.41 | 40.268 |
| 110 | 49.903 | 245.53 | 86.854 |
| 111 | 11.204 | 121.88 | 32.356 |
| 112 | 37.547 | 303.85 | 112.63 |
| 113 | 20.247 | 91.754 | 38.705 |
| 114 | 15.491 | 105.88 | 24.459 |
| 115 | 16.2 | 79.849 | 34.063 |
| 116 | 58.559 | 374.15 | 136.34 |
| 117 | 19.73 | 97.778 | 27.55 |
| 118 | 18.502 | 65.156 | 23.054 |
| 119 | 21.725 | 88.296 | 33.84 |
| 120 | 11.282 | 80.822 | 26.481 |
| 121 | 38.174 | 176.11 | 73.873 |
| 122 | 10.657 | 25.201 | 12.205 |
| 123 | 40.929 | 209.73 | 78.786 |
| 124 | 16.093 | 82.772 | 106.78 |
| 125 | 5.24 | 45.738 | 16.697 |
| 126 | 13.069 | 51.529 | 47.04 |
| 127 | 4.143 | 14.021 | 7.801 |
| 128 | 123.15 | 649.59 | 405.2 |
| 129 | 23.984 | 105.64 | 112.57 |
| 130 | 4.136 | 20.032 | 7.143 |
| 131 | 4.672 | 14.962 | 5.128 |
| 132 | 133.41 | | |
| 133 | 19.227 | 113.09 | 48.603 |
| 134 | 127.99 | 196.86 | |
| 135 | 1543.8 | | |
| 136 | 211.25 | 1302.7 | 407.28 |
| 137 | 4079.5 | | |
| 138 | 269.64 | | |
| 139 | 10000 | | |
| 140 | 10000 | | |
| 141 | 10000 | | |
| 142 | 322.5 | 1000 | |
| 143 | 1000 | 1000 | |
| 144 | 124.67 | 469.06 | 435.83 |
| 145 | 552.54 | 1000 | 1000 |
| 146 | 33.572 | 267.94 | 98.667 |
| 147 | 114.13 | | |
| 148 | 267.19 | | |
| 149 | 43.534 | | |
| 150 | 10000 | | |
| 151 | 220.03 | 948.57 | 392.55 |
| 152 | 45.76 | 132.18 | 61.594 |
| 153 | 119 | 214.58 | 124.14 |
| 154 | 50.564 | 132.36 | |
| 155 | 96.924 | 622.18 | 260.87 |
| 156 | 114.56 | | 145.39 |
| 157 | 13.661 | 71.458 | 34.998 |
| 158 | 31.739 | 162.98 | |
| 159 | 176.59 | 898.94 | 486.71 |
| 160 | 225.95 | 1135.7 | |
| 161 | 10000 | 10000 | |
| 162 | 88.223 | | 160.04 |
| 163 | 1000 | | 1000 |
| 164 | 27.63 | 245.17 | 73.178 |
| 165 | 7.348 | 47.415 | 19.059 |
| 166 | 24.063 | 55.932 | 33.095 |
| 167 | 21.715 | 52.202 | 30.777 |
| 168 | 7.132 | 13.808 | 10.154 |
| 169 | 6.681 | | 13.318 |
| 170 | 16.504 | | 31.092 |
| 173 | 7.338 | 26.523 | 13.329 |
| 182 | >10000 | | |
| 183 | >10000 | | |
| 184 | >10000 | | |
| 185 | >10000 | | |

Biological Assay 2: Oral Bioavailability and PK Studies

An oral dose of Example 2 was formulated in a sterile solution of 50% water, 37.5% PEG 300, and 12.5% DMSO at 1.0 mg/mL. The dosing group consisted of three fasted male Sprague Dawley rats. At dosing, the animals weighed between 0.26 and 0.27 kg. For the oral dosing group, the formulated dose was administered via oral gavage at 5.0 mL/kg for a dose of 5.0 mg/kg. Non-compartmental pharmacokinetic analysis was performed on the plasma concentration-time data.

TABLE 3

| Animal | Animal Wt (kg) | Target Conc (mg/mL) | Measured Conc (mg/mL) | Dose Vol (mL) | Dose (mg/kg) | Dose (nmol/kg) |
|---|---|---|---|---|---|---|
| 1 | 0.26 | 1.00 | 1.00 | 1.30 | 5.04 | 16344 |
| 2 | 0.26 | 1.00 | 1.00 | 1.30 | 4.96 | 16094 |
| 3 | 0.27 | 1.00 | 1.00 | 1.40 | 5.20 | 16881 |

Table 3 shows the mean plasma pharmacokinetic parameters of Example 2 following a PO dose of Example 2 at 5 mg/kg in SD rats (mean±SD, n=3). Table 4 shows the mean plasma pharmacokinetic parameters of Example 68 following a PO dose of Example 2 at 5 mg/kg in SD rats (mean±SD, n=3). As shown in Tables 4 and 5, the AUC$_{inf}$ of Example 2 was 1600±280 nM*h and the C$_{max}$ was 2390±246 nM. The AUC$_{inf}$ of Example 68 was 3250±242 nM·h and the C$_{max}$ was 2270±171 nM. The bioavailability of Example 68 was estimated to be 19.0%±1.4%.

TABLE 4

| | Rat | | | | |
|---|---|---|---|---|---|
| PO | 001 | 002 | 003 | Mean | SD |
| AUC$_{0-24\,h}$ (nM · h) | 1270 | 1550 | 1850 | 1560 | 288 |
| AUC$_{inf}$ (nM · h) | 1340 | 1570 | 1900 | 1600 | 280 |
| C$_{max}$ (nM) | 2540 | 2530 | 2110 | 2390 | 246 |
| T$_{max}$ (hr) | 0.25 | 0.25 | 0.50 | 0.33 | 0.14 |
| F (%) | NC | NC | NC | NC | NC |

TABLE 5

| PO | 001 | 002 | 003 | Mean | SD |
|---|---|---|---|---|---|
| $AUC_{0-24\ h}$ (nM · h) | 3150 | 3360 | 2930 | 3140 | 216 |
| $AUC_{inf}$ (nM · h) | 3320 | 3450 | 2980 | 3250 | 242 |
| $C_{max}$ (nM) | 2120 | 2220 | 2450 | 2270 | 171 |
| $T_{max}$ (hr) | 0.50 | 0.25 | 0.50 | 0.42 | 0.14 |
| *F (%) | 19.4 | 20.2 | 17.4 | 19.0 | 1.4 |

*Based on IV exposure ($AUC_{inf}$ = 3420 nM · hr) of Example 68 at 1.0 mg/kg from Table 7, below.

Figure 2:
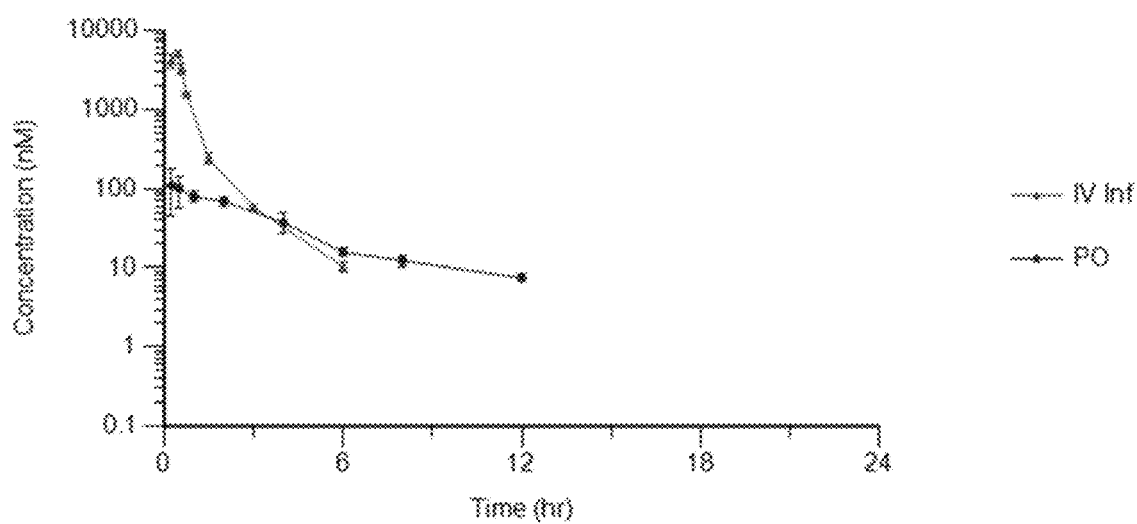
FIG. 2 shows the plasma concentration-time profiles of Example 68 following a 30-minute intravenous infusion at 1.0 mg/kg and a PO dose at 5.0 mg/kg in SD rats (mean±SD, n=3).

The apparent systemic clearance for Example 68 (CL=0.95±0.09 L/hr/kg) was low relative to the hepatic blood flow in rats (CL=4.0 L/hr/kg). The volume of distribution ($V_{ss}$=0.44±0.06 L/kg) was smaller than the volume of total body water (0.7 L/kg). The terminal $t_{1/2}$ of Example 68 was 1.02±0.06 hr and the mean residence time (MRT) was 0.47±0.02 hr. The oral bioavailability (% F) was estimated to be 2.3%±0.3%. See Table 7, Table 8 and FIG. 2.

TABLE 7

Mean plasma pharmacokinetic parameters of Example 68 following a 30-minute IV infusion at 1 mg/kg in SD rats (mean ± SD, n = 3).

| IV Parameter | A | B | C | Mean | SD |
|---|---|---|---|---|---|
| $AUC_{last}$ (nM · hr) | 3680 | 3090 | 3450 | 3400 | 296 |
| $AUC_{inf}$ (nM · hr) | 3690 | 3110 | 3460 | 3420 | 295 |
| $C_{max}$ (nM) | 4940 | 5100 | 5350 | 5130 | 208 |
| MRT (hr) | 0.47 | 0.49 | 0.44 | 0.47 | 0.02 |
| $t_{1/2}$ (hr) | 1.01 | 1.08 | 0.96 | 1.02 | 0.06 |
| $V_{ss}$ (L/kg) | 0.41 | 0.51 | 0.41 | 0.44 | 0.06 |
| CL (L/hr/kg) | 0.87 | 1.04 | 0.93 | 0.95 | 0.09 |

TABLE 8

Mean plasma pharmacokinetic parameters of Example 68 following a PO dose at 5 mg/kg in SD rats (mean ± SD, n = 3).

| Parameter | D | E | F | Mean | SD |
|---|---|---|---|---|---|
| $AUC_{last}$ (nM · hr) | 429 | 334 | 396 | 386 | 48 |
| $AUC_{inf}$ (nM · hr) | 485 | 383 | 479 | 449 | 57 |
| $C_{max}$ (nM) | 90.4 | 65.0 | 182 | 113 | 61.7 |
| $T_{max}$ (hr) | 0.25 | 2.00 | 0.25 | 0.83 | 1.01 |
| F (%) | 2.5 | 1.9 | 2.3 | 2.3 | 0.3 |

Figure 3:
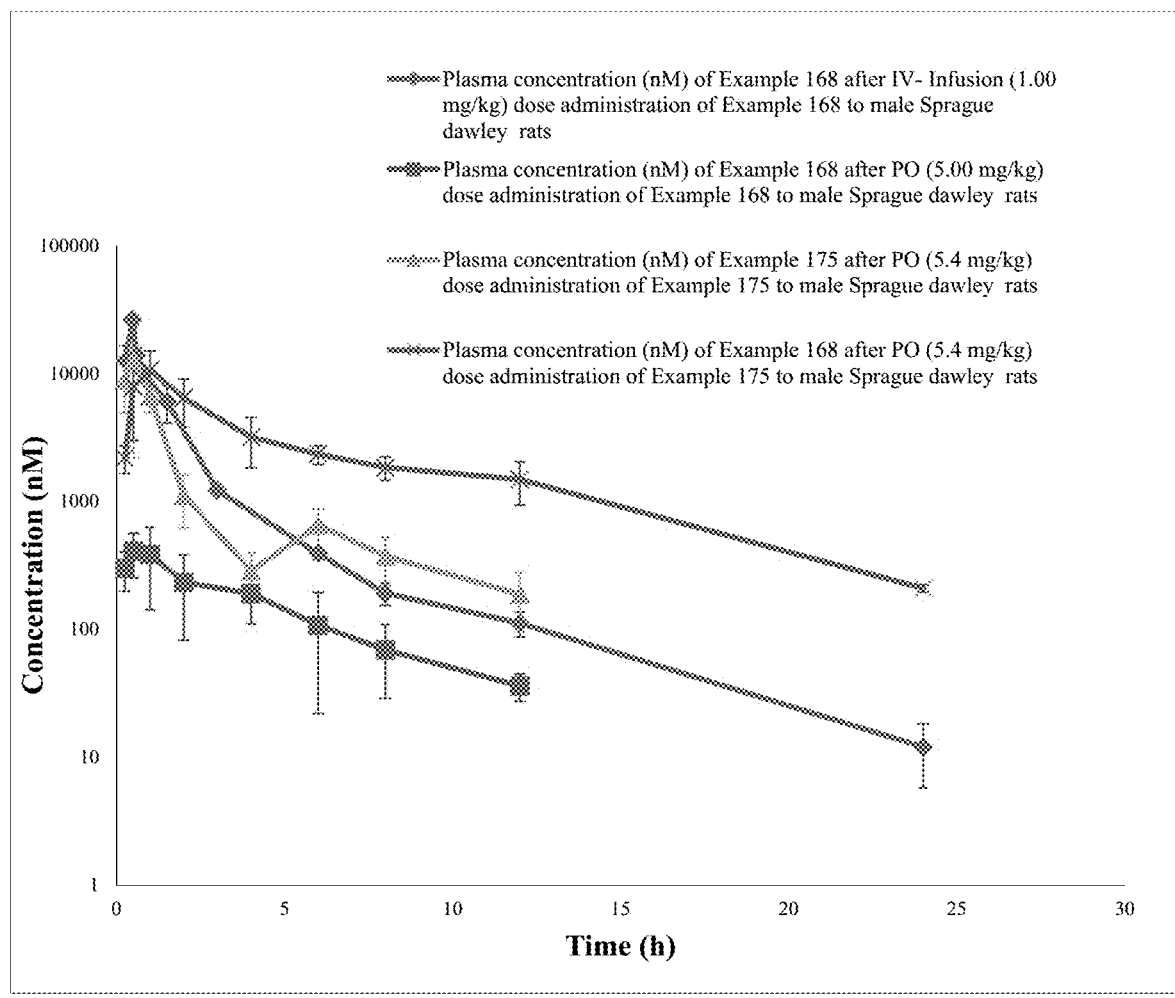
FIG. 3 shows the plasma concentration-time profiles of Example 168 and Example 175 in SD rats.
Figure 4:
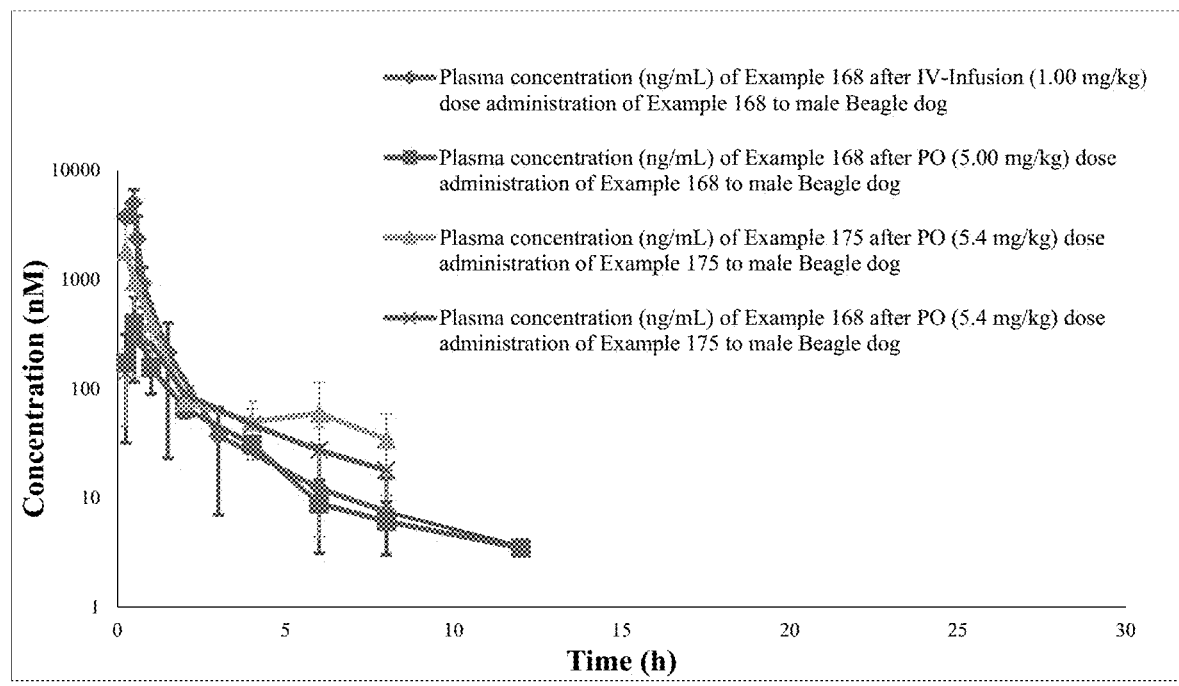
FIG. 4 shows the plasma concentration-time profiles of Example 168 and Example in 175 male Beagle dogs.

Example 168 or Example 175 was formulated in a sterile solution of 15% N-methyl-2-pyrrolidone, 55% PEG, and 30% water for oral administration or intravenous administration. The dosing group consisted of three fasted male SD rats or three fasted male beagle dogs. At dosing, the rats weighed between 0.2 and 0.3 kg, and the dogs weighed between 10.72 and 10.82 kg. For the oral dosing group, the formulated dose was administered via oral gavage at 5.0 mL/kg for a dose of 5.0 mg/kg or 5.4 mg/kg. For the intravenous dosing group, the formulated dose was 1.00 mg/kg. Non-compartmental pharmacokinetic analysis was performed on the plasma concentration-time data. Data from these studies are shown in FIG. 3 and FIG. 4.

The invention claimed is:
1. A compound of formula III:

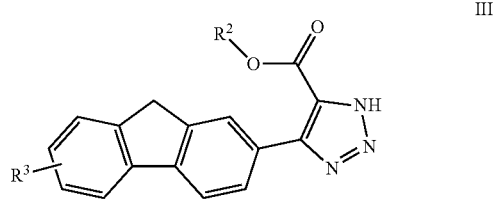

III or a pharmaceutically acceptable salt, tautomer, stereoisomer, mixture of stereoisomers, or deuterated analog thereof, wherein:

$R^2$ is hydrogen, —(CH$_2$CH$_2$O)$_{1-9}$CH$_2$CH$_2$OCH$_3$, $C_{1-6}$ alkyl optionally substituted with one to three $R^4$, cycloalkyl, or heteroaryl optionally substituted with one to three $R^5$;

each $R_3$ is independently aryl, heteroaryl, or heterocyclyl, wherein each $R_3$ is optionally substituted with one to three $R^6$;

each $R^4$ is independently halo, hydroxy, —OC$_{1-6}$alkyl, —NH$_2$, —NHC$_{1-6}$ alkyl, —N(C$_{1-6}$alkyl)$_2$, —OC(O)R$^a$, —OC(O)OR$^a$, —OP(O)(OR$^b$)$_2$, or monocyclic heterocyclyl; wherein each is optionally substituted with one to three $R_5$; provided only one $R^4$ is heterocyclyl;

each $R^5$ is independently cyano, halo, $C_{1-4}$ alkyl, hydroxy, —OC$_{1-4}$alkyl, $C_{1-4}$ haloalkyl, or —OC$_{1-4}$ haloalkyl;

each $R^6$ is independently cyano, halo, —C(O)R$^7$, —C(O)OR$^7$, —C(O)NR$^7$R$^8$, —S(O)$_2$NR$^7$R$^8$, —NR$^7$C(O)R$^8$, —OR$^7$, $C_{1-4}$ alkyl, —OC$_{1-4}$alkyl, $C_{1-4}$ haloalkyl, —OC$_{1-4}$ haloalkyl, phenyl, heterocyclyl, or heteroaryl; wherein each is optionally substituted with one to three $C_{1-4}$ alkyl, —C(O)OH or $C_{1-4}$ haloalkyl;

$R^7$ and $R^8$ are each independently hydrogen, $C_{1-4}$ alkyl or phenyl, pyridyl, or $R^7$ and $R^8$ together with the nitrogen atom to which they are attached form a heterocyclyl;

each $R^a$ is independently $C_{1-6}$ alkyl optionally substituted with —NH$_2$, —NHC$_{1-6}$ alkyl, —N(C$_{1-6}$alkyl)$_2$, or —OP(O)(OR$^b$)$_2$;

each $R^b$ is independently hydrogen or $C_{1-4}$ alkyl.

2. A compound of formula IV:

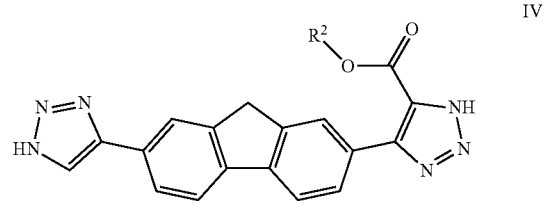

IV or a pharmaceutically acceptable salt, tautomer, stereoisomer, mixture of stereoisomers, or deuterated analog thereof, wherein:

$R^2$ is hydrogen, —(CH$_2$CH$_2$O)$_{1-9}$CH$_2$CH$_2$OCH$_3$, $C_{1-6}$ alkyl optionally substituted with one to three $R^4$, cycloalkyl, or heteroaryl optionally substituted with one to three $R^5$;

each $R^4$ is independently halo, hydroxy, —OC$_{1-6}$alkyl, —NH$_2$, —NHC$_{1-6}$ alkyl, —N(C$_{1-6}$alkyl)$_2$, —OC(O)R$^a$, —OC(O)OR$^a$, —OP(O)(OR$^b$)$_2$, or monocyclic heterocyclyl; wherein each is optionally substituted with one to three R⁵; provided only one R⁴ is heterocyclyl;

each R⁵ is independently cyano, halo, $C_{1-4}$ alkyl, hydroxy, —$OC_{1-4}$alkyl, $C_{1-4}$ haloalkyl, or —$OC_{1-4}$ haloalkyl;

each Rᵃ is independently $C_{1-6}$ alkyl optionally substituted with —NH₂, —NHC_{1-6} alkyl, —N(C_{1-6}alkyl)₂, or —OP(O)(ORᵇ)₂;

each Rᵇ is independently hydrogen or $C_{1-4}$ alkyl.

3. The compound of claim 2, wherein:
R² is hydrogen, $C_{1-6}$ alkyl optionally substituted with one to three R⁴, or cycloalkyl;
each R⁴ is independently —OC_{1-6}alkyl, —OC(O)Rᵃ, —OC(O)ORᵃ, —OP(O)(ORᵇ)₂, or monocyclic heterocyclyl;
each Rᵃ is independently $C_{1-6}$ alkyl optionally substituted with —NH₂ or —OP(O)(ORᵇ)₂; and
Rᵇ is hydrogen.

4. A compound selected from:

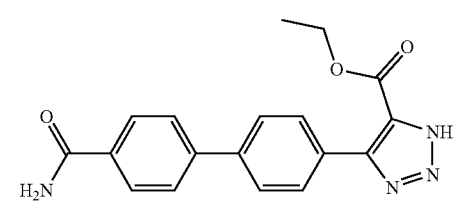

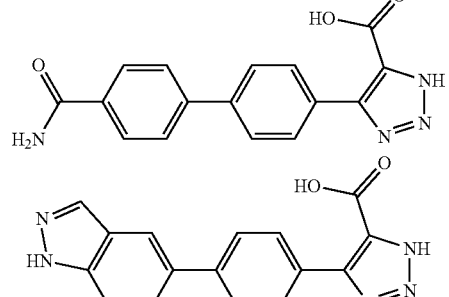

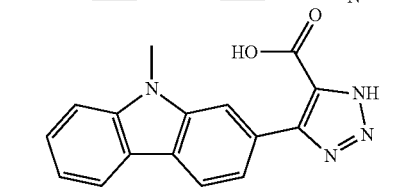

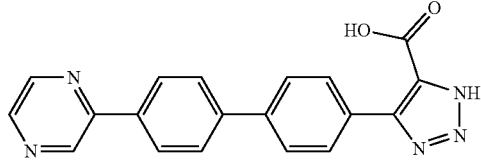

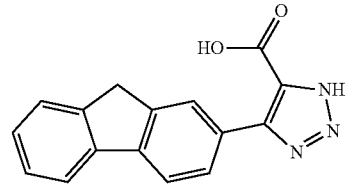

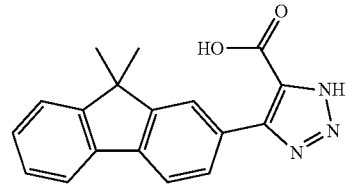

-continued

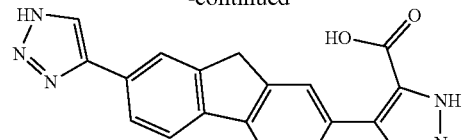

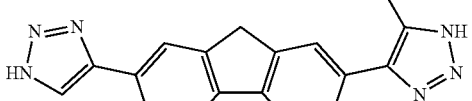

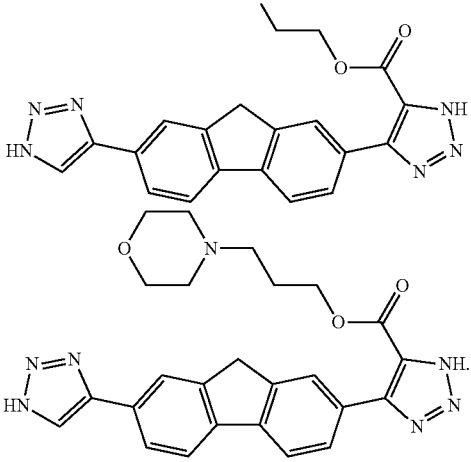

5. A compound having the structure:

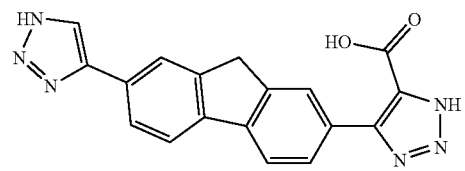 [SMILES: O=C(O)c1[nH]nnc1-c1ccc2c(c1)Cc1cc(-c3c[nH]nn3)ccc1-2]

or a pharmaceutically acceptable salt, tautomer, stereoisomer, mixture of stereoisomers, or deuterated analog thereof.

6. A compound having the structure:

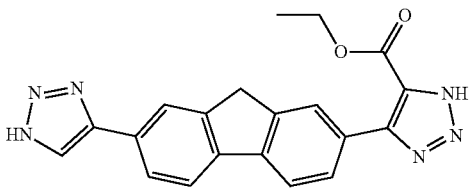 [SMILES: CCOC(=O)c1[nH]nnc1-c1ccc2c(c1)Cc1cc(-c3c[nH]nn3)ccc1-2]

or a pharmaceutically acceptable salt, tautomer, stereoisomer, mixture of stereoisomers, or deuterated analog thereof.

7. A pharmaceutical composition comprising the compound of claim 1 and a pharmaceutically acceptable excipient.

8. A pharmaceutical composition comprising the compound of claim 2 and a pharmaceutically acceptable excipient.

9. A pharmaceutical composition comprising the compound of claim 3 and a pharmaceutically acceptable excipient.

10. A pharmaceutical composition comprising the compound of claim 4 and a pharmaceutically acceptable excipient.

11. A pharmaceutical composition comprising the compound of claim 5 and a pharmaceutically acceptable excipient.

12. A pharmaceutical composition comprising the compound of claim 6 and a pharmaceutically acceptable excipient.

* * * * *

UNITED STATES PATENT AND TRADEMARK OFFICE
CERTIFICATE OF CORRECTION

PATENT NO. : 11,806,335 B2
APPLICATION NO. : 17/081940
DATED : November 7, 2023
INVENTOR(S) : Hongyan Guo et al.

Page 1 of 1

It is certified that error appears in the above-identified patent and that said Letters Patent is hereby corrected as shown below:

In the Claims

At Column 176, Claim number 1, Line number 28, after "each" insert --$R^4$--.

At Column 176, Claim number 1, Line number 36, after "each" insert --$R^6$--.

At Column 177, Claim number 2, Line number 1, after "each" insert --$R^4$--.

Signed and Sealed this
Twenty-ninth Day of April, 2025

Coke Morgan Stewart
*Acting Director of the United States Patent and Trademark Office*